(12) United States Patent
Rommelaere et al.

(10) Patent No.: US 11,840,566 B2
(45) Date of Patent: Dec. 12, 2023

(54) METHODS OF TREATING ASTHMA WITH POLYPEPTIDES TARGETING IL-13 AND TSLP

(71) Applicants: Ablynx N.V., Zwijnaarde (BE); Sanofi, Paris (FR)

(72) Inventors: Heidi Rommelaere, Ghent (BE); Ann Brigé, Ertvelde (BE); Sigrid Cornelis, St. Martens-Latem (BE); Bruno Dombrecht, Heusden (BE); Eric Lorent, Zwijnaarde (BE); Melanie Rieger, Zwijnaarde (BE); Timothy Soos, Bridgewater, NJ (US); John Park, Warthausen (DE); Bernd Weigle, Ingelheim am Rhein (DE); Klaus Erb, Ingelheim am Rhein (DE)

(73) Assignees: Ablynx N.V., Zwijnaarde (BE); Sanofi, Paris (FR)

( * ) Notice: Subject to any disclaimer, the term of this patent is extended or adjusted under 35 U.S.C. 154(b) by 193 days.

(21) Appl. No.: 17/530,800

(22) Filed: Nov. 19, 2021

(65) Prior Publication Data

US 2022/0177565 A1 Jun. 9, 2022

Related U.S. Application Data

(60) Division of application No. 17/208,046, filed on Mar. 22, 2021, now Pat. No. 11,208,476, which is a continuation of application No. 17/115,906, filed on Dec. 9, 2020, now abandoned.

(60) Provisional application No. 62/945,391, filed on Dec. 9, 2019.

(30) Foreign Application Priority Data

Jan. 27, 2020 (EP) .................... 20305064

(51) Int. Cl.
  *A61K 39/395* (2006.01)
  *C07K 16/24* (2006.01)
(52) U.S. Cl.
  CPC ...... *C07K 16/244* (2013.01); *C07K 2317/565* (2013.01)

(58) Field of Classification Search
  CPC .............. C07K 2319/00; A61K 39/395; A61K 2039/505; A61P 11/06
  See application file for complete search history.

(56) References Cited

U.S. PATENT DOCUMENTS

| 11,208,476 B2 | 12/2021 | Rommelaere et al. |
| 2009/0123478 A1 | 5/2009 | Monk et al. |
| 2021/0214431 A1 | 7/2021 | Rommelaere et al. |

FOREIGN PATENT DOCUMENTS

| WO | WO 2008/076321 A1 | 6/2008 |
| WO | WO 2012/175741 A2 | 12/2012 |
| WO | WO 2015/173325 A2 | 11/2015 |
| WO | WO 2017/087587 A1 | 5/2017 |
| WO | WO 2017/153402 A1 | 9/2017 |
| WO | WO 2018/091606 A1 | 5/2018 |
| WO | WO 2019/191519 A1 | 10/2019 |

OTHER PUBLICATIONS

Lin et al. Advanced Molecular Knowledge of Therapeutic Drugs and Natural Products Focusing on Inflammatory Cytokines in Asthma. Cells. Jul. 5, 2019;8(7):685.*
Rudikoff et al., Single amino acid substitution altering antigen-binding specificity. Proc Natl Acad Sci U S A. Mar. 1982;79(6):1979-83. doi: 10.1073/pnas.79.6.1979.
Venkataramani et al., Design and characterization of Zweimab and Doppelmab, high affinity dual antagonistic anti-TSLP/IL13 bispecific antibodies. Biochem Biophys Res Commun. Sep. 26, 2018;504(1):19-24. doi: 10.1016/j.bbrc.2018.08.064. Epub Aug. 17, 2018.

* cited by examiner

*Primary Examiner* — Dong Jiang
(74) *Attorney, Agent, or Firm* — Wolf, Greenfield & Sacks, P.C.

(57) ABSTRACT

The present technology aims at providing a novel type of drug for treating a subject suffering from an inflammatory disease. Specifically, the present technology provides polypeptides comprising at least four immunoglobulin single variable domains (ISVDs), characterized in that at least two ISVDs bind to IL-13 and at least two ISVDs binds to TSLP. The present technology also provides nucleic acids, vectors and compositions.

18 Claims, 14 Drawing Sheets

Specification includes a Sequence Listing.

SEQUENCE LISTING

```
<160> NUMBER OF SEQ ID NOS: 177

<210> SEQ ID NO 1
<211> LENGTH: 671
<212> TYPE: PRT
<213> ORGANISM: Artificial Sequence
<220> FEATURE:
<223> OTHER INFORMATION: F027400161-Synthetic

<400> SEQUENCE: 1

Asp Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Ser Ser Tyr
            20                  25                  30

Arg Met Gly Trp Phe Arg Gln Ala Pro Gly Lys Glu Arg Glu Phe Val
```

```
                35                  40                  45
Ala Ala Leu Ser Gly Asp Gly Tyr Ser Thr Tyr Thr Ala Asn Ser Val
 50                  55                  60
Lys Gly Arg Phe Thr Ile Ser Arg Asp Asn Ser Lys Asn Thr Val Tyr
 65                  70                  75                  80
Leu Gln Met Asn Ser Leu Arg Pro Glu Asp Thr Ala Leu Tyr Tyr Cys
                 85                  90                  95
Ala Ala Lys Leu Gln Tyr Val Ser Gly Trp Ser Tyr Asp Tyr Pro Tyr
                100                 105                 110
Trp Gly Gln Gly Thr Leu Val Thr Val Ser Ser Gly Gly Gly Gly Ser
                115                 120                 125
Gly Gly Gly Gly Ser Gly Gly Gly Ser Gly Gly Gly Gly Ser Gly
                130                 135                 140
Gly Gly Gly Ser Gly Gly Gly Ser Gly Gly Gly Gly Ser Glu Val
145                 150                 155                 160
Gln Leu Val Glu Ser Gly Gly Gly Val Val Gln Pro Gly Gly Ser Leu
                165                 170                 175
Arg Leu Ser Cys Ala Ala Ser Gly Phe Thr Phe Asn Asn Tyr Ala Met
                180                 185                 190
Lys Trp Val Arg Gln Ala Pro Gly Lys Gly Leu Glu Trp Val Ser Ser
                195                 200                 205
Ile Thr Thr Gly Gly Ser Thr Asp Tyr Ala Asp Ser Val Lys Gly
                210                 215                 220
Arg Phe Thr Ile Ser Arg Asp Asn Ser Lys Asn Thr Leu Tyr Leu Gln
225                 230                 235                 240
Met Asn Ser Leu Arg Pro Glu Asp Thr Ala Leu Tyr Tyr Cys Ala Asn
                245                 250                 255
Val Pro Phe Gly Tyr Tyr Ser Glu His Phe Ser Gly Leu Ser Phe Asp
                260                 265                 270
Tyr Arg Gly Gln Gly Thr Leu Val Thr Val Ser Ser Gly Gly Gly Gly
                275                 280                 285
Ser Gly Gly Gly Ser Glu Val Gln Leu Val Glu Ser Gly Gly Val
                290                 295                 300
Val Gln Pro Gly Gly Ser Leu Arg Leu Ser Cys Ala Ala Ser Gly Ser
305                 310                 315                 320
Gly Phe Gly Val Asn Ile Leu Tyr Trp Tyr Arg Gln Ala Ala Gly Ile
                325                 330                 335
Glu Arg Glu Leu Ile Ala Ser Ile Thr Ser Gly Gly Ile Thr Asn Tyr
                340                 345                 350
Val Asp Ser Val Lys Gly Arg Phe Thr Ile Ser Arg Asp Asn Ser Glu
                355                 360                 365
Asn Thr Met Tyr Leu Gln Met Asn Ser Leu Arg Ala Glu Asp Thr Gly
                370                 375                 380
Leu Tyr Tyr Cys Ala Ser Arg Asn Ile Phe Asp Gly Thr Thr Glu Trp
385                 390                 395                 400
Gly Gln Gly Thr Leu Val Thr Val Ser Ser Gly Gly Gly Ser Gly
                405                 410                 415
Gly Gly Ser Glu Val Gln Leu Val Glu Ser Gly Gly Gly Val Val Gln
                420                 425                 430
Pro Gly Gly Ser Leu Arg Leu Ser Cys Ala Ala Ser Gly Phe Thr Phe
                435                 440                 445
Arg Ser Phe Gly Met Ser Trp Val Arg Gln Ala Pro Gly Lys Gly Pro
                450                 455                 460
```

```
Glu Trp Val Ser Ser Ile Ser Gly Ser Gly Ser Asp Thr Leu Tyr Ala
465                 470                 475                 480

Asp Ser Val Lys Gly Arg Phe Thr Ile Ser Arg Asp Asn Ser Lys Asn
            485                 490                 495

Thr Leu Tyr Leu Gln Met Asn Ser Leu Arg Pro Glu Asp Thr Ala Leu
        500                 505                 510

Tyr Tyr Cys Thr Ile Gly Gly Ser Leu Ser Arg Ser Gln Gly Thr
            515                 520                 525

Leu Val Thr Val Ser Ser Gly Gly Gly Ser Gly Gly Gly Ser Glu
        530                 535                 540

Val Gln Leu Val Glu Ser Gly Gly Val Val Gln Pro Gly Gly Ser
545                 550                 555                 560

Leu Arg Leu Ser Cys Ala Ala Ser Gly Phe Thr Phe Ala Asp Tyr Asp
                565                 570                 575

Tyr Asp Ile Gly Trp Phe Arg Gln Ala Pro Gly Lys Glu Arg Glu Gly
            580                 585                 590

Val Ser Cys Ile Ser Asn Arg Asp Gly Ser Thr Tyr Tyr Ala Asp Ser
            595                 600                 605

Val Lys Gly Arg Phe Thr Ile Ser Arg Asp Asn Ser Lys Asn Thr Val
        610                 615                 620

Tyr Leu Gln Met Asn Ser Leu Arg Pro Glu Asp Thr Ala Leu Tyr Tyr
625                 630                 635                 640

Cys Ala Val Glu Ile His Cys Asp Asp Tyr Gly Val Glu Asn Phe Asp
                645                 650                 655

Phe Asp Pro Trp Gly Gln Gly Thr Leu Val Thr Val Ser Ala
            660                 665                 670

<210> SEQ ID NO 2
<211> LENGTH: 123
<212> TYPE: PRT
<213> ORGANISM: Artificial Sequence
<220> FEATURE:
<223> OTHER INFORMATION: 4B02-Synthetic

<400> SEQUENCE: 2

Asp Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Ser Ser Tyr
            20                  25                  30

Arg Met Gly Trp Phe Arg Gln Ala Pro Gly Lys Glu Arg Glu Phe Val
        35                  40                  45

Ala Ala Leu Ser Gly Asp Gly Tyr Ser Thr Tyr Thr Ala Asn Ser Val
    50                  55                  60

Lys Gly Arg Phe Thr Ile Ser Arg Asp Asn Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Lys Leu Gln Tyr Val Ser Gly Trp Ser Tyr Asp Tyr Pro Tyr
            100                 105                 110

Trp Gly Gln Gly Thr Leu Val Thr Val Ser Ser
        115                 120

<210> SEQ ID NO 3
<211> LENGTH: 126
<212> TYPE: PRT
<213> ORGANISM: Artificial Sequence
```

```
<220> FEATURE:
<223> OTHER INFORMATION: 4B06-Synthetic

<400> SEQUENCE: 3

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Asn Asn Tyr
            20                  25                  30

Ala Met Lys Trp Val Arg Gln Ala Pro Gly Lys Gly Leu Glu Trp Val
        35                  40                  45

Ser Ser Ile Thr Thr Gly Gly Ser Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Ala Asn Val Pro Phe Gly Tyr Tyr Ser Glu His Phe Ser Gly Leu Ser
            100                 105                 110

Phe Asp Tyr Arg Gly Gln Gly Thr Leu Val Thr Val Ser Ser
            115                 120                 125

<210> SEQ ID NO 4
<211> LENGTH: 117
<212> TYPE: PRT
<213> ORGANISM: Artificial Sequence
<220> FEATURE:
<223> OTHER INFORMATION: 501A02-Synthetic

<400> SEQUENCE: 4

Glu Val Gln Leu Val Glu Ser Gly Gly Gly Val Val Gln Pro Gly Gly
1               5                   10                  15

Ser Leu Arg Leu Ser Cys Ala Ala Ser Gly Ser Gly Phe Gly Val Asn
            20                  25                  30

Ile Leu Tyr Trp Tyr Arg Gln Ala Ala Gly Ile Glu Arg Glu Leu Ile
        35                  40                  45

Ala Ser Ile Thr Ser Gly Gly Ile Thr Asn Tyr Val Asp Ser Val Lys
    50                  55                  60

Gly Arg Phe Thr Ile Ser Arg Asp Asn Ser Glu Asn Thr Met Tyr Leu
65                  70                  75                  80

Gln Met Asn Ser Leu Arg Ala Glu Asp Thr Gly Leu Tyr Tyr Cys Ala
                85                  90                  95

Ser Arg Asn Ile Phe Asp Gly Thr Thr Glu Trp Gly Gln Gly Thr Leu
            100                 105                 110

Val Thr Val Ser Ser
        115

<210> SEQ ID NO 5
<211> LENGTH: 115
<212> TYPE: PRT
<213> ORGANISM: Artificial Sequence
<220> FEATURE:
<223> OTHER INFORMATION: ALB23002-Synthetic

<400> SEQUENCE: 5

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30
```

Gly Met Ser Trp Val Arg Gln Ala Pro Gly Lys Pro Glu Trp Val
            35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 6
<211> LENGTH: 127
<212> TYPE: PRT
<213> ORGANISM: Artificial Sequence
<220> FEATURE:
<223> OTHER INFORMATION: 529F10-Synthetic

<400> SEQUENCE: 6

Glu Val Gln Leu Val Glu Ser Gly Gly Gly Val Val Gln Pro Gly Gly
 1               5                  10                  15

Ser Leu Arg Leu Ser Cys Ala Ala Ser Gly Phe Thr Phe Ala Asp Tyr
            20                  25                  30

Asp Tyr Asp Ile Gly Trp Phe Arg Gln Ala Pro Gly Lys Glu Arg Glu
            35                  40                  45

Gly Val Ser Cys Ile Ser Asn Arg Asp Gly Ser Thr Tyr Tyr Ala Asp
 50                  55                  60

Ser Val Lys Gly Arg Phe Thr Ile Ser Arg Asp Asn Ser Lys Asn Thr
 65                  70                  75                  80

Val Tyr Leu Gln Met Asn Ser Leu Arg Pro Glu Asp Thr Ala Leu Tyr
                85                  90                  95

Tyr Cys Ala Val Glu Ile His Cys Asp Asp Tyr Gly Val Glu Asn Phe
            100                 105                 110

Asp Phe Asp Pro Trp Gly Gln Gly Thr Leu Val Thr Val Ser Ser
            115                 120                 125

<210> SEQ ID NO 7
<211> LENGTH: 10
<212> TYPE: PRT
<213> ORGANISM: Artificial Sequence
<220> FEATURE:
<223> OTHER INFORMATION: CDR1-Synthetic

<400> SEQUENCE: 7

Gly Arg Thr Phe Ser Ser Tyr Arg Met Gly
 1               5                  10

<210> SEQ ID NO 8
<211> LENGTH: 10
<212> TYPE: PRT
<213> ORGANISM: Artificial Sequence
<220> FEATURE:
<223> OTHER INFORMATION: CDR1-Synthetic

<400> SEQUENCE: 8

Gly Phe Thr Phe Asn Asn Tyr Ala Met Lys
 1               5                  10

```
<210> SEQ ID NO 9
<211> LENGTH: 10
<212> TYPE: PRT
<213> ORGANISM: Artificial Sequence
<220> FEATURE:
<223> OTHER INFORMATION: CDR1-Synthetic

<400> SEQUENCE: 9

Gly Ser Gly Phe Gly Val Asn Ile Leu Tyr
1               5                   10

<210> SEQ ID NO 10
<211> LENGTH: 10
<212> TYPE: PRT
<213> ORGANISM: Artificial Sequence
<220> FEATURE:
<223> OTHER INFORMATION: CDR1-Synthetic

<400> SEQUENCE: 10

Gly Phe Thr Phe Arg Ser Phe Gly Met Ser
1               5                   10

<210> SEQ ID NO 11
<211> LENGTH: 12
<212> TYPE: PRT
<213> ORGANISM: Artificial Sequence
<220> FEATURE:
<223> OTHER INFORMATION: CDR1-Synthetic

<400> SEQUENCE: 11

Gly Phe Thr Phe Ala Asp Tyr Asp Tyr Asp Ile Gly
1               5                   10

<210> SEQ ID NO 12
<211> LENGTH: 10
<212> TYPE: PRT
<213> ORGANISM: Artificial Sequence
<220> FEATURE:
<223> OTHER INFORMATION: CDR2-Synthetic

<400> SEQUENCE: 12

Ala Leu Ser Gly Asp Gly Tyr Ser Thr Tyr
1               5                   10

<210> SEQ ID NO 13
<211> LENGTH: 10
<212> TYPE: PRT
<213> ORGANISM: Artificial Sequence
<220> FEATURE:
<223> OTHER INFORMATION: CDR2-Synthetic

<400> SEQUENCE: 13

Ser Ile Thr Thr Gly Gly Gly Ser Thr Asp
1               5                   10

<210> SEQ ID NO 14
<211> LENGTH: 9
<212> TYPE: PRT
<213> ORGANISM: Artificial Sequence
<220> FEATURE:
<223> OTHER INFORMATION: CDR2-Synthetic

<400> SEQUENCE: 14

Ser Ile Thr Ser Gly Gly Ile Thr Asn
1               5

<210> SEQ ID NO 15
```

```
<211> LENGTH: 10
<212> TYPE: PRT
<213> ORGANISM: Artificial Sequence
<220> FEATURE:
<223> OTHER INFORMATION: CDR2-Synthetic

<400> SEQUENCE: 15

Ser Ile Ser Gly Ser Gly Ser Asp Thr Leu
1               5                   10

<210> SEQ ID NO 16
<211> LENGTH: 10
<212> TYPE: PRT
<213> ORGANISM: Artificial Sequence
<220> FEATURE:
<223> OTHER INFORMATION: CDR2-Synthetic

<400> SEQUENCE: 16

Cys Ile Ser Asn Arg Asp Gly Ser Thr Tyr
1               5                   10

<210> SEQ ID NO 17
<211> LENGTH: 14
<212> TYPE: PRT
<213> ORGANISM: Artificial Sequence
<220> FEATURE:
<223> OTHER INFORMATION: CDR3-Synthetic

<400> SEQUENCE: 17

Lys Leu Gln Tyr Val Ser Gly Trp Ser Tyr Asp Tyr Pro Tyr
1               5                   10

<210> SEQ ID NO 18
<211> LENGTH: 17
<212> TYPE: PRT
<213> ORGANISM: Artificial Sequence
<220> FEATURE:
<223> OTHER INFORMATION: CDR3-Synthetic

<400> SEQUENCE: 18

Val Pro Phe Gly Tyr Tyr Ser Glu His Phe Ser Gly Leu Ser Phe Asp
1               5                   10                  15

Tyr

<210> SEQ ID NO 19
<211> LENGTH: 9
<212> TYPE: PRT
<213> ORGANISM: Artificial Sequence
<220> FEATURE:
<223> OTHER INFORMATION: CDR3-Synthetic

<400> SEQUENCE: 19

Arg Asn Ile Phe Asp Gly Thr Thr Glu
1               5

<210> SEQ ID NO 20
<211> LENGTH: 6
<212> TYPE: PRT
<213> ORGANISM: Artificial Sequence
<220> FEATURE:
<223> OTHER INFORMATION: CDR3-Synthetic

<400> SEQUENCE: 20

Gly Gly Ser Leu Ser Arg
1               5
```

-continued

```
<210> SEQ ID NO 21
<211> LENGTH: 16
<212> TYPE: PRT
<213> ORGANISM: Artificial Sequence
<220> FEATURE:
<223> OTHER INFORMATION: CDR3-Synthetic

<400> SEQUENCE: 21

Glu Ile His Cys Asp Asp Tyr Gly Val Glu Asn Phe Asp Phe Asp Pro
1               5                   10                  15

<210> SEQ ID NO 22
<211> LENGTH: 25
<212> TYPE: PRT
<213> ORGANISM: Artificial Sequence
<220> FEATURE:
<223> OTHER INFORMATION: FR1-Synthetic

<400> SEQUENCE: 22

Asp Val Gln Leu Val Glu Ser Gly Gly Gly Val Val Gln Pro Gly Gly
1               5                   10                  15

Ser Leu Arg Leu Ser Cys Ala Ala Ser
            20                  25

<210> SEQ ID NO 23
<211> LENGTH: 25
<212> TYPE: PRT
<213> ORGANISM: Artificial Sequence
<220> FEATURE:
<223> OTHER INFORMATION: FR1-Synthetic

<400> SEQUENCE: 23

Glu Val Gln Leu Val Glu Ser Gly Gly Gly Val Val Gln Pro Gly Gly
1               5                   10                  15

Ser Leu Arg Leu Ser Cys Ala Ala Ser
            20                  25

<210> SEQ ID NO 24
<211> LENGTH: 14
<212> TYPE: PRT
<213> ORGANISM: Artificial Sequence
<220> FEATURE:
<223> OTHER INFORMATION: FR2-Synthetic

<400> SEQUENCE: 24

Trp Phe Arg Gln Ala Pro Gly Lys Glu Arg Glu Phe Val Ala
1               5                   10

<210> SEQ ID NO 25
<211> LENGTH: 14
<212> TYPE: PRT
<213> ORGANISM: Artificial Sequence
<220> FEATURE:
<223> OTHER INFORMATION: FR2-Synthetic

<400> SEQUENCE: 25

Trp Val Arg Gln Ala Pro Gly Lys Gly Leu Glu Trp Val Ser
1               5                   10

<210> SEQ ID NO 26
<211> LENGTH: 14
<212> TYPE: PRT
<213> ORGANISM: Artificial Sequence
<220> FEATURE:
<223> OTHER INFORMATION: FR2-Synthetic

<400> SEQUENCE: 26
```

Trp Tyr Arg Gln Ala Ala Gly Ile Glu Arg Glu Leu Ile Ala
1               5                  10

<210> SEQ ID NO 27
<211> LENGTH: 14
<212> TYPE: PRT
<213> ORGANISM: Artificial Sequence
<220> FEATURE:
<223> OTHER INFORMATION: FR2-Synthetic

<400> SEQUENCE: 27

Trp Val Arg Gln Ala Pro Gly Lys Gly Pro Glu Trp Val Ser
1               5                  10

<210> SEQ ID NO 28
<211> LENGTH: 14
<212> TYPE: PRT
<213> ORGANISM: Artificial Sequence
<220> FEATURE:
<223> OTHER INFORMATION: FR2-Synthetic

<400> SEQUENCE: 28

Trp Phe Arg Gln Ala Pro Gly Lys Glu Arg Glu Gly Val Ser
1               5                  10

<210> SEQ ID NO 29
<211> LENGTH: 39
<212> TYPE: PRT
<213> ORGANISM: Artificial Sequence
<220> FEATURE:
<223> OTHER INFORMATION: FR3-Synthetic

<400> SEQUENCE: 29

Thr Ala Asn Ser Val Lys Gly Arg Phe Thr Ile Ser Arg Asp Asn Ser
1               5                   10                  15

Lys Asn Thr Val Tyr Leu Gln Met Asn Ser Leu Arg Pro Glu Asp Thr
            20                  25                  30

Ala Leu Tyr Tyr Cys Ala Ala
        35

<210> SEQ ID NO 30
<211> LENGTH: 39
<212> TYPE: PRT
<213> ORGANISM: Artificial Sequence
<220> FEATURE:
<223> OTHER INFORMATION: FR3-Synthetic

<400> SEQUENCE: 30

Tyr Ala Asp Ser Val Lys Gly Arg Phe Thr Ile Ser Arg Asp Asn Ser
1               5                   10                  15

Lys Asn Thr Leu Tyr Leu Gln Met Asn Ser Leu Arg Pro Glu Asp Thr
            20                  25                  30

Ala Leu Tyr Tyr Cys Ala Asn
        35

<210> SEQ ID NO 31
<211> LENGTH: 39
<212> TYPE: PRT
<213> ORGANISM: Artificial Sequence
<220> FEATURE:
<223> OTHER INFORMATION: FR3-Synthetic

<400> SEQUENCE: 31

Tyr Val Asp Ser Val Lys Gly Arg Phe Thr Ile Ser Arg Asp Asn Ser

```
1               5                   10                  15
Glu Asn Thr Met Tyr Leu Gln Met Asn Ser Leu Arg Ala Glu Asp Thr
            20                  25                  30

Gly Leu Tyr Tyr Cys Ala Ser
            35
```

<210> SEQ ID NO 32
<211> LENGTH: 39
<212> TYPE: PRT
<213> ORGANISM: Artificial Sequence
<220> FEATURE:
<223> OTHER INFORMATION: FR3-Synthetic

<400> SEQUENCE: 32

```
Tyr Ala Asp Ser Val Lys Gly Arg Phe Thr Ile Ser Arg Asp Asn Ser
1               5                   10                  15

Lys Asn Thr Leu Tyr Leu Gln Met Asn Ser Leu Arg Pro Glu Asp Thr
            20                  25                  30

Ala Leu Tyr Tyr Cys Thr Ile
            35
```

<210> SEQ ID NO 33
<211> LENGTH: 39
<212> TYPE: PRT
<213> ORGANISM: Artificial Sequence
<220> FEATURE:
<223> OTHER INFORMATION: FR3-Synthetic

<400> SEQUENCE: 33

```
Tyr Ala Asp Ser Val Lys Gly Arg Phe Thr Ile Ser Arg Asp Asn Ser
1               5                   10                  15

Lys Asn Thr Val Tyr Leu Gln Met Asn Ser Leu Arg Pro Glu Asp Thr
            20                  25                  30

Ala Leu Tyr Tyr Cys Ala Val
            35
```

<210> SEQ ID NO 34
<211> LENGTH: 11
<212> TYPE: PRT
<213> ORGANISM: Artificial Sequence
<220> FEATURE:
<223> OTHER INFORMATION: FR4-Synthetic

<400> SEQUENCE: 34

```
Trp Gly Gln Gly Thr Leu Val Thr Val Ser Ser
1               5                   10
```

<210> SEQ ID NO 35
<211> LENGTH: 11
<212> TYPE: PRT
<213> ORGANISM: Artificial Sequence
<220> FEATURE:
<223> OTHER INFORMATION: FR4-Synthetic

<400> SEQUENCE: 35

```
Arg Gly Gln Gly Thr Leu Val Thr Val Ser Ser
1               5                   10
```

<210> SEQ ID NO 36
<211> LENGTH: 11
<212> TYPE: PRT
<213> ORGANISM: Artificial Sequence
<220> FEATURE:
<223> OTHER INFORMATION: FR4-Synthetic

```
<400> SEQUENCE: 36

Ser Ser Gln Gly Thr Leu Val Thr Val Ser Ser
1               5                   10

<210> SEQ ID NO 37
<211> LENGTH: 5
<212> TYPE: PRT
<213> ORGANISM: Artificial Sequence
<220> FEATURE:
<223> OTHER INFORMATION: CDR1-Synthetic

<400> SEQUENCE: 37

Ser Tyr Arg Met Gly
1               5

<210> SEQ ID NO 38
<211> LENGTH: 5
<212> TYPE: PRT
<213> ORGANISM: Artificial Sequence
<220> FEATURE:
<223> OTHER INFORMATION: CDR1-Synthetic

<400> SEQUENCE: 38

Asn Tyr Ala Met Lys
1               5

<210> SEQ ID NO 39
<211> LENGTH: 5
<212> TYPE: PRT
<213> ORGANISM: Artificial Sequence
<220> FEATURE:
<223> OTHER INFORMATION: CDR1-Synthetic

<400> SEQUENCE: 39

Val Asn Ile Leu Tyr
1               5

<210> SEQ ID NO 40
<211> LENGTH: 5
<212> TYPE: PRT
<213> ORGANISM: Artificial Sequence
<220> FEATURE:
<223> OTHER INFORMATION: CDR1-Synthetic

<400> SEQUENCE: 40

Ser Phe Gly Met Ser
1               5

<210> SEQ ID NO 41
<211> LENGTH: 7
<212> TYPE: PRT
<213> ORGANISM: Artificial Sequence
<220> FEATURE:
<223> OTHER INFORMATION: CDR1-Synthetic

<400> SEQUENCE: 41

Asp Tyr Asp Tyr Asp Ile Gly
1               5

<210> SEQ ID NO 42
<211> LENGTH: 17
<212> TYPE: PRT
<213> ORGANISM: Artificial Sequence
<220> FEATURE:
<223> OTHER INFORMATION: CDR2-Synthetic
```

```
<400> SEQUENCE: 42

Ala Leu Ser Gly Asp Gly Tyr Ser Thr Tyr Thr Ala Asn Ser Val Lys
1               5                   10                  15

Gly

<210> SEQ ID NO 43
<211> LENGTH: 17
<212> TYPE: PRT
<213> ORGANISM: Artificial Sequence
<220> FEATURE:
<223> OTHER INFORMATION: CDR2-Synthetic

<400> SEQUENCE: 43

Ser Ile Thr Thr Gly Gly Gly Ser Thr Asp Tyr Ala Asp Ser Val Lys
1               5                   10                  15

Gly

<210> SEQ ID NO 44
<211> LENGTH: 16
<212> TYPE: PRT
<213> ORGANISM: Artificial Sequence
<220> FEATURE:
<223> OTHER INFORMATION: CDR2-Synthetic

<400> SEQUENCE: 44

Ser Ile Thr Ser Gly Gly Ile Thr Asn Tyr Val Asp Ser Val Lys Gly
1               5                   10                  15

<210> SEQ ID NO 45
<211> LENGTH: 17
<212> TYPE: PRT
<213> ORGANISM: Artificial Sequence
<220> FEATURE:
<223> OTHER INFORMATION: CDR2-Synthetic

<400> SEQUENCE: 45

Ser Ile Ser Gly Ser Gly Ser Asp Thr Leu Tyr Ala Asp Ser Val Lys
1               5                   10                  15

Gly

<210> SEQ ID NO 46
<211> LENGTH: 17
<212> TYPE: PRT
<213> ORGANISM: Artificial Sequence
<220> FEATURE:
<223> OTHER INFORMATION: CDR2-Synthetic

<400> SEQUENCE: 46

Cys Ile Ser Asn Arg Asp Gly Ser Thr Tyr Tyr Ala Asp Ser Val Lys
1               5                   10                  15

Gly

<210> SEQ ID NO 47
<211> LENGTH: 30
<212> TYPE: PRT
<213> ORGANISM: Artificial Sequence
<220> FEATURE:
<223> OTHER INFORMATION: FR1-Synthetic

<400> SEQUENCE: 47

Asp Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Ser
```

<210> SEQ ID NO 48
<211> LENGTH: 30
<212> TYPE: PRT
<213> ORGANISM: Artificial Sequence
<220> FEATURE:
<223> OTHER INFORMATION: FR1-Synthetic

<400> SEQUENCE: 48

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Asn
            20                  25                  30

<210> SEQ ID NO 49
<211> LENGTH: 30
<212> TYPE: PRT
<213> ORGANISM: Artificial Sequence
<220> FEATURE:
<223> OTHER INFORMATION: FR1-Synthetic

<400> SEQUENCE: 49

Glu Val Gln Leu Val Glu Ser Gly Gly Gly Val Val Gln Pro Gly Gly
1               5                   10                  15

Ser Leu Arg Leu Ser Cys Ala Ala Ser Gly Ser Gly Phe Gly
            20                  25                  30

<210> SEQ ID NO 50
<211> LENGTH: 30
<212> TYPE: PRT
<213> ORGANISM: Artificial Sequence
<220> FEATURE:
<223> OTHER INFORMATION: FR1-Synthetic

<400> SEQUENCE: 50

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg
            20                  25                  30

<210> SEQ ID NO 51
<211> LENGTH: 30
<212> TYPE: PRT
<213> ORGANISM: Artificial Sequence
<220> FEATURE:
<223> OTHER INFORMATION: FR1-Synthetic

<400> SEQUENCE: 51

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ala
            20                  25                  30

<210> SEQ ID NO 52
<211> LENGTH: 32
<212> TYPE: PRT
<213> ORGANISM: Artificial Sequence
<220> FEATURE:
<223> OTHER INFORMATION: FR3-Synthetic

<400> SEQUENCE: 52

Arg Phe Thr Ile Ser Arg Asp Asn Ser Lys Asn Thr Val Tyr Leu Gln
1               5                   10                  15

Met Asn Ser Leu Arg Pro Glu Asp Thr Ala Leu Tyr Tyr Cys Ala Ala
            20                  25                  30

<210> SEQ ID NO 53
<211> LENGTH: 32
<212> TYPE: PRT
<213> ORGANISM: Artificial Sequence
<220> FEATURE:
<223> OTHER INFORMATION: FR3-Synthetic

<400> SEQUENCE: 53

Arg Phe Thr Ile Ser Arg Asp Asn Ser Lys Asn Thr Leu Tyr Leu Gln
1               5                   10                  15

Met Asn Ser Leu Arg Pro Glu Asp Thr Ala Leu Tyr Tyr Cys Ala Asn
            20                  25                  30

<210> SEQ ID NO 54
<211> LENGTH: 32
<212> TYPE: PRT
<213> ORGANISM: Artificial Sequence
<220> FEATURE:
<223> OTHER INFORMATION: FR3-Synthetic

<400> SEQUENCE: 54

Arg Phe Thr Ile Ser Arg Asp Asn Ser Glu Asn Thr Met Tyr Leu Gln
1               5                   10                  15

Met Asn Ser Leu Arg Ala Glu Asp Thr Gly Leu Tyr Tyr Cys Ala Ser
            20                  25                  30

<210> SEQ ID NO 55
<211> LENGTH: 32
<212> TYPE: PRT
<213> ORGANISM: Artificial Sequence
<220> FEATURE:
<223> OTHER INFORMATION: FR3-Synthetic

<400> SEQUENCE: 55

Arg Phe Thr Ile Ser Arg Asp Asn Ser Lys Asn Thr Leu Tyr Leu Gln
1               5                   10                  15

Met Asn Ser Leu Arg Pro Glu Asp Thr Ala Leu Tyr Tyr Cys Thr Ile
            20                  25                  30

<210> SEQ ID NO 56
<211> LENGTH: 32
<212> TYPE: PRT
<213> ORGANISM: Artificial Sequence
<220> FEATURE:
<223> OTHER INFORMATION: FR3-Synthetic

<400> SEQUENCE: 56

Arg Phe Thr Ile Ser Arg Asp Asn Ser Lys Asn Thr Val Tyr Leu Gln
1               5                   10                  15

Met Asn Ser Leu Arg Pro Glu Asp Thr Ala Leu Tyr Tyr Cys Ala Val
            20                  25                  30

<210> SEQ ID NO 57
<211> LENGTH: 115
<212> TYPE: PRT
<213> ORGANISM: Artificial Sequence
<220> FEATURE:
<223> OTHER INFORMATION: Alb8-Synthetic

<400> SEQUENCE: 57

Glu Val Gln Leu Val Glu Ser Gly Gly Gly Leu Val Gln Pro Gly Asn
1               5                   10                  15

-continued

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
            85                  90                  95

Thr Ile Gly Gly Ser Leu Ser Arg Ser Ser Gln Gly Thr Leu Val Thr
            100                 105                 110

Val Ser Ser
        115

<210> SEQ ID NO 58
<211> LENGTH: 115
<212> TYPE: PRT
<213> ORGANISM: Artificial Sequence
<220> FEATURE:
<223> OTHER INFORMATION: Alb23-Synthetic

<400> SEQUENCE: 58

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
            85                  90                  95

Thr Ile Gly Gly Ser Leu Ser Arg Ser Ser Gln Gly Thr Leu Val Thr
            100                 105                 110

Val Ser Ser
        115

<210> SEQ ID NO 59
<211> LENGTH: 116
<212> TYPE: PRT
<213> ORGANISM: Artificial Sequence
<220> FEATURE:
<223> OTHER INFORMATION: Alb129-Synthetic

<400> SEQUENCE: 59

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
50                  55                  60

Lys Gly Arg Phe Thr Ile Ser Arg Asp Asn Ala Lys Thr Thr Leu Tyr

```
                65                  70                  75                  80
Leu Gln Met Asn Ser Leu Arg Pro Glu Asp Thr Ala Thr Tyr Tyr Cys
                    85                  90                  95

Thr Ile Gly Gly Ser Leu Ser Arg Ser Ser Gln Gly Thr Leu Val Thr
                    100                 105                 110

Val Ser Ser Ala
        115

<210> SEQ ID NO 60
<211> LENGTH: 116
<212> TYPE: PRT
<213> ORGANISM: Artificial Sequence
<220> FEATURE:
<223> OTHER INFORMATION: Alb132-Synthetic

<400> SEQUENCE: 60

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
                20                  25                  30

Gly Met Ser Trp Val Arg Gln Ala Pro Gly Lys Gly Pro Glu Trp Val
                35                  40                  45

Ser Ser Ile Ser Gly Ser Gly Ser Asp Thr Leu Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Thr Tyr Tyr Cys
                    85                  90                  95

Thr Ile Gly Gly Ser Leu Ser Arg Ser Ser Gln Gly Thr Leu Val Thr
                    100                 105                 110

Val Ser Ser Ala
        115

<210> SEQ ID NO 61
<211> LENGTH: 115
<212> TYPE: PRT
<213> ORGANISM: Artificial Sequence
<220> FEATURE:
<223> OTHER INFORMATION: Alb11-Synthetic

<400> SEQUENCE: 61

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
                20                  25                  30

Gly Met Ser Trp Val Arg Gln Ala Pro Gly Lys Gly Leu Glu Trp Val
                35                  40                  45

Ser Ser Ile Ser Gly Ser Gly Ser Asp Thr Leu Tyr Ala Asp Ser Val
            50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                    85                  90                  95

Thr Ile Gly Gly Ser Leu Ser Arg Ser Ser Gln Gly Thr Leu Val Thr
                    100                 105                 110

Val Ser Ser
        115
```

<210> SEQ ID NO 62
<211> LENGTH: 116
<212> TYPE: PRT
<213> ORGANISM: Artificial Sequence
<220> FEATURE:
<223> OTHER INFORMATION: Alb11 (S112K)-A-Synthetic

<400> SEQUENCE: 62

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Lys
            100                 105                 110

Val Ser Ser Ala
        115

<210> SEQ ID NO 63
<211> LENGTH: 115
<212> TYPE: PRT
<213> ORGANISM: Artificial Sequence
<220> FEATURE:
<223> OTHER INFORMATION: Alb82-Synthetic

<400> SEQUENCE: 63

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 64
<211> LENGTH: 116
<212> TYPE: PRT
<213> ORGANISM: Artificial Sequence
<220> FEATURE:
<223> OTHER INFORMATION: Alb82-A-Synthetic

<400> SEQUENCE: 64

Glu Val Gln Leu Val Glu Ser Gly Gly Gly Val Val Gln Pro Gly Asn

```
1               5                   10                  15
Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
            85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 65
<211> LENGTH: 117
<212> TYPE: PRT
<213> ORGANISM: Artificial Sequence
<220> FEATURE:
<223> OTHER INFORMATION: Alb82-AA-Synthetic

<400> SEQUENCE: 65

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
            85                  90                  95

Thr Ile Gly Gly Ser Leu Ser Arg Ser Ser Gln Gly Thr Leu Val Thr
            100                 105                 110

Val Ser Ser Ala Ala
        115

<210> SEQ ID NO 66
<211> LENGTH: 118
<212> TYPE: PRT
<213> ORGANISM: Artificial Sequence
<220> FEATURE:
<223> OTHER INFORMATION: Alb82-AAA-Synthetic

<400> SEQUENCE: 66

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60
```

```
Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
                 85                  90                  95

Thr Ile Gly Gly Ser Leu Ser Arg Ser Ser Gln Gly Thr Leu Val Thr
            100                 105                 110

Val Ser Ser Ala Ala Ala
            115
```

<210> SEQ ID NO 67
<211> LENGTH: 116
<212> TYPE: PRT
<213> ORGANISM: Artificial Sequence
<220> FEATURE:
<223> OTHER INFORMATION: Alb82-G-Synthetic

<400> SEQUENCE: 67

```
Glu Val Gln Leu Val Glu Ser Gly Gly Gly Val Val Gln Pro Gly Asn
  1               5                  10                  15

Ser Leu Arg Leu Ser Cys Ala Ala Ser Gly Phe Thr Phe Ser Ser Phe
                 20                  25                  30

Gly Met Ser Trp Val Arg Gln Ala Pro Gly Lys Gly Leu Glu Trp Val
             35                  40                  45

Ser Ser Ile Ser Gly Ser Gly Ser Asp Thr Leu Tyr Ala Asp Ser Val
         50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
                 85                  90                  95

Thr Ile Gly Gly Ser Leu Ser Arg Ser Ser Gln Gly Thr Leu Val Thr
            100                 105                 110

Val Ser Ser Gly
            115
```

<210> SEQ ID NO 68
<211> LENGTH: 117
<212> TYPE: PRT
<213> ORGANISM: Artificial Sequence
<220> FEATURE:
<223> OTHER INFORMATION: Alb82-GG-Synthetic

<400> SEQUENCE: 68

```
Glu Val Gln Leu Val Glu Ser Gly Gly Gly Val Val Gln Pro Gly Asn
  1               5                  10                  15

Ser Leu Arg Leu Ser Cys Ala Ala Ser Gly Phe Thr Phe Ser Ser Phe
                 20                  25                  30

Gly Met Ser Trp Val Arg Gln Ala Pro Gly Lys Gly Leu Glu Trp Val
             35                  40                  45

Ser Ser Ile Ser Gly Ser Gly Ser Asp Thr Leu Tyr Ala Asp Ser Val
         50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
                 85                  90                  95

Thr Ile Gly Gly Ser Leu Ser Arg Ser Ser Gln Gly Thr Leu Val Thr
            100                 105                 110

Val Ser Ser Gly Gly
            115
```

<210> SEQ ID NO 69
<211> LENGTH: 118
<212> TYPE: PRT
<213> ORGANISM: Artificial Sequence
<220> FEATURE:
<223> OTHER INFORMATION: Alb82-GGG-Synthetic

<400> SEQUENCE: 69

```
Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly
        115
```

<210> SEQ ID NO 70
<211> LENGTH: 115
<212> TYPE: PRT
<213> ORGANISM: Artificial Sequence
<220> FEATURE:
<223> OTHER INFORMATION: Alb23002-Synthetic

<400> SEQUENCE: 70

```
Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser
        115
```

<210> SEQ ID NO 71
<211> LENGTH: 116
<212> TYPE: PRT
<213> ORGANISM: Artificial Sequence
<220> FEATURE:
<223> OTHER INFORMATION: Alb223-Synthetic

<400> SEQUENCE: 71

```
Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 72
<211> LENGTH: 3
<212> TYPE: PRT
<213> ORGANISM: Artificial Sequence
<220> FEATURE:
<223> OTHER INFORMATION: 3A linker-Synthetic

<400> SEQUENCE: 72

Ala Ala Ala
1

<210> SEQ ID NO 73
<211> LENGTH: 5
<212> TYPE: PRT
<213> ORGANISM: Artificial Sequence
<220> FEATURE:
<223> OTHER INFORMATION: 5GS linker-Synthetic

<400> SEQUENCE: 73

Gly Gly Gly Gly Ser
1               5

<210> SEQ ID NO 74
<211> LENGTH: 7
<212> TYPE: PRT
<213> ORGANISM: Artificial Sequence
<220> FEATURE:
<223> OTHER INFORMATION: 7GS linker-Synthetic

<400> SEQUENCE: 74

Ser Gly Gly Ser Gly Gly Ser
1               5

<210> SEQ ID NO 75
<211> LENGTH: 8
<212> TYPE: PRT
<213> ORGANISM: Artificial Sequence
<220> FEATURE:
<223> OTHER INFORMATION: 8GS linker-Synthetic

<400> SEQUENCE: 75

Gly Gly Gly Gly Ser Gly Gly Ser
1               5

<210> SEQ ID NO 76
<211> LENGTH: 9
```

```
<212> TYPE: PRT
<213> ORGANISM: Artificial Sequence
<220> FEATURE:
<223> OTHER INFORMATION: 9GS linker-Synthetic

<400> SEQUENCE: 76

Gly Gly Gly Gly Ser Gly Gly Gly Ser
1               5

<210> SEQ ID NO 77
<211> LENGTH: 10
<212> TYPE: PRT
<213> ORGANISM: Artificial Sequence
<220> FEATURE:
<223> OTHER INFORMATION: 10GS linker-Synthetic

<400> SEQUENCE: 77

Gly Gly Gly Gly Ser Gly Gly Gly Gly Ser
1               5                   10

<210> SEQ ID NO 78
<211> LENGTH: 15
<212> TYPE: PRT
<213> ORGANISM: Artificial Sequence
<220> FEATURE:
<223> OTHER INFORMATION: 15GS linker-Synthetic

<400> SEQUENCE: 78

Gly Gly Gly Gly Ser Gly Gly Gly Gly Ser Gly Gly Gly Gly Ser
1               5                   10                  15

<210> SEQ ID NO 79
<211> LENGTH: 18
<212> TYPE: PRT
<213> ORGANISM: Artificial Sequence
<220> FEATURE:
<223> OTHER INFORMATION: 18GS linker-Synthetic

<400> SEQUENCE: 79

Gly Gly Gly Gly Ser Gly Gly Gly Gly Ser Gly Gly Gly Gly Ser Gly
1               5                   10                  15

Gly Ser

<210> SEQ ID NO 80
<211> LENGTH: 20
<212> TYPE: PRT
<213> ORGANISM: Artificial Sequence
<220> FEATURE:
<223> OTHER INFORMATION: 20GS linker-Synthetic

<400> SEQUENCE: 80

Gly Gly Gly Gly Ser Gly Gly Gly Gly Ser Gly Gly Gly Gly Ser Gly
1               5                   10                  15

Gly Gly Gly Ser
            20

<210> SEQ ID NO 81
<211> LENGTH: 25
<212> TYPE: PRT
<213> ORGANISM: Artificial Sequence
<220> FEATURE:
<223> OTHER INFORMATION: 25GS linker-Synthetic

<400> SEQUENCE: 81

Gly Gly Gly Gly Ser Gly Gly Gly Gly Ser Gly Gly Gly Gly Ser Gly
1               5                   10                  15
```

Gly Gly Gly Ser Gly Gly Gly Ser
        20              25

<210> SEQ ID NO 82
<211> LENGTH: 30
<212> TYPE: PRT
<213> ORGANISM: Artificial Sequence
<220> FEATURE:
<223> OTHER INFORMATION: 30GS linker-Synthetic

<400> SEQUENCE: 82

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Ser
        20                  25                  30

<210> SEQ ID NO 83
<211> LENGTH: 35
<212> TYPE: PRT
<213> ORGANISM: Artificial Sequence
<220> FEATURE:
<223> OTHER INFORMATION: 35GS linker-Synthetic

<400> SEQUENCE: 83

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
        20                  25                  30

Gly Gly Ser
        35

<210> SEQ ID NO 84
<211> LENGTH: 40
<212> TYPE: PRT
<213> ORGANISM: Artificial Sequence
<220> FEATURE:
<223> OTHER INFORMATION: 40GS linker-Synthetic

<400> SEQUENCE: 84

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
        20                  25                  30

Gly Gly Ser Gly Gly Gly Gly Ser
        35                  40

<210> SEQ ID NO 85
<211> LENGTH: 15
<212> TYPE: PRT
<213> ORGANISM: Artificial Sequence
<220> FEATURE:
<223> OTHER INFORMATION: G1 hinge-Synthetic

<400> SEQUENCE: 85

Glu Pro Lys Ser Cys Asp Lys Thr His Thr Cys Pro Pro Cys Pro
1               5                   10                  15

<210> SEQ ID NO 86
<211> LENGTH: 24
<212> TYPE: PRT
<213> ORGANISM: Artificial Sequence
<220> FEATURE:
<223> OTHER INFORMATION: 9GS-G1 hinge-Synthetic

```
<400> SEQUENCE: 86

Gly Gly Gly Gly Ser Gly Gly Gly Ser Glu Pro Lys Ser Cys Asp Lys
1               5                   10                  15
Thr His Thr Cys Pro Pro Cys Pro
            20

<210> SEQ ID NO 87
<211> LENGTH: 12
<212> TYPE: PRT
<213> ORGANISM: Artificial Sequence
<220> FEATURE:
<223> OTHER INFORMATION: Llama upper long hinge region-Synthetic

<400> SEQUENCE: 87

Glu Pro Lys Thr Pro Lys Pro Gln Pro Ala Ala Ala
1               5                   10

<210> SEQ ID NO 88
<211> LENGTH: 62
<212> TYPE: PRT
<213> ORGANISM: Artificial Sequence
<220> FEATURE:
<223> OTHER INFORMATION: G3 hinge-Synthetic

<400> SEQUENCE: 88

Glu Leu Lys Thr Pro Leu Gly Asp Thr Thr His Thr Cys Pro Arg Cys
1               5                   10                  15
Pro Glu Pro Lys Ser Cys Asp Thr Pro Pro Cys Pro Arg Cys Pro
            20                  25                  30
Glu Pro Lys Ser Cys Asp Thr Pro Pro Cys Pro Arg Cys Pro Glu
        35                  40                  45
Pro Lys Ser Cys Asp Thr Pro Pro Cys Pro Arg Cys Pro
    50                  55                  60

<210> SEQ ID NO 89
<211> LENGTH: 4
<212> TYPE: PRT
<213> ORGANISM: Artificial Sequence
<220> FEATURE:
<223> OTHER INFORMATION: Motif-Synthetic

<400> SEQUENCE: 89

Lys Glu Arg Glu
1

<210> SEQ ID NO 90
<211> LENGTH: 4
<212> TYPE: PRT
<213> ORGANISM: Artificial Sequence
<220> FEATURE:
<223> OTHER INFORMATION: Motif-Synthetic

<400> SEQUENCE: 90

Lys Gln Arg Glu
1

<210> SEQ ID NO 91
<211> LENGTH: 4
<212> TYPE: PRT
<213> ORGANISM: Artificial Sequence
<220> FEATURE:
<223> OTHER INFORMATION: Motif-Synthetic

<400> SEQUENCE: 91
```

```
Gly Leu Glu Trp
1

<210> SEQ ID NO 92
<211> LENGTH: 5
<212> TYPE: PRT
<213> ORGANISM: Artificial Sequence
<220> FEATURE:
<223> OTHER INFORMATION: Motif-Synthetic

<400> SEQUENCE: 92

Lys Glu Arg Glu Leu
1               5

<210> SEQ ID NO 93
<211> LENGTH: 5
<212> TYPE: PRT
<213> ORGANISM: Artificial Sequence
<220> FEATURE:
<223> OTHER INFORMATION: Motif-Synthetic

<400> SEQUENCE: 93

Lys Glu Arg Glu Phe
1               5

<210> SEQ ID NO 94
<211> LENGTH: 5
<212> TYPE: PRT
<213> ORGANISM: Artificial Sequence
<220> FEATURE:
<223> OTHER INFORMATION: Motif-Synthetic

<400> SEQUENCE: 94

Lys Gln Arg Glu Leu
1               5

<210> SEQ ID NO 95
<211> LENGTH: 5
<212> TYPE: PRT
<213> ORGANISM: Artificial Sequence
<220> FEATURE:
<223> OTHER INFORMATION: Motif-Synthetic

<400> SEQUENCE: 95

Lys Gln Arg Glu Phe
1               5

<210> SEQ ID NO 96
<211> LENGTH: 5
<212> TYPE: PRT
<213> ORGANISM: Artificial Sequence
<220> FEATURE:
<223> OTHER INFORMATION: Motif-Synthetic

<400> SEQUENCE: 96

Lys Glu Arg Glu Gly
1               5

<210> SEQ ID NO 97
<211> LENGTH: 5
<212> TYPE: PRT
<213> ORGANISM: Artificial Sequence
<220> FEATURE:
<223> OTHER INFORMATION: Motif-Synthetic

<400> SEQUENCE: 97

Lys Gln Arg Glu Trp
```

```
1               5

<210> SEQ ID NO 98
<211> LENGTH: 5
<212> TYPE: PRT
<213> ORGANISM: Artificial Sequence
<220> FEATURE:
<223> OTHER INFORMATION: Motif-Synthetic

<400> SEQUENCE: 98

Lys Gln Arg Glu Gly
1               5

<210> SEQ ID NO 99
<211> LENGTH: 4
<212> TYPE: PRT
<213> ORGANISM: Artificial Sequence
<220> FEATURE:
<223> OTHER INFORMATION: Motif-Synthetic

<400> SEQUENCE: 99

Thr Glu Arg Glu
1

<210> SEQ ID NO 100
<211> LENGTH: 5
<212> TYPE: PRT
<213> ORGANISM: Artificial Sequence
<220> FEATURE:
<223> OTHER INFORMATION: Motif-Synthetic

<400> SEQUENCE: 100

Thr Glu Arg Glu Leu
1               5

<210> SEQ ID NO 101
<211> LENGTH: 4
<212> TYPE: PRT
<213> ORGANISM: Artificial Sequence
<220> FEATURE:
<223> OTHER INFORMATION: Motif-Synthetic

<400> SEQUENCE: 101

Thr Gln Arg Glu
1

<210> SEQ ID NO 102
<211> LENGTH: 5
<212> TYPE: PRT
<213> ORGANISM: Artificial Sequence
<220> FEATURE:
<223> OTHER INFORMATION: Motif-Synthetic

<400> SEQUENCE: 102

Thr Gln Arg Glu Leu
1               5

<210> SEQ ID NO 103
<211> LENGTH: 4
<212> TYPE: PRT
<213> ORGANISM: Artificial Sequence
<220> FEATURE:
<223> OTHER INFORMATION: Motif-Synthetic

<400> SEQUENCE: 103

Lys Glu Cys Glu
1
```

<210> SEQ ID NO 104
<211> LENGTH: 5
<212> TYPE: PRT
<213> ORGANISM: Artificial Sequence
<220> FEATURE:
<223> OTHER INFORMATION: Motif-Synthetic

<400> SEQUENCE: 104

Lys Glu Cys Glu Leu
1               5

<210> SEQ ID NO 105
<211> LENGTH: 5
<212> TYPE: PRT
<213> ORGANISM: Artificial Sequence
<220> FEATURE:
<223> OTHER INFORMATION: Motif-Synthetic

<400> SEQUENCE: 105

Lys Glu Cys Glu Arg
1               5

<210> SEQ ID NO 106
<211> LENGTH: 4
<212> TYPE: PRT
<213> ORGANISM: Artificial Sequence
<220> FEATURE:
<223> OTHER INFORMATION: Motif-Synthetic

<400> SEQUENCE: 106

Lys Gln Cys Glu
1

<210> SEQ ID NO 107
<211> LENGTH: 5
<212> TYPE: PRT
<213> ORGANISM: Artificial Sequence
<220> FEATURE:
<223> OTHER INFORMATION: Motif-Synthetic

<400> SEQUENCE: 107

Lys Gln Cys Glu Leu
1               5

<210> SEQ ID NO 108
<211> LENGTH: 4
<212> TYPE: PRT
<213> ORGANISM: Artificial Sequence
<220> FEATURE:
<223> OTHER INFORMATION: Motif-Synthetic

<400> SEQUENCE: 108

Arg Glu Arg Glu
1

<210> SEQ ID NO 109
<211> LENGTH: 5
<212> TYPE: PRT
<213> ORGANISM: Artificial Sequence
<220> FEATURE:
<223> OTHER INFORMATION: Motif-Synthetic

<400> SEQUENCE: 109

Arg Glu Arg Glu Gly
1               5

```
<210> SEQ ID NO 110
<211> LENGTH: 4
<212> TYPE: PRT
<213> ORGANISM: Artificial Sequence
<220> FEATURE:
<223> OTHER INFORMATION: Motif-Synthetic

<400> SEQUENCE: 110

Arg Gln Arg Glu
1

<210> SEQ ID NO 111
<211> LENGTH: 5
<212> TYPE: PRT
<213> ORGANISM: Artificial Sequence
<220> FEATURE:
<223> OTHER INFORMATION: Motif-Synthetic

<400> SEQUENCE: 111

Arg Gln Arg Glu Leu
1               5

<210> SEQ ID NO 112
<211> LENGTH: 5
<212> TYPE: PRT
<213> ORGANISM: Artificial Sequence
<220> FEATURE:
<223> OTHER INFORMATION: Motif-Synthetic

<400> SEQUENCE: 112

Arg Gln Arg Glu Phe
1               5

<210> SEQ ID NO 113
<211> LENGTH: 5
<212> TYPE: PRT
<213> ORGANISM: Artificial Sequence
<220> FEATURE:
<223> OTHER INFORMATION: Motif-Synthetic

<400> SEQUENCE: 113

Arg Gln Arg Glu Trp
1               5

<210> SEQ ID NO 114
<211> LENGTH: 4
<212> TYPE: PRT
<213> ORGANISM: Artificial Sequence
<220> FEATURE:
<223> OTHER INFORMATION: Motif-Synthetic

<400> SEQUENCE: 114

Gln Glu Arg Glu
1

<210> SEQ ID NO 115
<211> LENGTH: 5
<212> TYPE: PRT
<213> ORGANISM: Artificial Sequence
<220> FEATURE:
<223> OTHER INFORMATION: Motif-Synthetic

<400> SEQUENCE: 115

Gln Glu Arg Glu Gly
1               5
```

<210> SEQ ID NO 116
<211> LENGTH: 4
<212> TYPE: PRT
<213> ORGANISM: Artificial Sequence
<220> FEATURE:
<223> OTHER INFORMATION: Motif-Synthetic

<400> SEQUENCE: 116

Gln Gln Arg Glu
1

<210> SEQ ID NO 117
<211> LENGTH: 5
<212> TYPE: PRT
<213> ORGANISM: Artificial Sequence
<220> FEATURE:
<223> OTHER INFORMATION: Motif-Synthetic

<400> SEQUENCE: 117

Gln Gln Arg Glu Trp
1               5

<210> SEQ ID NO 118
<211> LENGTH: 5
<212> TYPE: PRT
<213> ORGANISM: Artificial Sequence
<220> FEATURE:
<223> OTHER INFORMATION: Motif-Synthetic

<400> SEQUENCE: 118

Gln Gln Arg Glu Leu
1               5

<210> SEQ ID NO 119
<211> LENGTH: 5
<212> TYPE: PRT
<213> ORGANISM: Artificial Sequence
<220> FEATURE:
<223> OTHER INFORMATION: Motif-Synthetic

<400> SEQUENCE: 119

Gln Gln Arg Glu Phe
1               5

<210> SEQ ID NO 120
<211> LENGTH: 4
<212> TYPE: PRT
<213> ORGANISM: Artificial Sequence
<220> FEATURE:
<223> OTHER INFORMATION: Motif-Synthetic

<400> SEQUENCE: 120

Lys Gly Arg Glu
1

<210> SEQ ID NO 121
<211> LENGTH: 5
<212> TYPE: PRT
<213> ORGANISM: Artificial Sequence
<220> FEATURE:
<223> OTHER INFORMATION: Motif-Synthetic

<400> SEQUENCE: 121

Lys Gly Arg Glu Gly
1               5

<210> SEQ ID NO 122

```
<211> LENGTH: 4
<212> TYPE: PRT
<213> ORGANISM: Artificial Sequence
<220> FEATURE:
<223> OTHER INFORMATION: Motif-Synthetic

<400> SEQUENCE: 122

Lys Asp Arg Glu
1

<210> SEQ ID NO 123
<211> LENGTH: 5
<212> TYPE: PRT
<213> ORGANISM: Artificial Sequence
<220> FEATURE:
<223> OTHER INFORMATION: Motif-Synthetic

<400> SEQUENCE: 123

Lys Asp Arg Glu Val
1               5

<210> SEQ ID NO 124
<211> LENGTH: 5
<212> TYPE: PRT
<213> ORGANISM: Artificial Sequence
<220> FEATURE:
<223> OTHER INFORMATION: Motif-Synthetic

<400> SEQUENCE: 124

Asp Glu Cys Lys Leu
1               5

<210> SEQ ID NO 125
<211> LENGTH: 5
<212> TYPE: PRT
<213> ORGANISM: Artificial Sequence
<220> FEATURE:
<223> OTHER INFORMATION: Motif-Synthetic

<400> SEQUENCE: 125

Asn Val Cys Glu Leu
1               5

<210> SEQ ID NO 126
<211> LENGTH: 4
<212> TYPE: PRT
<213> ORGANISM: Artificial Sequence
<220> FEATURE:
<223> OTHER INFORMATION: Motif-Synthetic

<400> SEQUENCE: 126

Gly Val Glu Trp
1

<210> SEQ ID NO 127
<211> LENGTH: 4
<212> TYPE: PRT
<213> ORGANISM: Artificial Sequence
<220> FEATURE:
<223> OTHER INFORMATION: Motif-Synthetic

<400> SEQUENCE: 127

Glu Pro Glu Trp
1

<210> SEQ ID NO 128
<211> LENGTH: 4
```

```
<212> TYPE: PRT
<213> ORGANISM: Artificial Sequence
<220> FEATURE:
<223> OTHER INFORMATION: Motif-Synthetic

<400> SEQUENCE: 128

Gly Leu Glu Arg
1

<210> SEQ ID NO 129
<211> LENGTH: 4
<212> TYPE: PRT
<213> ORGANISM: Artificial Sequence
<220> FEATURE:
<223> OTHER INFORMATION: Motif-Synthetic

<400> SEQUENCE: 129

Asp Gln Glu Trp
1

<210> SEQ ID NO 130
<211> LENGTH: 4
<212> TYPE: PRT
<213> ORGANISM: Artificial Sequence
<220> FEATURE:
<223> OTHER INFORMATION: Motif-Synthetic

<400> SEQUENCE: 130

Asp Leu Glu Trp
1

<210> SEQ ID NO 131
<211> LENGTH: 4
<212> TYPE: PRT
<213> ORGANISM: Artificial Sequence
<220> FEATURE:
<223> OTHER INFORMATION: Motif-Synthetic

<400> SEQUENCE: 131

Gly Ile Glu Trp
1

<210> SEQ ID NO 132
<211> LENGTH: 4
<212> TYPE: PRT
<213> ORGANISM: Artificial Sequence
<220> FEATURE:
<223> OTHER INFORMATION: Motif-Synthetic

<400> SEQUENCE: 132

Glu Leu Glu Trp
1

<210> SEQ ID NO 133
<211> LENGTH: 4
<212> TYPE: PRT
<213> ORGANISM: Artificial Sequence
<220> FEATURE:
<223> OTHER INFORMATION: Motif-Synthetic

<400> SEQUENCE: 133

Gly Pro Glu Trp
1

<210> SEQ ID NO 134
<211> LENGTH: 4
<212> TYPE: PRT
```

```
<213> ORGANISM: Artificial Sequence
<220> FEATURE:
<223> OTHER INFORMATION: Motif-Synthetic

<400> SEQUENCE: 134

Glu Trp Leu Pro
1

<210> SEQ ID NO 135
<211> LENGTH: 4
<212> TYPE: PRT
<213> ORGANISM: Artificial Sequence
<220> FEATURE:
<223> OTHER INFORMATION: Motif-Synthetic

<400> SEQUENCE: 135

Gly Pro Glu Arg
1

<210> SEQ ID NO 136
<211> LENGTH: 4
<212> TYPE: PRT
<213> ORGANISM: Artificial Sequence
<220> FEATURE:
<223> OTHER INFORMATION: Motif-Synthetic

<400> SEQUENCE: 136

Gly Leu Glu Arg
1

<210> SEQ ID NO 137
<211> LENGTH: 4
<212> TYPE: PRT
<213> ORGANISM: Artificial Sequence
<220> FEATURE:
<223> OTHER INFORMATION: Motif-Synthetic

<400> SEQUENCE: 137

Glu Leu Glu Trp
1

<210> SEQ ID NO 138
<211> LENGTH: 5
<212> TYPE: PRT
<213> ORGANISM: Artificial Sequence
<220> FEATURE:
<223> OTHER INFORMATION: C-terminus-Synthetic

<400> SEQUENCE: 138

Val Thr Val Ser Ser
1               5

<210> SEQ ID NO 139
<211> LENGTH: 5
<212> TYPE: PRT
<213> ORGANISM: Artificial Sequence
<220> FEATURE:
<223> OTHER INFORMATION: C-terminus-Synthetic

<400> SEQUENCE: 139

Val Lys Val Ser Ser
1               5

<210> SEQ ID NO 140
<211> LENGTH: 5
<212> TYPE: PRT
<213> ORGANISM: Artificial Sequence
```

<220> FEATURE:
<223> OTHER INFORMATION: C-terminus-Synthetic

<400> SEQUENCE: 140

Val Gln Val Ser Ser
1               5

<210> SEQ ID NO 141
<211> LENGTH: 6
<212> TYPE: PRT
<213> ORGANISM: Artificial Sequence
<220> FEATURE:
<223> OTHER INFORMATION: C-terminus-Synthetic

<400> SEQUENCE: 141

Val Thr Val Ser Ser Ala
1               5

<210> SEQ ID NO 142
<211> LENGTH: 6
<212> TYPE: PRT
<213> ORGANISM: Artificial Sequence
<220> FEATURE:
<223> OTHER INFORMATION: C-terminus-Synthetic

<400> SEQUENCE: 142

Val Lys Val Ser Ser Ala
1               5

<210> SEQ ID NO 143
<211> LENGTH: 6
<212> TYPE: PRT
<213> ORGANISM: Artificial Sequence
<220> FEATURE:
<223> OTHER INFORMATION: C-terminus-Synthetic

<400> SEQUENCE: 143

Val Gln Val Ser Ser Ala
1               5

<210> SEQ ID NO 144
<211> LENGTH: 123
<212> TYPE: PRT
<213> ORGANISM: Artificial Sequence
<220> FEATURE:
<223> OTHER INFORMATION: F0107004B02-Synthetic

<400> SEQUENCE: 144

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Arg Met Gly Trp Phe Arg Gln Ala Pro Gly Lys Glu Arg Glu Phe Val
        35                  40                  45

Ala Ala Leu Ser Gly Asp Gly Tyr Ser Thr Tyr Thr Ala Asn Ser Val
    50                  55                  60

Asn Ser Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Ala Lys Leu Gln Tyr Val Ser Gly Trp Ser Tyr Asp Tyr Pro Tyr
            100                 105                 110

Trp Gly Gln Gly Thr Leu Val Thr Val Ser Ser

<210> SEQ ID NO 145
<211> LENGTH: 126
<212> TYPE: PRT
<213> ORGANISM: Artificial Sequence
<220> FEATURE:
<223> OTHER INFORMATION: F0107004B06-Synthetic

<400> SEQUENCE: 145

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Ala Met Lys Trp Val Arg Gln Ala Pro Gly Lys Gly Leu Glu Trp Val
        35                  40                  45

Ser Ser Ile Thr Thr Gly Gly Ser Thr Asp Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Asn Val Pro Phe Gly Tyr Tyr Ser Glu His Phe Ser Gly Leu Ser
            100                 105                 110

Phe Asp Tyr Arg Gly Gln Gly Thr Leu Val Thr Val Ser Ser
        115                 120                 125

<210> SEQ ID NO 146
<211> LENGTH: 117
<212> TYPE: PRT
<213> ORGANISM: Artificial Sequence
<220> FEATURE:
<223> OTHER INFORMATION: F0107501A02-Synthetic

<400> SEQUENCE: 146

Glu Val Gln Leu Val Glu Ser Gly Gly Gly Leu Val Gln Ala Gly Glu
1               5                   10                  15

Ser Leu Arg Leu Ser Cys Ala Ala Ser Gly Ser Gly Phe Gly Val Asn
            20                  25                  30

Ile Leu Tyr Trp Tyr Arg Gln Ala Ala Gly Ile Glu Arg Glu Leu Ile
        35                  40                  45

Ala Ser Ile Thr Ser Gly Gly Ile Thr Asn Tyr Val Asp Ser Val Lys
    50                  55                  60

Gly Arg Phe Thr Ile Ser Arg Asp Asn Ala Glu Asn Thr Met Tyr Leu
65                  70                  75                  80

Gln Met Asn Ser Leu Lys Ala Glu Asp Thr Gly Val Tyr Tyr Cys Ala
                85                  90                  95

Ser Arg Asn Ile Phe Asp Gly Thr Thr Glu Trp Gly Gln Gly Thr Leu
            100                 105                 110

Val Thr Val Ser Ser
        115

<210> SEQ ID NO 147
<211> LENGTH: 127
<212> TYPE: PRT
<213> ORGANISM: Artificial Sequence
<220> FEATURE:
<223> OTHER INFORMATION: F0107529F10-Synthetic

<400> SEQUENCE: 147

```
Glu Val Gln Leu Val Glu Ser Gly Gly Gly Leu Val Gln Ala Gly
1               5                   10                  15

Ser Leu Arg Leu Ser Cys Ala Ala Ser Gly Phe Thr Phe Ala Asp Tyr
            20                  25                  30

Asp Tyr Asp Ile Gly Trp Phe Arg Gln Ala Pro Gly Lys Glu Arg Glu
        35                  40                  45

Gly Val Ser Cys Ile Ser Asn Arg Asp Gly Ser Thr Tyr Tyr Thr Asp
    50                  55                  60

Ser Val Lys Gly Arg Phe Thr Ile Ser Asp Asn Ala Lys Asn Thr
65                  70                  75                  80

Val Ser Leu Gln Met Asn Ser Leu Lys Pro Glu Asp Thr Ala Val Tyr
                85                  90                  95

Tyr Cys Ala Val Glu Ile His Cys Asp Asp Tyr Gly Val Glu Asn Phe
            100                 105                 110

Asp Phe Asp Pro Trp Gly Gln Gly Thr Leu Val Thr Val Ser Ser
        115                 120                 125
```

<210> SEQ ID NO 148
<211> LENGTH: 284
<212> TYPE: PRT
<213> ORGANISM: Artificial Sequence
<220> FEATURE:
<223> OTHER INFORMATION: F010700003-Synthetic

<400> SEQUENCE: 148

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Ala Met Lys Trp Val Arg Gln Ala Pro Gly Lys Gly Leu Glu Trp Val
        35                  40                  45

Ser Ser Ile Thr Thr Gly Gly Gly Ser Thr Asp Tyr Ala Asp Ser Val
    50                  55                  60

Lys Gly Arg Phe Thr Ile Ser Arg Asp Asn Arg Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Asn Val Pro Phe Gly Tyr Tyr Ser Glu His Phe Ser Gly Leu Ser
            100                 105                 110

Phe Asp Tyr Arg Gly Gln Gly Thr Leu Val Thr Val Ser Ser Gly Gly
        115                 120                 125

Gly Gly Ser Gly Gly Gly Gly Ser Gly Gly Gly Gly Ser Gly Gly Gly
    130                 135                 140

Gly Ser Gly Gly Gly Gly Ser Gly Gly Gly Ser Gly Gly Gly Gly
145                 150                 155                 160

Ser Glu Val Gln Leu Val Glu Ser Gly Gly Gly Leu Val Gln Ala Gly
                165                 170                 175

Gly Ser Leu Arg Leu Ser Cys Ala Ala Ser Gly Arg Thr Phe Ser Ser
            180                 185                 190

Tyr Arg Met Gly Trp Phe Arg Gln Ala Pro Gly Lys Glu Arg Glu Phe
        195                 200                 205

Val Ala Ala Leu Ser Gly Asp Gly Tyr Ser Tyr Thr Ala Asn Ser
    210                 215                 220

Val Asn Ser Arg Phe Thr Ile Ser Arg Asp Asn Ala Lys Asn Thr Val
225                 230                 235                 240
```

```
Tyr Leu Gln Met Asn Ser Leu Lys Pro Glu Asp Thr Ala Ile Tyr Tyr
                245                 250                 255

Cys Ala Ala Lys Leu Gln Tyr Val Ser Gly Trp Ser Tyr Asp Tyr Pro
            260                 265                 270

Tyr Trp Gly Gln Gly Thr Leu Val Thr Val Ser Ser
        275                 280

<210> SEQ ID NO 149
<211> LENGTH: 281
<212> TYPE: PRT
<213> ORGANISM: Artificial Sequence
<220> FEATURE:
<223> OTHER INFORMATION: F010700014-Synthetic

<400> SEQUENCE: 149

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Arg Met Gly Trp Phe Arg Gln Ala Pro Gly Lys Glu Arg Glu Phe Val
        35                  40                  45

Ala Ala Leu Ser Gly Asp Gly Tyr Ser Thr Tyr Thr Ala Asn Ser Val
    50                  55                  60

Asn Ser Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Ala Lys Leu Gln Tyr Val Ser Gly Trp Ser Tyr Asp Tyr Pro Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Ser Gly Gly Gly Gly Ser Gly
            130                 135                 140

Gly Gly Gly Ser Gly Gly Gly Ser Gly Gly Gly Gly Ser Glu Val
145                 150                 155                 160

Gln Leu Val Glu Ser Gly Gly Gly Leu Val Gln Ala Gly Gly Ser Leu
                165                 170                 175

Arg Leu Ser Cys Ala Ala Ser Gly Arg Thr Phe Ser Ser Tyr Arg Met
            180                 185                 190

Gly Trp Phe Arg Gln Ala Pro Gly Lys Glu Arg Glu Phe Val Ala Ala
        195                 200                 205

Leu Ser Gly Asp Gly Tyr Ser Thr Tyr Thr Ala Asn Ser Val Asn Ser
    210                 215                 220

Arg Phe Thr Ile Ser Arg Asp Asn Ala Lys Asn Thr Val Tyr Leu Gln
225                 230                 235                 240

Met Asn Ser Leu Lys Pro Glu Asp Thr Ala Ile Tyr Tyr Cys Ala Ala
                245                 250                 255

Lys Leu Gln Tyr Val Ser Gly Trp Ser Tyr Asp Tyr Pro Tyr Trp Gly
            260                 265                 270

Gln Gly Thr Leu Val Thr Val Ser Ser
        275                 280

<210> SEQ ID NO 150
<211> LENGTH: 284
<212> TYPE: PRT
<213> ORGANISM: Artificial Sequence
```

<220> FEATURE:
<223> OTHER INFORMATION: F010700029-Synthetic

<400> SEQUENCE: 150

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Arg Met Gly Trp Phe Arg Gln Ala Pro Gly Lys Glu Arg Glu Phe Val
        35                  40                  45

Ala Ala Leu Ser Gly Asp Gly Tyr Ser Thr Tyr Thr Ala Asn Ser Val
    50                  55                  60

Asn Ser Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Ala Lys Leu Gln Tyr Val Ser Gly Trp Ser Tyr Asp Tyr Pro Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Ser Gly Gly Gly Gly Ser Gly
    130                 135                 140

Gly Gly Ser Gly Gly Gly Ser Gly Gly Gly Ser Glu Val
145                 150                 155                 160

Gln Leu Val Glu Ser Gly Gly Leu Val Gln Pro Gly Gly Ser Leu
                165                 170                 175

Arg Leu Ser Cys Ala Ala Ser Gly Phe Thr Phe Asn Asn Tyr Ala Met
            180                 185                 190

Lys Trp Val Arg Gln Ala Pro Gly Lys Gly Leu Glu Trp Val Ser Ser
        195                 200                 205

Ile Thr Thr Gly Gly Ser Thr Asp Tyr Ala Asp Ser Val Lys Gly
    210                 215                 220

Arg Phe Thr Ile Ser Arg Asp Asn Arg Lys Asn Thr Leu Tyr Leu Gln
225                 230                 235                 240

Met Asn Ser Leu Lys Pro Glu Asp Thr Ala Val Tyr Tyr Cys Ala Asn
                245                 250                 255

Val Pro Phe Gly Tyr Tyr Ser Glu His Phe Ser Gly Leu Ser Phe Asp
            260                 265                 270

Tyr Arg Gly Gln Gly Thr Leu Val Thr Val Ser Ser
        275                 280

<210> SEQ ID NO 151
<211> LENGTH: 287
<212> TYPE: PRT
<213> ORGANISM: Artificial Sequence
<220> FEATURE:
<223> OTHER INFORMATION: F010700031-Synthetic

<400> SEQUENCE: 151

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Ala Met Lys Trp Val Arg Gln Ala Pro Gly Lys Gly Leu Glu Trp Val
        35                  40                  45

Ser Ser Ile Thr Thr Gly Gly Gly Ser Thr Asp Tyr Ala Asp Ser Val

Lys Gly Arg Phe Thr Ile Ser Arg Asp Asn Arg Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Asn Val Pro Phe Gly Tyr Tyr Ser Glu His Phe Ser Gly Leu Ser
            100                 105                 110

Phe Asp Tyr Arg Gly Gln Gly Thr Leu Val Thr Val Ser Ser Gly Gly
        115                 120                 125

Gly Gly Ser Gly Gly Gly Gly Ser Gly Gly Gly Gly Ser Gly Gly Gly
    130                 135                 140

Gly Ser Gly Gly Gly Ser Gly Gly Gly Ser Gly Gly Gly
145                 150                 155                 160

Ser Glu Val Gln Leu Val Glu Ser Gly Gly Leu Val Gln Pro Gly
                165                 170                 175

Gly Ser Leu Arg Leu Ser Cys Ala Ala Ser Gly Phe Thr Phe Asn Asn
        180                 185                 190

Tyr Ala Met Lys Trp Val Arg Gln Ala Pro Gly Lys Gly Leu Glu Trp
    195                 200                 205

Val Ser Ser Ile Thr Thr Gly Gly Ser Thr Asp Tyr Ala Asp Ser
210                 215                 220

Val Lys Gly Arg Phe Thr Ile Ser Arg Asp Asn Arg Lys Asn Thr Leu
225                 230                 235                 240

Tyr Leu Gln Met Asn Ser Leu Lys Pro Glu Asp Thr Ala Val Tyr Tyr
                245                 250                 255

Cys Ala Asn Val Pro Phe Gly Tyr Tyr Ser Glu His Phe Ser Gly Leu
            260                 265                 270

Ser Phe Asp Tyr Arg Gly Gln Gly Thr Leu Val Thr Val Ser Ser
        275                 280                 285

<210> SEQ ID NO 152
<211> LENGTH: 279
<212> TYPE: PRT
<213> ORGANISM: Artificial Sequence
<220> FEATURE:
<223> OTHER INFORMATION: F010703842-Synthetic

<400> SEQUENCE: 152

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Ala Asp Tyr
            20                  25                  30

Asp Tyr Asp Ile Gly Trp Phe Arg Gln Ala Pro Gly Lys Glu Arg Glu
        35                  40                  45

Gly Val Ser Cys Ile Ser Asn Arg Asp Gly Ser Thr Tyr Tyr Thr Asp
    50                  55                  60

Ser Val Lys Gly Arg Phe Thr Ile Ser Ser Asp Asn Ala Lys Asn Thr
65                  70                  75                  80

Val Ser Leu Gln Met Asn Ser Leu Lys Pro Glu Asp Thr Ala Val Tyr
                85                  90                  95

Tyr Cys Ala Val Glu Ile His Cys Asp Asp Tyr Gly Val Glu Asn Phe
            100                 105                 110

Asp Phe Asp Pro Trp Gly Gln Gly Thr Leu Val Thr Val Ser Ser Gly
        115                 120                 125

Gly Gly Gly Ser Gly Gly Gly Gly Ser Gly Gly Gly Gly Ser Gly Gly

```
                130                 135                 140
Gly Gly Ser Gly Gly Gly Ser Gly Gly Gly Ser Gly Gly
145                 150                 155                 160

Gly Ser Glu Val Gln Leu Val Glu Ser Gly Gly Leu Val Gln Ala
                165                 170                 175

Gly Glu Ser Leu Arg Leu Ser Cys Ala Ala Ser Gly Ser Phe Gly
                180                 185                 190

Val Asn Ile Leu Tyr Trp Tyr Arg Gln Ala Ala Gly Ile Glu Arg Glu
                195                 200                 205

Leu Ile Ala Ser Ile Thr Ser Gly Gly Ile Thr Asn Tyr Val Asp Ser
        210                 215                 220

Val Lys Gly Arg Phe Thr Ile Ser Arg Asp Asn Ala Glu Asn Thr Met
225                 230                 235                 240

Tyr Leu Gln Met Asn Ser Leu Lys Ala Glu Asp Thr Gly Val Tyr Tyr
                245                 250                 255

Cys Ala Ser Arg Asn Ile Phe Asp Gly Thr Thr Glu Trp Gly Gln Gly
                260                 265                 270

Thr Leu Val Thr Val Ser Ser
        275

<210> SEQ ID NO 153
<211> LENGTH: 279
<212> TYPE: PRT
<213> ORGANISM: Artificial Sequence
<220> FEATURE:
<223> OTHER INFORMATION: F027400016-Synthetic

<400> SEQUENCE: 153

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Gly Phe Gly Val Asn
                20                  25                  30

Ile Leu Tyr Trp Tyr Arg Gln Ala Pro Gly Lys Gln Arg Glu Leu Ile
            35                  40                  45

Ala Ser Ile Thr Ser Gly Gly Ile Thr Asn Tyr Val Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Pro Glu Asp Thr Ala Leu Tyr Tyr Cys Ala
                85                  90                  95

Ser Arg Asn Ile Phe Asp Gly Thr Thr Glu Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Ser Gly Gly Gly Gly Ser Gly Gly Gly Gly Ser Gly Gly
    130                 135                 140

Gly Gly Ser Gly Gly Gly Gly Ser Glu Val Gln Leu Val Glu Ser Gly
145                 150                 155                 160

Gly Gly Val Val Gln Pro Gly Gly Ser Leu Arg Leu Ser Cys Ala Ala
                165                 170                 175

Ser Gly Phe Thr Phe Ala Asp Tyr Asp Tyr Asp Ile Gly Trp Phe Arg
            180                 185                 190

Gln Ala Pro Gly Lys Glu Arg Glu Gly Val Ser Cys Ile Ser Asn Arg
        195                 200                 205

Asp Gly Ser Thr Tyr Tyr Ala Asp Ser Val Lys Gly Arg Phe Thr Ile
```

```
            210                 215                 220
Ser Arg Asp Asn Ser Lys Asn Thr Val Tyr Leu Gln Met Asn Ser Leu
225                 230                 235                 240

Arg Pro Glu Asp Thr Ala Leu Tyr Tyr Cys Ala Val Glu Ile His Cys
                245                 250                 255

Asp Asp Tyr Gly Val Glu Asn Phe Phe Asp Pro Trp Gly Gln Gly
            260                 265                 270

Thr Leu Val Thr Val Ser Ser
            275
```

<210> SEQ ID NO 154
<211> LENGTH: 284
<212> TYPE: PRT
<213> ORGANISM: Artificial Sequence
<220> FEATURE:
<223> OTHER INFORMATION: F010700003-SO-Synthetic

<400> SEQUENCE: 154

```
Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Asn Asn Tyr
            20                  25                  30

Ala Met Lys Trp Val Arg Gln Ala Pro Gly Lys Gly Leu Glu Trp Val
        35                  40                  45

Ser Ser Ile Thr Thr Gly Gly Ser Thr Asp Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Ala Asn Val Pro Phe Gly Tyr Tyr Ser Glu His Phe Ser Gly Leu Ser
            100                 105                 110

Phe Asp Tyr Arg Gly Gln Gly Thr Leu Val Thr Val Ser Ser Gly Gly
        115                 120                 125

Gly Gly Ser Gly Gly Gly Gly Ser Gly Gly Gly Gly Ser Gly Gly Gly
130                 135                 140

Gly Ser Gly Gly Gly Gly Ser Gly Gly Gly Gly Ser Gly Gly Gly Gly
145                 150                 155                 160

Ser Glu Val Gln Leu Val Glu Ser Gly Gly Gly Val Val Gln Pro Gly
                165                 170                 175

Gly Ser Leu Arg Leu Ser Cys Ala Ala Ser Gly Arg Thr Phe Ser Ser
            180                 185                 190

Tyr Arg Met Gly Trp Phe Arg Gln Ala Pro Gly Lys Glu Arg Glu Phe
        195                 200                 205

Val Ala Ala Leu Ser Gly Asp Gly Tyr Ser Thr Tyr Thr Ala Asn Ser
210                 215                 220

Val Lys Gly Arg Phe Thr Ile Ser Arg Asp Asn Ser Lys Asn Thr Val
225                 230                 235                 240

Tyr Leu Gln Met Asn Ser Leu Arg Pro Glu Asp Thr Ala Leu Tyr Tyr
                245                 250                 255

Cys Ala Ala Lys Leu Gln Tyr Val Ser Gly Trp Ser Tyr Asp Tyr Pro
            260                 265                 270

Tyr Trp Gly Gln Gly Thr Leu Val Thr Val Ser Ser
        275                 280
```

```
<210> SEQ ID NO 155
<211> LENGTH: 281
<212> TYPE: PRT
<213> ORGANISM: Artificial Sequence
<220> FEATURE:
<223> OTHER INFORMATION: F010700014-SO-Synthetic

<400> SEQUENCE: 155

Asp Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Ser Ser Tyr
            20                  25                  30

Arg Met Gly Trp Phe Arg Gln Ala Pro Gly Lys Glu Arg Glu Phe Val
        35                  40                  45

Ala Ala Leu Ser Gly Asp Gly Tyr Ser Thr Tyr Thr Ala Asn Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Lys Leu Gln Tyr Val Ser Gly Trp Ser Tyr Asp Tyr Pro Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Ser Gly Gly Gly Gly Ser Gly
    130                 135                 140

Gly Gly Ser Gly Gly Gly Ser Gly Gly Gly Ser Glu Val
145                 150                 155                 160

Gln Leu Val Glu Ser Gly Gly Gly Val Val Gln Pro Gly Gly Ser Leu
                165                 170                 175

Arg Leu Ser Cys Ala Ala Ser Gly Arg Thr Phe Ser Ser Tyr Arg Met
            180                 185                 190

Gly Trp Phe Arg Gln Ala Pro Gly Lys Glu Arg Glu Phe Val Ala Ala
        195                 200                 205

Leu Ser Gly Asp Gly Tyr Ser Thr Tyr Thr Ala Asn Ser Val Lys Gly
    210                 215                 220

Arg Phe Thr Ile Ser Arg Asp Asn Ser Lys Asn Thr Val Tyr Leu Gln
225                 230                 235                 240

Met Asn Ser Leu Arg Pro Glu Asp Thr Ala Leu Tyr Tyr Cys Ala Ala
                245                 250                 255

Lys Leu Gln Tyr Val Ser Gly Trp Ser Tyr Asp Tyr Pro Tyr Trp Gly
            260                 265                 270

Gln Gly Thr Leu Val Thr Val Ser Ser
        275                 280

<210> SEQ ID NO 156
<211> LENGTH: 284
<212> TYPE: PRT
<213> ORGANISM: Artificial Sequence
<220> FEATURE:
<223> OTHER INFORMATION: F010700029-SO-Synthetic

<400> SEQUENCE: 156

Asp Val Gln Leu Val Glu Ser Gly Gly Gly Val Val Gln Pro Gly Gly
1               5                   10                  15

Ser Leu Arg Leu Ser Cys Ala Ser Gly Arg Thr Phe Ser Ser Tyr
            20                  25                  30
```

```
Arg Met Gly Trp Phe Arg Gln Ala Pro Gly Lys Glu Arg Glu Phe Val
             35                  40                  45

Ala Ala Leu Ser Gly Asp Gly Tyr Ser Thr Tyr Thr Ala Asn Ser Val
 50                      55                  60

Lys Gly Arg Phe Thr Ile Ser Arg Asp Asn Ser Lys Asn Thr Val Tyr
 65                  70                  75                  80

Leu Gln Met Asn Ser Leu Arg Pro Glu Asp Thr Ala Leu Tyr Tyr Cys
                 85                  90                  95

Ala Ala Lys Leu Gln Tyr Val Ser Gly Trp Ser Tyr Asp Tyr Pro Tyr
            100                 105                 110

Trp Gly Gln Gly Thr Leu Val Thr Val Ser Ser Gly Gly Gly Gly Ser
            115                 120                 125

Gly Gly Gly Gly Ser Gly Gly Gly Ser Gly Gly Gly Gly Ser Gly
130                 135                 140

Gly Gly Ser Gly Gly Gly Ser Gly Gly Gly Ser Glu Val
145                 150                 155                 160

Gln Leu Val Glu Ser Gly Gly Val Val Gln Pro Gly Gly Ser Leu
            165                 170                 175

Arg Leu Ser Cys Ala Ala Ser Gly Phe Thr Phe Asn Asn Tyr Ala Met
            180                 185                 190

Lys Trp Val Arg Gln Ala Pro Gly Lys Gly Leu Glu Trp Val Ser Ser
            195                 200                 205

Ile Thr Thr Gly Gly Gly Ser Thr Asp Tyr Ala Asp Ser Val Lys Gly
            210                 215                 220

Arg Phe Thr Ile Ser Arg Asp Asn Ser Lys Asn Thr Leu Tyr Leu Gln
225                 230                 235                 240

Met Asn Ser Leu Arg Pro Glu Asp Thr Ala Leu Tyr Tyr Cys Ala Asn
                245                 250                 255

Val Pro Phe Gly Tyr Tyr Ser Glu His Phe Ser Gly Leu Ser Phe Asp
            260                 265                 270

Tyr Arg Gly Gln Gly Thr Leu Val Thr Val Ser Ser
            275                 280

<210> SEQ ID NO 157
<211> LENGTH: 287
<212> TYPE: PRT
<213> ORGANISM: Artificial Sequence
<220> FEATURE:
<223> OTHER INFORMATION: F010700031-SO-Synthetic

<400> SEQUENCE: 157

Glu Val Gln Leu Val Glu Ser Gly Gly Val Val Gln Pro Gly Gly
 1               5                  10                  15

Ser Leu Arg Leu Ser Cys Ala Ala Ser Gly Phe Thr Phe Asn Asn Tyr
                 20                  25                  30

Ala Met Lys Trp Val Arg Gln Ala Pro Gly Lys Gly Leu Glu Trp Val
             35                  40                  45

Ser Ser Ile Thr Thr Gly Gly Gly Ser Thr Asp Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Leu Tyr Tyr Cys
                 85                  90                  95

Ala Asn Val Pro Phe Gly Tyr Tyr Ser Glu His Phe Ser Gly Leu Ser
                100                 105                 110
```

```
Phe Asp Tyr Arg Gly Gln Gly Thr Leu Val Thr Val Ser Gly Gly
            115                 120                 125
Gly Gly Ser Gly Gly Gly Ser Gly Gly Gly Ser Gly Gly Gly
        130                 135                 140
Gly Ser Gly Gly Gly Ser Gly Gly Gly Ser Gly Gly Gly Gly
145                 150                 155                 160
Ser Glu Val Gln Leu Val Glu Ser Gly Gly Val Val Gln Pro Gly
                165                 170                 175
Gly Ser Leu Arg Leu Ser Cys Ala Ala Ser Gly Phe Thr Phe Asn Asn
                180                 185                 190
Tyr Ala Met Lys Trp Val Arg Gln Ala Pro Lys Gly Leu Glu Trp
            195                 200                 205
Val Ser Ser Ile Thr Thr Gly Gly Ser Thr Asp Tyr Ala Asp Ser
        210                 215                 220
Val Lys Gly Arg Phe Thr Ile Ser Arg Asp Asn Ser Lys Asn Thr Leu
225                 230                 235                 240
Tyr Leu Gln Met Asn Ser Leu Arg Pro Glu Asp Thr Ala Leu Tyr Tyr
                245                 250                 255
Cys Ala Asn Val Pro Phe Gly Tyr Tyr Ser Glu His Phe Ser Gly Leu
                260                 265                 270
Ser Phe Asp Tyr Arg Gly Gln Gly Thr Leu Val Thr Val Ser Ser
            275                 280                 285

<210> SEQ ID NO 158
<211> LENGTH: 279
<212> TYPE: PRT
<213> ORGANISM: Artificial Sequence
<220> FEATURE:
<223> OTHER INFORMATION: F010703842-SO-Synthetic

<400> SEQUENCE: 158

Glu Val Gln Leu Val Glu Ser Gly Gly Gly Val Val Gln Pro Gly Gly
1               5                   10                  15
Ser Leu Arg Leu Ser Cys Ala Ala Ser Gly Phe Thr Phe Ala Asp Tyr
            20                  25                  30
Asp Tyr Asp Ile Gly Trp Phe Arg Gln Ala Pro Gly Lys Glu Arg Glu
        35                  40                  45
Gly Val Ser Cys Ile Ser Asn Arg Asp Gly Ser Thr Tyr Tyr Ala Asp
    50                  55                  60
Ser Val Lys Gly Arg Phe Thr Ile Ser Arg Asp Asn Ser Lys Asn Thr
65                  70                  75                  80
Val Tyr Leu Gln Met Asn Ser Leu Arg Pro Glu Asp Thr Ala Leu Tyr
                85                  90                  95
Tyr Cys Ala Val Glu Ile His Cys Asp Asp Tyr Gly Val Glu Asn Phe
            100                 105                 110
Asp Phe Asp Pro Trp Gly Gln Gly Thr Leu Val Thr Val Ser Ser Gly
        115                 120                 125
Gly Gly Gly Ser Gly Gly Gly Gly Ser Gly Gly Gly Gly Ser Gly Gly
    130                 135                 140
Gly Gly Ser Gly Gly Gly Gly Ser Gly Gly Gly Gly Ser Gly Gly Gly
145                 150                 155                 160
Gly Ser Glu Val Gln Leu Val Glu Ser Gly Gly Val Val Gln Pro
                165                 170                 175
Gly Gly Ser Leu Arg Leu Ser Cys Ala Ala Ser Gly Ser Gly Phe Gly
            180                 185                 190
```

```
Val Asn Ile Leu Tyr Trp Tyr Arg Gln Ala Ala Gly Ile Glu Arg Glu
        195                 200                 205

Leu Ile Ala Ser Ile Thr Ser Gly Gly Ile Thr Asn Tyr Val Asp Ser
    210                 215                 220

Val Lys Gly Arg Phe Thr Ile Ser Arg Asp Asn Ser Glu Asn Thr Met
225                 230                 235                 240

Tyr Leu Gln Met Asn Ser Leu Arg Ala Glu Asp Thr Gly Leu Tyr Tyr
                245                 250                 255

Cys Ala Ser Arg Asn Ile Phe Asp Gly Thr Thr Glu Trp Gly Gln Gly
                260                 265                 270

Thr Leu Val Thr Val Ser Ser
        275

<210> SEQ ID NO 159
<211> LENGTH: 279
<212> TYPE: PRT
<213> ORGANISM: Artificial Sequence
<220> FEATURE:
<223> OTHER INFORMATION: F027400016-SO-Synthetic

<400> SEQUENCE: 159

Glu Val Gln Leu Val Glu Ser Gly Gly Gly Val Val Gln Pro Gly Gly
1               5                   10                  15

Ser Leu Arg Leu Ser Cys Ala Ala Ser Gly Ser Gly Phe Gly Val Asn
            20                  25                  30

Ile Leu Tyr Trp Tyr Arg Gln Ala Ala Gly Ile Glu Arg Glu Leu Ile
        35                  40                  45

Ala Ser Ile Thr Ser Gly Gly Ile Thr Asn Tyr Val Asp Ser Val Lys
    50                  55                  60

Gly Arg Phe Thr Ile Ser Arg Asp Asn Ser Glu Asn Thr Met Tyr Leu
65                  70                  75                  80

Gln Met Asn Ser Leu Arg Ala Glu Asp Thr Gly Leu Tyr Tyr Cys Ala
                85                  90                  95

Ser Arg Asn Ile Phe Asp Gly Thr Thr Glu Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Ser Gly Gly Gly Ser Gly Gly Gly Ser Gly Gly Gly Ser Gly
    130                 135                 140

Gly Gly Ser Gly Gly Gly Ser Glu Val Gln Leu Val Glu Ser Gly
145                 150                 155                 160

Gly Gly Val Val Gln Pro Gly Gly Ser Leu Arg Leu Ser Cys Ala Ala
                165                 170                 175

Ser Gly Phe Thr Phe Ala Asp Tyr Asp Tyr Asp Ile Gly Trp Phe Arg
            180                 185                 190

Gln Ala Pro Gly Lys Glu Arg Glu Gly Val Ser Cys Ile Ser Asn Arg
        195                 200                 205

Asp Gly Ser Thr Tyr Tyr Ala Asp Ser Val Lys Gly Arg Phe Thr Ile
    210                 215                 220

Ser Arg Asp Asn Ser Lys Asn Thr Val Tyr Leu Gln Met Asn Ser Leu
225                 230                 235                 240

Arg Pro Glu Asp Thr Ala Leu Tyr Tyr Cys Ala Val Glu Ile His Cys
                245                 250                 255

Asp Asp Tyr Gly Val Glu Asn Phe Asp Phe Asp Pro Trp Gly Gln Gly
            260                 265                 270
```

Thr Leu Val Thr Val Ser Ser
        275

<210> SEQ ID NO 160
<211> LENGTH: 117
<212> TYPE: PRT
<213> ORGANISM: Artificial Sequence
<220> FEATURE:
<223> OTHER INFORMATION: F010704076-Synthetic

<400> SEQUENCE: 160

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Gly Phe Gly Val Asn
            20                  25                  30

Ile Leu Tyr Trp Tyr Arg Gln Ala Ala Gly Ile Glu Arg Glu Leu Ile
        35                  40                  45

Ala Ser Ile Thr Ser Gly Gly Ile Thr Asn Tyr Val Asp Ser Val Lys
    50                  55                  60

Gly Arg Phe Thr Ile Ser Arg Asp Asn Ser Glu Asn Thr Met Tyr Leu
65                  70                  75                  80

Gln Met Asn Ser Leu Arg Ala Glu Asp Thr Gly Val Tyr Tyr Cys Ala
                85                  90                  95

Ser Arg Asn Ile Phe Asp Gly Thr Thr Glu Trp Gly Gln Gly Thr Leu
            100                 105                 110

Val Thr Val Ser Ser
        115

<210> SEQ ID NO 161
<211> LENGTH: 127
<212> TYPE: PRT
<213> ORGANISM: Artificial Sequence
<220> FEATURE:
<223> OTHER INFORMATION: F010704099-Synthetic

<400> SEQUENCE: 161

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ala Asp Tyr
            20                  25                  30

Asp Tyr Asp Ile Gly Trp Phe Arg Gln Ala Pro Gly Lys Glu Arg Glu
        35                  40                  45

Gly Val Ser Cys Ile Ser Asn Arg Asp Gly Ser Thr Tyr Tyr Ala Asp
    50                  55                  60

Ser Val Lys Gly Arg Phe Thr Ile Ser Arg Asp Asn Ser Lys Asn Thr
65                  70                  75                  80

Val Tyr Leu Gln Met Asn Ser Leu Arg Pro Glu Asp Thr Ala Val Tyr
                85                  90                  95

Tyr Cys Ala Val Glu Ile His Cys Asp Asp Tyr Gly Val Glu Asn Phe
            100                 105                 110

Asp Phe Asp Pro Trp Gly Gln Gly Thr Leu Val Thr Val Ser Ser
        115                 120                 125

<210> SEQ ID NO 162
<211> LENGTH: 126
<212> TYPE: PRT
<213> ORGANISM: Artificial Sequence
<220> FEATURE:
<223> OTHER INFORMATION: F027100019-Synthetic -continued

<400> SEQUENCE: 162

Asp Val Gln Leu Val Glu Ser Gly Gly Val Val Gln Pro Gly Gly
1               5                   10                  15

Ser Leu Arg Leu Ser Cys Ala Ala Ser Gly Arg Thr Phe Ser Ser Tyr
            20                  25                  30

Arg Met Gly Trp Phe Arg Gln Ala Pro Gly Lys Glu Arg Glu Phe Val
        35                  40                  45

Ala Ala Leu Ser Gly Asp Gly Tyr Ser Thr Tyr Thr Ala Asn Ser Val
50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Lys Leu Gln Tyr Val Ser Gly Trp Ser Tyr Asp Tyr Pro Tyr
            100                 105                 110

Trp Gly Gln Gly Thr Leu Val Thr Val Ser Ser Ala Ala Ala
        115                 120                 125

<210> SEQ ID NO 163
<211> LENGTH: 126
<212> TYPE: PRT
<213> ORGANISM: Artificial Sequence
<220> FEATURE:
<223> OTHER INFORMATION: F027100183-Synthetic

<400> SEQUENCE: 163

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Asn Asn Tyr
            20                  25                  30

Ala Met Lys Trp Val Arg Gln Ala Pro Gly Lys Gly Leu Glu Trp Val
        35                  40                  45

Ser Ser Ile Thr Thr Gly Gly Ser Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Ala Asn Val Pro Phe Gly Tyr Tyr Ser Glu His Phe Ser Gly Leu Ser
            100                 105                 110

Phe Asp Tyr Arg Gly Gln Gly Thr Leu Val Thr Val Ser Ser
        115                 120                 125

<210> SEQ ID NO 164
<211> LENGTH: 127
<212> TYPE: PRT
<213> ORGANISM: Artificial Sequence
<220> FEATURE:
<223> OTHER INFORMATION: F027400021-Synthetic

<400> SEQUENCE: 164

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ala Asp Tyr
            20                  25                  30

Asp Tyr Asp Ile Gly Trp Phe Arg Gln Ala Pro Gly Lys Glu Arg Glu
        35                  40                  45

Gly Val Ser Cys Ile Ser Asn Arg Asp Gly Ser Thr Tyr Tyr Ala Asp
        50              55                  60

Ser Val Lys Gly Arg Phe Thr Ile Ser Arg Asp Asn Ser Lys Asn Thr
65                  70                  75                  80

Val Tyr Leu Gln Met Asn Ser Leu Arg Pro Glu Asp Thr Ala Leu Tyr
                    85                  90                  95

Tyr Cys Ala Val Glu Ile His Cys Asp Tyr Gly Val Glu Asn Phe
                100                 105                 110

Asp Phe Asp Pro Trp Gly Gln Gly Thr Leu Val Thr Val Ser Ser
            115                 120                 125

<210> SEQ ID NO 165
<211> LENGTH: 117
<212> TYPE: PRT
<213> ORGANISM: Artificial Sequence
<220> FEATURE:
<223> OTHER INFORMATION: F027400160-Synthetic

<400> SEQUENCE: 165

Glu Val Gln Leu Val Glu Ser Gly Gly Gly Val Val Gln Pro Gly Gly
1               5                   10                  15

Ser Leu Arg Leu Ser Cys Ala Ala Ser Gly Ser Gly Phe Gly Val Asn
            20                  25                  30

Ile Leu Tyr Trp Tyr Arg Gln Ala Ala Gly Ile Glu Arg Glu Leu Ile
        35                  40                  45

Ala Ser Ile Thr Ser Gly Gly Ile Thr Asn Tyr Val Asp Ser Val Lys
    50                  55                  60

Gly Arg Phe Thr Ile Ser Arg Asp Asn Ser Glu Asn Thr Met Tyr Leu
65                  70                  75                  80

Gln Met Asn Ser Leu Arg Ala Glu Asp Thr Gly Leu Tyr Tyr Cys Ala
                85                  90                  95

Ser Arg Asn Ile Phe Asp Gly Thr Thr Glu Trp Gly Gln Gly Thr Leu
                100                 105                 110

Val Thr Val Ser Ser
        115

<210> SEQ ID NO 166
<211> LENGTH: 5
<212> TYPE: PRT
<213> ORGANISM: Artificial Sequence
<220> FEATURE:
<223> OTHER INFORMATION: C-terminus-Synthetic

<400> SEQUENCE: 166

Val Thr Val Lys Ser
1               5

<210> SEQ ID NO 167
<211> LENGTH: 5
<212> TYPE: PRT
<213> ORGANISM: Artificial Sequence
<220> FEATURE:
<223> OTHER INFORMATION: C-terminus-Synthetic

<400> SEQUENCE: 167

Val Thr Val Gln Ser
1               5

<210> SEQ ID NO 168
<211> LENGTH: 5
<212> TYPE: PRT

```
<213> ORGANISM: Artificial Sequence
<220> FEATURE:
<223> OTHER INFORMATION: C-terminus-Synthetic

<400> SEQUENCE: 168

Val Lys Val Lys Ser
1               5

<210> SEQ ID NO 169
<211> LENGTH: 5
<212> TYPE: PRT
<213> ORGANISM: Artificial Sequence
<220> FEATURE:
<223> OTHER INFORMATION: C-terminus-Synthetic

<400> SEQUENCE: 169

Val Lys Val Gln Ser
1               5

<210> SEQ ID NO 170
<211> LENGTH: 5
<212> TYPE: PRT
<213> ORGANISM: Artificial Sequence
<220> FEATURE:
<223> OTHER INFORMATION: C-terminus-Synthetic

<400> SEQUENCE: 170

Val Gln Val Lys Ser
1               5

<210> SEQ ID NO 171
<211> LENGTH: 5
<212> TYPE: PRT
<213> ORGANISM: Artificial Sequence
<220> FEATURE:
<223> OTHER INFORMATION: C-terminus-Synthetic

<400> SEQUENCE: 171

Val Gln Val Gln Ser
1               5

<210> SEQ ID NO 172
<211> LENGTH: 6
<212> TYPE: PRT
<213> ORGANISM: Artificial Sequence
<220> FEATURE:
<223> OTHER INFORMATION: C-terminus-Synthetic

<400> SEQUENCE: 172

Val Thr Val Lys Ser Ala
1               5

<210> SEQ ID NO 173
<211> LENGTH: 6
<212> TYPE: PRT
<213> ORGANISM: Artificial Sequence
<220> FEATURE:
<223> OTHER INFORMATION: C-terminus-Synthetic

<400> SEQUENCE: 173

Val Thr Val Gln Ser Ala
1               5

<210> SEQ ID NO 174
<211> LENGTH: 6
<212> TYPE: PRT
<213> ORGANISM: Artificial Sequence
```

```
<220> FEATURE:
<223> OTHER INFORMATION: C-terminus-Synthetic

<400> SEQUENCE: 174

Val Lys Val Lys Ser Ala
1               5

<210> SEQ ID NO 175
<211> LENGTH: 6
<212> TYPE: PRT
<213> ORGANISM: Artificial Sequence
<220> FEATURE:
<223> OTHER INFORMATION: C-terminus-Synthetic

<400> SEQUENCE: 175

Val Lys Val Gln Ser Ala
1               5

<210> SEQ ID NO 176
<211> LENGTH: 6
<212> TYPE: PRT
<213> ORGANISM: Artificial Sequence
<220> FEATURE:
<223> OTHER INFORMATION: C-terminus-Synthetic

<400> SEQUENCE: 176

Val Gln Val Lys Ser Ala
1               5

<210> SEQ ID NO 177
<211> LENGTH: 6
<212> TYPE: PRT
<213> ORGANISM: Artificial Sequence
<220> FEATURE:
<223> OTHER INFORMATION: C-terminus-Synthetic

<400> SEQUENCE: 177

Val Gln Val Gln Ser Ala
1               5
```

METHODS OF TREATING ASTHMA WITH POLYPEPTIDES TARGETING IL-13 AND TSLP

RELATED APPLICATIONS

This application is a division of U.S. application Ser. No. 17/208,046, filed Mar. 22, 2021, which is a continuation of U.S. application Ser. No. 17/115,906, filed Dec. 9, 2020, which claims the benefit under 35 U.S.C. § 119(e) of U.S. Provisional Application Ser. No. 62/945,391, filed Dec. 9, 2019, the entire contents of each of which are incorporated by reference herein in its entirety.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Nov. 15, 2021, is named A0848.70215US04-SEQ-JRV, and is 99,569 bytes in size.

DESCRIPTION

Field of the Present Technology

The present technology relates to polypeptides targeting IL-13 and TSLP. It also relates to nucleic acid molecules encoding the polypeptide and vectors comprising the nucleic acids, and to compositions comprising the polypeptide, nucleic acid or vector. The present technology further relates to these products for use in a method of treating a subject suffering from an inflammatory disease. Moreover, the present technology relates to method of producing these products.

Technological Background

While necessary for host-defense, unrestrained immune responses can lead to a range of inflammatory diseases such as asthma, atopic dermatitis and rheumatoid arthritis. A cascade of immune responses mediated by the innate and adaptive arms of the immune system (e.g., antigen recognition, antigen processing, antigen presentation, cytokine production, antibody production, target cell killing) drive the initiation and propagation of a range of immunological diseases. Inflammatory diseases are often chronic and can even be life-threatening. Allergic and atopic diseases such as asthma and atopic dermatitis are driven predominantly by type 2 immune responses and characterized by salient features of type 2 immunity such as high IgE production and eosinophilia.

Thymic stromal lymphopoietin (TSLP) and Interleukin-13 (IL-13) are soluble cytokine targets produced by stromal and/or immune cells (Ziegler & Artis, Nat Rev Immunol (2010) 11:289, Gieseck III et al., Nat Rev Immunol (2018) 18:62). Human TSLP and IL-13 drive distinct, overlapping and synergistic aspects of type 2 immunity, type 2 inflammatory diseases such as asthma and atopic dermatitis as well as a broad array of immunological diseases.

The signalling of TSLP begins through a heterodimeric receptor complex composed of the thymic stromal lymphopoietin receptor (TSLPR) and the IL-7R alpha chain (IL-7R$\alpha$). Similarly, IL-13 signalling starts by binding to a heterodimeric receptor complex consisting of alpha IL-4 receptor (IL-4R$\alpha$) and alpha Interleukin-13 receptor (IL-13R1a). The high affinity of IL-13 to the IL-13R1 leads to their complex formation which further increase the probability of a heterodimer formation to IL-4R$\alpha$.

TSLP drives the maturation of dendritic cells, development and proliferation of mast cells, as well as activating other immune cells such as basophils and innate lymphoid cells (ILC2). Similarly, IL-13 exerts a range of immunopathologies such as epithelial barrier disruption, mucus production from mucosal-epithelial surfaces, airway remodeling as well as the induction of eosinophil recruiting chemokines such as eotaxin. These mechanisms are central to the initiation and propagation of the type 2 inflammatory response and are central to the development of a range of immunopathologies in diseases such as atopic dermatitis and asthma.

Currently, patients with moderate/severe asthma are inadequately responding to presently available standard of care treatments, including biological such as anti-IL4R$\alpha$ monoclonal antibody Dupixent (dupilumab; marketed), anti-IL5s (marketed), anti-IgE monoclonal antibody Xolair (omalizumab; marketed), in particular in asthma patients with a low-eosinophilic phenotype. Although antagonistic monoclonal antibodies against TSLP (tezepelumab) and IL-13 (lebrikizumab) are presently undergoing clinical trials, there are no active clinical development programs that target both TSLP and IL-13. Dual targeting of TSLP and IL-13 with a single agent has the potential to confer efficacy in both low-type 2 and high-type 2 asthma as well as atopic dermatitis, with the potential to confer efficacy in sub-populations within these indications where a single monospecific agent therapy may not be fully efficacious. Accordingly, there is still an unmet medical need for the treatment of type 2 inflammatory diseases such as asthma and atopic dermatitis that is not only more efficacious but also conveniently applicable to the patient.

Such therapy may comprise targeting multiple disease factors, such as IL-13 and TSLP.

Targeting multiple disease factors may be achieved for example by co-administration or combinatorial use of two separate biologicals, e.g. antibodies binding to different therapeutic targets. However, co-administration or combinatorial use of separate biologicals can be challenging, both from a practical and a commercial point of view. For example, two injections of separate products result in a more inconvenient and more painful treatment regime to the patients which may negatively affect compliance. With regard to a single injection of two separate products, it can be difficult or impossible to provide formulations that allow for acceptable viscosity at the required concentrations and suitable stability of both products. Additionally, co-administration and co-formulation requires production of two separate drugs which can increase overall costs.

Bispecific antibodies that are able to bind to two different antigens have been suggested as one strategy for addressing such limitations associated with co-administration or combinatorial use of separate biologicals, such as antibodies.

Bispecific antibody constructs have been proposed in multiple formats. For example, bispecific antibody formats may involve the chemical conjugation of two antibodies or fragments thereof (Brennan, M, et al., Science, 1985. 229 (4708): p. 81-83; Glennie, M. J., et al., J Immunol, 1987. 139(7): p. 2367-2375).

Disadvantages of such bispecific antibody formats include, however, high viscosity at high concentration, making e.g. subcutaneous administration challenging, and in that each binding unit requires the interaction of two variable domains for specific and high affinity binding, comprising implications on polypeptide stability and efficiency of production. Such bispecific antibody formats may also potentially lead to Chemistry, Manufacturing and Control (CMC) issues related to mispairing of the light chains or mispairing of the heavy chains.

SUMMARY OF THE PRESENT TECHNOLOGY

In some embodiments, the present technology relates to a polypeptide targeting specifically IL-13 and TSLP at the same time leading to an increased efficiency of modulating a type 2 inflammatory response as compared to monospecific anti-IL-13 or anti-TSLP polypeptides in vitro. In some embodiments, the polypeptides are efficiently produced (e.g. in microbial hosts). Furthermore, in some embodiments, such polypeptides have limited reactivity to pre-existing antibodies in the subject to be treated (i.e., antibodies present in the subject before the first treatment with the antibody construct). In other embodiments such polypeptides exhibit a half-life in the subject to be treated that is long enough such that consecutive treatments can be conveniently spaced apart.

In one embodiment, the present technology provides a polypeptide comprising or consisting of at least one immunoglobulin single variable domain (ISVD) that specifically binds to IL-13. In a further embodiment, the polypeptide of the present technology comprises or consists of at least two ISVDs that specifically bind to IL-13, wherein the two ISVDs are optionally linked via a peptidic linker. In one embodiment, the two ISVDs specifically binding to IL-13 are distinct ISVDs. Moreover, in one embodiment the polypeptide further comprises one or more other groups, residues, moieties or binding units, optionally linked via one or more peptidic linkers, in which said one or more other groups, residues, moieties or binding units provide the polypeptide with increased half-life, compared to the corresponding polypeptide without said one or more other groups, residues, moieties or binding units. For example, the binding unit can be an ISVD that binds to a (human) serum protein, such as human serum albumin.

In another aspect, the polypeptide of the present technology comprises or consists of at least one ISVD that specifically binds to TSLP. In a further embodiment, the polypeptide of the present technology comprises or consists of at least two ISVDs that specifically bind to TSLP, wherein the two ISVDs are optionally linked via a peptidic linker. In one embodiment, the two ISVDs specifically binding to TSLP are distinct ISVDs. Moreover, in one embodiment the polypeptide further comprises one or more other groups, residues, moieties or binding units, optionally linked via one or more peptidic linkers, in which said one or more other groups, residues, moieties or binding units provide the polypeptide with increased half-life, compared to the corresponding polypeptide without said one or more other groups, residues, moieties or binding units. For example, the binding unit can be an ISVD that binds to a (human) serum protein, such as human serum albumin.

In another embodiment, the polypeptide of the present technology comprises or consists of at least four ISVDs, wherein at least two ISVDs specifically bind to IL-13 and at least two ISVDs specifically bind to TSLP. In one embodiment, the at least two ISVDs specifically binding to IL-13 specifically bind to human IL-13 and the at least two ISVDs specifically binding to TSLP specifically bind to human TSLP. In one embodiment, the at least two ISVDs specifically binding to IL-13 are distinct ISVDs and the at least two ISVDs binding to TSLP are distinct ISVDs. In another embodiment, the polypeptide comprising or consisting of at least four ISVDs further comprises one or more other groups, residues, moieties or binding units, optionally linked via one or more peptidic linkers, in which said one or more other groups, residues, moieties or binding units provide the polypeptide with increased half-life, compared to the corresponding polypeptide without said one or more other groups, residues, moieties or binding units. For example, the binding unit can be an ISVD that binds to a (human) serum protein, such as human serum albumin.

Also provided is a nucleic acid molecule capable of expressing the polypeptide of the present technology, a nucleic acid or vector comprising the nucleic acid, and a composition comprising the polypeptide, the nucleic acid or the vector. In one embodiment, the composition is a pharmaceutical composition.

Also provided is a host or host cell comprising the nucleic acid or vector that encodes the polypeptide according to the present technology.

Further provided is a method for producing the polypeptide according to present technology, said method at least comprising the steps of:
  a. expressing, in a suitable host cell or host organism or in another suitable expression system, a nucleic acid comprising a nucleotide sequence that encodes a polypeptide of the present technology; optionally followed by:
  b. isolating and/or purifying the polypeptide according to the present technology.

Moreover, the present technology provides the polypeptide, the composition comprising the polypeptide, or the composition comprising the nucleic acid or vector comprising the nucleotide sequence that encodes the polypeptide, for use as a medicament. In one embodiment, the polypeptide or composition is for use in the treatment of an inflammatory disease, such as a type 2 inflammatory disease. In one embodiment, the type 2 inflammatory disease is selected from atopic dermatitis and asthma.

In addition, provided is a method of treating an inflammatory disease, such as a type 2 inflammatory disease, wherein said method comprises administering, to a subject in need thereof, a pharmaceutically active amount of the polypeptide or a composition according to the present technology. In one embodiment, the type 2 inflammatory disease is selected from atopic dermatitis and asthma. In one embodiment, the method further comprises administering one or more additional therapeutic agents.

Further provided is the use of the polypeptide or composition of the present technology in the preparation of a pharmaceutical composition for treating an inflammatory disease, such as a type 2 inflammatory disease. In one embodiment, the type 2 inflammatory disease is selected from atopic dermatitis and asthma.

In particular, the present technology provides the following embodiments:

Embodiment 1. A polypeptide, a composition comprising the polypeptide, or a composition comprising a nucleic acid comprising a nucleotide sequence that encodes the polypeptide, for use as a medicament, wherein the polypeptide comprises or consists of at least one immunoglobulin single variable domain (ISVD), wherein said ISVD comprises three complementarity determining regions (CDR1 to CDR3, respectively), and wherein the at least one ISVD comprises:
  a) a CDR1 that is the amino acid sequence of SEQ ID NO: 7 or an amino acid sequence with 2 or 1 amino acid difference(s) with SEQ ID NO: 7;

a CDR2 that is the amino acid sequence of SEQ ID NO: 12 or an amino acid sequence with 2 or 1 amino acid difference(s) with SEQ ID NO: 12; and a CDR3 that is the amino acid sequence of SEQ ID NO: 17 or an amino acid sequence with 2 or 1 amino acid difference(s) with SEQ ID NO: 17, b) a CDR1 that is the amino acid sequence of SEQ ID NO: 8 or an amino acid sequence with 2 or 1 amino acid difference(s) with SEQ ID NO: 8;

a CDR2 that is the amino acid sequence of SEQ ID NO: 13 or an amino acid sequence with 2 or 1 amino acid difference(s) with SEQ ID NO: 13; and a CDR3 that is the amino acid sequence of SEQ ID NO: 18 or an amino acid sequence with 2 or 1 amino acid difference(s) with SEQ ID NO: 18, c) a CDR1 that is the amino acid sequence of SEQ ID NO: 9 or an amino acid sequence with 2 or 1 amino acid difference(s) with SEQ ID NO: 9;

a CDR2 that is the amino acid sequence of SEQ ID NO: 14 or an amino acid sequence with 2 or 1 amino acid difference(s) with SEQ ID NO: 14; and a CDR3 that is the amino acid sequence of SEQ ID NO: 19 or an amino acid sequence with 2 or 1 amino acid difference(s) with SEQ ID NO: 19, or d) a CDR1 that is the amino acid sequence of SEQ ID NO: 11 or an amino acid sequence with 2 or 1 amino acid difference(s) with SEQ ID NO: 11;

a CDR2 that is the amino acid sequence of SEQ ID NO: 16 or an amino acid sequence with 2 or 1 amino acid difference(s) with SEQ ID NO: 16; and a CDR3 that is the amino acid sequence of SEQ ID NO: 21 or an amino acid sequence with 2 or 1 amino acid difference(s) with SEQ ID NO: 21.

Embodiment 2. The polypeptide or composition for use according to embodiment 1, wherein the at least one ISVD comprises:

a) a CDR1 that is the amino acid sequence of SEQ ID NO: 7, a CDR2 that is the amino acid sequence of SEQ ID NO: 12 and a CDR3 that is the amino acid sequence of SEQ ID NO: 17, b) a CDR1 that is the amino acid sequence of SEQ ID NO: 8, a CDR2 that is the amino acid sequence of SEQ ID NO: 13 and a CDR3 that is the amino acid sequence of SEQ ID NO: 18, c) a CDR1 that is the amino acid sequence of SEQ ID NO: 9, a CDR2 that is the amino acid sequence of SEQ ID NO: 14 and a CDR3 that is the amino acid sequence of SEQ ID NO: 19, or d) a CDR1 that is the amino acid sequence of SEQ ID NO: 11, a CDR2 that is the amino acid sequence of SEQ ID NO: 16 and a CDR3 that is the amino acid sequence of SEQ ID NO: 21.

Embodiment 3. The polypeptide or composition for use according to any of embodiments 1 or 2, wherein the amino acid sequence of the at least one ISVD comprises:

a) a sequence identity of more than 90% with SEQ ID NO: 2, b) a sequence identity of more than 90% with SEQ ID NO: 3, c) a sequence identity of more than 90% identity with SEQ ID NO: 4, or d) a sequence identity of more than 90% identity with SEQ ID NO: 6.

Embodiment 4. The polypeptide or composition for use according to any of embodiments 1 to 3, wherein said at least one ISVD comprises:

a) the amino acid sequence of SEQ ID NO: 2, b) the amino acid sequence of SEQ ID NO: 3, c) the amino acid sequence of SEQ ID NO: 4, or d) the amino acid sequence of SEQ ID NO: 6.

Embodiment 5. The polypeptide or composition for use according to embodiment 1, wherein the polypeptide comprises or consists of at least two ISVDs, wherein each of said ISVDs comprises three complementarity determining regions (CDR1 to CDR3, respectively), wherein the at least two ISVDs are optionally linked via one or more peptidic linkers, and wherein:

a) a first and a second ISVD comprises
 i. a CDR1 that is the amino acid sequence of SEQ ID NO: 7 or an amino acid sequence with 2 or 1 amino acid difference(s) with SEQ ID NO: 7;
 ii. a CDR2 that is the amino acid sequence of SEQ ID NO: 12 or an amino acid sequence with 2 or 1 amino acid difference(s) with SEQ ID NO: 12; and
 iii. a CDR3 that is the amino acid sequence of SEQ ID NO: 17 or an amino acid sequence with 2 or 1 amino acid difference(s) with SEQ ID NO: 17, b) a first and a second ISVD comprises
 i. a CDR1 that is the amino acid sequence of SEQ ID NO: 8 or an amino acid sequence with 2 or 1 amino acid difference(s) with SEQ ID NO: 8;
 ii. a CDR2 that is the amino acid sequence of SEQ ID NO: 13 or an amino acid sequence with 2 or 1 amino acid difference(s) with SEQ ID NO: 13; and
 iii. a CDR3 that is the amino acid sequence of SEQ ID NO: 18 or an amino acid sequence with 2 or 1 amino acid difference(s) with SEQ ID NO: 18, c) a first ISVD comprises
 i. a CDR1 that is the amino acid sequence of SEQ ID NO: 7 or an amino acid sequence with 2 or 1 amino acid difference(s) with SEQ ID NO: 7;
 ii. a CDR2 that is the amino acid sequence of SEQ ID NO: 12 or an amino acid sequence with 2 or 1 amino acid difference(s) with SEQ ID NO: 12; and
 iii. a CDR3 that is the amino acid sequence of SEQ ID NO: 17 or an amino acid sequence with 2 or 1 amino acid difference(s) with SEQ ID NO: 17, and a second ISVD comprises
 iv. a CDR1 that is the amino acid sequence of SEQ ID NO: 8 or an amino acid sequence with 2 or 1 amino acid difference(s) with SEQ ID NO: 8;
 v. a CDR2 that is the amino acid sequence of SEQ ID NO: 13 or an amino acid sequence with 2 or 1 amino acid difference(s) with SEQ ID NO: 13; and
 vi. a CDR3 that is the amino acid sequence of SEQ ID NO: 18 or an amino acid sequence with 2 or 1 amino acid difference(s) with SEQ ID NO: 18, d) a first ISVD comprises
 i. a CDR1 that is the amino acid sequence of SEQ ID NO: 8 or an amino acid sequence with 2 or 1 amino acid difference(s) with SEQ ID NO: 8;
 ii. a CDR2 that is the amino acid sequence of SEQ ID NO: 13 or an amino acid sequence with 2 or 1 amino acid difference(s) with SEQ ID NO: 13; and
 iii. a CDR3 that is the amino acid sequence of SEQ ID NO: 18 or an amino acid sequence with 2 or 1 amino acid difference(s) with SEQ ID NO: 18, and a second ISVD comprises
 iv. a CDR1 that is the amino acid sequence of SEQ ID NO: 7 or an amino acid sequence with 2 or 1 amino acid difference(s) with SEQ ID NO: 7;
 v. a CDR2 that is the amino acid sequence of SEQ ID NO: 12 or an amino acid sequence with 2 or 1 amino acid difference(s) with SEQ ID NO: 12; and vi. a CDR3 that is the amino acid sequence of SEQ ID NO: 17 or an amino acid sequence with 2 or 1 amino acid difference(s) with SEQ ID NO: 17,
e) a first ISVD comprises
  i. a CDR1 that is the amino acid sequence of SEQ ID NO: 11 or an amino acid sequence with 2 or 1 amino acid difference(s) with SEQ ID NO: 11;
  ii. a CDR2 that is the amino acid sequence of SEQ ID NO: 16 or an amino acid sequence with 2 or 1 amino acid difference(s) with SEQ ID NO: 16; and
  iii. a CDR3 that is the amino acid sequence of SEQ ID NO: 21 or an amino acid sequence with 2 or 1 amino acid difference(s) with SEQ ID NO: 21, and
a second ISVD comprises
  iv. a CDR1 that is the amino acid sequence of SEQ ID NO: 9 or an amino acid sequence with 2 or 1 amino acid difference(s) with SEQ ID NO: 9;
  v. a CDR2 that is the amino acid sequence of SEQ ID NO: 14 or an amino acid sequence with 2 or 1 amino acid difference(s) with SEQ ID NO: 14; and
  vi. a CDR3 that is the amino acid sequence of SEQ ID NO: 19 or an amino acid sequence with 2 or 1 amino acid difference(s) with SEQ ID NO: 19, or
f) a first ISVD comprises
  i. a CDR1 that is the amino acid sequence of SEQ ID NO: 9 or an amino acid sequence with 2 or 1 amino acid difference(s) with SEQ ID NO: 9;
  ii. a CDR2 that is the amino acid sequence of SEQ ID NO: 14 or an amino acid sequence with 2 or 1 amino acid difference(s) with SEQ ID NO: 14; and
  iii. a CDR3 that is the amino acid sequence of SEQ ID NO: 19 or an amino acid sequence with 2 or 1 amino acid difference(s) with SEQ ID NO: 19, and/or
a second ISVD comprises
  iv. a CDR1 that is the amino acid sequence of SEQ ID NO: 11 or an amino acid sequence with 2 or 1 amino acid difference(s) with SEQ ID NO: 11;
  v. a CDR2 that is the amino acid sequence of SEQ ID NO: 16 or an amino acid sequence with 2 or 1 amino acid difference(s) with SEQ ID NO: 16; and
  vi. a CDR3 that is the amino acid sequence of SEQ ID NO: 21 or an amino acid sequence with 2 or 1 amino acid difference(s) with SEQ ID NO: 21, wherein the order of the ISVDs indicates their relative position to each other considered from the N-terminus to the C-terminus of said polypeptide.

Embodiment 6. The polypeptide or composition for use according to embodiment 5, wherein:
a) the first and the second ISVD comprises a CDR1 that is the amino acid sequence of SEQ ID NO: 7, a CDR2 that is the amino acid sequence of SEQ ID NO: 12 and a CDR3 that is the amino acid sequence of SEQ ID NO: 17,
b) the first and the second ISVD comprises a CDR1 that is the amino acid sequence of SEQ ID NO: 8, a CDR2 that is the amino acid sequence of SEQ ID NO: 13 and a CDR3 that is the amino acid sequence of SEQ ID NO: 18,
c) the first ISVD comprises a CDR1 that is the amino acid sequence of SEQ ID NO: 7, a CDR2 that is the amino acid sequence of SEQ ID NO: 12 and a CDR3 that is the amino acid sequence of SEQ ID NO: 17, and the second ISVD comprises a CDR1 that is the amino acid sequence of SEQ ID NO: 8, a CDR2 that is the amino acid sequence of SEQ ID NO: 13 and a CDR3 that is the amino acid sequence of SEQ ID NO: 18,
d) the first ISVD comprises a CDR1 that is the amino acid sequence of SEQ ID NO: 8, a CDR2 that is the amino acid sequence of SEQ ID NO: 13 and a CDR3 that is the amino acid sequence of SEQ ID NO: 18, and the second ISVD comprises a CDR1 that is the amino acid sequence of SEQ ID NO: 7, a CDR2 that is the amino acid sequence of SEQ ID NO: 12 and a CDR3 that is the amino acid sequence of SEQ ID NO: 17,
e) the first ISVD comprises a CDR1 that is the amino acid sequence of SEQ ID NO: 11, a CDR2 that is the amino acid sequence of SEQ ID NO: 16 and a CDR3 that is the amino acid sequence of SEQ ID NO: 21, and the second ISVD comprises a CDR1 that is the amino acid sequence of SEQ ID NO: 9, a CDR2 that is the amino acid sequence of SEQ ID NO: 14 and a CDR3 that is the amino acid sequence of SEQ ID NO: 19, or
f) the first ISVD comprises a CDR1 that is the amino acid sequence of SEQ ID NO: 9, a CDR2 that is the amino acid sequence of SEQ ID NO: 14 and a CDR3 that is the amino acid sequence of SEQ ID NO: 19, and the second ISVD comprises a CDR1 that is the amino acid sequence of SEQ ID NO: 11, a CDR2 that is the amino acid sequence of SEQ ID NO: 16 and a CDR3 that is the amino acid sequence of SEQ ID NO: 21.

Embodiment 7. The polypeptide or composition for use according to any of embodiments 5 or 6, wherein:
a) the amino acid sequence of the first and the second ISVD comprises a sequence identity of more than 90% with SEQ ID NO: 2,
b) the amino acid sequence of the first and the second ISVD comprises a sequence identity of more than 90% with SEQ ID NO: 3,
c) the amino acid sequence of the first ISVD comprises a sequence identity of more than 90% with SEQ ID NO: 2, and the second ISVD comprises a sequence identity of more than 90% identity with SEQ ID NO: 3,
d) the amino acid sequence of the first ISVD comprises a sequence identity of more than 90% with SEQ ID NO: 3, and the second ISVD comprises a sequence identity of more than 90% identity with SEQ ID NO: 2,
e) the amino acid sequence of the first ISVD comprises a sequence identity of more than 90% with SEQ ID NO: 6, and the second ISVD comprises a sequence identity of more than 90% identity with SEQ ID NO: 4,
f) the amino acid sequence of the first ISVD comprises a sequence identity of more than 90% with SEQ ID NO: 4, and the second ISVD comprises a sequence identity of more than 90% identity with SEQ ID NO: 6.

Embodiment 8. The polypeptide or composition for use according to any of embodiments 5 to 7, wherein:
a) the first and the second ISVD comprises the amino acid sequence of SEQ ID NO: 2,
b) the first and the second ISVD comprises the amino acid sequence of SEQ ID NO: 3,
c) the first ISVD comprises the amino acid sequence of SEQ ID NO: 2, and the second ISVD comprises the amino acid sequence of SEQ ID NO: 3,
d) the first ISVD comprises the amino acid sequence of SEQ ID NO: 3, and the second ISVD comprises the amino acid sequence of SEQ ID NO: 2,
e) the first ISVD comprises the amino acid sequence of SEQ ID NO: 6, and the second ISVD comprises the amino acid sequence of SEQ ID NO: 4, or
f) the first ISVD comprises the amino acid sequence of SEQ ID NO: 4, and the second ISVD comprises the amino acid sequence of SEQ ID NO: 6.

Embodiment 9. The polypeptide according to any of embodiments 5 to 8, wherein the polypeptide comprises or consists of:
- a) the amino acid sequence of SEQ ID NO: 148,
- b) the amino acid sequence of SEQ ID NO: 149,
- c) the amino acid sequence of SEQ ID NO: 150,
- d) the amino acid sequence of SEQ ID NO: 151,
- e) the amino acid sequence of SEQ ID NO: 152,
- f) the amino acid sequence of SEQ ID NO: 153,
- g) the amino acid sequence of SEQ ID NO: 154,
- h) the amino acid sequence of SEQ ID NO: 155,
- i) the amino acid sequence of SEQ ID NO: 156,
- j) the amino acid sequence of SEQ ID NO: 157,
- k) the amino acid sequence of SEQ ID NO: 158, or
- l) the amino acid sequence of SEQ ID NO: 159.

Embodiment 10. The polypeptide or composition for use according to any of embodiments 1 or 5, wherein the polypeptide comprises or consists of at least four ISVDs, wherein each of said ISVDs comprises three complementarity determining regions (CDR1 to CDR3, respectively), wherein the at least four ISVDs are optionally linked via one or more peptidic linkers, and wherein:
- a) a first ISVD comprises
  - i. a CDR1 that is the amino acid sequence of SEQ ID NO: 7 or an amino acid sequence with 2 or 1 amino acid difference(s) with SEQ ID NO: 7;
  - ii. a CDR2 that is the amino acid sequence of SEQ ID NO: 12 or an amino acid sequence with 2 or 1 amino acid difference(s) with SEQ ID NO: 12; and
  - iii. a CDR3 that is the amino acid sequence of SEQ ID NO: 17 or an amino acid sequence with 2 or 1 amino acid difference(s) with SEQ ID NO: 17;
- b) a second ISVD comprises
  - iv. a CDR1 that is the amino acid sequence of SEQ ID NO: 8 or an amino acid sequence with 2 or 1 amino acid difference(s) with SEQ ID NO: 8;
  - v. a CDR2 that is the amino acid sequence of SEQ ID NO: 13 or an amino acid sequence with 2 or 1 amino acid difference(s) with SEQ ID NO: 13; and
  - vi. a CDR3 that is the amino acid sequence of SEQ ID NO: 18 or an amino acid sequence with 2 or 1 amino acid difference(s) with SEQ ID NO: 18;
- c) a third ISVD comprises
  - vii. a CDR1 that is the amino acid sequence of SEQ ID NO: 9 or an amino acid sequence with 2 or 1 amino acid difference(s) with SEQ ID NO: 9;
  - viii. a CDR2 that is the amino acid sequence of SEQ ID NO: 14 or an amino acid sequence with 2 or 1 amino acid difference(s) with SEQ ID NO: 14; and
  - ix. a CDR3 that is the amino acid sequence of SEQ ID NO: 19 or an amino acid sequence with 2 or 1 amino acid difference(s) with SEQ ID NO: 19; and
- d) a fourth ISVD comprises
  - x. a CDR1 that is the amino acid sequence of SEQ ID NO: 11 or an amino acid sequence with 2 or 1 amino acid difference(s) with SEQ ID NO: 11;
  - xi. a CDR2 that is the amino acid sequence of SEQ ID NO: 16 or an amino acid sequence with 2 or 1 amino acid difference(s) with SEQ ID NO: 16; and
  - xii. a CDR3 that is the amino acid sequence of SEQ ID NO: 21 or an amino acid sequence with 2 or 1 amino acid difference(s) with SEQ ID NO: 21, wherein the order of the ISVDs indicates their relative position to each other considered from the N-terminus to the C-terminus of said polypeptide.

Embodiment 11. The composition for use according to any one of embodiments 1 to 10, which is a pharmaceutical composition which further comprises at least one pharmaceutically acceptable carrier, diluent or excipient and/or adjuvant, and optionally comprises one or more further pharmaceutically active polypeptides and/or compounds.

Embodiment 12. The polypeptide or composition for use according to embodiment 10 or 11, wherein:
- a) said first ISVD comprises a CDR1 that is the amino acid sequence of SEQ ID NO: 7, a CDR2 that is the amino acid sequence of SEQ ID NO: 12 and a CDR3 that is the amino acid sequence of SEQ ID NO: 17;
- b) said second ISVD comprises a CDR1 that is the amino acid sequence of SEQ ID NO: 8, a CDR2 that is the amino acid sequence of SEQ ID NO: 13 and a CDR3 that is the amino acid sequence of SEQ ID NO: 18;
- c) said third ISVD comprises a CDR1 that is the amino acid sequence of SEQ ID NO: 9, a CDR2 that is the amino acid sequence of SEQ ID NO: 14 and a CDR3 that is the amino acid sequence of SEQ ID NO: 19; and
- d) said fourth ISVD comprises a CDR1 that is the amino acid sequence of SEQ ID NO: 11, a CDR2 that is the amino acid sequence of SEQ ID NO: 16 and a CDR3 that is the amino acid sequence of SEQ ID NO: 21.

Embodiment 13. The polypeptide or composition for use according to any of embodiments 10 to 12, wherein:
- a) the amino acid sequence of said first ISVD comprises a sequence identity of more than 90% with SEQ ID NO: 2;
- b) the amino acid sequence of said second ISVD comprises a sequence identity of more than 90% with SEQ ID NO: 3;
- c) the amino acid sequence of said third ISVD comprises a sequence identity of more than 90% identity with SEQ ID NO: 4; and
- d) the amino acid sequence of said fourth ISVD comprises a sequence identity of more than 90% identity with SEQ ID NO: 6.

Embodiment 14. The polypeptide or composition for use according to any of embodiments 10 to 13, wherein:
- a) said first ISVD comprises the amino acid sequence of SEQ ID NO: 2;
- b) said second ISVD comprises the amino acid sequence of SEQ ID NO: 3;
- c) said third ISVD comprises the amino acid sequence of SEQ ID NO: 4; and
- d) said fourth ISVD comprises the amino acid sequence of SEQ ID NO: 6.

Embodiment 15. The polypeptide or composition for use according to any of embodiments 1 to 14, wherein said polypeptide further comprises one or more other groups, residues, moieties or binding units, optionally linked via one or more peptidic linkers, in which said one or more other groups, residues, moieties or binding units provide the polypeptide with increased half-life, compared to the corresponding polypeptide without said one or more other groups, residues, moieties or binding units.

Embodiment 16. The polypeptide or composition for use according to embodiment 15, in which said one or more other groups, residues, moieties or binding units that provide the polypeptide with increased half-life is chosen from the group consisting of a polyethylene glycol molecule, serum proteins or fragments thereof, binding units that can bind to serum proteins, an Fc portion, and small proteins or peptides that can bind to serum proteins.

Embodiment 17. The polypeptide or composition for use according to any one of embodiments 15 to 16, in which said one or more other binding units that provide the polypeptide with increased half-life is chosen from the group consisting of binding units that can bind to serum albumin (such as human serum albumin) or a serum immunoglobulin (such as IgG).

Embodiment 18. The polypeptide or composition for use according to embodiment 17, in which said binding unit that provides the polypeptide with increased half-life is an ISVD that can bind to human serum albumin.

Embodiment 19. The polypeptide or composition for use according to embodiment 18, wherein the ISVD binding to human serum albumin comprises
  i. a CDR1 that is the amino acid sequence of SEQ ID NO: 10 or an amino acid sequence with 2 or 1 amino acid difference(s) with SEQ ID NO: 10;
  ii. a CDR2 that is the amino acid sequence of SEQ ID NO: 15 or an amino acid sequence with 2 or 1 amino acid difference(s) with SEQ ID NO: 15; and
  iii. a CDR3 that is the amino acid sequence of SEQ ID NO: 20 or an amino acid sequence with 2 or 1 amino acid difference(s) with SEQ ID NO: 20.

Embodiment 20. The polypeptide or composition for use according to any of embodiments 18 to 19, wherein the ISVD binding to human serum albumin comprises a CDR1 that is the amino acid sequence of SEQ ID NO: 10, a CDR2 that is the amino acid sequence of SEQ ID NO: 15 and a CDR3 that is the amino acid sequence of SEQ ID NO: 20.

Embodiment 21. The polypeptide or composition for use according to any of embodiments 18 to 20, wherein the amino acid sequence of said ISVD binding to human serum albumin comprises a sequence identity of more than 90% with SEQ ID NO: 5.

Embodiment 22. The polypeptide or composition for use according to any of embodiments 18 to 21, wherein said ISVD binding to human serum albumin comprises the amino acid sequence of SEQ ID NO: 5.

Embodiment 23. The polypeptide or composition for use according to any of embodiments 10 to 22, wherein the amino acid sequence of the polypeptide comprises a sequence identity of more than 90% with SEQ ID NO: 1.

Embodiment 24. The polypeptide or composition for use according to any of embodiments 10 to 23, wherein the polypeptide comprises or consists of the amino acid sequence of SEQ ID NO: 1.

Embodiment 25. The polypeptide or composition for use according to any of embodiments 1 to 24, for use in the treatment of an inflammatory disease, such as a type 2 inflammatory disease.

Embodiment 26. The polypeptide or composition for use according to embodiment 25, wherein the type 2 inflammatory disease is selected from asthma and atopic dermatitis.

Embodiment 27. A polypeptide that comprises or consists of at least one immunoglobulin single variable domain (ISVD), wherein said ISVD comprises three complementarity determining regions (CDR1 to CDR3, respectively); and wherein the at least one ISVD comprises:
  a) a CDR1 that is the amino acid sequence of SEQ ID NO: 7 or an amino acid sequence with 2 or 1 amino acid difference(s) with SEQ ID NO: 7;
    a CDR2 that is the amino acid sequence of SEQ ID NO: 12 or an amino acid sequence with 2 or 1 amino acid difference(s) with SEQ ID NO: 12; and
    a CDR3 that is the amino acid sequence of SEQ ID NO: 17 or an amino acid sequence with 2 or 1 amino acid difference(s) with SEQ ID NO: 17,
  b) a CDR1 that is the amino acid sequence of SEQ ID NO: 8 or an amino acid sequence with 2 or 1 amino acid difference(s) with SEQ ID NO: 8;
    a CDR2 that is the amino acid sequence of SEQ ID NO: 13 or an amino acid sequence with 2 or 1 amino acid difference(s) with SEQ ID NO: 13; and
    a CDR3 that is the amino acid sequence of SEQ ID NO: 18 or an amino acid sequence with 2 or 1 amino acid difference(s) with SEQ ID NO: 18,
  c) a CDR1 that is the amino acid sequence of SEQ ID NO: 9 or an amino acid sequence with 2 or 1 amino acid difference(s) with SEQ ID NO: 9;
    a CDR2 that is the amino acid sequence of SEQ ID NO: 14 or an amino acid sequence with 2 or 1 amino acid difference(s) with SEQ ID NO: 14; and
    a CDR3 that is the amino acid sequence of SEQ ID NO: 19 or an amino acid sequence with 2 or 1 amino acid difference(s) with SEQ ID NO: 19, or
  d) a CDR1 that is the amino acid sequence of SEQ ID NO: 11 or an amino acid sequence with 2 or 1 amino acid difference(s) with SEQ ID NO: 11;
    a CDR2 that is the amino acid sequence of SEQ ID NO: 16 or an amino acid sequence with 2 or 1 amino acid difference(s) with SEQ ID NO: 16; and
    a CDR3 that is the amino acid sequence of SEQ ID NO: 21 or an amino acid sequence with 2 or 1 amino acid difference(s) with SEQ ID NO: 21.

Embodiment 28. The polypeptide according to embodiment 27, wherein the at least one ISVD comprises:
  a) a CDR1 that is the amino acid sequence of SEQ ID NO: 7, a CDR2 that is the amino acid sequence of SEQ ID NO: 12 and a CDR3 that is the amino acid sequence of SEQ ID NO: 17,
  b) a CDR1 that is the amino acid sequence of SEQ ID NO: 8, a CDR2 that is the amino acid sequence of SEQ ID NO: 13 and a CDR3 that is the amino acid sequence of SEQ ID NO: 18,
  c) a CDR1 that is the amino acid sequence of SEQ ID NO: 9, a CDR2 that is the amino acid sequence of SEQ ID NO: 14 and a CDR3 that is the amino acid sequence of SEQ ID NO: 19, or
  d) a CDR1 that is the amino acid sequence of SEQ ID NO: 11, a CDR2 that is the amino acid sequence of SEQ ID NO: 16 and a CDR3 that is the amino acid sequence of SEQ ID NO: 21.

Embodiment 29. The polypeptide according to any of embodiments 27 or 28, wherein the amino acid sequence of the at least one ISVD comprises:
  a) a sequence identity of more than 90% with SEQ ID NO: 2,
  b) a sequence identity of more than 90% with SEQ ID NO: 3,
  c) a sequence identity of more than 90% identity with SEQ ID NO: 4, or
  d) a sequence identity of more than 90% identity with SEQ ID NO: 6.

Embodiment 30. The polypeptide according to any of embodiments 27 to 29, wherein said at least one ISVD comprises:
  a) the amino acid sequence of SEQ ID NO: 2,
  b) the amino acid sequence of SEQ ID NO: 3,
  c) the amino acid sequence of SEQ ID NO: 4, or
  d) the amino acid sequence of SEQ ID NO: 6.

Embodiment 31. The polypeptide according to embodiment 1 or 27, wherein the polypeptide comprises or consists of at least two ISVDs, wherein each of said ISVDs comprises three complementarity determining regions (CDR1 to CDR3, respectively), wherein the at least two ISVDs are optionally linked via one or more peptidic linkers, and wherein:

a) a first and a second ISVD comprises
   i. a CDR1 that is the amino acid sequence of SEQ ID NO: 7 or an amino acid sequence with 2 or 1 amino acid difference(s) with SEQ ID NO: 7;
   ii. a CDR2 that is the amino acid sequence of SEQ ID NO: 12 or an amino acid sequence with 2 or 1 amino acid difference(s) with SEQ ID NO: 12; and
   iii. a CDR3 that is the amino acid sequence of SEQ ID NO: 17 or an amino acid sequence with 2 or 1 amino acid difference(s) with SEQ ID NO: 17,
b) a first and a second ISVD comprises
   i. a CDR1 that is the amino acid sequence of SEQ ID NO: 8 or an amino acid sequence with 2 or 1 amino acid difference(s) with SEQ ID NO: 8;
   ii. a CDR2 that is the amino acid sequence of SEQ ID NO: 13 or an amino acid sequence with 2 or 1 amino acid difference(s) with SEQ ID NO: 13; and
   iii. a CDR3 that is the amino acid sequence of SEQ ID NO: 18 or an amino acid sequence with 2 or 1 amino acid difference(s) with SEQ ID NO: 18,
c) a first ISVD comprises
   i. a CDR1 that is the amino acid sequence of SEQ ID NO: 7 or an amino acid sequence with 2 or 1 amino acid difference(s) with SEQ ID NO: 7;
   ii. a CDR2 that is the amino acid sequence of SEQ ID NO: 12 or an amino acid sequence with 2 or 1 amino acid difference(s) with SEQ ID NO: 12; and
   iii. a CDR3 that is the amino acid sequence of SEQ ID NO: 17 or an amino acid sequence with 2 or 1 amino acid difference(s) with SEQ ID NO: 17, and
a second ISVD comprises
   iv. a CDR1 that is the amino acid sequence of SEQ ID NO: 8 or an amino acid sequence with 2 or 1 amino acid difference(s) with SEQ ID NO: 8;
   v. a CDR2 that is the amino acid sequence of SEQ ID NO: 13 or an amino acid sequence with 2 or 1 amino acid difference(s) with SEQ ID NO: 13; and
   vi. a CDR3 that is the amino acid sequence of SEQ ID NO: 18 or an amino acid sequence with 2 or 1 amino acid difference(s) with SEQ ID NO: 18,
d) a first ISVD comprises
   i. a CDR1 that is the amino acid sequence of SEQ ID NO: 8 or an amino acid sequence with 2 or 1 amino acid difference(s) with SEQ ID NO: 8;
   ii. a CDR2 that is the amino acid sequence of SEQ ID NO: 13 or an amino acid sequence with 2 or 1 amino acid difference(s) with SEQ ID NO: 13; and
   iii. a CDR3 that is the amino acid sequence of SEQ ID NO: 18 or an amino acid sequence with 2 or 1 amino acid difference(s) with SEQ ID NO: 18, and
a second ISVD comprises
   iv. a CDR1 that is the amino acid sequence of SEQ ID NO: 7 or an amino acid sequence with 2 or 1 amino acid difference(s) with SEQ ID NO: 7;
   v. a CDR2 that is the amino acid sequence of SEQ ID NO: 12 or an amino acid sequence with 2 or 1 amino acid difference(s) with SEQ ID NO: 12; and
   vi. a CDR3 that is the amino acid sequence of SEQ ID NO: 17 or an amino acid sequence with 2 or 1 amino acid difference(s) with SEQ ID NO: 17,
e) a first ISVD comprises
   i. a CDR1 that is the amino acid sequence of SEQ ID NO: 11 or an amino acid sequence with 2 or 1 amino acid difference(s) with SEQ ID NO: 11;
   ii. a CDR2 that is the amino acid sequence of SEQ ID NO: 16 or an amino acid sequence with 2 or 1 amino acid difference(s) with SEQ ID NO: 16; and
   iii. a CDR3 that is the amino acid sequence of SEQ ID NO: 21 or an amino acid sequence with 2 or 1 amino acid difference(s) with SEQ ID NO: 21, and
a second ISVD comprises
   iv. a CDR1 that is the amino acid sequence of SEQ ID NO: 9 or an amino acid sequence with 2 or 1 amino acid difference(s) with SEQ ID NO: 9;
   v. a CDR2 that is the amino acid sequence of SEQ ID NO: 14 or an amino acid sequence with 2 or 1 amino acid difference(s) with SEQ ID NO: 14; and
   vi. a CDR3 that is the amino acid sequence of SEQ ID NO: 19 or an amino acid sequence with 2 or 1 amino acid difference(s) with SEQ ID NO: 19, or
f) a first ISVD comprises
   i. a CDR1 that is the amino acid sequence of SEQ ID NO: 9 or an amino acid sequence with 2 or 1 amino acid difference(s) with SEQ ID NO: 9;
   ii. a CDR2 that is the amino acid sequence of SEQ ID NO: 14 or an amino acid sequence with 2 or 1 amino acid difference(s) with SEQ ID NO: 14; and
   iii. a CDR3 that is the amino acid sequence of SEQ ID NO: 19 or an amino acid sequence with 2 or 1 amino acid difference(s) with SEQ ID NO: 19, and
a second ISVD comprises
   iv. a CDR1 that is the amino acid sequence of SEQ ID NO: 11 or an amino acid sequence with 2 or 1 amino acid difference(s) with SEQ ID NO: 11;
   v. a CDR2 that is the amino acid sequence of SEQ ID NO: 16 or an amino acid sequence with 2 or 1 amino acid difference(s) with SEQ ID NO: 16; and
   vi. a CDR3 that is the amino acid sequence of SEQ ID NO: 21 or an amino acid sequence with 2 or 1 amino acid difference(s) with SEQ ID NO: 21,
wherein the order of the ISVDs indicates their relative position to each other considered from the N-terminus to the C-terminus of said polypeptide.

Embodiment 32. The polypeptide according to embodiment 31, wherein:
a) the first and the second ISVD comprises a CDR1 that is the amino acid sequence of SEQ ID NO: 7, a CDR2 that is the amino acid sequence of SEQ ID NO: 12 and a CDR3 that is the amino acid sequence of SEQ ID NO: 17,
b) the first and the second ISVD comprises a CDR1 that is the amino acid sequence of SEQ ID NO: 8, a CDR2 that is the amino acid sequence of SEQ ID NO: 13 and a CDR3 that is the amino acid sequence of SEQ ID NO: 18,
c) the first ISVD comprises a CDR1 that is the amino acid sequence of SEQ ID NO: 7, a CDR2 that is the amino acid sequence of SEQ ID NO: 12 and a CDR3 that is the amino acid sequence of SEQ ID NO: 17, and the second ISVD comprises a CDR1 that is the amino acid sequence of SEQ ID NO: 8, a CDR2 that is the amino acid sequence of SEQ ID NO: 13 and a CDR3 that is the amino acid sequence of SEQ ID NO: 18,
d) the first ISVD comprises a CDR1 that is the amino acid sequence of SEQ ID NO: 8, a CDR2 that is the amino acid sequence of SEQ ID NO: 13 and a CDR3 that is the amino acid sequence of SEQ ID NO: 18, and the second ISVD comprises a CDR1 that is the amino acid sequence of SEQ ID NO: 7, a CDR2 that is the amino acid sequence of SEQ ID NO: 12 and a CDR3 that is the amino acid sequence of SEQ ID NO: 17,
e) the first ISVD comprises a CDR1 that is the amino acid sequence of SEQ ID NO: 11, a CDR2 that is the amino acid sequence of SEQ ID NO: 16 and a CDR3 that is the amino acid sequence of SEQ ID NO: 21, and the second ISVD comprises a CDR1 that is the amino acid sequence of SEQ ID NO: 9, a CDR2 that is the amino acid sequence of SEQ ID NO: 14 and a CDR3 that is the amino acid sequence of SEQ ID NO: 19, or
f) the first ISVD comprises a CDR1 that is the amino acid sequence of SEQ ID NO: 9, a CDR2 that is the amino acid sequence of SEQ ID NO: 14 and a CDR3 that is the amino acid sequence of SEQ ID NO: 19, and the second ISVD comprises a CDR1 that is the amino acid sequence of SEQ ID NO: 11, a CDR2 that is the amino acid sequence of SEQ ID NO: 16 and a CDR3 that is the amino acid sequence of SEQ ID NO: 21.

Embodiment 33. The polypeptide according to any of embodiments 31 or 32, wherein:
a) the amino acid sequence of the first and the second ISVD comprises a sequence identity of more than 90% with SEQ ID NO: 2,
b) the amino acid sequence of the first and the second ISVD comprises a sequence identity of more than 90% with SEQ ID NO: 3,
c) the amino acid sequence of the first ISVD comprises a sequence identity of more than 90% with SEQ ID NO: 2, and the second ISVD comprises a sequence identity of more than 90% identity with SEQ ID NO: 3,
d) the amino acid sequence of the first ISVD comprises a sequence identity of more than 90% with SEQ ID NO: 3, and the second ISVD comprises a sequence identity of more than 90% identity with SEQ ID NO: 2,
e) the amino acid sequence of the first ISVD comprises a sequence identity of more than 90% with SEQ ID NO: 6, and the second ISVD comprises a sequence identity of more than 90% identity with SEQ ID NO: 4,
f) the amino acid sequence of the first ISVD comprises a sequence identity of more than 90% with SEQ ID NO: 4, and the second ISVD comprises a sequence identity of more than 90% identity with SEQ ID NO: 6.

Embodiment 34. The polypeptide according to any of embodiments 31 to 33, wherein:
a) the first and the second ISVD comprises the amino acid sequence of SEQ ID NO: 2,
b) the first and the second ISVD comprises the amino acid sequence of SEQ ID NO: 3,
c) the first ISVD comprises the amino acid sequence of SEQ ID NO: 2, and the second ISVD comprises the amino acid sequence of SEQ ID NO: 3,
d) the first ISVD comprises the amino acid sequence of SEQ ID NO: 3, and the second ISVD comprises the amino acid sequence of SEQ ID NO: 2,
e) the first ISVD comprises the amino acid sequence of SEQ ID NO: 6, and the second ISVD comprises the amino acid sequence of SEQ ID NO: 4, or
f) the first ISVD comprises the amino acid sequence of SEQ ID NO: 4, and the second ISVD comprises the amino acid sequence of SEQ ID NO: 6.

Embodiment 35. The polypeptide according to any of embodiments 31 to 34, wherein the polypeptide comprises or consists of:
a) the amino acid sequence of SEQ ID NO: 148,
b) the amino acid sequence of SEQ ID NO: 149,
c) the amino acid sequence of SEQ ID NO: 150,
d) the amino acid sequence of SEQ ID NO: 151,
e) the amino acid sequence of SEQ ID NO: 152,
f) the amino acid sequence of SEQ ID NO: 153,
g) the amino acid sequence of SEQ ID NO: 154,
h) the amino acid sequence of SEQ ID NO: 155,
i) the amino acid sequence of SEQ ID NO: 156,
j) the amino acid sequence of SEQ ID NO: 157,
k) the amino acid sequence of SEQ ID NO: 158, or
l) the amino acid sequence of SEQ ID NO: 159.

Embodiment 36. The polypeptide according to any of embodiments 27 or 31, wherein the polypeptide comprises or consists of at least four ISVDs, wherein each of said ISVDs comprises three complementarity determining regions (CDR1 to CDR3, respectively), wherein the at least four ISVDs are optionally linked via one or more peptidic linkers, and wherein:
a) a first ISVD comprises
 i. a CDR1 that is the amino acid sequence of SEQ ID NO: 7 or an amino acid sequence with 2 or 1 amino acid difference(s) with SEQ ID NO: 7;
 ii. a CDR2 that is the amino acid sequence of SEQ ID NO: 12 or an amino acid sequence with 2 or 1 amino acid difference(s) with SEQ ID NO: 12; and
 iii. a CDR3 that is the amino acid sequence of SEQ ID NO: 17 or an amino acid sequence with 2 or 1 amino acid difference(s) with SEQ ID NO: 17;
b) a second ISVD comprises
 iv. a CDR1 that is the amino acid sequence of SEQ ID NO: 8 or an amino acid sequence with 2 or 1 amino acid difference(s) with SEQ ID NO: 8;
 v. a CDR2 that is the amino acid sequence of SEQ ID NO: 13 or an amino acid sequence with 2 or 1 amino acid difference(s) with SEQ ID NO: 13; and
 vi. a CDR3 that is the amino acid sequence of SEQ ID NO: 18 or an amino acid sequence with 2 or 1 amino acid difference(s) with SEQ ID NO: 18;
c) a third ISVD comprises
 vii. a CDR1 that is the amino acid sequence of SEQ ID NO: 9 or an amino acid sequence with 2 or 1 amino acid difference(s) with SEQ ID NO: 9;
 viii. a CDR2 that is the amino acid sequence of SEQ ID NO: 14 or an amino acid sequence with 2 or 1 amino acid difference(s) with SEQ ID NO: 14; and
 ix. a CDR3 that is the amino acid sequence of SEQ ID NO: 19 or an amino acid sequence with 2 or 1 amino acid difference(s) with SEQ ID NO: 19; and
d) a fourth ISVD comprises
 x. a CDR1 that is the amino acid sequence of SEQ ID NO: 11 or an amino acid sequence with 2 or 1 amino acid difference(s) with SEQ ID NO: 11;
 xi. a CDR2 that is the amino acid sequence of SEQ ID NO: 16 or an amino acid sequence with 2 or 1 amino acid difference(s) with SEQ ID NO: 16; and
 xii. a CDR3 that is the amino acid sequence of SEQ ID NO: 21 or an amino acid sequence with 2 or 1 amino acid difference(s) with SEQ ID NO: 21,
wherein the order of the ISVDs indicates their relative position to each other considered from the N-terminus to the C-terminus of said polypeptide.

Embodiment 37. The polypeptide according to embodiment 36, wherein:
a) said first ISVD comprises a CDR1 that is the amino acid sequence of SEQ ID NO: 7, a CDR2 that is the amino acid sequence of SEQ ID NO: 12 and a CDR3 that is the amino acid sequence of SEQ ID NO: 17;
b) said second ISVD comprises a CDR1 that is the amino acid sequence of SEQ ID NO: 8, a CDR2 that is the amino acid sequence of SEQ ID NO: 13 and a CDR3 that is the amino acid sequence of SEQ ID NO: 18;
c) said third ISVD comprises a CDR1 that is the amino acid sequence of SEQ ID NO: 9, a CDR2 that is the amino acid sequence of SEQ ID NO: 14 and a CDR3 that is the amino acid sequence of SEQ ID NO: 19; and d) said fourth ISVD comprises a CDR1 that is the amino acid sequence of SEQ ID NO: 11, a CDR2 that is the amino acid sequence of SEQ ID NO: 16 and a CDR3 that is the amino acid sequence of SEQ ID NO: 21.

Embodiment 38. The polypeptide according to any of embodiments 36 or 37, wherein:
a) the amino acid sequence of said first ISVD comprises a sequence identity of more than 90% with SEQ ID NO: 2;
b) the amino acid sequence of said second ISVD comprises a sequence identity of more than 90% with SEQ ID NO: 3;
c) the amino acid sequence of said third ISVD comprises a sequence identity of more than 90% identity with SEQ ID NO: 4; and
d) the amino acid sequence of said fourth ISVD comprises a sequence identity of more than 90% identity with SEQ ID NO: 6.

Embodiment 39. The polypeptide according to any of embodiments 36 to 38, wherein:
a) said first ISVD comprises the amino acid sequence of SEQ ID NO: 2;
b) said second ISVD comprises the amino acid sequence of SEQ ID NO: 3;
c) said third ISVD comprises the amino acid sequence of SEQ ID NO: 4; and
d) said fourth ISVD comprises the amino acid sequence of SEQ ID NO: 6.

Embodiment 40. The polypeptide according to any of embodiments 27 to 39, wherein said polypeptide further comprises one or more other groups, residues, moieties or binding units, optionally linked via one or more peptidic linkers, in which said one or more other groups, residues, moieties or binding units provide the polypeptide with increased half-life, compared to the corresponding polypeptide without said one or more other groups, residues, moieties or binding units.

Embodiment 41. The polypeptide according to embodiment 40, in which said one or more other groups, residues, moieties or binding units that provide the polypeptide with increased half-life is chosen from the group consisting of a polyethylene glycol molecule, serum proteins or fragments thereof, binding units that can bind to serum proteins, an Fc portion, and small proteins or peptides that can bind to serum proteins.

Embodiment 42. The polypeptide according to any one of embodiments 40 to 41, in which said one or more other binding units that provide the polypeptide with increased half-life is chosen from the group consisting of binding units that can bind to serum albumin (such as human serum albumin) or a serum immunoglobulin (such as IgG).

Embodiment 43. The polypeptide according to embodiment 42, in which said binding unit that provides the polypeptide with increased half-life is an ISVD that can bind to human serum albumin.

Embodiment 44. The polypeptide according to embodiment 43, wherein the ISVD binding to human serum albumin comprises
i. a CDR1 that is the amino acid sequence of SEQ ID NO: 10 or an amino acid sequence with 2 or 1 amino acid difference(s) with SEQ ID NO: 10;
ii. a CDR2 that is the amino acid sequence of SEQ ID NO: 15 or an amino acid sequence with 2 or 1 amino acid difference(s) with SEQ ID NO: 15; and
iii. a CDR3 that is the amino acid sequence of SEQ ID NO: 20 or an amino acid sequence with 2 or 1 amino acid difference(s) with SEQ ID NO: 20.

Embodiment 45. The polypeptide according to any of embodiments 43 to 44, wherein the ISVD binding to human serum albumin comprises a CDR1 that is the amino acid sequence of SEQ ID NO:10, a CDR2 that is the amino acid sequence of SEQ ID NO: 15 and a CDR3 that is the amino acid sequence of SEQ ID NO: 20.

Embodiment 46. The polypeptide according to any of embodiments 43 to 45, wherein the amino acid sequence of said ISVD binding to human serum albumin comprises a sequence identity of more than 90% with SEQ ID NO: 5.

Embodiment 47. The polypeptide according to any of embodiments 43 to 46, wherein said ISVD binding to human serum albumin comprises the amino acid sequence of SEQ ID NO: 5.

Embodiment 48. The polypeptide according to any of embodiments 36 to 47, wherein the amino acid sequence of the polypeptide comprises a sequence identity of more than 90% with SEQ ID NO: 1.

Embodiment 49. The polypeptide according to any of embodiments 36 to 48, wherein the polypeptide comprises or consists of the amino acid sequence of SEQ ID NO: 1.

Embodiment 50. A nucleic acid comprising a nucleotide sequence that encodes a polypeptide according to any of embodiments 27 to 49, or a polypeptide according to embodiments 36 to 49.

Embodiment 51. A host or host cell comprising a nucleic acid according to embodiment 50.

Embodiment 52. A method for producing a polypeptide according to any of embodiments 27 to 49, or a polypeptide according to embodiments 36 to 49, said method at least comprising the steps of:
a) expressing, in a suitable host cell or host organism or in another suitable expression system, a nucleic acid according to embodiment 50; optionally followed by:
b) isolating and/or purifying the polypeptide according to any of embodiments 27 to 49, or the polypeptide according to embodiments 36 to 49.

Embodiment 53. A composition comprising at least one polypeptide according to any of embodiments 27 to 49, or at least one polypeptide according to embodiments 36 to 49, or a nucleic acid according to embodiment 50.

Embodiment 54. The composition according to embodiment 53, which is a pharmaceutical composition which further comprises at least one pharmaceutically acceptable carrier, diluent or excipient and/or adjuvant, and optionally comprises one or more further pharmaceutically active polypeptides and/or compounds.

Embodiment 55. A method of treating an inflammatory disease, such as a type 2 inflammatory disease, wherein said method comprises administering, to a subject in need thereof, a pharmaceutically active amount of a polypeptide according to any of embodiments 27 to 49, or according to embodiments 36 to 49, or a composition according to any of embodiments 53 to 54.

Embodiment 56. The method according to embodiment 55, wherein the type 2 inflammatory disease is selected from asthma and atopic dermatitis.

Embodiment 57. Use of a polypeptide according to any of embodiments 27 to 49, or according to embodiments 36 to 49, or a composition according to any of embodiments 53 to 54, in the preparation of a pharmaceutical composition for treating an inflammatory disease, such as a type 2 inflammatory disease.

Embodiment 58. Use of the polypeptide or a composition according to embodiments 57, wherein the type 2 inflammatory disease is selected from asthma and atopic dermatitis.

DETAILED DESCRIPTION OF THE PRESENT TECHNOLOGY

Figure 1:
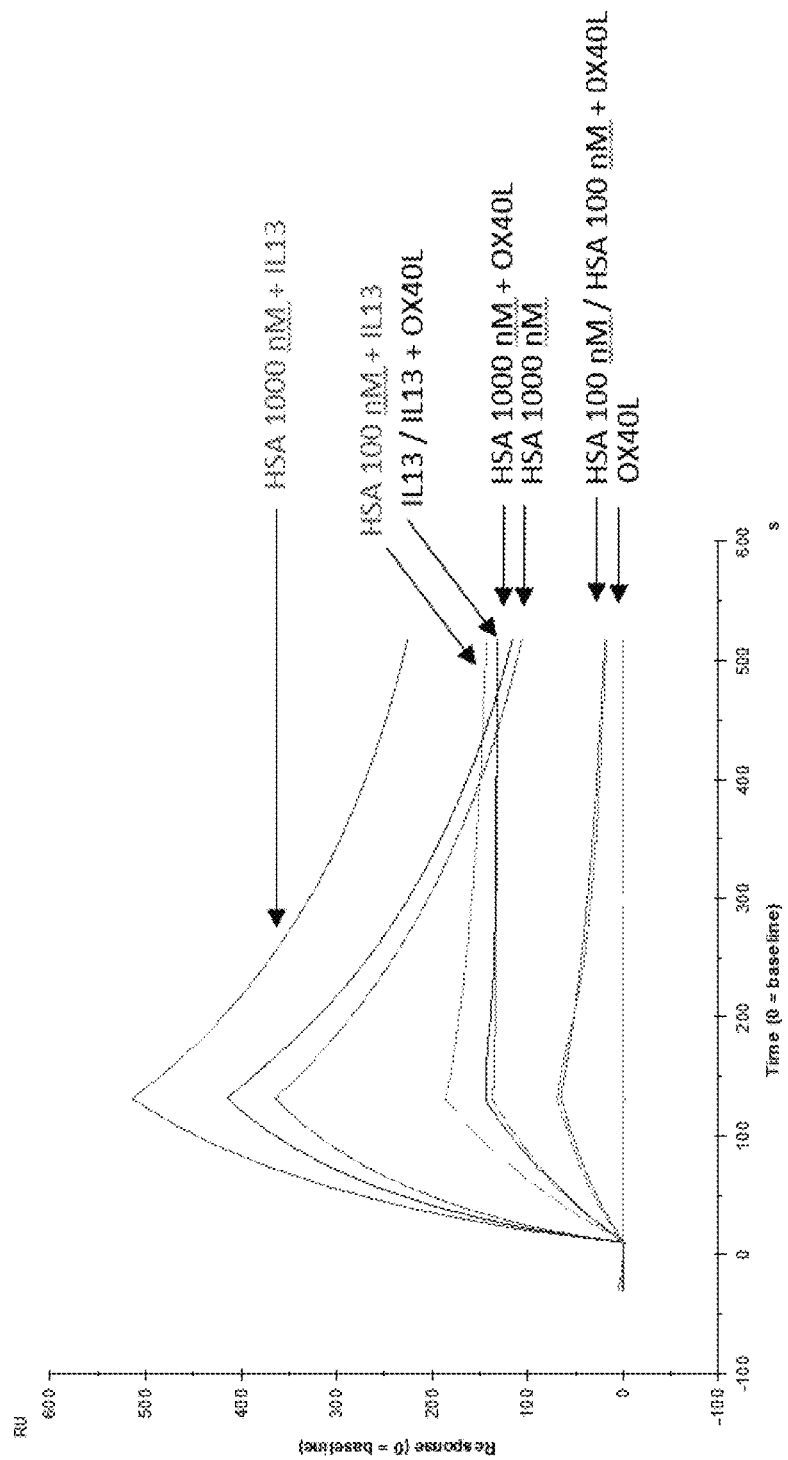
FIG. 1: Sensorgram showing simultaneous binding of IL13 and HSA to F027400161 captured via TSLP.

The present technology aims at providing a novel type of drug for treating inflammatory diseases, such as atopic dermatitis and asthma.

In some embodiments, the present technology relates to a polypeptide targeting IL-13 and TSLP at the same time leading to an increased efficiency of modulating a type 2 inflammatory response as compared to monospecific anti-IL-13 or anti-TSLP polypeptides in vitro and/or in vivo. In some embodiments, the polypeptides are efficiently produced (e.g. in microbial hosts). Furthermore, in some embodiments, such polypeptides could be shown to have limited reactivity to pre-existing antibodies in the subject to be treated (i.e. antibodies present in the subject before the first treatment with the antibody construct). In other embodiments such polypeptides exhibit a half-life in the subject to be treated that is long enough such that consecutive treatments can be conveniently spaced apart.

5.1 The Polypeptides of the Present Technology

Monospecific-Monovalent Polypeptides

In one embodiment, the polypeptide of the present technology is monospecific and monovalent.

The term "monospecific" refers to the binding to one (specific) type of target molecule(s). A monospecific polypeptide of the present technology thus specifically binds to IL-13. Another monospecific polypeptide of the present technology specifically binds to TSLP.

The term "monovalent" indicates the presence of only one binding units/building block that (specifically) targets a molecule, such as ISVDs.

Accordingly, in one aspect, the present technology provides a monospecific-monovalent polypeptide comprising or consisting of one ISVD that specifically binds to IL-13, which comprises three complementarity determining regions (CDR1 to CDR3, respectively). The ISVD can be selected from an ISVD comprising:
  a) a CDR1 that is the amino acid sequence of SEQ ID NO: 7 or an amino acid sequence with 2 or 1 amino acid difference(s) with SEQ ID NO: 7, a CDR2 that is the amino acid sequence of SEQ ID NO: 12 or an amino acid sequence with 2 or 1 amino acid difference(s) with SEQ ID NO: 12, and a CDR3 that is the amino acid sequence of SEQ ID NO: 17 or an amino acid sequence with 2 or 1 amino acid difference(s) with SEQ ID NO: 17; or
  b) a CDR1 that is the amino acid sequence of SEQ ID NO: 8 or an amino acid sequence with 2 or 1 amino acid difference(s) with SEQ ID NO: 8, a CDR2 that is the amino acid sequence of SEQ ID NO: 13 or an amino acid sequence with 2 or 1 amino acid difference(s) with SEQ ID NO: 13, and a CDR3 that is the amino acid sequence of SEQ ID NO: 18 or an amino acid sequence with 2 or 1 amino acid difference(s) with SEQ ID NO: 18.

In one embodiment of this aspect of the present technology, the ISVD specifically binds to human IL-13.

In a further embodiment, the ISVD specifically binding to IL-13 is selected from an ISVD comprising:
  a) a CDR1 that is the amino acid sequence of SEQ ID NO: 7, a CDR2 that is the amino acid sequence of SEQ ID NO: 12 and a CDR3 that is the amino acid sequence of SEQ ID NO: 17; or
  b) a CDR1 that is the amino acid sequence of SEQ ID NO: 8, a CDR2 that is the amino acid sequence of SEQ ID NO: 13 and a CDR3 that is the amino acid sequence of SEQ ID NO: 18.

In a further embodiment of this aspect of the present technology, the ISVD specifically binding to IL-13 is selected from an ISVD comprising:
  a) a sequence identity of more than 90% with SEQ ID NO: 2; or
  b) a sequence identity of more than 90% with SEQ ID NO: 3.

In one embodiment, the ISVD specifically binding to IL-13 is selected from an ISVD comprising the amino acid sequence of SEQ ID NO: 2; or the amino acid sequence of SEQ ID NO: 3.

In another aspect the present technology provides a monospecific-monovalent polypeptide comprising or consisting of one ISVD that specifically binds to TSLP, which comprises three complementarity determining regions (CDR1 to CDR3, respectively). The ISVD can be selected from an ISVD comprising:
  a) a CDR1 that is the amino acid sequence of SEQ ID NO: 9 or an amino acid sequence with 2 or 1 amino acid difference(s) with SEQ ID NO: 9, a CDR2 that is the amino acid sequence of SEQ ID NO: 14 or an amino acid sequence with 2 or 1 amino acid difference(s) with SEQ ID NO: 14, and a CDR3 that is the amino acid sequence of SEQ ID NO: 19 or an amino acid sequence with 2 or 1 amino acid difference(s) with SEQ ID NO: 19; or
  b) a CDR1 that is the amino acid sequence of SEQ ID NO: 11 or an amino acid sequence with 2 or 1 amino acid difference(s) with SEQ ID NO: 11, a CDR2 that is the amino acid sequence of SEQ ID NO: 16 or an amino acid sequence with 2 or 1 amino acid difference(s) with SEQ ID NO: 16, and a CDR3 that is the amino acid sequence of SEQ ID NO: 21 or an amino acid sequence with 2 or 1 amino acid difference(s) with SEQ ID NO: 21.

In one embodiment of this aspect of the present technology, the ISVD specifically binds to human TSLP.

In a further embodiment, the ISVD specifically binding to TSLP is selected from an ISVD comprising:
  a) a CDR1 that is the amino acid sequence of SEQ ID NO: 9, a CDR2 that is the amino acid sequence of SEQ ID NO: 14 and a CDR3 that is the amino acid sequence of SEQ ID NO: 19; or
  b) a CDR1 that is the amino acid sequence of SEQ ID NO: 11, a CDR2 that is the amino acid sequence of SEQ ID NO: 16 and a CDR3 that is the amino acid sequence of SEQ ID NO: 21.

In a further embodiment of this aspect of the present technology, the ISVD specifically binding to TSLP is selected from an ISVD comprising:
  a) a sequence identity of more than 90% with SEQ ID NO: 4; or
  b) a sequence identity of more than 90% with SEQ ID NO: 6.

In one embodiment, the ISVD specifically binding to TSLP is selected from an ISVD comprising the amino acid sequence of SEQ ID NO: 4; or the amino acid sequence of SEQ ID NO: 6.

Monospecific-Multivalent Polypeptides

In another aspect, the polypeptide of the present technology is monospecific and at least bivalent, but can also be e.g., trivalent, tetravalent, pentavalent, hexavalent, etc.

The terms "bivalent", "trivalent", "tetravalent", "pentavalent", or "hexavalent" all fall under the term "multivalent" and indicate the presence of two, three, four, five or six binding units/building blocks, respectively, such as ISVDs.

Accordingly, in one aspect the present technology provides a monospecific-bivalent polypeptide comprising or consisting of two ISVDs that specifically bind to IL-13, wherein each of the two ISVDs comprises three complementarity determining regions (CDR1 to CDR3, respectively), wherein the two ISVDs are optionally linked via one or more peptidic linkers, and wherein:
  a) a first and a second ISVD comprises a CDR1 that is the amino acid sequence of SEQ ID NO: 7 or an amino acid sequence with 2 or 1 amino acid difference(s) with SEQ ID NO: 7, a CDR2 that is the amino acid sequence of SEQ ID NO: 12 or an amino acid sequence with 2 or 1 amino acid difference(s) with SEQ ID NO: 12, and a CDR3 that is the amino acid sequence of SEQ ID NO: 17 or an amino acid sequence with 2 or 1 amino acid difference(s) with SEQ ID NO: 17;
  b) a first and a second ISVD comprises a CDR1 that is the amino acid sequence of SEQ ID NO: 8 or an amino acid sequence with 2 or 1 amino acid difference(s) with SEQ ID NO: 8, a CDR2 that is the amino acid sequence of SEQ ID NO: 13 or an amino acid sequence with 2 or 1 amino acid difference(s) with SEQ ID NO: 13, and a CDR3 that is the amino acid sequence of SEQ ID NO:

18 or an amino acid sequence with 2 or 1 amino acid difference(s) with SEQ ID NO: 18;
c) a first ISVD comprises a CDR1 that is the amino acid sequence of SEQ ID NO: 7 or an amino acid sequence with 2 or 1 amino acid difference(s) with SEQ ID NO: 7, a CDR2 that is the amino acid sequence of SEQ ID NO: 12 or an amino acid sequence with 2 or 1 amino acid difference(s) with SEQ ID NO: 12, and a CDR3 that is the amino acid sequence of SEQ ID NO: 17 or an amino acid sequence with 2 or 1 amino acid difference(s) with SEQ ID NO: 17, and
  a second ISVD comprises a CDR1 that is the amino acid sequence of SEQ ID NO: 8 or an amino acid sequence with 2 or 1 amino acid difference(s) with SEQ ID NO: 8, a CDR2 that is the amino acid sequence of SEQ ID NO: 13 or an amino acid sequence with 2 or 1 amino acid difference(s) with SEQ ID NO: 13, and a CDR3 that is the amino acid sequence of SEQ ID NO: 18 or an amino acid sequence with 2 or 1 amino acid difference(s) with SEQ ID NO: 18; or
d) a first ISVD comprises a CDR1 that is the amino acid sequence of SEQ ID NO: 8 or an amino acid sequence with 2 or 1 amino acid difference(s) with SEQ ID NO: 8, a CDR2 that is the amino acid sequence of SEQ ID NO: 13 or an amino acid sequence with 2 or 1 amino acid difference(s) with SEQ ID NO: 13, and a CDR3 that is the amino acid sequence of SEQ ID NO: 18 or an amino acid sequence with 2 or 1 amino acid difference(s) with SEQ ID NO: 18, and
  a second ISVD comprises a CDR1 that is the amino acid sequence of SEQ ID NO: 7 or an amino acid sequence with 2 or 1 amino acid difference(s) with SEQ ID NO: 7, a CDR2 that is the amino acid sequence of SEQ ID NO: 12 or an amino acid sequence with 2 or 1 amino acid difference(s) with SEQ ID NO: 12, and a CDR3 that is the amino acid sequence of SEQ ID NO: 17 or an amino acid sequence with 2 or 1 amino acid difference(s) with SEQ ID NO: 17.

In one embodiment of this aspect of the present technology, the ISVDs are linked via one or more peptidic linkers. In one embodiment, the two ISVDs specifically bind human IL13.

In a further embodiment, the monospecific-bivalent polypeptide comprises or consists of two ISVDs that specifically bind to IL-13, wherein:
a) the first and the second ISVD comprises a CDR1 that is the amino acid sequence of SEQ ID NO: 7, a CDR2 that is the amino acid sequence of SEQ ID NO: 12 and a CDR3 that is the amino acid sequence of SEQ ID NO: 17;
b) the first and the second ISVD comprises a CDR1 that is the amino acid sequence of SEQ ID NO: 8, a CDR2 that is the amino acid sequence of SEQ ID NO: 13 and a CDR3 that is the amino acid sequence of SEQ ID NO: 18;
c) the first ISVD comprises a CDR1 that is the amino acid sequence of SEQ ID NO: 7, a CDR2 that is the amino acid sequence of SEQ ID NO: 12 and a CDR3 that is the amino acid sequence of SEQ ID NO: 17, and the second ISVD comprises a CDR1 that is the amino acid sequence of SEQ ID NO: 8, a CDR2 that is the amino acid sequence of SEQ ID NO: 13 and a CDR3 that is the amino acid sequence of SEQ ID NO: 18; or
d) the first ISVD comprises a CDR1 that is the amino acid sequence of SEQ ID NO: 8, a CDR2 that is the amino acid sequence of SEQ ID NO: 13 and a CDR3 that is the amino acid sequence of SEQ ID NO: 18, and the second ISVD comprises a CDR1 that is the amino acid sequence of SEQ ID NO: 7, a CDR2 that is the amino acid sequence of SEQ ID NO: 12 and a CDR3 that is the amino acid sequence of SEQ ID NO: 17.

In a further embodiment of this aspect of the present technology, the monospecific-bivalent polypeptide comprises or consists of two ISVDs that specifically bind to IL-13, wherein:
a) the amino acid sequence of the first and the second ISVD comprises a sequence identity of more than 90% with SEQ ID NO: 2;
b) the amino acid sequence of the first and the second ISVD comprises a sequence identity of more than 90% with SEQ ID NO: 3;
c) the amino acid sequence of the first ISVD comprises a sequence identity of more than 90% with SEQ ID NO: 2 and the second ISVD comprises a sequence identity of more than 90% identity with SEQ ID NO: 3; or
d) the amino acid sequence of the first ISVD comprises a sequence identity of more than 90% with SEQ ID NO: 3 and the second ISVD comprises a sequence identity of more than 90% identity with SEQ ID NO: 2.

In one embodiment, the monospecific-bivalent polypeptide comprises or consists of two ISVDs that specifically bind to IL-13, wherein:
a) the first and the second ISVD comprise the amino acid sequence of SEQ ID NO: 2;
b) the first and the second ISVD comprise the amino acid sequence of SEQ ID NO: 3:
c) the first ISVD comprises the amino acid sequence of SEQ ID NO: 2 and the second ISVD comprises the amino acid sequence of SEQ ID NO: 3; or
d) the first ISVD comprises the amino acid sequence of SEQ ID NO: 3 and the second ISVD comprises the amino acid sequence of SEQ ID NO: 2.

In another aspect the present technology provides a monospecific-bivalent polypeptide comprising or consisting of two ISVDs that specifically bind to TSLP, wherein each of the two ISVDs comprises three complementarity determining regions (CDR1 to CDR3, respectively), wherein the two ISVDs are optionally linked via one or more peptidic linkers, and wherein:
a) a first ISVD comprises a CDR1 that is the amino acid sequence of SEQ ID NO: 11 or an amino acid sequence with 2 or 1 amino acid difference(s) with SEQ ID NO: 11, a CDR2 that is the amino acid sequence of SEQ ID NO: 16 or an amino acid sequence with 2 or 1 amino acid difference(s) with SEQ ID NO: 16, and a CDR3 that is the amino acid sequence of SEQ ID NO: 21 or an amino acid sequence with 2 or 1 amino acid difference(s) with SEQ ID NO: 21, and
  a second ISVD comprises a CDR1 that is the amino acid sequence of SEQ ID NO: 9 or an amino acid sequence with 2 or 1 amino acid difference(s) with SEQ ID NO: 9, a CDR2 that is the amino acid sequence of SEQ ID NO: 14 or an amino acid sequence with 2 or 1 amino acid difference(s) with SEQ ID NO: 14, and a CDR3 that is the amino acid sequence of SEQ ID NO: 19 or an amino acid sequence with 2 or 1 amino acid difference(s) with SEQ ID NO: 19, or
b) a first ISVD comprises a CDR1 that is the amino acid sequence of SEQ ID NO: 9 or an amino acid sequence with 2 or 1 amino acid difference(s) with SEQ ID NO: 9, a CDR2 that is the amino acid sequence of SEQ ID NO: 14 or an amino acid sequence with 2 or 1 amino acid difference(s) with SEQ ID NO: 14, and a CDR3 that is the amino acid sequence of SEQ ID NO: 19 or an amino acid sequence with 2 or 1 amino acid difference(s) with SEQ ID NO: 19, and a second ISVD comprises a CDR1 that is the amino acid sequence of SEQ ID NO: 11 or an amino acid sequence with 2 or 1 amino acid difference(s) with SEQ ID NO: 11, a CDR2 that is the amino acid sequence of SEQ ID NO: 16 or an amino acid sequence with 2 or 1 amino acid difference(s) with SEQ ID NO: 16, and a CDR3 that is the amino acid sequence of SEQ ID NO: 21 or an amino acid sequence with 2 or 1 amino acid difference(s) with SEQ ID NO: 21.

In one embodiment of this aspect of the present technology, the ISVDs are linked via one or more peptidic linkers. In one embodiment, the two ISVDs specifically bind human TSLP.

In a further embodiment, the monospecific-bivalent polypeptide comprises or consists of two ISVDs that specifically bind to TSLP, wherein:
a) the first ISVD comprises a CDR1 that is the amino acid sequence of SEQ ID NO: 11, a CDR2 that is the amino acid sequence of SEQ ID NO: 16 and a CDR3 that is the amino acid sequence of SEQ ID NO: 21, and the second ISVD comprises a CDR1 that is the amino acid sequence of SEQ ID NO: 9, a CDR2 that is the amino acid sequence of SEQ ID NO: 14 and a CDR3 that is the amino acid sequence of SEQ ID NO: 19, or
b) the first ISVD comprises a CDR1 that is the amino acid sequence of SEQ ID NO: 9, a CDR2 that is the amino acid sequence of SEQ ID NO: 14 and a CDR3 that is the amino acid sequence of SEQ ID NO: 19, and the second ISVD comprises a CDR1 that is the amino acid sequence of SEQ ID NO:11, a CDR2 that is the amino acid sequence of SEQ ID NO: 16 and a CDR3 that is the amino acid sequence of SEQ ID NO: 21.

In a further embodiment of this aspect of the present technology, the monospecific-bivalent polypeptide comprises or consists of two ISVDs that specifically bind to TSLP, wherein:
a) the amino acid sequence of the first ISVD comprises a sequence identity of more than 90% with SEQ ID NO: 6 and the second ISVD comprises a sequence identity of more than 90% identity with SEQ ID NO: 4, or
b) the amino acid sequence of the first ISVD comprises a sequence identity of more than 90% with SEQ ID NO: 4 and the second ISVD comprises a sequence identity of more than 90% identity with SEQ ID NO: 6.

In one embodiment, the monospecific-bivalent polypeptide comprises or consists of two ISVDs that specifically bind to TSLP, wherein:
a) the first ISVD comprises the amino acid sequence of SEQ ID NO: 6 and the second ISVD comprises the amino acid sequence of SEQ ID NO: 4; or
b) the first ISVD comprises the amino acid sequence of SEQ ID NO: 4 and the second ISVD comprises the amino acid sequence of SEQ ID NO: 6.

The terms "first ISVD" and "second ISVD" in this regard only indicate the relative position of the specifically recited ISVDs binding to IL-13/TSLP to each other, wherein the numbering is started from the N-terminus of the polypeptide of the present technology. The "first ISVD" is thus closer to the N-terminus than the "second ISVD". Accordingly, the "second ISVD" is thus closer to the C-terminus than the "first ISVD". Since the numbering is thus not absolute and only indicates the relative position of the two ISVDs it does not exclude the possibility that additional binding units/building blocks such as ISVDs binding to IL-13 and TSLP, respectively, can be present in the polypeptide. Moreover, it does not exclude the possibility that other binding units/building blocks such as ISVDs can be placed in between. For instance, as described further below (see in particular, section "multispecific-multivalent polypeptides" and 5.4 "(In vivo) half-life extension"), the polypeptide can further comprise another ISVD binding to human serum albumin that can even be located between the "first ISVD" and "second ISVD" (such a construct is then referred to as multispecific as described in the subsequent section).

In one embodiment, the (at least two) ISVDs of the monospecific-multivalent polypeptides, in particular of the above described monospecific-bivalent polypeptides, are linked via peptidic linkers. The use of peptidic linkers to connect two or more (poly)peptides is well known in the art. Exemplary peptidic linkers that can be used with the monospecific-multivalent polypeptides, in particular with the above described monospecific-bivalent polypeptides are shown in Table A-5. One often used class of peptidic linkers is known as the "Gly-Ser" or "GS" linkers. These are linkers that essentially consist of glycine (G) and serine (S) residues, and usually comprise one or more repeats of a peptide motif such as the GGGGS (SEQ ID NO: 73) motif (for example, comprising the formula (Gly-Gly-Gly-Gly-Ser)$_n$ in which n may be 1, 2, 3, 4, 5, 6, 7 or more). Some often used examples of such GS linkers are 9GS linkers (GGGGSGGGS, SEQ ID NO: 76) 15GS linkers (n=3) and 35GS linkers (n=7). Reference is for example made to Chen et al., Adv. Drug Deliv. Rev. 2013 Oct. 15; 65(10): 1357-1369; and Klein et al., Protein Eng. Des. Sel. (2014) 27 (10): 325-330. In one embodiment of the present technology, the ISVDs of the monospecific-multivalent polypeptides, in particular the monospecific-bivalent polypeptides of the present technology are linked via a linker set forth in Table A-5. In one embodiment, the (at least) two ISVDs are linked via a 35GS linker(s).

Accordingly, in one embodiment, the monospecific-bivalent polypeptide comprises or consists of:
a) the amino acid sequence of SEQ ID NO: 148,
b) the amino acid sequence of SEQ ID NO: 149,
c) the amino acid sequence of SEQ ID NO: 150,
d) the amino acid sequence of SEQ ID NO: 151,
e) the amino acid sequence of SEQ ID NO: 152,
f) the amino acid sequence of SEQ ID NO: 153,
g) the amino acid sequence of SEQ ID NO: 154,
h) the amino acid sequence of SEQ ID NO: 155,
i) the amino acid sequence of SEQ ID NO: 156,
j) the amino acid sequence of SEQ ID NO: 157,
k) the amino acid sequence of SEQ ID NO: 158, or
l) the amino acid sequence of SEQ ID NO: 159.

Multispecific-Multivalent Polypeptides

In a further aspect, the polypeptide of the present technology is at least bispecific, but can also be e.g., trispecific, tetraspecific, pentaspecific, etc. Moreover, the polypeptide is at least bivalent, but can also be e.g., trivalent, tetravalent, pentavalent, hexavalent, etc.

The terms "bispecific", "trispecific", "tetraspecific", "pentaspecific", etc., all fall under the term "multispecific" and refer to binding to two, three, four, five, etc., different target molecules, respectively.

The terms "bivalent", "trivalent", "tetravalent", "pentavalent", "hexavalent", etc. all fall under the term "multivalent" and indicate the presence of two, three, four, five, six, etc., binding units/building blocks, respectively, such as ISVDs.

For example, the polypeptide may be bispecific-tetravalent, such as a polypeptide comprising or consisting of at least four ISVDs, wherein at least two ISVD specifically bind to IL-13 and at least two ISVDs specifically bind to TSLP. In one embodiment, IL-13 and TSLP are human IL-13 and human TSLP. In another example, the polypeptide may be trispecific-pentavalent, such as a polypeptide comprising or consisting of five ISVDs, wherein two ISVDs specifically bind to human IL-13, two ISVDs specifically bind to human TSLP and one ISVD binds to human serum albumin. Such a polypeptide may at the same time be biparatopic, for example if two ISVDs bind two different epitopes on human IL-13 or human TSLP. The term "biparatopic" refers to binding to two different parts (e.g., epitopes) of the same target molecule. In one embodiment, the trispecific-pentavalent polypeptide of the present technology is e.g., ISVD construct F027400161, comprising two ISVDs specifically binding to human IL-13, two ISVDs specifically binding to human TSLP, one ISVD binding to human serum albumin, and which is biparatopic for both binding to IL-13 and TSLP.

In one embodiment, the multispecific-multivalent polypeptide comprises or consists of at least four ISVDs, wherein each of said ISVDs comprises three complementarity determining regions (CDR1 to CDR3, respectively), wherein the at least four ISVDs are optionally linked via one or more peptidic linkers, and wherein:
  a) a first ISVD that specifically binds IL-13 and comprises a CDR1 that is the amino acid sequence of SEQ ID NO: 7 or an amino acid sequence with 2 or 1 amino acid difference(s) with SEQ ID NO: 7, a CDR2 that is the amino acid sequence of SEQ ID NO: 12 or an amino acid sequence with 2 or 1 amino acid difference(s) with SEQ ID NO: 12, and a CDR3 that is the amino acid sequence of SEQ ID NO: 17 or an amino acid sequence with 2 or 1 amino acid difference(s) with SEQ ID NO: 17;
  b) a second ISVD that specifically binds IL-13 and comprises a CDR1 that is the amino acid sequence of SEQ ID NO: 8 or an amino acid sequence with 2 or 1 amino acid difference(s) with SEQ ID NO: 8, a CDR2 that is the amino acid sequence of SEQ ID NO: 13 or an amino acid sequence with 2 or 1 amino acid difference(s) with SEQ ID NO: 13, and a CDR3 that is the amino acid sequence of SEQ ID NO: 18 or an amino acid sequence with 2 or 1 amino acid difference(s) with SEQ ID NO: 18;
  c) a third ISVD that specifically binds TSLP and comprises a CDR1 that is the amino acid sequence of SEQ ID NO: 9 or an amino acid sequence with 2 or 1 amino acid difference(s) with SEQ ID NO: 9, a CDR2 that is the amino acid sequence of SEQ ID NO: 14 or an amino acid sequence with 2 or 1 amino acid difference(s) with SEQ ID NO: 14, and a CDR3 that is the amino acid sequence of SEQ ID NO: 19 or an amino acid sequence with 2 or 1 amino acid difference(s) with SEQ ID NO: 19, and
  d) a fourth ISVD that specifically binds TSLP and comprises a CDR1 that is the amino acid sequence of SEQ ID NO: 11 or an amino acid sequence with 2 or 1 amino acid difference(s) with SEQ ID NO: 11, a CDR2 that is the amino acid sequence of SEQ ID NO: 16 or an amino acid sequence with 2 or 1 amino acid difference(s) with SEQ ID NO: 16, and a CDR3 that is the amino acid sequence of SEQ ID NO: 21 or an amino acid sequence with 2 or 1 amino acid difference(s) with SEQ ID NO: 21.

In one embodiment, the IL-13 and TSLP bound by said polypeptide is human IL-13 and human TSLP, respectively.

In a further embodiment of the multispecific-multivalent polypeptide:
  a) said first ISVD comprises a CDR1 that is the amino acid sequence of SEQ ID NO: 7, a CDR2 that is the amino acid sequence of SEQ ID NO: 12 and a CDR3 that is the amino acid sequence of SEQ ID NO: 17;
  b) said second ISVD comprises a CDR1 that is the amino acid sequence of SEQ ID NO: 8, a CDR2 that is the amino acid sequence of SEQ ID NO: 13 and a CDR3 that is the amino acid sequence of SEQ ID NO: 18;
  c) said third ISVD comprises a CDR1 that is the amino acid sequence of SEQ ID NO: 9, a CDR2 that is the amino acid sequence of SEQ ID NO: 14 and a CDR3 that is the amino acid sequence of SEQ ID NO: 19; and
  d) said fourth ISVD comprises a CDR1 that is the amino acid sequence of SEQ ID NO: 11, a CDR2 that is the amino acid sequence of SEQ ID NO: 16 and a CDR3 that is the amino acid sequence of SEQ ID NO: 21.

In a further aspect of the multispecific-multivalent polypeptide:
  a) the amino acid sequence of said first ISVD comprises a sequence identity of more than 90% with SEQ ID NO: 2;
  b) the amino acid sequence of said second ISVD comprises a sequence identity of more than 90% with SEQ ID NO: 3;
  c) the amino acid sequence of said third ISVD comprises a sequence identity of more than 90% identity with SEQ ID NO: 4; and
  d) the amino acid sequence of said fourth ISVD comprises a sequence identity of more than 90% identity with SEQ ID NO: 6.

In one embodiment of the multispecific-multivalent polypeptide:
  a) the first ISVD comprises the amino acid sequence of SEQ ID NO: 2;
  b) the second ISVD comprises the amino acid sequence of SEQ ID NO: 3;
  c) the third ISVD comprises the amino acid sequence of SEQ ID NO: 4; and
  d) the fourth ISVD comprises the amino acid sequence of SEQ ID NO: 6.

The terms "first ISVD", "second ISVD", "third ISVD", etc., in this regard only indicate the relative position of the ISVDs to each other, wherein the numbering is started from the N-terminus of the polypeptide of the present technology. The "first ISVD" is thus closer to the N-terminus than the "second ISVD", whereas the "second ISVD" is closer to the N-terminus than the "third ISVD". Accordingly, the ISVD arrangement is inverse when considered from the C-terminus. Since the numbering is not absolute and only indicates the relative position of the at least four ISVDs it is not excluded that other binding units/building blocks such as additional ISVDs binding to IL-13 or TSLP, or ISVDs binding to another target may be present in the polypeptide. Moreover, it does not exclude the possibility that other binding units/building blocks such as ISVDs can be placed in between. For instance, as described further below (see in particular, section 5.4 "(In vivo) half-life extension" below), the polypeptide can further comprise another ISVD binding to human serum albumin that can even be located between e.g. the "third ISVD" and "fourth ISVD".

In another aspect the present technology provides a bispecific-bivalent polypeptide comprising an ISVD that specifically binds to IL-13 or TSLP as described in detail for the monospecific-monovalent polypeptides above (section 5.1; "Monospecific-monovalent polypeptides") and an ISVD binding to human serum albumin as described in detail below (section 5.4; "(In vivo) half-life extension").

In another aspect the present technology provides a bispecific-trivalent polypeptide comprising the monospecific-bivalent polypeptides above (section 5.1; "monospecific-bivalent polypeptides") and an ISVD binding to human serum albumin as described in detail below (section 5.4; "(In vivo) half-life extension").

The components, such as the ISVDs, of said multispecific-multivalent polypeptide may be linked to each other by one or more suitable linkers, such as peptidic linkers.

The use of linkers to connect two or more (poly)peptides is well known in the art. Exemplary peptidic linkers are shown in Table A-5. One often used class of peptidic linker are known as the "Gly-Ser" or "GS" linkers. These are linkers that essentially consist of glycine (G) and serine (S) residues, and usually comprise one or more repeats of a peptide motif such as the GGGGS (SEQ ID NO: 73) motif (for example, comprising the formula (Gly-Gly-Gly-Gly-Ser)$_n$, in which n may be 1, 2, 3, 4, 5, 6, 7 or more). Some often used examples of such GS linkers are 9GS linkers (GGGGSGGGS, SEQ ID NO: 76) 15GS linkers (n=3) (SEQ ID NO: 78) and 35GS linkers (n=7) (SEQ ID NO: 83). Reference is for example made to Chen et al., Adv. Drug Deliv. Rev. 2013 Oct. 15; 65(10): 1357-1369; and Klein et al., Protein Eng. Des. Sel. (2014) 27 (10): 325-330. In the polypeptide(s) of the present technology, the 9GS (SEQ ID NO: 76) and 35GS (SEQ ID NO: 83) linkers are used to link the components of the polypeptide to each other.

In one aspect of the multispecific-multivalent polypeptide of the present technology, the polypeptide comprising or consisting of at least four ISVDs, comprises the at least two ISVDs specifically binding to IL-13 and at least two ISVDs specifically binding to TSLP. In this aspect of the present technology, the at least two ISVDs binding to IL-13 are linked via a 35GS linker, whereas the at least two ISVDs specifically binding to TSLP are linked via a 9GS linker. In one embodiment, the at least two ISVDs specifically binding to TSLP are separated by an ISVD binding to albumin (9GS-Alb-9GS) (as described in section 5.4 "(In vivo) half-life extension" below). The inventors surprisingly found that such a configuration can increase the production yield of the polypeptide.

Accordingly, in one embodiment, the polypeptide comprises or consists of the following, in the order starting from the N-terminus of the polypeptide: a first ISVD specifically binding to IL-13, a second ISVD specifically binding to IL-13, a first ISVD specifically binding to TSLP, an optional binding unit providing the polypeptide with increased half-life as defined herein, and a second ISVD specifically binding to TSLP. In one embodiment, the binding unit providing the polypeptide with increased half-life is an ISVD.

In a further embodiment, the polypeptide comprises or consists of the following, in the order starting from the N-terminus of the polypeptide: an ISVD specifically binding to IL-13, a linker, a second ISVD specifically binding to IL-13, a linker, a first ISVD specifically binding to TSLP, a linker, an ISVD binding to human serum albumin, a linker, and a second ISVD specifically binding to TSLP. In one specific embodiment, the linker between the two ISVDs binding to IL-13 is a 35GS linker, whereas the other linkers are 9GS linkers.

Such configurations of the polypeptide can provide for increased production yield, good CMC characteristics, such as sufficient solubility and biophysical stability, strong potencies with regard to modulation of a type 2 immune response as well as low binding to pre-existing antibodies.

In one embodiment, the multispecific-multivalent polypeptide of the present technology exhibits reduced binding by pre-existing antibodies in human serum. To this end, in one embodiment, the polypeptide comprises a valine (V) at amino acid position 11 and a leucine (L) at amino acid position 89 (according to Kabat numbering) in at least one ISVD. In one embodiment, the polypeptide comprises a valine (V) at amino acid position 11 and a leucine (L) at amino acid position 89 (according to Kabat numbering) in each ISVD. In another embodiment, the polypeptide comprises an extension of 1 to 5 (naturally occurring) amino acids, such as a single alanine (A) extension, at the C-terminus of the C-terminal ISVD. The C-terminus of an ISVD is normally VTVSS (SEQ ID NO: 138). In another embodiment, the polypeptide comprises a lysine (K) or glutamine (Q) at position 110 (according to Kabat numbering) in at least one ISVD. In another embodiment, the ISVD comprises a lysine (K) or glutamine (Q) at position 112 (according to Kabat numbering) in at least on ISVD. In these embodiments, the C-terminus of the ISVD is VKVSS (SEQ ID NO: 139), VQVSS (SEQ ID NO: 140), VTVKS (SEQ ID NO:166), VTVQS (SEQ ID NO:167), VKVKS (SEQ ID NO:168), VKVQS (SEQ ID NO:169), VQVKS (SEQ ID NO:170), or VQVQS (SEQ ID NO:171) such that after addition of a single alanine the C-terminus of the polypeptide for example comprises the sequence VTVSSA (SEQ ID NO: 141), VKVSSA (SEQ ID NO: 142), VQVSSA (SEQ ID NO: 143), VTVKSA (SEQ ID NO:172), VTVQSA (SEQ ID NO:173), VKVKSA (SEQ ID NO:174), VKVQSA (SEQ ID NO:175), VQVKSA (SEQ ID NO:176), or VQVQSA (SEQ ID NO:177). In one embodiment, the C-terminus comprises VTVSSA (SEQ ID NO: 141). In another embodiment, the polypeptide comprises a valine (V) at amino acid position 11 and a leucine (L) at amino acid position 89 (according to Kabat numbering) in each ISVD, optionally a lysine (K) or glutamine (Q) at position 110 (according to Kabat numbering) in at least one ISVD and comprises an extension of 1 to 5 (naturally occurring) amino acids, such as a single alanine (A) extension, at the C-terminus of the C-terminal ISVD (such that the C-terminus of the polypeptide for example has the sequence VTVSSA (SEQ ID NO: 141), VKVSSA (SEQ ID NO: 142) or VQVSSA (SEQ ID NO: 143), such as VTVSSA (SEQ ID NO: 141)). See e.g. WO2012/175741 and WO2015/173325 for further information in this regard.

In one embodiment, the multispecific-multivalent polypeptide of the present technology comprises or consists of an amino acid sequence comprising a sequence identity of more than 90%, such as more than 95% or more than 99%, with SEQ ID NO: 1, wherein the CDRs of the five ISVDs are as defined in items A to E (or A' to E' if using the Kabat definition) set forth in sections "5.2 Immunoglobulin single variable domains" and "5.4 (In vivo) half-life extension" below, respectively, wherein in particular:

the first ISVD specifically binding to IL-13 has a CDR1 that is the amino acid sequence of SEQ ID NO: 7, a CDR2 that is the amino acid sequence of SEQ ID NO: 12 and a CDR3 that is the amino acid sequence of SEQ ID NO: 17;

the second ISVD specifically binding to IL-13 has a CDR1 that is the amino acid sequence of SEQ ID NO: 8, a CDR2 that is the amino acid sequence of SEQ ID NO: 13 and a CDR3 that is the amino acid sequence of SEQ ID NO: 18;

the third ISVD specifically binding to TSLP has a CDR1 that is the amino acid sequence of SEQ ID NO: 9, a CDR2 that is the amino acid sequence of SEQ ID NO: 14 and a CDR3 that is the amino acid sequence of SEQ ID NO: 19;

the fourth ISVD specifically binding to TSLP has a CDR1 that is the amino acid sequence of SEQ ID NO: 11, a CDR2 that is the amino acid sequence of SEQ ID NO: 16 and a CDR3 that is the amino acid sequence of SEQ ID NO: 21; and the ISVD binding to human serum albumin has a CDR1 that is the amino acid sequence of SEQ ID NO: 10, a CDR2 that is the amino acid sequence of SEQ ID NO: 15 and a CDR3 that is the amino acid sequence of SEQ ID NO: 20, or alternatively if using the Kabat definition:

the first ISVD specifically binding to IL-13 has a CDR1 that is the amino acid sequence of SEQ ID NO: 37, a CDR2 that is the amino acid sequence of SEQ ID NO: 42 and a CDR3 that is the amino acid sequence of SEQ ID NO: 17;

the second ISVD specifically binding to IL-13 has a CDR1 that is the amino acid sequence of SEQ ID NO: 38, a CDR2 that is the amino acid sequence of SEQ ID NO: 43 and a CDR3 that is the amino acid sequence of SEQ ID NO: 18;

the third ISVD specifically binding to TSLP has a CDR1 that is the amino acid sequence of SEQ ID NO: 39, a CDR2 that is the amino acid sequence of SEQ ID NO: 44 and a CDR3 that is the amino acid sequence of SEQ ID NO: 19;

the fourth ISVD specifically binding to TSLP has a CDR1 that is the amino acid sequence of SEQ ID NO: 41, a CDR2 that is the amino acid sequence of SEQ ID NO: 46 and a CDR3 that is the amino acid sequence of SEQ ID NO: 21; and the ISVD binding to human serum albumin has a CDR1 that is the amino acid sequence of SEQ ID NO: 40, a CDR2 that is the amino acid sequence of SEQ ID NO: 45 and a CDR3 that is the amino acid sequence of SEQ ID NO: 20.

In another embodiment, the polypeptide comprises or consists of the amino acid sequence of SEQ ID NO: 1. In another embodiment, the polypeptide consists of the amino acid sequence of SEQ ID NO: 1.

In one embodiment, the polypeptide of the present technology has at least half the binding affinity, or at least the same binding affinity, to human IL-13 and to human TSLP as compared to a polypeptide consisting of the amino acid of SEQ ID NO: 1 wherein the binding affinity is measured using the same method, such as Surface Plasmon Resonance (SPR).

5.2 Immunoglobulin Single Variable Domains

The term "immunoglobulin single variable domain" (ISVD), interchangeably used with "single variable domain", defines immunoglobulin molecules wherein the antigen binding site is present on, and formed by, a single immunoglobulin domain. This sets ISVDs apart from "conventional" immunoglobulins (e.g. monoclonal antibodies) or their fragments (such as Fab, Fab', F(ab')$_2$, scFv, di-scFv), wherein two immunoglobulin domains, in particular two variable domains, interact to form an antigen binding site. Typically, in conventional immunoglobulins, a heavy chain variable domain ($V_H$) and a light chain variable domain ($V_L$) interact to form an antigen binding site. In this case, the complementarity determining regions (CDRs) of both $V_H$ and $V_L$ will contribute to the antigen binding site, i.e. a total of 6 CDRs will be involved in antigen binding site formation.

In view of the above definition, the antigen-binding domain of a conventional 4-chain antibody (such as an IgG, IgM, IgA, IgD or IgE molecule; known in the art) or of a Fab fragment, a F(ab')$_2$ fragment, an Fv fragment such as a disulphide linked Fv or a scFv fragment, or a diabody (all known in the art) derived from such conventional 4-chain antibody, would normally not be regarded as an ISVD, as, in these cases, binding to the respective epitope of an antigen would normally not occur by one (single) immunoglobulin domain but by a pair of (associating) immunoglobulin domains such as light and heavy chain variable domains, i.e., by a $V_H$-$V_L$ pair of immunoglobulin domains, which jointly bind to an epitope of the respective antigen.

In contrast, ISVDs are capable of specifically binding to an epitope of the antigen without pairing with an additional immunoglobulin variable domain. The binding site of an ISVD is formed by a single $V_H$, a single $V_{HH}$ or single $V_L$ domain.

As such, the single variable domain may be a light chain variable domain sequence (e.g., a $V_L$-sequence) or a suitable fragment thereof; or a heavy chain variable domain sequence (e.g., a $V_H$-sequence or $V_{HH}$ sequence) or a suitable fragment thereof; as long as it is capable of forming a single antigen binding unit (i.e., a functional antigen binding unit that essentially consists of the single variable domain, such that the single antigen binding domain does not need to interact with another variable domain to form a functional antigen binding unit).

An ISVD can for example be a heavy chain ISVD, such as a $V_H$, $V_{HH}$, including a camelized $V_H$ or humanized $V_{HH}$. In one embodiment, it is a $V_{HH}$, including a camelized $V_H$ or humanized $V_{HH}$. Heavy chain ISVDs can be derived from a conventional four-chain antibody or from a heavy chain antibody.

For example, the ISVD may be a single domain antibody (or an amino acid sequence that is suitable for use as a single domain antibody), a "dAb" or dAb (or an amino acid sequence that is suitable for use as a dAb) or a Nanobody® (as defined herein, and including but not limited to a $V_{HH}$); other single variable domains, or any suitable fragment of any one thereof.

In particular, the ISVD may be a Nanobody® (such as a $V_{HH}$, including a humanized $V_{HH}$ or camelized $V_H$) or a suitable fragment thereof. Nanobody®, Nanobodies® and Nanoclone® are registered trademarks of Ablynx N.V.

"$V_{HH}$ domains", also known as $V_{HH}$s, $V_{HH}$ antibody fragments, and $V_{HH}$ antibodies, have originally been described as the antigen binding immunoglobulin variable domain of "heavy chain antibodies" (i.e., of "antibodies devoid of light chains"; Hamers-Casterman et al. Nature 363: 446-448, 1993). The term "$V_{HH}$ domain" has been chosen in order to distinguish these variable domains from the heavy chain variable domains that are present in conventional 4-chain antibodies (which are referred to herein as "$V_H$ domains") and from the light chain variable domains that are present in conventional 4-chain antibodies (which are referred to herein as "$V_L$ domains"). For a further description of $V_{HH}$'s, reference is made to the review article by Muyldermans (Reviews in Molecular Biotechnology 74: 277-302, 2001).

Typically, the generation of immunoglobulins involves the immunization of experimental animals, fusion of immunoglobulin producing cells to create hybridomas and screening for the desired specificities. Alternatively, immunoglobulins can be generated by screening of naïve or synthetic libraries e.g. by phage display.

The generation of immunoglobulin sequences, such as Nanobodies®, has been described extensively in various publications, among which WO 94/04678, Hamers-Casterman et al. 1993 and Muyldermans et al. 2001 can be exemplified. In these methods, camelids are immunized with the target antigen in order to induce an immune response against said target antigen. The repertoire of Nanobodies obtained from said immunization is further screened for Nanobodies that bind the target antigen.

In these instances, the generation of antibodies requires purified antigen for immunization and/or screening. Antigens can be purified from natural sources, or in the course of recombinant production.

Immunization and/or screening for immunoglobulin sequences can be performed using peptide fragments of such antigens.

The present technology may use immunoglobulin sequences of different origin, comprising mouse, rat, rabbit, donkey, human and camelid immunoglobulin sequences. The present technology also includes fully human, humanized or chimeric sequences. For example, the present technology comprises camelid immunoglobulin sequences and humanized camelid immunoglobulin sequences, or camelized domain antibodies, e.g. camelized dAb as described by Ward et al (see for example WO 94/04678 and Davies and Riechmann (1994 and 1996)). Moreover, the present technology also uses fused immunoglobulin sequences, e.g. forming a multivalent and/or multispecific construct (for multivalent and multispecific polypeptides containing one or more $V_{HH}$ domains and their preparation, reference is also made to Conrath et al., J. Biol. Chem., Vol. 276, 10. 7346-7350, 2001, as well as to for example WO 96/34103 and WO 99/23221), and immunoglobulin sequences comprising tags or other functional moieties, e.g. toxins, labels, radiochemicals, etc., which are derivable from the immunoglobulin sequences of the present technology.

A "humanized $V_{HH}$" comprises an amino acid sequence that corresponds to the amino acid sequence of a naturally occurring $V_{HH}$ domain, but that has been "humanized", i.e. by replacing one or more amino acid residues in the amino acid sequence of said naturally occurring $V_{HH}$ sequence (and in particular in the framework sequences) by one or more of the amino acid residues that occur at the corresponding position(s) in a $V_H$ domain from a conventional 4-chain antibody from a human being (e.g. indicated above). This can be performed in a manner known per se, which will be clear to the skilled person, for example on the basis of the further description herein and the prior art (e.g. WO 2008/020079). Again, it should be noted that such humanized $V_{HH}$s can be obtained in any suitable manner known per se and thus are not strictly limited to polypeptides that have been obtained using a polypeptide that comprises a naturally occurring VHH domain as a starting material.

A "camelized $V_H$" comprises an amino acid sequence that corresponds to the amino acid sequence of a naturally occurring $V_H$ domain, but that has been "camelized", i.e. by replacing one or more amino acid residues in the amino acid sequence of a naturally occurring $V_H$ domain from a conventional 4-chain antibody by one or more of the amino acid residues that occur at the corresponding position(s) in a $V_{HH}$ domain of a heavy chain antibody. This can be performed in a manner known per se, which will be clear to the skilled person, for example on the basis of the further description herein and the prior art (e.g. WO 2008/020079). Such "camelizing" substitutions are usually inserted at amino acid positions that form and/or are present at the $V_H$-$V_L$ interface, and/or at the so-called Camelidae hallmark residues, as defined herein (see for example WO 94/04678 and Davies and Riechmann (1994 and 1996), supra). In one embodiment, the $V_H$ sequence that is used as a starting material or starting point for generating or designing the camelized $V_H$ is a $V_H$ sequence from a mammal, or the $V_H$ sequence of a human being, such as a $V_H3$ sequence. However, it should be noted that such camelized $V_H$ can be obtained in any suitable manner known per se and thus are not strictly limited to polypeptides that have been obtained using a polypeptide that comprises a naturally occurring $V_H$ domain as a starting material.

The structure of an ISVD sequence can be considered to be comprised of four framework regions ("FRs"), which are referred to in the art and herein as "Framework region 1" ("FR1"); as "Framework region 2" ("FR2"); as "Framework region 3" ("FR3"); and as "Framework region 4" ("FR4"), respectively; which framework regions are interrupted by three complementary determining regions ("CDRs"), which are referred to in the art and herein as "Complementarity Determining Region 1" ("CDR1"); as "Complementarity Determining Region 2" ("CDR2"); and as "Complementarity Determining Region 3" ("CDR3"), respectively.

As further described in paragraph q) on pages 58 and 59 of WO 08/020079, the amino acid residues of an ISVD can be numbered according to the general numbering for $V_H$ domains given by Kabat et al. ("Sequence of proteins of immunological interest", US Public Health Services, NIH Bethesda, MD, Publication No. 91), as applied to $V_{HH}$ domains from Camelids in the article of Riechmann and Muyldermans, 2000 (J. Immunol. Methods 240 (1-2): 185-195; see for example FIG. 2 of this publication). It should be noted that—as is well known in the art for $V_H$ domains and for $V_{HH}$ domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. The total number of amino acid residues in a $V_H$ domain and a $V_{HH}$ domain will usually be in the range of from 110 to 120, often between 112 and 115. It should however be noted that smaller and longer sequences may also be suitable for the purposes described herein.

In the present application, unless indicated otherwise, CDR sequences were determined according to the AbM definition as described in Kontermann and Dübel (Eds. 2010, Antibody Engineering, vol 2, Springer Verlag Heidelberg Berlin, Martin, Chapter 3, pp. 33-51). According to this method, FR1 comprises the amino acid residues at positions 1-25, CDR1 comprises the amino acid residues at positions 26-35, FR2 comprises the amino acids at positions 36-49, CDR2 comprises the amino acid residues at positions 50-58, FR3 comprises the amino acid residues at positions 59-94, CDR3 comprises the amino acid residues at positions 95-102, and FR4 comprises the amino acid residues at positions 103-113.

Determination of CDR regions may also be done according to different methods. In the CDR determination according to Kabat, FR1 of an ISVD comprises the amino acid residues at positions 1-30, CDR1 of an ISVD comprises the amino acid residues at positions 31-35, FR2 of an ISVD comprises the amino acids at positions 36-49, CDR2 of an ISVD comprises the amino acid residues at positions 50-65, FR3 of an ISVD comprises the amino acid residues at positions 66-94, CDR3 of an ISVD comprises the amino acid residues at positions 95-102, and FR4 of an ISVD comprises the amino acid residues at positions 103-113.

In such an immunoglobulin sequence, the framework sequences may be any suitable framework sequences, and examples of suitable framework sequences will be clear to the skilled person, for example on the basis the standard handbooks and the further disclosure and prior art mentioned herein.

The framework sequences are a suitable combination of immunoglobulin framework sequences or framework sequences that have been derived from immunoglobulin framework sequences (for example, by humanization or camelization). For example, the framework sequences may be framework sequences derived from a light chain variable domain (e.g. a $V_L$-sequence) and/or from a heavy chain variable domain (e.g. a $V_H$-sequence or $V_{HH}$ sequence). In one aspect, the framework sequences are either framework sequences that have been derived from a $V_{HH}$-sequence (in which said framework sequences may optionally have been partially or fully humanized) or are conventional $V_H$ sequences that have been camelized (as defined herein).

In particular, the framework sequences present in the ISVD sequence used in the present technology may contain one or more of hallmark residues (as defined herein), such that the ISVD sequence is a Nanobody®, such as a $V_{HH}$, including a humanized $V_{HH}$ or camelized $V_H$. Some non-limiting examples of (suitable combinations of) such framework sequences will become clear from the further disclosure herein.

Again, as generally described herein for the immunoglobulin sequences, it is also possible to use suitable fragments (or combinations of fragments) of any of the foregoing, such as fragments that contain one or more CDR sequences, suitably flanked by and/or linked via one or more framework sequences (for example, in the same order as these CDR's and framework sequences may occur in the full-sized immunoglobulin sequence from which the fragment has been derived).

However, it should be noted that the present technology is not limited as to the origin of the ISVD sequence (or of the nucleotide sequence used to express it), nor as to the way that the ISVD sequence or nucleotide sequence is (or has been) generated or obtained. Thus, the ISVD sequences may be naturally occurring sequences (from any suitable species) or synthetic or semi-synthetic sequences. In a specific but non-limiting aspect, the ISVD sequence is a naturally occurring sequence (from any suitable species) or a synthetic or semi-synthetic sequence, including but not limited to "humanized" (as defined herein) immunoglobulin sequences (such as partially or fully humanized mouse or rabbit immunoglobulin sequences, and in particular partially or fully humanized $V_{HH}$ sequences), "camelized" (as defined herein) immunoglobulin sequences, as well as immunoglobulin sequences that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing.

Similarly, nucleotide sequences may be naturally occurring nucleotide sequences or synthetic or semi-synthetic sequences, and may for example be sequences that are isolated by PCR from a suitable naturally occurring template (e.g. DNA or RNA isolated from a cell), nucleotide sequences that have been isolated from a library (and in particular, an expression library), nucleotide sequences that have been prepared by introducing mutations into a naturally occurring nucleotide sequence (using any suitable technique known per se, such as mismatch PCR), nucleotide sequence that have been prepared by PCR using overlapping primers, or nucleotide sequences that have been prepared using techniques for DNA synthesis known per se.

As described above, an ISVD may be a Nanobody® or a suitable fragment thereof. For a general description of Nanobodies, reference is made to the further description below, as well as to the prior art cited herein. In this respect, it should however be noted that this description and the prior art mainly described Nanobodies of the so-called "$V_H3$ class" (i.e. Nanobodies with a high degree of sequence homology to human germline sequences of the $V_H3$ class such as DP-47, DP-51 or DP-29). It should however be noted that the present technology in its broadest sense can generally use any type of Nanobody, and for example also uses the Nanobodies belonging to the so-called "$V_H4$ class" (i.e. Nanobodies with a high degree of sequence homology to human germline sequences of the $V_H4$ class such as DP-78), as for example described in WO 2007/118670.

Generally, Nanobodies (in particular $V_{HH}$ sequences, including (partially) humanized $V_{HH}$ sequences and camelized $V_H$ sequences) can be characterized by the presence of one or more "Hallmark residues" (as described herein) in one or more of the framework sequences (again as further described herein). Thus, generally, a Nanobody can be defined as an immunoglobulin sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which one or more of the Hallmark residues are as further defined herein.

In particular, a Nanobody can be an immunoglobulin sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which the framework sequences are as further defined herein.

More in particular, a Nanobody can be an immunoglobulin sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

one or more of the amino acid residues at positions 11, 37, 44, 45, 47, 83, 84, 103, 104 and 108 according to the Kabat numbering are chosen from the Hallmark residues mentioned in Table A-0 below.

TABLE A-0

Hallmark Residues in Nanobodies

| Position | Human $V_H3$ | Hallmark Residues |
|---|---|---|
| 11 | L, V; predominantly L | L, S, V, M, W, F, T, Q, E, A, R, G, K, Y, N, P, I; preferably L |
| 37 | V, I, F; usually V | $F^{(1)}$, Y, V, L, A, H, S, I, W, C, N, G, D, T, P, preferably $F^{(1)}$ or Y |
| $44^{(8)}$ | G | $E^{(3)}$, $Q^{(3)}$, $G^{(2)}$, D, A, K, R, L, P, S, V, H, T, N, W, M, I; preferably $G^{(2)}$, $E^{(3)}$ or $Q^{(3)}$; most preferably $G^{(2)}$ or $Q^{(3)}$. |
| $45^{(8)}$ | L | $L^{(2)}$, $R^{(3)}$, P, H, F, G, Q, S, E, T, Y, C, I, D, V; preferably $L^{(2)}$ or $R^{(3)}$ |
| $47^{(8)}$ | W, Y | $F^{(1)}$, $L^{(1)}$ or $W^{(2)}$ G, I, S, A, V, M, R, Y, E, P, T, C, H, K, Q, N, D; preferably $W^{(2)}$, $L^{(1)}$ or $F^{(1)}$ |
| 83 | R or K; usually R | R, $K^{(5)}$, T, $E^{(5)}$, Q, N, S, I, V, G, M, L, A, D, Y, H; preferably K or R; most preferably K |
| 84 | A, T, D; predominantly A | $P^{(5)}$, S, H, L, A, V, I, T, F, D, R, Y, N, Q, G, E; preferably P |
| 103 | W | $W^{(4)}$, $R^{(6)}$, G, S, K, A, M, Y, L, F, T, N, V, Q, $P^{(6)}$, E, C; preferably W |
| 104 | G | G, A, S, T, D, P, N, E, C, L; preferably G |
| 108 | L, M or T; predominantly L | Q, $L^{(7)}$, R, P, E, K, S, T, M, A, H; preferably Q or $L^{(7)}$ |

Notes:
$^{(1)}$In particular, but not exclusively, in combination with KERE or KQRE at positions 43-46.
$^{(2)}$Usually as GLEW at positions 44-47.
$^{(3)}$Usually as KERE or KQRE at positions 43-46, e.g. as KEREL, KEREF, KQREL, KQREF, KEREG, KQREW or KQREG at positions 43-47. Alternatively, also sequences such as TERE (for example TEREL), TQRE (for example TQREL), KECE (for example KECEL or KECER), KQCE (for example KQCEL), RERE (for example REREG), RQRE (for example RQREL, RQREF or RQREW), QERE (for example QEREG), QQRE, (for example QQREW, QQREL or QQREF), KGRE (for example KGREG), KDRE (for example KDREV) are possible. Some other possible, but less preferred sequences include for example DECKL and NVCEL.
$^{(4)}$With both GLEW at positions 44-47 and KERE or KQRE at positions 43-46.
$^{(5)}$Often as KP or EP at positions 83-84 of naturally occurring $V_{HH}$ domains.
$^{(6)}$In particular, but not exclusively, in combination with GLEW at positions 44-47.
$^{(7)}$With the proviso that when positions 44-47 are GLEW, position 108 is always Q in (non-humanized) $V_{HH}$ sequences that also contain a W at 103.
$^{(8)}$The GLEW group also contains GLEW-like sequences at positions 44-47, such as for example GVEW, EPEW, GLER, DQEW, DLEW, GIEW, ELEW, GPEW, EWLP, GPER, GLER and ELEW.

The present technology inter alia uses ISVDs that can bind to IL-13 or TSLP. In the context of the present technology, "binding to" a certain target molecule has the usual meaning in the art as understood in the context of antibodies and their respective antigens.

The multispecific-multivalent polypeptide of the present technology may comprise two or more ISVDs specifically binding to IL-13 and two or more ISVDs specifically binding to TSLP. For example, the polypeptide may comprise two ISVDs that specifically bind to IL-13 and two ISVDs that specifically bind to TSLP.

In some embodiments, at least one ISVD can functionally block its target molecule. For example, targeting moieties can block the interaction between IL-13 and IL-13Rα1 (Interleukin 13 receptor, alpha 1) and/or the interaction between IL-13/IL-13Rα1 complex and IL-4Rα (alpha interleukin-4 receptor), or can block the interaction between TSLP and TSLPR (TSLP receptor) and/or TSLP/TSLPR complex and IL-7Rα (Interleukin-7 receptor subunit alpha). Accordingly, in one embodiment, the polypeptide of the present technology comprises at least two ISVDs that specifically bind to IL-13 and functionally block its interaction with IL-13Rα1 and/or the interaction between IL-13/IL-13Rα1 complex and IL-4Rα, and two ISVDs that specifically bind to TSLP and functionally block its interaction with TSLPR and/or the interaction between TSLP/TSLPR complex and IL-7Rα.

The ISVDs used in the present technology form part of a polypeptide of the present technology, which comprises or consists of at least four ISVDs, such that the polypeptide can specifically bind to IL-13 and TSLP.

Accordingly, the target molecules of the at least four ISVDs as used in the polypeptide of the present technology are IL-13 and TSLP. Examples are mammalian IL-13 and TSLP. Besides human IL-13 (Uniprot accession P35225) and human TSLP (Uniprot accession Q969D9), the versions from other species are also amenable to the present technology, for example IL-13 and TSLP from mice, rats, rabbits, cats, dogs, goats, sheep, horses, pigs, non-human primates, such as cynomolgus monkeys (also referred to herein as "cyno"), or camelids, such as llama or alpaca.

Specific examples of ISVDs specifically binding to IL-13 that can be used in the present technology are as described in the following items A and B:

A. An ISVD that specifically binds to human IL-13 and comprises
  i. a CDR1 that is the amino acid sequence of SEQ ID NO: 7 or an amino acid sequence with 2 or 1 amino acid difference(s) with SEQ ID NO: 7;
  ii. a CDR2 that is the amino acid sequence of SEQ ID NO: 12 or an amino acid sequence with 2 or 1 amino acid difference(s) with SEQ ID NO: 12; and
  iii. a CDR3 that is the amino acid sequence of SEQ ID NO: 17 or an amino acid sequence with 2 or 1 amino acid difference(s) with SEQ ID NO: 17.

In one embodiment, the ISVD comprises a CDR1 that is the amino acid sequence of SEQ ID NO: 7, a CDR2 that is the amino acid sequence of SEQ ID NO: 12 and a CDR3 that is the amino acid sequence of SEQ ID NO: 17.

B. An ISVD that specifically binds to human IL-13 and comprises
  i. a CDR1 that is the amino acid sequence of SEQ ID NO: 8 or an amino acid sequence with 2 or 1 amino acid difference(s) with SEQ ID NO: 8;
  ii. a CDR2 that is the amino acid sequence of SEQ ID NO: 13 or an amino acid sequence with 2 or 1 amino acid difference(s) with SEQ ID NO: 13; and
  iii. a CDR3 that is the amino acid sequence of SEQ ID NO: 18 or an amino acid sequence with 2 or 1 amino acid difference(s) with SEQ ID NO: 18.

In one embodiment, the ISVD comprises a CDR1 that is the amino acid sequence of SEQ ID NO: 8, a CDR2 that is the amino acid sequence of SEQ ID NO: 13 and a CDR3 that is the amino acid sequence of SEQ ID NO: 18.

Examples of such an ISVD that specifically binds to human IL-13 have one or more, or all, framework regions as indicated for construct 4B02 or 4B06, respectively, in Table A-2 (in addition to the CDRs as defined in the preceding items A and B, respectively). In one embodiment, it is an ISVD comprising or consisting of the full amino acid sequence of construct 4B02 or construct 4B06 (SEQ ID NOs: 2 and 3, respectively; see Table A-1 and A-2).

In another embodiment, the amino acid sequence of the ISVD(s) specifically binding to human IL-13 may have a sequence identity of more than 90%, such as more than 95% or more than 99%, with SEQ ID NO: 2 or 3 respectively, wherein the CDRs are as defined in the preceding item A or B, respectively. In one embodiment, the ISVD specifically binding to IL-13 comprises or consists of the amino acid sequence of SEQ ID NO: 2 or 3.

When such an ISVD binding to IL-13 has 2 or 1 amino acid difference in at least one CDR relative to a corresponding reference CDR sequence (item A or B above), the ISVD has at least half the binding affinity, or at least the same binding affinity to human IL-13 as the construct 4B02 or 4B06 set forth in SEQ ID NO: 2 or 3, respectively, wherein the binding affinity is measured using the same method, such as SPR.

Specific examples of ISVDs specifically binding to TSLP that can be used in the present technology are as described in the following items C and D:

C. An ISVD that specifically binds to human TSLP and comprises
- i. a CDR1 that is the amino acid sequence of SEQ ID NO: 9 or an amino acid sequence with 2 or 1 amino acid difference(s) with SEQ ID NO: 9;
- ii. a CDR2 that is the amino acid sequence of SEQ ID NO: 14 or an amino acid sequence with 2 or 1 amino acid difference(s) with SEQ ID NO: 14; and
- iii. a CDR3 that is the amino acid sequence of SEQ ID NO: 19 or an amino acid sequence with 2 or 1 amino acid difference(s) with SEQ ID NO: 19.

In one embodiment, the ISVD comprises a CDR1 that is the amino acid sequence of SEQ ID NO: 9, a CDR2 that is the amino acid sequence of SEQ ID NO: 14 and a CDR3 that is the amino acid sequence of SEQ ID NO: 19.

D. An ISVD that specifically binds to human TSLP and comprises
- i. a CDR1 that is the amino acid sequence of SEQ ID NO: 11 or an amino acid sequence with 2 or 1 amino acid difference(s) with SEQ ID NO: 11;
- ii. a CDR2 that is the amino acid sequence of SEQ ID NO: 16 or an amino acid sequence with 2 or 1 amino acid difference(s) with SEQ ID NO: 16; and
- iii. a CDR3 that is the amino acid sequence of SEQ ID NO: 21 or an amino acid sequence with 2 or 1 amino acid difference(s) with SEQ ID NO: 21.

In one embodiment, the ISVD comprises a CDR1 that is the amino acid sequence of SEQ ID NO: 11, a CDR2 that is the amino acid sequence of SEQ ID NO: 16 and a CDR3 that is the amino acid sequence of SEQ ID NO: 21.

Examples of such an ISVD that specifically binds to human TSLP have one or more, or all, framework regions as indicated for construct 501A02 and 529F10, respectively, in Table A-2 (in addition to the CDRs as defined in the preceding items C and D). In one embodiment, it is an ISVD comprising or consisting of the full amino acid sequence of construct 501A02 or 529F10 (SEQ ID NOs: 4 or 6, see Table A-1 and A-2).

In another embodiment, the amino acid sequence of an ISVD(s) specifically binding to human TSLP may have a sequence identity of more than 90%, such as more than 95% or more than 99%, with SEQ ID NO: 4 or 6, respectively, wherein the CDRs are as defined in the preceding item C or D. In one embodiment, the ISVD binding to human TSLP comprises or consists of the amino acid sequence of SEQ ID NOs: 4 or 6.

When such an ISVD binding to human TSLP has 2 or 1 amino acid difference in at least one CDR relative to a corresponding reference CDR sequence (item C or D above), the ISVD has at least half the binding affinity, or at least the same binding affinity to human TSLP as construct 501A02 or 529F10 set forth in SEQ ID NO: 4 and 6, respectively, wherein the binding affinity is measured using the same method, such as SPR.

In an embodiment, each of the ISVDs as defined under items A to D above is comprised in the polypeptide of the present technology.

Such a polypeptide of the present technology comprising each of the ISVDs as defined under items A to D above has at least half the binding affinity, or at least the same binding affinity, to human IL-13 and to human TSLP as a polypeptide consisting of the amino acid of SEQ ID NO: 1, wherein the binding affinity is measured using the same method, such as SPR.

The SEQ ID NOs referred to in the above items A to D and item E below (see section 5.4 "(In vivo) half-life extension") are based on the CDR definition according to the AbM definition (see Table A-2). It is noted that the SEQ ID NOs defining the same CDRs according to the Kabat definition (see Table A-2.1) can likewise be used in the above items A to D and item E below (see section 5.4 "(In vivo) half-life extension").

Accordingly, the specific examples of ISVDs specifically binding to IL-13 or TSLP that can be used in the present technology are as described above using the AbM definition can be also described using the Kabat definition as set forth in items A' to D' below:

A'. An ISVD that specifically binds to human IL-13 and comprises
- i. a CDR1 that is the amino acid sequence of SEQ ID NO: 37 or an amino acid sequence with 2 or 1 amino acid difference(s) with SEQ ID NO: 37;
- ii. a CDR2 that is the amino acid sequence of SEQ ID NO: 42 or an amino acid sequence with 2 or 1 amino acid difference(s) with SEQ ID NO: 42; and
- iii. a CDR3 that is the amino acid sequence of SEQ ID NO: 17 or an amino acid sequence with 2 or 1 amino acid difference(s) with SEQ ID NO: 17.

In one embodiment, the ISVD comprises a CDR1 that is the amino acid sequence of SEQ ID NO: 37, a CDR2 that is the amino acid sequence of SEQ ID NO: 42 and a CDR3 that is the amino acid sequence of SEQ ID NO: 17.

B'. An ISVD that specifically binds to human IL-13 and comprises
- i. a CDR1 that is the amino acid sequence of SEQ ID NO: 38 or an amino acid sequence with 2 or 1 amino acid difference(s) with SEQ ID NO: 38;
- ii. a CDR2 that is the amino acid sequence of SEQ ID NO: 43 or an amino acid sequence with 2 or 1 amino acid difference(s) with SEQ ID NO: 43; and
- iii. a CDR3 that is the amino acid sequence of SEQ ID NO: 18 or an amino acid sequence with 2 or 1 amino acid difference(s) with SEQ ID NO: 18.

In one embodiment, the ISVD comprises a CDR1 that is the amino acid sequence of SEQ ID NO: 38, a CDR2 that is the amino acid sequence of SEQ ID NO: 43 and a CDR3 that is the amino acid sequence of SEQ ID NO: 18.

Examples of such an ISVD(s) that specifically binds to human IL-13 have one or more, or all, framework regions as indicated for construct 4B02 or 4B06, respectively, in Table A-2-1 (in addition to the CDRs as defined in the preceding items A' and B', respectively). In one embodiment it is an ISVD comprising or consisting of the full amino acid sequence of construct 4B02 or construct 4B06 (SEQ ID NOs: 2 and 3, respectively; see Table A-1 and A-2-1).

C'. An ISVD that specifically binds to human TSLP and comprises
  i. a CDR1 that is the amino acid sequence of SEQ ID NO: 39 or an amino acid sequence with 2 or 1 amino acid difference(s) with SEQ ID NO: 39;
  ii. a CDR2 that is the amino acid sequence of SEQ ID NO: 44 or an amino acid sequence with 2 or 1 amino acid difference(s) with SEQ ID NO: 44; and
  iii. a CDR3 that is the amino acid sequence of SEQ ID NO: 19 or an amino acid sequence with 2 or 1 amino acid difference(s) with SEQ ID NO: 19.

In one embodiment, the ISVD comprises a CDR1 that is the amino acid sequence of SEQ ID NO: 39, a CDR2 that is the amino acid sequence of SEQ ID NO: 44 and a CDR3 that is the amino acid sequence of SEQ ID NO: 19.

D'. An ISVD that specifically binds to human TSLP and comprises
  i. a CDR1 that is the amino acid sequence of SEQ ID NO: 41 or an amino acid sequence with 2 or 1 amino acid difference(s) with SEQ ID NO: 41;
  ii. a CDR2 that is the amino acid sequence of SEQ ID NO: 46 or an amino acid sequence with 2 or 1 amino acid difference(s) with SEQ ID NO: 46; and
  iii. a CDR3 that is the amino acid sequence of SEQ ID NO: 21 or an amino acid sequence with 2 or 1 amino acid difference(s) with SEQ ID NO: 21.

In one embodiment, the ISVD comprises a CDR1 that is the amino acid sequence of SEQ ID NO: 41, a CDR2 that is the amino acid sequence of SEQ ID NO: 46 and a CDR3 that is the amino acid sequence of SEQ ID NO: 21.

Examples of such an ISVD(s) that specifically binds to human TSLP have one or more, or all, framework regions as indicated for construct 501A02 and 529F10, respectively, in Table A-2-1 (in addition to the CDRs as defined in the preceding items C' and D'). In one embodiment, it is an ISVD comprising or consisting of the full amino acid sequence of construct 501A02 or 529F10 (SEQ ID NOs: 4 or 6, see Table A-1 and A-2-1).

The percentage of "sequence identity" between a first amino acid sequence and a second amino acid sequence may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (i.e. at a single position).

Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

An "amino acid difference" as used herein refers to a deletion, insertion or substitution of a single amino acid residue vis-à-vis a reference sequence. In one embodiment, an "amino acid difference" is a substitution.

In one embodiment, amino acid substitutions are conservative substitutions. Such conservative substitutions are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp.

In one embodiment, conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

5.3 Specificity

The terms "specificity", "binding specifically" or "specific binding" refer to the number of different target molecules, such as antigens, from the same organism to which a particular binding unit, such as an ISVD, can bind with sufficiently high affinity (see below). "Specificity", "binding specifically" or "specific binding" are used interchangeably herein with "selectivity", "binding selectively" or "selective binding". Binding units, such as ISVDs, specifically bind to their designated targets.

The specificity/selectivity of a binding unit can be determined based on affinity. The affinity denotes the strength or stability of a molecular interaction. The affinity is commonly given as by the KD, or dissociation constant, which has units of mol/liter (or M). The affinity can also be expressed as an association constant, KA, which equals 1/KD and has units of (mol/liter)$^{-1}$ (or M$^{-1}$).

The affinity is a measure for the binding strength between a moiety and a binding site on the target molecule: the lower the value of the KD, the stronger the binding strength between a target molecule and a targeting moiety.

Typically, binding units used in the present technology (such as ISVDs) will bind to their targets with a dissociation constant (KD) of $10^{-5}$ to $10^{-12}$ moles/liter or less, or $10^{-2}$ to $10^{-12}$ moles/liter or less, or $10^{-8}$ to $10^{-12}$ moles/liter (i.e. with an association constant (KA) of $10^5$ to $10^{12}$ liter/moles or more, or $10^{-8}$ to $10^{12}$ liter/moles or more, or $10^8$ to $10^{12}$ liter/moles).

Any KD value greater than $10^{-4}$ mol/liter (or any KA value lower than $10^4$ liters/mol) is generally considered to indicate non-specific binding.

The KD for biological interactions, such as the binding of immunoglobulin sequences to an antigen, which are considered specific are typically in the range of $10^{-5}$ moles/liter (10000 nM or 10 μM) to $10^{-12}$ moles/liter (0.001 nM or 1 pM) or less.

Accordingly, specific/selective binding may mean that—using the same measurement method, e.g. SPR—a binding unit (or polypeptide comprising the same) binds to IL13 and/or TSLP with a KD value of $10^{-5}$ to $10^{-12}$ moles/liter or less and binds to related cytokines with a KD value greater than $10^{-4}$ moles/liter. Examples of IL13 related targets are human IL4. Examples of related cytokines for TSLP are human IL7. Thus, in an embodiment of the present technology, at least two ISVDs comprised in the polypeptide binds to IL13 with a KD value of $10^{-5}$ to $10^{-12}$ moles/liter or less and binds to IL4 of the same species with a KD value greater than $10^{-4}$ moles/liter, and at least two ISVDs comprised in the polypeptide bind to TSLP with a KD value of $10^{-5}$ to $10^{-12}$ moles/liter or less and binds to human IL7 of the same species with a KD value greater than $10^{-4}$ moles/liter.

Thus, the polypeptide of the present technology has at least half the binding affinity, or at least the same binding affinity, to human IL13 and to human TSLP as compared to a polypeptide consisting of the amino acid of SEQ ID NO: 1, wherein the binding affinity is measured using the same method, such as SPR.

Specific binding to a certain target from a certain species does not exclude that the binding unit can also specifically bind to the analogous target from a different species. For example, specific binding to human IL13 does not exclude that the binding unit (or a polypeptide comprising the same) can also specifically bind to IL13 from cynomolgus monkeys. Likewise, for example, specific binding to human TSLP does not exclude that the binding unit (or a polypeptide comprising the same) can also specifically bind to TSLP from cynomolgus monkeys ("cyno").

Specific binding of a binding unit to its designated target can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as the other techniques mentioned herein.

The dissociation constant may be the actual or apparent dissociation constant, as will be clear to the skilled person. Methods for determining the dissociation constant will be clear to the skilled person, and for example include the techniques mentioned below. In this respect, it will also be clear that it may not be possible to measure dissociation constants of more than $10^{-4}$ moles/liter or $10^{-3}$ moles/liter (e.g. of $10^{-2}$ moles/liter). Optionally, as will also be clear to the skilled person, the (actual or apparent) dissociation constant may be calculated on the basis of the (actual or apparent) association constant (KA), by means of the relationship [KD=1/KA].

The affinity of a molecular interaction between two molecules can be measured via different techniques known per se, such as the well-known surface plasmon resonance (SPR) biosensor technique (see for example Ober et al. 2001, Intern. Immunology 13: 1551-1559). The term "surface plasmon resonance", as used herein, refers to an optical phenomenon that allows for the analysis of real-time biospecific interactions by detection of alterations in protein concentrations within a biosensor matrix, where one molecule is immobilized on the biosensor chip and the other molecule is passed over the immobilized molecule under flow conditions yielding $k_{on}$, $k_{off}$ measurements and hence $K_D$ (or $K_A$) values. This can for example be performed using the well-known BIAcore® system (BIAcore International AB, a GE Healthcare company, Uppsala, Sweden and Piscataway, NJ). For further descriptions, see Jonsson et al. (1993, Ann. Biol. Clin. 51: 19-26), Jonsson et al. (1991 Biotechniques 11: 620-627), Johnsson et al. (1995, J. Mol. Recognit. 8: 125-131), and Johnnson et al. (1991, Anal. Biochem. 198: 268-277).

Another well-known biosensor technique to determine affinities of biomolecular interactions is bio-layer interferometry (BLI) (see for example Abdiche et al. 2008, Anal. Biochem. 377: 209-217). The term "bio-layer Interferometry" or "BLI", as used herein, refers to a label-free optical technique that analyzes the interference pattern of light reflected from two surfaces: an internal reference layer (reference beam) and a layer of immobilized protein on the biosensor tip (signal beam). A change in the number of molecules bound to the tip of the biosensor causes a shift in the interference pattern, reported as a wavelength shift (nm), the magnitude of which is a direct measure of the number of molecules bound to the biosensor tip surface. Since the interactions can be measured in real-time, association and dissociation rates and affinities can be determined. BLI can for example be performed using the well-known Octet® Systems (ForteBio, a division of Pall Life Sciences, Menlo Park, USA).

Alternatively, affinities can be measured in Kinetic Exclusion Assay (KinExA) (see for example Drake et al. 2004, Anal. Biochem., 328: 35-43), using the KinExA® platform (Sapidyne Instruments Inc, Boise, USA). The term "KinExA", as used herein, refers to a solution-based method to measure true equilibrium binding affinity and kinetics of unmodified molecules. Equilibrated solutions of an antibody/antigen complex are passed over a column with beads precoated with antigen (or antibody), allowing the free antibody (or antigen) to bind to the coated molecule. Detection of the antibody (or antigen) thus captured is accomplished with a fluorescently labeled protein binding the antibody (or antigen).

The GYROLAB® immunoassay system provides a platform for automated bioanalysis and rapid sample turnaround (Fraley et al. 2013, Bioanalysis 5: 1765-74).

5.4 (In Vivo) Half-Life Extension

The polypeptide may further comprise one or more other groups, residues, moieties or binding units, optionally linked via one or more peptidic linkers, in which said one or more other groups, residues, moieties or binding units provide the polypeptide with increased (in vivo) half-life, compared to the corresponding polypeptide without said one or more other groups, residues, moieties or binding units. In vivo half-life extension means, for example, that the polypeptide has an increased half-life in a mammal, such as a human subject, after administration. Half-life can be expressed for example as t1/2beta.

The type of groups, residues, moieties or binding units is not generally restricted and may for example be chosen from the group consisting of a polyethylene glycol molecule, serum proteins or fragments thereof, binding units that can bind to serum proteins, an Fc portion, and small proteins or peptides that can bind to serum proteins.

More specifically, said one or more other groups, residues, moieties or binding units that provide the polypeptide with increased half-life can be chosen from the group consisting of binding units that can bind to serum albumin, such as human serum albumin, or a serum immunoglobulin, such as IgG. In one embodiment, said one or more other binding units that provide the polypeptide with increased half-life is a binding unit that can bind to human serum albumin. In one embodiment, the binding unit is an ISVD.

For example, WO 04/041865 describes Nanobodies® binding to serum albumin (and in particular against human serum albumin) that can be linked to other proteins (such as one or more other Nanobodies binding to a desired target) in order to increase the half-life of said protein.

The international application WO 06/122787 describes a number of Nanobodies® against (human) serum albumin. These Nanobodies® include the Nanobody® called Alb-1 (SEQ ID NO: 52 in WO 06/122787) and humanized variants thereof, such as Alb-8 (SEQ ID NO: 62 in WO 06/122787). Again, these can be used to extend the half-life of therapeutic proteins and polypeptide and other therapeutic entities or moieties.

Moreover, WO2012/175400 describes a further improved version of Alb-1, called Alb-23.

In one embodiment, the polypeptide comprises a serum albumin binding moiety selected from Alb-1, Alb-3, Alb-4, Alb-5, Alb-6, Alb-7, Alb-8, Alb-9, Alb-10 and Alb-23. In one embodiment, the serum albumin binding moiety is Alb-8 or Alb-23 or its variants, as shown in pages 7-9 of WO2012/175400 and the albumin binders described in WO 2012/175741, WO2015/173325, WO2017/080850, WO2017/085172, WO2018/104444, WO2018/134235, WO2018/134234. Some serum albumin binders are also shown in Table A-4. In one embodiment, a further component of the polypeptide of the present technology is as described in item E:

E. An ISVD that binds to human serum albumin and comprises
  i. a CDR1 that is the amino acid sequence of SEQ ID NO: 10 or an amino acid sequence with 2 or 1 amino acid difference(s) with SEQ ID NO: 10;
  ii. a CDR2 that is the amino acid sequence of SEQ ID NO: 15 or an amino acid sequence with 2 or 1 amino acid difference(s) with SEQ ID NO: 15; and
  iii. a CDR3 that is the amino acid sequence of SEQ ID NO: 20 or an amino acid sequence with 2 or 1 amino acid difference(s) with SEQ ID NO: 20.
  In one embodiment, the ISVD comprises a CDR1 that is the amino acid sequence of SEQ ID NO: 10, a CDR2 that is the amino acid sequence of SEQ ID NO: 15 and a CDR3 that is the amino acid sequence of SEQ ID NO: 20.

Examples of such an ISVD that binds to human serum albumin have one or more, or all, framework regions as indicated for construct ALB23002 in Table A-2 (in addition to the CDRs as defined in the preceding item E). In one embodiment, it is an ISVD comprising or consisting of the full amino acid sequence of construct ALB23002 (SEQ ID NO: 5, see Table A-1 and A-2).

Item E can be also described using the Kabat definition as:
E'. An ISVD that binds to human serum albumin and comprises
  i. a CDR1 that is the amino acid sequence of SEQ ID NO: 40 or an amino acid sequence with 2 or 1 amino acid difference(s) with SEQ ID NO: 40;
  ii. a CDR2 that is the amino acid sequence of SEQ ID NO: 45 or an amino acid sequence with 2 or 1 amino acid difference(s) with SEQ ID NO: 45; and
  iii. a CDR3 that is the amino acid sequence of SEQ ID NO: 20 or an amino acid sequence with 2 or 1 amino acid difference(s) with SEQ ID NO: 20.
  In one embodiment, the ISVD comprises a CDR1 that is the amino acid sequence of SEQ ID NO: 40, a CDR2 that is the amino acid sequence of SEQ ID NO: 45 and a CDR3 that is the amino acid sequence of SEQ ID NO: 20.

Examples of such an ISVD that binds to human serum albumin have one or more, or all, framework regions as indicated for construct ALB23002 in Table A-2-1 (in addition to the CDRs as defined in the preceding item E'). In one embodiment, it is an ISVD comprising or consisting of the full amino acid sequence of construct ALB23002 (SEQ ID NO: 5, see Table A-1 and A-2-1).

In a further embodiment, the amino acid sequence of an ISVD binding to human serum albumin may have a sequence identity of more than 90%, such as more than 95% or more than 99%, with SEQ ID NO: 5, wherein the CDRs are as defined in the preceding item E or E'. In one embodiment, the ISVD binding to human serum albumin has the amino acid sequence of SEQ ID NO: 5.

When such an ISVD binding to human serum albumin has 2 or 1 amino acid difference in at least one CDR relative to a corresponding reference CDR sequence (item E above), the ISVD has at least half the binding affinity, or at least the same binding affinity to human serum albumin as construct ALB23002 set forth in SEQ ID NO: 5, wherein the binding affinity is measured using the same method, such as SPR.

In one embodiment, when such an ISVD binding to human serum albumin has a C-terminal position it exhibits a C-terminal alanine (A) or glycine (G) extension. In one embodiment, such and ISVD is selected from SEQ ID NOs: 59, 60, 62, 64, 65, 66, 67, 68, 69 and 71 (see table A-4 below). In one embodiment, the ISVD binding to human serum albumin has another position than the C-terminal position (i.e. is not the C-terminal ISVD of the polypeptide of the present technology). In one embodiment, such an ISVD is selected from SEQ ID NOs: 5, 57, 58, 61, and 63 (see table A-4 below).

5.5 Nucleic Acid Molecules

Also provided is a nucleic acid molecule encoding the polypeptide of the present technology.

A "nucleic acid molecule" (used interchangeably with "nucleic acid") is a chain of nucleotide monomers linked to each other via a phosphate backbone to form a nucleotide sequence. A nucleic acid may be used to transform/transfect a host cell or host organism, e.g. for expression and/or production of a polypeptide. Suitable hosts or host cells for production purposes will be clear to the skilled person, and may for example be any suitable fungal, prokaryotic or eukaryotic cell or cell line or any suitable fungal, prokaryotic or eukaryotic organism. A host or host cell comprising a nucleic acid encoding the polypeptide of the present technology is also encompassed by the present technology.

A nucleic acid may be for example DNA, RNA, or a hybrid thereof, and may also comprise (e.g. chemically) modified nucleotides, like PNA. It can be single- or double-stranded. In one embodiment, it is in the form of double-stranded DNA. For example, the nucleotide sequences of the present technology may be genomic DNA, cDNA.

The nucleic acids of the present technology can be prepared or obtained in a manner known per se, and/or can be isolated from a suitable natural source. Nucleotide sequences encoding naturally occurring (poly)peptides can for example be subjected to site-directed mutagenesis, so as to provide a nucleic acid molecule encoding polypeptide with sequence variation. Also, as will be clear to the skilled person, to prepare a nucleic acid, also several nucleotide sequences, such as at least one nucleotide sequence encoding a targeting moiety and for example nucleic acids encoding one or more linkers can be linked together in a suitable manner.

Techniques for generating nucleic acids will be clear to the skilled person and may for instance include, but are not limited to, automated DNA synthesis; site-directed mutagenesis; combining two or more naturally occurring and/or synthetic sequences (or two or more parts thereof), introduction of mutations that lead to the expression of a truncated expression product; introduction of one or more restriction sites (e.g. to create cassettes and/or regions that may easily be digested and/or ligated using suitable restriction enzymes), and/or the introduction of mutations by means of a PCR reaction using one or more "mismatched" primers.

5.6 Vectors

Also provided is a vector comprising the nucleic acid molecule encoding the polypeptide of the present technology. A vector as used herein is a vehicle suitable for carrying genetic material into a cell. A vector includes naked nucleic acids, such as plasmids or mRNAs, or nucleic acids embedded into a bigger structure, such as liposomes or viral vectors.

Vectors generally comprise at least one nucleic acid that is optionally linked to one or more regulatory elements, such as for example one or more suitable promoter(s), enhancer(s), terminator(s), etc.). In one embodiment, the vector is an expression vector, i.e. a vector suitable for expressing an encoded polypeptide or construct under suitable conditions, e.g. when the vector is introduced into a (e.g. human) cell. For DNA-based vectors, this usually includes the presence of elements for transcription (e.g. a promoter and a polyA signal) and translation (e.g. Kozak sequence).

In one embodiment, in the vector, said at least one nucleic acid and said regulatory elements are "operably linked" to each other, by which is generally meant that they are in a functional relationship with each other. For instance, a promoter is considered "operably linked" to a coding sequence if said promoter is able to initiate or otherwise control/regulate the transcription and/or the expression of a coding sequence (in which said coding sequence should be understood as being "under the control of" said promotor). Generally, when two nucleotide sequences are operably linked, they will be in the same orientation and usually also in the same reading frame. They will usually also be essentially contiguous, although this may also not be required.

In one embodiment, any regulatory elements of the vector are such that they are capable of providing their intended biological function in the intended host cell or host organism.

For instance, a promoter, enhancer or terminator should be "operable" in the intended host cell or host organism, by which is meant that for example said promoter should be capable of initiating or otherwise controlling/regulating the transcription and/or the expression of a nucleotide sequence—e.g. a coding sequence—to which it is operably linked.

5.7 Compositions

The present technology also provides a composition comprising at least one polypeptide of the present technology, at least one nucleic acid molecule encoding a polypeptide of the present technology or at least one vector comprising such a nucleic acid molecule. The composition may be a pharmaceutical composition. The composition may further comprise at least one pharmaceutically acceptable carrier, diluent or excipient and/or adjuvant, and optionally comprise one or more further pharmaceutically active polypeptides and/or compounds.

5.8 Host Organisms

The present technology also pertains to host cells or host organisms comprising the polypeptide of the present technology, the nucleic acid encoding the polypeptide of the present technology, and/or the vector comprising the nucleic acid molecule encoding the polypeptide of the present technology.

Suitable host cells or host organisms are clear to the skilled person, and are for example any suitable fungal, prokaryotic or eukaryotic cell or cell line or any suitable fungal, prokaryotic or eukaryotic organism. Specific examples include HEK293 cells, CHO cells, *Escherichia coli* or *Pichia pastoris*. In one embodiment, the host is *Pichia pastoris*.

5.9 Methods and Uses of the Polypeptide

The present technology also provides a method for producing the polypeptide of the present technology. The method may comprise transforming/transfecting a host cell or host organism with a nucleic acid encoding the polypeptide, expressing the polypeptide in the host, optionally followed by one or more isolation and/or purification steps. Specifically, the method may comprise:

a) expressing, in a suitable host cell or host organism or in another suitable expression system, a nucleic acid sequence encoding the polypeptide; optionally followed by:

b) isolating and/or purifying the polypeptide.

Suitable host cells or host organisms for production purposes will be clear to the skilled person, and may for example be any suitable fungal, prokaryotic or eukaryotic cell or cell line or any suitable fungal, prokaryotic or eukaryotic organism. Specific examples include HEK293 cells, CHO cells, *Escherichia coli* or *Pichia pastoris*. In one embodiment, the host is *Pichia pastoris*.

The polypeptide of the present technology, a nucleic acid molecule or vector as described, or a composition comprising the polypeptide of the present technology, nucleic acid molecule or vector are useful as a medicament.

Accordingly, the present technology provides the polypeptide of the present technology, a nucleic acid molecule or vector as described, or a composition comprising the polypeptide of the present technology, nucleic acid molecule or vector for use as a medicament.

Also provided is the polypeptide of the present technology, a nucleic acid molecule or vector as described, or a composition comprising the polypeptide of the present technology, nucleic acid molecule or vector for use in the (prophylactic or therapeutic). treatment of an inflammatory disease.

Further provided is a (prophylactic and/or therapeutic) method of treating an inflammatory disease, wherein said method comprises administering, to a subject in need thereof, a pharmaceutically active amount of the polypeptide of the present technology, a nucleic acid molecule or vector as described, or a composition comprising the polypeptide of the present technology, nucleic acid molecule or vector.

Further provided is the use of the polypeptide of the present technology, a nucleic acid molecule or vector as described, or a composition comprising the polypeptide of the present technology, nucleic acid molecule or vector in the preparation of a pharmaceutical composition. In one embodiment, the prepared pharmaceutical composition is for treating an inflammatory disease.

The inflammatory disease is a type 2 inflammatory disease such as atopic dermatitis and asthma.

A "subject" as referred to in the context of the present technology can be any animal, and more specifically a mammal. Among mammals, a distinction can be made between humans and non-human mammals. Non-human animals may be for example companion animals (e.g. dogs, cats), livestock (e.g. bovine, equine, ovine, caprine, or porcine animals), or animals used generally for research purposes and/or for producing antibodies (e.g. mice, rats, rabbits, cats, dogs, goats, sheep, horses, pigs, non-human primates, such as cynomolgus monkeys, or camelids, such as llama or alpaca).

In the context of prophylactic and/or therapeutic purposes, the subject can be any animal, and more specifically any mammal. In one embodiment, the subject is a human subject.

Substances (including polypeptides, nucleic acid molecules and vectors) or compositions may be administered to a subject by any suitable route of administration, for example by enteral (such as oral or rectal) or parenteral (such as epicutaneous, sublingual, buccal, nasal, intra-articular, intradermal, intramuscular, intraperitoneal, intravenous, subcutaneous, transdermal, or transmucosal) administration. In one embodiment, substances are administered by parenteral administration, such as intramuscular, subcutaneous or intradermal administration. In one embodiment, subcutaneous administration is used.

An effective amount of a polypeptide, a nucleic acid molecule or vector as described, or a composition comprising the polypeptide, nucleic acid molecule or vector can be administered to a subject in order to provide the intended treatment results.

One or more doses can be administered. If more than one dose is administered, the doses can be administered in suitable intervals in order to maximize the effect of the polypeptide, composition, nucleic acid molecule or vector.

TABLE A-1

Amino acid sequences of the different monovalent $V_{HH}$ building blocks identified within the pentavalent polypeptide F027400161 ("ID" refers to the SEQ ID NO as used herein)

| Name | ID | Amino acid sequence |
|---|---|---|
| 4B02 | 2 | DVQLVESGGGVVQPGGSLRLSCAASGRTFSSYRMGWFRQAPGKEREFVAALSGDGYSTYTANSVKGRFTISRDNSKNTVYLQMNSLRPEDTALYYCAAKLQYVSGWSYDYPYWGQGTLVTVSS |
| 4B06 | 3 | EVQLVESGGGVVQPGGSLRLSCAASGFTFNNYAMKWVRQAPGKGLEWVSSITTGGGSTDYADSVKGRFTISRDNSKNTLYLQMNSLRPEDTALYYCANVPFGYYSEHFSGLSFDYRGQGTLVTVSS |
| 501A02 | 4 | EVQLVESGGGVVQPGGSLRLSCAASGSGFGVNILYWYRQAAGIERELIASITSGGITNYVDSVKGRFTISRDNSENTMYLQMNSLRAEDTGLYYCASRNIFDGTTEWGQGTLVTVSS |
| ALB23002 | 5 | EVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLSRSSQGTLVTVSS |
| 529F10 | 6 | EVQLVESGGGVVQPGGSLRLSCAASGFTFADYDYDIGWFRQAPGKEREGVSCISNRDGSTYYADSVKGRFTISRDNSKNTVYLQMNSLRPEDTALYYCAVEIHCDDYGVENFDFDPWGQGTLVTVSS |

TABLE A-2

Sequences for CDRs according to AbM definition and frameworks ("ID" refers to the given SEQ ID NO)

| ID | $V_{HH}$ | ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|---|
| 2 | 4B02 | 22 | DVQLVESGGGVVQPGGSLRLSCAAS | 7 | GRTFSSYRMG | 24 | WFRQAPGKEREFVA | 12 | ALSGDGYSTY | 29 | TANSVKGRFTISRDNSKNTVYLQMNSLRPEDTALYYCAA | 17 | KLQYVSGWSYDYPY | 34 | WGQGTLVTVSS |
| 3 | 4B06 | 23 | EVQLVESGGGVVQPGGSLRLSCAAS | 8 | GFTFNNYAMK | 25 | WVRQAPGKGLEWVS | 13 | SITTGGGSTD | 30 | YADSVKGRFTISRDNSKNTLYLQMNSLRPEDTALYYCAN | 18 | VPFGYYSEHFSGLSFDY | 35 | RGQGTLVTVSS |
| 4 | 501A02 | 23 | EVQLVESGGGVVQPGGSLRLSCAAS | 9 | GSGFGVNILY | 26 | WYRQAAGIERELIA | 14 | SITSGGITN | 31 | YVDSVKGRFTISRDNSENTMYLQMNSLRAEDTGLYYCAS | 19 | RNIFDGTTE | 34 | WGQGTLVTVSS |
| 5 | ALB23002 | 23 | EVQLVESGGGVVQPGGSLRLSCAAS | 10 | GFTFRSFGMS | 27 | WVRQAPGKGPEWVS | 15 | SISGSGSDTL | 32 | YADSVKGRFTISRDNSKNTLYLQMNSLRPEDTALYYCTI | 20 | GGSLSR | 36 | SSQGTLVTVSS |
| 6 | 529F10 | 23 | EVQLVESGGGVVQPGGSLRLSCAAS | 11 | GFTFADYDYDIG | 28 | WFRQAPGKEREGVS | 16 | CISNRDGSTY | 33 | YADSVKGRFTISRDNSKNTVYLQMNSLRPEDTALYYCAV | 21 | EIHCDDYGVENFDFDP | 34 | WGQGTLVTVSS |

TABLE A-2.1

Sequences for CDRs according to Kabat definition and frameworks ("ID" refers to the given SEQ ID NO)

| ID | V<sub>HH</sub> | ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|---|
| 2 | 4B02 | 47 | DVQLVES GGGVVQP GGSLRLSC AASGRTFS | 37 | SYRMG | 24 | WFRQ APGKE REFVA | 42 | ALSGDG YSTYTAN SVKG | 52 | RFTISRDNS KNTVYLQMN SLRPEDTAL YYCAA | 17 | KLQYV SGWSY DYPY | 34 | WGQGT LVTVS S |
| 3 | 4B06 | 48 | EVQLVESG GGVVQPGG SLRLSCAA SGFTFN | 38 | NYAMK | 25 | WVRQA PGKGL EWVS | 43 | SITTGGG STDYADS VKG | 53 | RFTISRDNS KNTLYLQMN SLRPEDTAL YYCAN | 18 | VPFGY YSEHF SGLSF DY | 35 | RGQGT LVTVS S |
| 4 | 501A02 | 49 | EVQLVESG GGVVQPGG SLRLSCAA SGSGFG | 39 | VNILY | 26 | WYRQA AGIER ELIA | 44 | SITSGG ITNYVD SVKG | 54 | RFTISRDNS ENTMYLQMN SLRAEDTGL YYCAS | 19 | RNIFD GTTE | 34 | WGQGT LVTVS S |
| 5 | ALB23002 | 50 | EVQLVESG GGVVQPGG SLRLSCAA SGFTFR | 40 | SFGMS | 27 | WVRQA PGKGP EWVS | 45 | SISGSGS DTLYADS VKG | 55 | RFTISRDNS KNTLYLQMN SLRPEDTAL YYCTI | 20 | GGSLS R | 36 | SSQGT LVTVS S |
| 6 | 529F10 | 51 | EVQLVESG GGVVQPGG SLRLSCAA SGFTFA | 41 | DYDYD IG | 28 | WFRQA PGKER EGVS | 46 | CISNRDG STYYADS VKG | 56 | RFTISRDNS KNTVYLQMN SLRPEDTAL YYCAV | 21 | EIHCD DYGVE NFDFP D | 34 | WGQGT LVTVS S |

TABLE A-3

Amino acid sequences of selected multivalent polypeptide ("ID" refers to the given SEQ ID NO)

| Name | ID | Amino acid sequence |
|---|---|---|
| F027400161 | 1 | DVQLVESGGGVVQPGGSLRLSCAASGRTFSSYRMGWFRQAPGKEREFVAALSGDGYSTYTANSVKGRFTISRDNSKNTVYLQMNSLR PEDTALYYCAAKLQYVSGWSYDYPYWGQGTLVTVSSGGGGSGGGGSGGGGSGGGGSGGGGSGGGGSEVQLVESGGGVVQPGG SLRLSCAASGFTFNNYAMKWVRQAPGKGLEWVSSITTGGGSTDYADSVKGRFTISRDNSKNTLYLQMNSLRPEDTALYYCANVPFGY YSEHFSGLSFDYRGQGTLVTVSSGGGGSGGGSEVQLVESGGGVVQPGGSLRLSCAASGSGFGVNILYWYRQAAGIERELIASITSGG ITNYVDSVKGRFTISRDNSENTMYLQMNSLRAEDTGLYYCASRNIFDGTTEWGQGTLVTVSSGGGGSGGGSEVQLVESGGGVVQPGG SLRLSCAASGFTFRSFGMSWVRQAPGKGPEWVSSISGSGSDTLYADSVKGRFTISRDNSKNTLYLQMNSLRPEDTALYYCTIGGSLS RSSQGTLVTVSSGGGGSGGGSEVQLVESGGGVVQPGGSLRLSCAASGFTFADYDYDIGWFRQAPGKEREGVSCISNRDGSTYYADSV KGRFTISRDNSKNTVYLQMNSLRPEDTALYYCAVEIHCDDYGVENFDFDPWGQGTLVTVSSA |

TABLE A-4

Serum albumin binding ISVD sequences ("ID" refers to the SEQ ID NO as used herein)

| Name | ID | Amino acid sequence |
|---|---|---|
| Alb8 | 57 | EVQLVESGGGLVQPGNSLRLSCAASGFTFSSFGMSWVRQAPGKGLEWVSSISG SGSDTLYADSVKGRFTISRDNAKTTLYLQMNSLRPEDTAVYYCTIGGSLSRSSQGT LVTVSS |
| Alb23 | 58 | EVQLLESGGGLVQPGGSLRLSCAASGFTFRSFGMSWVRQAPGKGPEWVSSISG SGSDTLYADSVKGRFTISRDNSKNTLYLQMNSLRPEDTAVYYCTIGGSLSRSSQG TLVTVSS |
| Alb129 | 59 | EVQLVESGGGVVQPGNSLRLSCAASGFTFSSFGMSWVRQAPGKGLEWVSSISG SGSDTLYADSVKGRFTISRDNAKTTLYLQMNSLRPEDTATYYCTIGGSLSRSSQGT LVTVSSA |
| Alb132 | 60 | EVQLVESGGGVVQPGGSLRLSCAASGFTFRSFGMSWVRQAPGKGPEWVSSIS GSGSDTLYADSVKGRFTISRDNSKNTLYLQMNSLRPEDTATYYCTIGGSLSRSSQ GTLVTVSSA |
| Alb11 | 61 | EVQLVESGGGLVQPGNSLRLSCAASGFTFSSFGMSWVRQAPGKGLEWVSSISG SGSDTLYADSVKGRFTISRDNAKTTLYLQMNSLRPEDTAVYYCTIGGSLSRSSQGT LVTVSS |

TABLE A-4-continued

Serum albumin binding ISVD sequences ("ID" refers to the SEQ ID NO as used herein)

| Name | ID | Amino acid sequence |
|---|---|---|
| Alb11 (S110K)-A | 62 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVKVSSA |
| Alb82 | 63 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSS |
| Alb82-A | 64 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSA |
| Alb82-AA | 65 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSAA |
| Alb82-AAA | 66 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSAAA |
| Alb82-G | 67 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSG |
| Alb82-GG | 68 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSGG |
| Alb82-GGG | 69 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSGGG |
| Alb23002 | 5 | EVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLSRSSQGTLVTVSS |
| Alb223 | 71 | EVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLSRSSQGTLVTVSSA |

TABLE A-5

Linker sequences ("ID" refers to the SEQ ID NO as used herein)

| Name | ID | Amino acid sequence |
|---|---|---|
| 3A linker | 72 | AAA |
| 5GS linker | 73 | GGGGS |
| 7GS linker | 74 | SGGSGGS |
| 8GS linker | 75 | GGGGSGGS |
| 9GS linker | 76 | GGGGSGGGS |
| 10GS linker | 77 | GGGGSGGGGS |
| 15GS linker | 78 | GGGGSGGGGSGGGGS |
| 18GS linker | 79 | GGGGSGGGGSGGGGSGGS |
| 20GS linker | 80 | GGGGSGGGGSGGGGSGGGGS |
| 25GS linker | 81 | GGGGSGGGGSGGGGSGGGGSGGGGS |
| 30GS linker | 82 | GGGGSGGGGSGGGGSGGGGSGGGGSGGGGS |
| 35GS linker | 83 | GGGGSGGGGSGGGGSGGGGSGGGGSGGGGSGGGGS |
| 40GS linker | 84 | GGGGSGGGGSGGGGSGGGGSGGGGSGGGGSGGGGSGGGGS |
| G1 hinge | 85 | EPKSCDKTHTCPPCP |
| 9GS-G1 hinge | 86 | GGGGSGGGSEPKSCDKTHTCPPCP |
| Llama upper long hinge region | 87 | EPKTPKPQPAAA |
| G3 hinge | 88 | ELKTPLGDTTHTCPRCPEPKSCDTPPPCPRCPEPKSCDTPPPCPRCPEPKSCDTPPPCPRCP |

TABLE A-6

Amino acid sequences of selected monospecific multivalent polypeptides ("ID" refers to the given SEQ ID NO)

| Name | ID | Amino acid sequence |
|---|---|---|
| F010700003 [F0107004B06-35GS-F0107004B02][1] | 148 | EVQLVESGGGLVQPGGSLRLSCAASGFTFNNYAMKWVRQAPGKGLEWVSSIT TGGGSTDYADSVKGRFTISRDNRKNTLYLQMNSLKPEDTAVYYCANVPFGYYSE HFSGLSFDYRGQGTLVTVSSGGGGSGGGGSGGGGSGGGGSGGGGSGGGGS GGGGSEVQLVESGGGLVQAGGSLRLSCAASGRTFSSYRMGWFRQAPGKEREF VAALSGDGYSTYTANSVNSRFTISRDNAKNTVYLQMNSLKPEDTAIYYCAAKLQ YVSGWSYDYPYWGQGTLVTVSS |
| F010700014 [F0107004B02-35GS-F0107004B02][1] | 149 | EVQLVESGGGLVQAGGSLRLSCAASGRTFSSYRMGWFRQAPGKEREFVAALS GDGYSTYTANSVNSRFTISRDNAKNTVYLQMNSLKPEDTAIYYCAAKLQYVSG WSYDYPYWGQGTLVTVSSGGGGSGGGGSGGGGSGGGGSGGGGSGGGGSG GGGSEVQLVESGGGLVQAGGSLRLSCAASGRTFSSYRMGWFRQAPGKEREFV AALSGDGYSTYTANSVNSRFTISRDNAKNTVYLQMNSLKPEDTAIYYCAAKLQY VSGWSYDYPYWGQGTLVTVSS |
| F010700029 [F0107004B02-35GS-F0107004B06][1] | 150 | EVQLVESGGGLVQAGGSLRLSCAASGRTFSSYRMGWFRQAPGKEREFVAALS GDGYSTYTANSVNSRFTISRDNAKNTVYLQMNSLKPEDTAIYYCAAKLQYVSG WSYDYPYWGQGTLVTVSSGGGGSGGGGSGGGGSGGGGSGGGGSGGGGSG GGGSEVQLVESGGGLVQPGGSLRLSCAASGFTFNNYAMKWVRQAPGKGLEW VSSITTGGGSTDYADSVKGRFTISRDNRKNTLYLQMNSLKPEDTAVYYCANVPF GYYSEHFSGLSFDYRGQGTLVTVSS |
| F010700031 [F0107004B06-35GS-F0107004B06][1] | 151 | EVQLVESGGGLVQPGGSLRLSCAASGFTFNNYAMKWVRQAPGKGLEWVSSIT TGGGSTDYADSVKGRFTISRDNRKNTLYLQMNSLKPEDTAVYYCANVPFGYYSE HFSGLSFDYRGQGTLVTVSSGGGGSGGGGSGGGGSGGGGSGGGGSGGGGS GGGGSEVQLVESGGGLVQPGGSLRLSCAASGFTFNNYAMKWVRQAPGKGLE WVSSITTGGGSTDYADSVKGRFTISRDNRKNTLYLQMNSLKPEDTAVYYCANV PFGYYSEHFSGLSFDYRGQGTLVTVSS |
| F010703842 [F0107529F10-35GS-F0107501A02][1] | 152 | EVQLVESGGGLVQAGGSLRLSCAASGFTFADYDYDIGWFRQAPGKEREGVSCI SNRDGSTYYTDSVKGRFTISSDNAKNTVSLQMNSLKPEDTAVYYCAVEIHCDDY GVENFDFDPWGQGTLVTVSSGGGGSGGGGSGGGGSGGGGSGGGGSGGGG SGGGGSEVQLVESGGGLVQAGESLRLSCAASGSGFGVNILYWYRQAAGIERELI ASITSGGITNYVDSVKGRFTISRDNAENTMYLQMNSLKAEDTGVYYCASRNIFD GTTEWGQGTLVTVSS |
| F027400016 [F0107501A02 (E1D, L11V, A14P, E16G, A41P, I43K, E44Q, A74S, E75K, M78L, K83R, A84P, G88A, V89L)*-35GS-529F10)][1] | 153 | DVQLVESGGGVVQPGGSLRLSCAASGSGFGVNILYWYRQAPGKQRELIASITSG GITNYVDSVKGRFTISRDNSKNTLYLQMNSLRPEDTALYYCASRNIFDGTTEWG QGTLVTVSSGGGGSGGGGSGGGGSGGGGSGGGGSGGGGSGGGGSEVQLVE SGGGVVQPGGSLRLSCAASGFTFADYDYDIGWFRQAPGKEREGVSCISNRDGS TYYADSVKGRFTISRDNSKNTVYLQMNSLRPEDTALYYCAVEIHCDDYGVENFD FDPWGQGTLVTVSS |
| F010700003-SO [4B06-35GS-4B02(D1E)*][1] | 154 | EVQLVESGGGVVQPGGSLRLSCAASGFTFNNYAMKWVRQAPGKGLEWVSSIT TGGGSTDYADSVKGRFTISRDNSKNTLYLQMNSLRPEDTALYYCANVPFGYYSE HFSGLSFDYRGQGTLVTVSSGGGGSGGGGSGGGGSGGGGSGGGGSGGGGS GGGGSEVQLVESGGGVVQPGGSLRLSCAASGRTFSSYRMGWFRQAPGKEREF VAALSGDGYSTYTANSVKGRFTISRDNSKNTVYLQMNSLRPEDTALYYCAAKLQ YVSGWSYDYPYWGQGTLVTVSS |
| F010700014-SO [4B02-35GS-4B02(D1E*)][1] | 155 | DVQLVESGGGVVQPGGSLRLSCAASGRTFSSYRMGWFRQAPGKEREFVAALS GDGYSTYTANSVKGRFTISRDNSKNTVYLQMNSLRPEDTALYYCAAKLQYVSG WSYDYPYWGQGTLVTVSSGGGGSGGGGSGGGGSGGGGSGGGGSGGGGSG GGGSEVQLVESGGGVVQPGGSLRLSCAASGRTFSSYRMGWFRQAPGKEREEV AALSGDGYSTYTANSVKGRFTISRDNSKNTVYLQMNSLRPEDTALYYCAAKLQY VSGWSYDYPYWGQGTLVTVSS |
| F010700029-SO [4B02-35GS-4B06][1] | 156 | DVQLVESGGGVVQPGGSLRLSCAASGRTFSSYRMGWFRQAPGKEREFVAALS GDGYSTYTANSVKGRFTISRDNSKNTVYLQMNSLRPEDTALYYCAAKLQYVSG WSYDYPYWGQGTLVTVSSGGGGSGGGGSGGGGSGGGGSGGGGSGGGGSG GGGSEVQLVESGGGVVQPGGSLRLSCAASGFTFNNYAMKWVRQAPGKGLE WVSSITTGGGSTDYADSVKGRFTISRDNSKNTLYLQMNSLRPEDTALYYCANVP FGYYSEHFSGLSFDYRGQGTLVTVSS |
| F010700031-SO [4B06-35GS-4B06][1] | 157 | EVQLVESGGGVVQPGGSLRLSCAASGFTFNNYAMKWVRQAPGKGLEWVSSIT TGGGSTDYADSVKGRFTISRDNSKNTLYLQMNSLRPEDTALYYCANVPFGYYSE HFSGLSFDYRGQGTLVTVSSGGGGSGGGGSGGGGSGGGGSGGGGSGGGGS GGGGSEVQLVESGGGVVQPGGSLRLSCAASGFTFNNYAMKWVRQAPGKGLE WVSSITTGGGSTDYADSVKGRFTISRDNSKNTLYLQMNSLRPEDTALYYCANVP FGYYSEHFSGLSFDYRGQGTLVTVSS |
| F010703842-SO [529F10-35GS-501A02][1] | 158 | EVQLVESGGGVVQPGGSLRLSCAASGFTFADYDYDIGWFRQAPGKEREGVSCI SNRDGSTYYADSVKGRFTISRDNSKNTVYLQMNSLRPEDTALYYCAVEIHCDDY GVENFDFDPWGQGTLVTVSSGGGGSGGGGSGGGGSGGGGSGGGGSGGGG |

TABLE A-6-continued

Amino acid sequences of selected monospecific multivalent polypeptides ("ID" refers to the given SEQ ID NO)

| Name | ID | Amino acid sequence |
|---|---|---|
| | | SGGGGSEVQLVESGGGVVQPGGSLRLSCAASGSGFGVNILYWYRQAAGIEREL IASITSGGITNYVDSVKGRFTISRDNSENTMYLQMNSLRAEDTGLYYCASRNIFD GTTEWGQGTLVTVSS |
| F027400016-SO [501A02-35GS-529F10][1] | 159 | EVQLVESGGGVVQPGGSLRLSCAASGSGFGVNILYWYRQAAGIERELIASITSG GITNYVDSVKGRFTISRDNSENTMYLQMNSLRAEDTGLYYCASRNIFDGTTEW GQGTLVTVSSGGGGSGGGGSGGGGSGGGGSGGGGSGGGGSGGGGSEVQLV ESGGGVVQPGGSLRLSCAASGFTFADYDYDIGWFRQAPGKEREGVSCISNRDG STYYADSVKGRFTISRDNSKNTVYLQMNSLRPEDTALYYCAVEIHCDDYGVENF DFDPWGQGTLVTVSS |

[1] [ ] indicates the monovalent building blocks and their linkage which were used for the bivalent construct.
*( ) indicates the amino acid substitutions introduced into the (parental) monovalent building block (e.g.: 4B02(D1E) means that the monovalent building block 4B02 (SEQ ID NO: 2) contains a D1E substitution).

EXAMPLES

6.1 Generation of Monovalent ISVDs Specifically Binding to IL-13 and TSLP, Respectively

6.1.1 Example 1: Immunizations

Three llamas were immunized with recombinant human IL-13 (Peprotech, cat nr 200-13, *E. coli*-derived) according to standard protocols, with the aim to induce a heavy-chain antibody dependent humoral immune response. In addition, these llamas were boosted with human/cyno IL-13 from another source (Sino Biological, cat nrs 10369-HNAC and 11057-CNAH, mammalian cell derived).

Another three llamas were immunized with recombinant hTSLP-Fc. In addition, these llamas were boosted with cyno TSLP-Fc. Two additional llamas were immunized with hTSLP alternated with cyno TSLP-Fc.

Immune blood (PBL) samples were taken at regular intervals, and total RNA was prepared from the isolated B-cells. The humoral immune response was monitored during the immunization process by comparing the antigen specific serum titers of a sample collected prior to initiation of immunization and a serum sample typically collected after multiple antigen administrations. Briefly, 96-well Maxisorp plates were coated with human IL-13 (Sino Biological, cat nr 10369-HNAC) or human TSLP. Recombinant human TSLP is commercially available, such as from R&D Systems (cat nr 1398-TS). After blocking and adding diluted serum samples, the presence of anti-IL-13 and anti-TSLP ISVDs was demonstrated by using HRP (horseradish peroxidase) conjugated goat anti-llama immunoglobulin (Bethyl Laboratories Inc.) and a subsequent enzymatic reaction in the presence of the substrate TMB (3,3',5,5'-tetramentylbenzidine).

6.1.2 Example 2: Library Construction and Phage Display Selections

Peripheral blood mononuclear cells were prepared from the blood samples using Ficoll-Hypaque according to the manufacturer's instructions. Total RNA extracted from these cells and from lymph nodes was used as starting material for RT-PCR to amplify ISVD encoding gene fragments. These fragments were cloned into phagemid vector pAX212. Phage was prepared according to standard protocols (Antibody Phage Display: Methods and Protocols (First Edition, 2002, O'Brian and Aitken eds., Humana Press, Totowa, NJ) and stored after filter sterilization at 4° C. until further use. Five phage libraries were constructed for IL13, with library sizes between $6.1 \times 10^8$ and $1.3 \times 10^9$, and a percentage of insert ranging from 87 to 96%. Five phage libraries were constructed for TSLP, with library sizes between $4.2 \times 10^8$ and $9.8 \times 10^8$, and a percentage of insert ranging from 91 to 100%.

To identify ISVDs recognizing human and cyno IL-13, the phage libraries were incubated with 50 nM soluble biotinylated hIL13-Fc in presence of IgG from human serum (Sigma, 14506). Complexes of hIL-13-Fc and phage were captured from solution on streptavidin coated magnetic beads. After extensive washing with PBS/0.05% Tween20, bound phage were eluted by addition of trypsin (1 mg/ml). Outputs of these round 1 selections were incubated with 0.05, 0.5 or 5 nM soluble biotinylated hIL-13-Fc or cyno IL-13-Fc. Not enriched outputs from the round 2 selections were further incubated with a 0.005, 0.05, 0.5 or 5 nM soluble biotinylated human or cyno IL-13-Fc in round 3. Individual clones from enriched round 2 and round 3 selections were picked.

To identify ISVDs recognizing human and cyno TSLP, the phage libraries were incubated with 50 nM soluble biotinylated hTSLP-Fc in presence of IgG from human serum (Sigma, 14506) or with 500 nM biotinylated hTSLP or with 500 nM biotinylated cyno TSLP. The human and cyno TSLP sequences are known (Uniprot accession Uniprot accession Q969D9 and NCBI RefSeq XP_005557555.1, respectively). Recombinant protein was used to perform the assay. Complexes of TSLP and phage were captured from solution on streptavidin coated magnetic beads. After extensive washing with PBS/0.05% Tween20, bound phage were eluted by addition of trypsin (1 mg/ml). Outputs of these round 1 selections were incubated with 5 nM soluble biotinylated hILTSLP-Fc or cyno TLSP-Fc or 0.5 nM biotinylated hTSLP. Outputs from the round 2 selections were incubated with 0.05, 0.5 or 5 nM soluble biotinylated human TSLP, TSLP-Fc or cyno TSLP-Fc. From each round individual clones from the enriched outputs were picked.

All individual clones were grown in 96 deep well plates (1 ml volume). ISVD expression was induced by adding IPTG to a final concentration of 1 mM. Periplasmic extracts were prepared by freezing the cell pellets and dissolving them in 100 μl PBS. Cell debris was removed by centrifugation.

As a control, selected periplasmic extracts were screened in an ELISA for binding to human and cyno IL13-Fc, respectively TSLP-Fc. The assessment was performed in a Spectraplate 384-HB (PerkinElmer) in a 25 μl format. The antigens were coated overnight at 1 μg/ml in PBS at 4° C. Wells were blocked with a casein solution (1%). After addition of a 5-fold dilution of peri plasmic extracts, ISVD binding was detected using mouse anti-Flag-HRP (Sigma) and a subsequent enzymatic reaction in the presence of substrate esTMB (3,3',5,5'-tetramentylbenzidine).

6.1.3 Example 3: Screening for Blocking ISVDs in Periplasmic Extracts by AlphaScreen Assays Using Human IL13 and Human TSLP In order to determine the blocking capacity of the ISVDs, crude periplasmic extracts were screened in different protein-based competition assays using the AlphaScreen technology (PerkinElmer, Waltham, MA USA). Fluorescence was measured using the EnVision Multilabel Plate Reader (PerkinElmer) using an excitation wavelength of 680 nm and an emission wavelength of 520 nm.

In the hIL-13:hIL-13Rα1 binary complex AlphaScreen, it was investigated if ISVDs could block the interaction between hIL-13 and the hIL-13Rα1 extracellular domain. To this end, dilutions of the periplasmic extracts were pre-incubated with biotinylated hIL-13 (Peprotech cat nr 200-13). To this mixture, hIL-13Rα1-hFc (R&D systems; cat nr 146-IR) and anti hFc-coupled Acceptor beads were added and further incubated for 1 hour at room temperature, followed by addition of streptavidin-coupled Donor beads and an additional 1-hour incubation. When the binary complex is formed, Acceptor and Donor beads are brought into proximity and upon laser excitation a detectable signal is generated. Decrease in the AlphaScreen signal indicates that the binding of biotinylated hIL-13 to hIL-13Rα1 is blocked by the ISVD present in the periplasmic extract. In a similar set-up it was investigated if ISVDs could block the interaction between hTSLP (eBioscience, cat nr 10-8499) and the hTSLPR extracellular domain (R&D systems cat nr 981-TR).

In the hIL-13:hIL-13Rα1:hIL4Rα ternary complex AlphaScreen, it was screened if ISVDs could block the recruitment of hIL4Rα to the hIL13:hIL13Rα1 binary complex. hIL-13 binds to hIL-13Rα1 and this binary complex recruits hIL4Rα, resulting in formation of the ternary complex hIL-13:hIL-13Rα1:hIL4Rα. Dilutions of the periplasmic extracts were pre-incubated with hIL-13 (Peprotech cat nr 200-13) and biotinylated huIL4Rα (R&D Systems; cat nr 230-4R/CF). To this mixture, hIL-13Rα1-hFc (R&D systems; cat nr 146-IR) and anti hFc-coupled Acceptor beads were added and further incubated for 1 hour at room temperature, followed by addition of streptavidin-coupled Donor beads and an additional 1-hour incubation. When the ternary complex is formed, Acceptor and Donor beads are brought into proximity and upon laser excitation a detectable signal is generated. Decrease in the AlphaScreen signal indicates that the formation of the ternary complex is blocked by the ISVD present in the periplasmic extract. Similarly, it was investigated if ISVDs could block the formation of the hTSLP:hTSLPR:hIL7Rα complex (hIL7Rα source=Sino Biological cat nr 1095-H08H).

Based on the Alphascreen analysis (Table 3 and Table 4), a number of blocking ISVDs were selected and sequenced (Table 1 and Table 2).

TABLE 1

Amino acid sequences of functional anti-IL-13 ISVDs.

| ISVD ID | SEQUENCE |
|---|---|
| F0107004B02 (SEQ ID NO: 144) | EVQLVESGGGLVQAGGSLRLSCAASGRTFSS YRMGWFRQAPGKEREFVAALSGDGYSTYTAN SVNSRFTISRDNAKNTVYLQMNSLKPEDTAI YYCAAKLQYVSGWSYDYPYWGQGTLVTVSS |
| F0107004B06 (SEQ ID NO: 145) | EVQLVESGGGLVQPGGSLRLSCAASGFTFNN YAMKWVRQAPGKGLEWVSSITTGGGSTDYAD SVKGRFTISRDNRKNTLYLQMNSLKPEDTAV YYCANVPFGYYSEHFSGLSFDYRGQGTLVTV SS |

TABLE 2

Amino acid sequences of functional anti-TSLP ISVDs.

| ISVD ID | SEQUENCE |
|---|---|
| F0107501A02 (SEQ ID NO: 146) | EVQLVESGGGLVQAGESLRLSCAASGSGFGVN ILYWYRQAAGIERELIASITSGGITNYVDSVK GRFTISRDNAENTMYLQMNSLKAEDTGVYYCA SRNIFDGTTEWGQGTLVTVSS |
| F0107529F10 (SEQ ID NO: 147) | EVQLVESGGGLVQAGGSLRLSCAASGFTFADY DYDIGWFRQAPGKEREGVSCISNRDGSTYYTD SVKGRFTISSDNAKNTVSLQMNSLKPEDTAVY YCAVEIHCDDYGVENFDFDPWGQGTLVTVSS |

6.1.4 Example 4: Surface Plasmon Resonance Analysis of Periplasmic Extracts on IL13 and TSLP Off-rates of the periplasmic extracts containing anti-IL13 or anti-TSLP ISVDs were measured by Surface Plasmon Resonance (SPR) using a Proteon XPR36 instrument (Bio-Rad Laboratories, Inc.). Phosphate buffered saline (PBS), pH7.4 supplemented with 0.005% Tween20 was used as running buffer and the experiments were performed at 25° C.

hIL13-Fc, cyno IL13-Fc, hTSLP-Fc and cyno TSLP-Fc were immobilized on ProteOn GLC Sensor Chips by amine coupling using EDC and NHS at flow rate 30 μl/min for activation. IL13 proteins were injected at 10 μg/ml in ProteOn Acetate buffer at pH5.0. TSLP proteins were injected at 5 μg/mL in ProteOn Acetate Buffer at pH5.5. After immobilization, surfaces were deactivated with ethanolamine.

Periplasmic extracts of the ISVD candidates were diluted 10 times in PBS-Tween20 (0.1%) and injected for 2 minutes at 45 μl/min and allowed to dissociate for 900 seconds. Between different samples, the surfaces were regenerated with a 2 minute injection of Phosphoric Acid (0.425%) at 45 μl/min, in case of IL13, or with a 1 minute injection of Glycine pH3.0 (5 mM)/SDS(0.25%) at 45 μL/min, in case of TSLP. From the sensorgrams obtained for the different periplasmic extracts off-rates were calculated.

Off-rate analysis on hIL-13-Fc and cyno IL-13-Fc is shown in Table 3.

TABLE 3

Summary of the screening results of anti-IL-13 ISVDs F0107004602 and F0107004606.

| ISVD ID | IL-13-IL-13Rα1 AlphaScreen (% inhibition) | IL13-IL-13Rα1-IL4Rα AlphaScreen (% inhibition) | $k_{off}$ hIL-13-Fc (1/s) | $k_{off}$ cyno IL-13-Fc (1/s) |
|---|---|---|---|---|
| F0107004602 | 37 | 61 | 1.7E−03 | 1.1E−03 |
| F0107004606 | 21 | 66 | 6.3E−03 | 8.9E−03 |

Off-rate analysis on hTSLP-Fc and cyno TSLP-Fc is shown in Table 4.

TABLE 4

Summary of the screening results of anti-TSLP ISVDs F0107501A02 and F0107529F10.

| ISVD ID | TSLP-TSLPR AlphaScreen (% inhibition) | TSLP-TSLPR-IL7Rα AlphaScreen (% inhibition) | $k_{off}$ hTSLP-Fc (1/s) | $k_{off}$ cyno TSLP-Fc (1/s) |
|---|---|---|---|---|
| F0107501A02 | 92 | 97 | 3.6E−05 | 6.6E−04 |
| F0107529F10 | 99 | 99 | <5E−05 | 1.8E−03 |

6.1.5 Example 5: Expression and Purification of Anti-IL-13 and Anti-TSLP ISVDs Anti-IL-13 ISVDs and anti-TSLP ISVDs were selected for expression and purification, based on their blocking capacity in AlphaScreen assays and off-rate values. Sequences are shown in Tables 1 and 2.

ISVDs were expressed in *E. coli* TG1 cells as c-myc, His6-tagged proteins. Expression was induced by addition of 1 mM IPTG and allowed to continue for 3 h at 37° C. After spinning the cell cultures, periplasmic extracts were prepared by freeze-thawing the pellets and resuspension in dPBS. These extracts were used as starting material for immobilized metal affinity chromatography (IMAC) using Nickel Sepharose™ 6 FF columns (Atoll). ISVDs were eluted from the column with 250 mM imidazole and subsequently desalted towards dPBS. For the cell-based assays described below, endotoxins were removed by gel filtration in the presence of 50 mM Octylβ-D-glucopyranoside (OGP, Sigma). Endotoxin levels were determined using a standard LAL-assay.

6.1.6 Example 6: Blocking Capacity of Purified Anti-IL13 and Anti-TSLP ISVDs in AlphaScreen Assays The binary and ternary complex AlphaScreen assays, as described in example 3, were used to determine the IC50 values of the anti-IL-13 and anti-TSLP ISVDs, purified as described in Example 5. Instead of dilutions of the periplasmic extracts, a dilution series of each purified ISVD starting from 500 nM down to 1.8 pM was pre-incubated with IL-13 or TSLP.

The tested anti-IL-13 ISVDs inhibited the formation of the ternary complex and partially blocked the binary complex with IC50 values as shown in Table 5.

TABLE 5

IC50 values for the blocking anti-IL13 ISVDs as determined in the binary and ternary complex AlphaScreen assays.

| | IL-13-IL-13Rα1 AlphaScreen | | IL-13-IL-13Rα1-IL4Rα AlphaScreen | |
|---|---|---|---|---|
| ISVD ID | IC50 (M) | % Inhibition | IC50 (M) | % Inhibition |
| F0107004602 | 4.0E−09 | 82 | 1.7E−09 | 100 |
| F0107004606 | 6.1E−08 | 55 | 6.7E−09 | 100 |

The tested anti-TSLP ISVDs fully inhibited the formation of the ternary complex, and also inhibited the formation of the binary complex, with IC50 values as shown in Table 6.

TABLE 6

IC50 values for the blocking anti-TSLP ISVDs as determined in the binary and ternary complex AlphaScreen assays.

| | TSLP-TSLPR AlphaScreen | | TSLP-TSLPR-IL7Rα AlphaScreen | |
|---|---|---|---|---|
| ISVD ID | IC50 (M) | % Inhibition | IC50 (M) | % Inhibition |
| F0107501A02 | 3.00E−10 | 97 | 3.50E−10 | 100 |
| F0107529F10 | 1.30E−11 | 100 | 1.80E−10 | 100 |

6.1.7 Example 7: Blocking Capacity of Purified Anti-IL-13 and Anti-TSLP ISVDs in Cell—Based Assays The inhibitory potency of the anti-IL-13 ISVDs was determined in a cell-based assay monitoring IL-13 mediated proliferation of TF-1 cells. To this end, TF-1 cells were cultured in RPMI 1640 medium with the addition of ⅕ HEPES, ¹⁄₅₀₀ Na-Pyruvate, ¹⁄₅₀₀ Glutamax and 2 ng/mL recombinant human GM-CSF. TF-1 cells were seeded at 40.000 cells per well in growth medium w/o GM-CSF. A dilution series of the purified anti-IL-13 ISVDs or reference compounds was added. After 15 min incubation at 37° C., 200 pM of IL-13 (Peprotech cat nr 200-13) was added. After 96 hours, proliferation of the TF-1 cells was determined with Cell Titer 96 Aqueous One Solution (Promega #G3580) on an EnVision Multilabel Reader (Perkin Elmer).

The ISVDs shown in Table 7 inhibit IL-13-induced TF1 proliferation.

TABLE 7

Overview of IC50 values of anti-IL-13 monovalent ISVDs in IL-13-induced TF-1 proliferation assay.

| compound | IC50 (M) |
|---|---|
| F0107004602 | 2.7E−08 |
| F0107004606 | 1.0E−05 |
| anti-hIL-13 reference mAb2 | 4.1E−10 |
| anti-hIL-13 reference mAb3 | 9.2E−11 |
| anti-hIL-13 reference mAb1 | 2.2E−11 |

The blocking potency of the anti-TSLP ISVDs was determined in a cell-based assay monitoring TSLP mediated proliferation of BaF3 cells transfected with plasmids encoding hTSLPR and hIL7Rα. Cells were seeded at a density of 20.000 cells/well in RPMI 1640 growth medium in cell culture treated white 96 well plates. A dilution series of anti-TSLP ISVDs were added, followed by addition of 50 pM hTLSP-Fc or 50 pM cyno TSLP-Fc for stimulation of the cells. The human and cyno TSLP sequences are known (Uniprot accession Uniprot accession Q969D9 and NCBI RefSeq XP_005557555.1, respectively). Recombinant protein was used to perform the assay.

After incubation for 72 hours, cell density and viability was monitored using the CellTiter-Glo® Luminescent Cell Viability Assay (Promega, G7571/G7572/G7573) and read-out on an EnVision Multilabel Reader (Perkin Elmer). Results are shown in Table 8.

TABLE 8

Potency and efficacy of anti-TSLP monovalent ISVDs in TSLP-induced BaF3 cell proliferation assay.

| ISVD ID | IC50 (M) hTSLP-Fc | % inhibition hTSLP-Fc | IC50 (M) cyno TSLP-Fc | % inhibition cyno TSLP-Fc |
|---|---|---|---|---|
| F0107501A02 | >1.0E−06 | 46 | >1.0E−06 | 10 |
| F0107529F10 | ND | ND | ND | ND |

ND = not determined

6.1.8 Example 8: Binding Affinity of Purified Anti-IL-13 and Anti-TSLP ISVDs to Human and Cyno IL-13 and TSLP Full binding kinetic study by SPR was performed on a BIAcore T100 instrument (GE Healthcare).

For IL-13, around 2000 RU of hIL13-Fc or 4000 RU cyno IL13-Fc was immobilized directly on a CM5 sensor chip. The ISVDs were then injected at different concentrations (between 3 μM and 12 nM) for 120s and allowed to dissociate for 900s. Regeneration of the hIL-13-Fc and cyno IL-13-Fc surfaces were performed using a 47s injection of 0.85% $H_3PO_4$:MilliQ (1:1).

For TSLP, around 8000 RU of anti-huIgG antibody (GE Healthcare) was immobilized directly on a CM5 sensor chip. hTSLP-Fc (at 1 μg/mL) or cyno TSLP-Fc (at 0.75 μg/mL) were floated and captured for 120s over the chip. The ISVDs were then injected at different concentrations (between 0.4 nM and 3000 nM) for 120s and allowed to dissociate for 900s.

Evaluation of the binding curves was done using BIAcore T100 Evaluation software V2.0.3. Kinetic analysis was performed by fitting a 1:1 interaction model (Langmuir binding) (Rmax=global; RI=constant=0, offset=0). Interactions which could not meet the acceptance criteria for the 1:1 interaction model, were fitted using the heterogeneous ligand fit model (RI=constant=0, offset=0).

Kinetic data are shown in Table 9 for IL-13 ISVDs and in Table 10 for TSLP ISVDs.

TABLE 9

KD determination of monovalent anti-IL13 ISVDs via SPR.

| Sample | Surface | % major interaction present | $k_a$ (1/Ms) | $k_d$ (1/s) | $K_D$ (M) | Model used for fitting of binding curves |
|---|---|---|---|---|---|---|
| F0107004B02 | hIL13-Fc | 80 | 2.2E+04 | 2.4E−02 | 1.1E−06 | heterogeneous ligand fit |
|  | cyno IL13-Fc | 81 | 1.8E+04 | 3.4E−02 | 1.9E−06 | heterogeneous ligand fit |

TABLE 10

KD determination of monovalent anti-TSLP ISVDs via SPR.

| | hTSLP-Fc | | | cyno TSLP-Fc | | |
|---|---|---|---|---|---|---|
| ID | $k_a$ (1/Ms) | $k_d$ (1/s) | $K_D$ (M) | $k_a$ (1/Ms) | $k_d$ (1/s) | $K_D$ (M) |
| F0107501A02 | 1.1E+05 | 5.7E−05 | 5.1E−10 | 7.3E+04 | 1.8E−03 | 2.5E−08 |
| F0107529F10 | 1.2E+07 | 4.2E−04 | 3.5E−11 | 8.7E+05 | 1.5E−03 | 1.7E−09 |

6.2 Generation of Monospecific Multivalent Polypeptides Binding to IL-13 and TSLP, Respectively

6.2.1 Example 10: Generation and In Vitro Characterization of Wild-Type Anti-IL-13 Bivalent or Biparatopic ISVD Constructs The selected anti-IL-13 ISVDs (F0107004B02 and F0107004B06) were formatted into biparatopic and bivalent ISVD constructs. The building blocks in the constructs are genetically linked by a flexible 35GS (GlySer) linker. ISVDs were expressed as FLAG3-HIS6-tagged protein in *Pichia pastoris* (amino acid sequences are shown in Table 14). Induction of ISVD construct expression occurred by stepwise addition of methanol. Clarified medium with secreted ISVD construct was used as starting material for immobilized metal affinity chromatography (IMAC) followed by desalting resulting in 90% purity as assessed by SDS-PAGE.

The biparatopic and bivalent IL-13 constructs were characterised in the binary and ternary complex blocking AlphaScreen assays (as described in example 6) as well as in the TF-1 proliferation assay (as described in example 7). An overview of the generated constructs and their blocking potencies in the binary and ternary AlphaScreen assay and in the TF-1 proliferation assay is shown in Table 11. The biparatopic construct displays excellent potencies against hIL-13 and cyIL-13, similar to the potency of anti-hIL-13 reference mAb1. Also bivalent constructs improve in potency, but not to the same extent as the biparatopic construct F010700029 in the TF1 proliferation assay. In addition, the bivalent constructs do not reach full inhibition in the IL13-IL13Rα1 Alphascreen.

TABLE 11

Overview of potency of different anti-IL-13 constructs in the Alphascreen assays and of potency and efficacy in the TF-1 proliferation assay. ND = not determined

| | | IL13-IL13Rα1 | | IL13-IL13Rα1-IL4Rα | | TF1 proliferation assay IC50 (M) | |
|---|---|---|---|---|---|---|---|
| | | AlphaScreen | | AlphaScreen | | 200 pM | |
| ISVD construct ID | ISVD construct description | IC50 (M) | % inhibition | IC50 (M) | % inhibition | 200 pM hIL13 | cyno IL13 |
| F010700003 | F0107004B06-35GS-F0107004B02 | 1.3E−10 | 99 | 3.40E−09 | 100 | 1.20E−08 | ND |
| F010700014 | F0107004B02-35GS-F0107004B02 | 2.7E−10 | 84 | 4.80E−09 | 98 | 9.40E−08 | ND |
| F010700029 | F0107004B02-35GS-F0107004B06 | 3.1E−10 | 99 | 3.00E−09 | 100 | 2.00E−11 | 2.50E−10 |
| F010700031 | F0107004B06-35GS-F0107004B06 | No fit | partial | 6.60E−10 | 99 | 1.00E−07 | ND |
| anti-hIL-13 reference mAb1 | | ND | ND | ND | ND | 1.50E−11 | 1.30E−10 |

The most potent anti-IL-13 biparatopic ISVD construct was tested in the IL-13 induced A549 eotaxin release assay. To this end A549 suspension cells were cultured in Ham's F12K medium supplemented with 10% FCS. Cells were seeded into a 96 well plate at 200.000 cells/well. The next day 200 pM hIL-13 (Sino Biological cat nr 10369-HNAC) or cyno IL-13 (Sino Biological cat nr 11057-CNAH) were added, followed by a dilution series of the ISVD constructs. After 24 h, Eotaxin-3 was determined in the supernatants using the MSD ELISA (Human Eotaxin-3 Tissue Culture Kit (Meso Scale, K151ABB-1)). Results are shown in Table 12.

TABLE 12

Potency of F010700029 in the IL-13-mediated Aa549 eotaxin release assay. Inhibition was 100%.

| ISVD construct ID | ISVD construct description | IC50 (M) hIL-13 | IC50 (M) cyno IL-13 |
|---|---|---|---|
| F010700029 | F0107004602-35GS-F0107004606 | 2.10E−10 | 1.50E−10 |
| anti-h1L-13 reference mAb1 | | 8.00E−11 | 7.00E−11 |

Competition ELISA was used to test if anti-IL-13 monovalent and biparatopic ISVD constructs inhibit binding of hIL-13 to IL13Rα2. IL13Rα2 (SinoBiological cat nr 10350-H08H) was coated on a 384 well Spectraplate (Perkin Elmer). hIL13-Fc (SinoBiological, cat nr 10369-H01H) was mixed with serial dilutions of ISVD constructs or positive control compound IL-13Rα2 and incubated for 1 hour. After washing and blocking, the coated receptor was incubated with the IL13-Fc ISVD/control mix and incubated for 1 hour. After washing, the presence of bound IL-13-Fc was detected using anti-human IgG-peroxidase antibody and a subsequent enzymatic reaction in the presence of substrate esTMB. In the case the ISVD inhibits the IL-13-IL-13Rα2 interaction, detection of IL-13-Fc disappears in a dose dependent manner. Results are shown in Table 13.

TABLE 13 capacity of anti-IL-13 monovalent and biparatopic ISVD constructs to inhibit IL-13-IL-13Rα2 complex formation in a competition ELISA

| Compound | construct description | % inhibition of IL13-IL13Rα2 complex formation | IC50 (M) |
|---|---|---|---|
| F010704602 | — | 37 | 4.9E−08 |
| F010704606 | — | 49 | No fit |
| F027100271 | F0107004602-9GS-ALB23002-9GS-F0107004606 | 53 | No fit |
| IL-13Rα2 | — | 100 | 7.9E−09 |

TABLE 14

Amino acids sequences of wild-type anti-IL13 biparatopic and bivalent ISVD constructs.

| ISVD construct ID | ISVD construct description | Sequence |
|---|---|---|
| F010700003 (SEQ ID NO: 148) | F0107004B06-35GS-F0107004B02 | EVQLVESGGGLVQPGGSLRLSCAASGFTFNNYAMKWVRQAPGKGLEWVSSITTGGGSTDYADSVKGRFTISRDNRKNTLYLQMNSLKPEDTAVYYCANVPFGYYSEHFSGLSFDYRGQGTLVTVSSGGGGSGGGGSGGGGSGGGGSGGGGSGGGGSGGGGSEVQLVESGGGLVQAGGSLRLSCAASGRTFSSYRMGWFRQAPGKEREFVAALSGDGYSTYTANSVNSRFTISRDNAKNTVYLQMNSLKPEDTAIYYCAAKLQYVSGWSYDYPYWGQGTLVTVSS |
| F010700014 (SEQ ID NO: 149) | F0107004B02-35G5-F0107004B02 | EVQLVESGGGLVQAGGSLRLSCAASGRTFSSYRMGWFRQAPGKEREFVAALSGDGYSTYTANSVNSRFTISRDNAKNTVYLQMNSLKPEDTAIYYCAAKLQYVSGWSYDYPYWGQGTLVTVSSGGGGSGGGGSGGGGSGGGGSGGGGSGGGGSGGGGSEVQLVESGGGLVQAGGSLRLSCAASGRTFSSYRMGWFRQAPGKEREFVAALSGDGYSTYTANSV |

TABLE 14-continued

Amino acids sequences of wild-type anti-IL13 biparatopic and bivalent ISVD constructs.

| ISVD construct ID | ISVD construct description | Sequence |
|---|---|---|
| | | NSRFTISRDNAKNTVYLQMNSLKPEDTAIYYCAAKLQYVSGWSYDYPYWGQGTLVTVSS |
| F010700029 (SEQ ID NO: 150) | F0107004B02-35G5-F0107004B06 | EVQLVESGGGLVQAGGSLRLSCAASGRTFSSYRMGWFRQAPGKEREFVAALSGDGYSTYTANSVNSRFTISRDNAKNTVYLQMNSLKPEDTAIYYCAAKLQYVSGWSYDYPYWGQGTLVTVSSGGGGSGGGGSGGGGSGGGGSGGGGSGGGGSGGGGSEVQLVESGGGLVQPGGSLRLSCAASGFTFNNYAMKWVRQAPGKGLEWVSSITTGGGSTDYADSVKGRFTISRDNRKNTLYLQMNSLKPEDTAVYYCANVPFGYYSEHFSGLSFDYRGQGTLVTVSS |
| F010700031 (SEQ ID NO: 151) | F0107004B06-35G5-F0107004B06 | EVQLVESGGGLVQPGGSLRLSCAASGFTFNNYAMKWVRQAPGKGLEWVSSITTGGGSTDYADSVKGRFTISRDNRKNTLYLQMNSLKPEDTAVYYCANVPFGYYSEHFSGLSFDYRGQGTLVTVSSGGGGSGGGGSGGGGSGGGGSGGGGSGGGGSEVQLVESGGGLVQPGGSLRLSCAASGFTFNNYAMKWVRQAPGKGLEWVSSITTGGGSTDYADSVKGRFTISRDNRKNTLYLQMNSLKPEDTAVYYCANVPFGYYSEHFSGLSFDYRGQGTLVTVSS |

6.2.2 Example 11: Generation and Characterization of Wild-Type Biparatopic Anti-TSLP ISVD Constructs The selected TSLPR blockers (F0107501A02 and F0107529F10) were combined into biparatopic ISVD constructs. The constructs were expressed as FLAG3-HIS6-tagged protein in *Pichia pastoris* (amino acid sequences are shown in Table 16). Induction of ISVD construct expression occurred by stepwise addition of methanol. Clarified medium with secreted ISVD construct was used as starting material for immobilized metal affinity chromatography (IMAC) followed by desalting resulting in 90% purity as assessed by SDS-PAGE.

The biparatopic constructs were titrated as purified proteins against 50 or 5 pM hTSLP and 50 or 5 pM cyno TSLP in the BaF3 proliferation assay (as described in example 7) and compared to different anti-TSLP reference compounds (anti-hTSLP reference mAb2 and anti-hTSLP reference mAb1). The data is summarized in Table 15 (hTSLP and cyno TSLP). The biparatopic constructs clearly outperform the reference mAbs. The biparatopic construct with F0107501A02 at the N-terminus shows improved reactivity towards cyno TSLP compared to the construct with F0107501A02 at the C-terminus.

TABLE 15

Overview of IC50 values (M) of different biparatopic anti-TSLP formats in the human and cyno TSLP, respectively, mediated BaF3 proliferation assay.

| ISVD construct ID | ISVD construct description | IC50 (M) hTSP | IC50 (M) cyno TSLP | Conc TSLP used for stimulation (pM) |
|---|---|---|---|---|
| F010703842 | F0107529F10-35GS-F0107501A02 | 4.8E−11 | 3.9E−09 | 50 |
| F027400016 | F0107501A02 (E1D, L11V, A14P, E16G, A41P, I43K, E44Q, A74S, E75K, M78L, K83R, A84P, G88A, V89L)*-35GS-529F10 | 4.6E−12 | 6.0E−11 | 5 |
| anti-hTSLP reference mAb2 | | 1.6E−10 | >1.0E−07 | 50 |
| anti-hTSLP reference mAb1 | | 5.5E−10 | 3.8E−09 | 5 |

*( ) indicates the amino acid substitutions introduced into the (parental) monovalent building block.

TABLE 16

Amino acids sequences of biparatopic anti-TSLP ISVD constructs F010703842 and F027400016.

| ISVD construct ID | ISVD construct description | Sequence |
|---|---|---|
| F010703842 (SEQ ID NO: 152) | F0107529F10-35GS-F0107501A02 | EVQLVESGGGLVQAGGSLRLSCAASGFTFADYDYDIGWFRQAPGKEREGVSCISNRDGSTYYTDSVKGRFTISSDNAKNTVSLQMNSLKPEDTAVYYCAVEIHCDDYGVENFDFDPWGQGTLVTVSSGGGGSGGGGSGGGGSGGGGSGGGGSGGGGSGGGGSEVQLVESGGGLVQAGESLRLSCAASGSGFGVNILYWYRQAAGIERELIASITSGGITNYVDSVKGRFTISRDNAENTMYLQMNSLKAEDTGVYYCASRNIFDGTTEWGQGTLVTVSS |
| F027400016 (SEQ ID NO: 153) | F0107501A02 (E1D, L11V, A14P, E16G, A41P, I43K, E44Q, A74S, E75K, M78L, K83R, A84P, G88A, V89L)*-35GS-529F10 | DVQLVESGGGVVQPGGSLRLSCAASGSGFGVNILYWYRQAPGKQRELIASITSGGITNYVDSVKGRFTISRDNSKNTLYLQMNSLRPEDTALYYCASRNIFDGTTEWGQGTLVTVSSGGGGSGGGGSGGGGSGGGGSGGGGSGGGGSEVQLVESGGGVVQPGGSLRLSCAASGFTFADYDYDIGWFRQAPGKEREGVSCISNRDGSTYYADSVKGRFTISRDNSKNTVYLQMNSLRPEDTALYYCAVEIHCDDYGVENFDFDPWGQGTLVTVSS |

*( ) indicates the amino acid substitutions introduced into the (parental) monovalent building block.

6.3 Sequence Optimization of the Anti-IL-13 and Anti-TSLP Monovalent ISVDs

6.3.1 Example 12: Sequence Optimization of Anti-IL-13 and Anti-TSLP Monovalent ISVDs Anti-IL-13 ISVDs F0107004B02 and F0107004B06 and anti-TSLP ISVDs F0107501A02 and F0107529F10 were further sequence optimized.

Sequence optimization involves replacing one or more specific amino acid residues in the sequence in order to improve one or more (desired) properties of the ISVDs.

Some examples of such sequence optimization are mentioned in the further description herein and for example include, without limitation:

1) Substitutions in parental wild type ISVD sequences to yield ISVD sequences that are more identical to the human VH3-JH germline consensus sequences, a process called humanization. To this end, specific amino acids, with the exception of the so-called hallmark residues, in the FRs that differ between the ISVD and the human VH3-JH germline consensus are altered to the human counterpart in such a way that the protein structure, activity and stability are kept intact.
2) Substitutions towards the llama germline to increase the stability of the ISVD, which is defined as camelisation. To this end, the parental wild type ISVD amino acid sequence is aligned to the llama IGHV germline amino acid sequence of the ISVD (identified as the top hit from a BlastP analysis of the ISVD against the llama IGHV germlines).
3) Substitutions that improve long-term stability or properties under storage, substitutions that increase expression levels in a desired host cell or host organism, and/or substitutions that remove or reduce (undesired) post-translational modification(s) (such as glycosylation or phosphorylation), again depending on the desired host cell or host organism. To avoid N-terminal pyroglutamate formation, standardly an E1D mutation is introduced in the N-terminal building block of a multivalent Nb, without impact on potency or stability. During sequence optimization of the building blocks, the E1D mutation is therefore not consistently introduced.
4) Mutations on position 11 towards Val and on position 89 towards Leu to minimize the binding of any naturally occurring pre-existing antibody activity.

F0107004B02 and F0107004B06

Sequence optimisation of anti-IL-13 ISVD F0107004B02 resulted in a final sequence optimised variant F027100019, which comprises 8 amino acid substitutions (i.e. E1D, L11V, A14P, N64K, S65G, A74S, K83R, I89L) compared to the parental ISVD F107004B02. Sequence optimisation of anti-IL-13 ISVD F0107004B06 resulted in a final sequence optimised variant F027100183, which comprises 4 amino acid substitutions (i.e. L11V, R74S, K83R, V89L) compared to the parental ISVD F107004B06.

The sequence optimised variants were assembled from oligonucleotides using a PCR overlap extension method. The variants were expressed in E. coli and purified by IMAC and desalting. F027100019 and F027100183 were evaluated for their hIL-13 binding capacity by surface plasmon resonance, using hIL-13 from Peprotech (cat nr 200-13). Additionally, F027100019 was tested for its neutralizing activity in the eotaxin release assay. Monomeric behavior of both variants was monitored by Size Exclusion-HPLC (SE-HPLC). Thermal stability of the variants was tested in a thermal shift assay (TSA) using the Lightcycler (Roche). In this assay, the parental ISVDs and their variants are incubated at different pH's in the presence of sypro orange and a temperature gradient is applied. When the ISVDs start denaturing, sypro orange binds and the measured fluorescence increases suddenly, as such a melting temperature can be determined for a certain pH. Results are summarized in Table 17 and Table 18.

TABLE 17 results of the analysis of the sequence optimization variant F027100019 of anti-IL-13 ISVD F0107004B02. nd = not determined, * measured on hIL-13-Fc

| ISVD ID | Mutation(s) | IC50 (nM) Eotaxin release assay | Kon hIL-13 (1/Ms) | Koff hIL-13 (1/s) | KD hIL-13 (M) | Tm (° C.) at pH 7 TSA | SE-HPLC % main peak |
|---|---|---|---|---|---|---|---|
| F0107004B02 | WT | nd | 2.20E+04* | 2.40E−02* | 1.10E−06* | 67 | 94 |
| F027100019 | E1D, L11V, A14P, N64K, S65G, A74S, K83R, I89L | 47 | 3.50E+04 | 1.20E−03 | 3.40E−08 | 70 | 100 |

F027100019 exhibited good potency in the Eotaxin release assay and its affinity to hIL-13 was determined to be 34 nM in SPR. The Tm of F027100019 is 3° C. higher than for the parental ISVD F0107004B2. The % framework identity in the framework regions for F027100019 is 85% based on the AbM definition (see Antibody Engineering, Volt by Kontermann & Dübel (Eds), Springer Verlag Heidelberg Berlin, 2010) and 86% based on the Kabat definition.

TABLE 18 results of the analysis of the sequence optimization variant of anti-IL13 ISVD F0107004B06. Nd = not determined

| ISVD ID | Mutation(s) | Kon hIL-13 (1/Ms) | Koff hIL-13 (1/s) | KD hIL-13 (M) | Tm (° C.) at pH 7 TSA | SE-HPLC % main peak |
|---|---|---|---|---|---|---|
| F0107004B06 | WT | 2.50E+05 | 3.30E−03 | 2.60E−08 | nd | nd |
| F027100183 | L11V, R74S, K83R, V89L | 2.80E+05 | 7.50E−03 | 2.70E−08 | 61 | 100 |

Affinity of F027100183 is similar compared to the WT sequence and the variant has a Tm of 61° C. The variant elutes as a 100% monomeric peak on SE-HPLC. The % framework identity in the framework regions for F027100183 is 94.4% based on the AbM definition and 93.1% based on the Kabat definition.

F0107529F10

Sequence optimisation of anti-TSLP ISVD F0107529F10 resulted in a final sequence optimised variant F027400021, which comprises 8 amino acid substitutions (i.e., L11V, A14P, T60A, S71R, A74S, S79Y, K83R, V89L) compared to the parental ISVD F0107529F10. Sequence optimisation of anti-TSLP ISVD F0107501A02 resulted in a final sequence optimised variant F027400160, which comprises 6 amino acid substitutions (i.e., L11V, A14P, E16G, A74S, K83R, V89L) compared to the parental ISVD F0107501A02.

The sequence optimised variants were assembled from oligonucleotides using a PCR overlap extension method. The constructs were expressed in *E. coli* and purified by IMAC and desalting. The variants were evaluated for their binding capacity to human and cyno TSLP by surface plasmon resonance. Monomeric behaviour of all variants was monitored by Size Exclusion-HPLC (SE-HPLC) and the thermal stability in a thermal shift assay (TSA). Additionally, the variants of F0107501A02 were tested for their blocking activity on hTSLP in the ternary complex Alphascreen. Results are summarized in Table 19 and Table 20.

TABLE 19

Results of the analysis of the sequence optimization variants of anti-TSLP ISVD F0107529F10, nd = not determined

| ISVD ID | Mutations | koff hTSLP (s-1) | koff cyno TSLP (s-1) | $K_D$ hTSLP-hFc (M) | $K_D$ cyno TSLP-hFc (M) | Tm (° C.) at pH 7 TSA | SE-HPLC % main peak |
|---|---|---|---|---|---|---|---|
| F0107529F10 | WT | 6.60E−05 | 1.80E−03 | 3.50E−11 | 1.70E−09 | 64.0 | nd |
| F010704099 | A14P, T60A, S71R, A74S, S79Y, K83R | 7.70E−05 | 1.80E−03 | 3.80E−11 | 3.30E−09 | 75.4 | 100 |
| F027400021 | L11V, A14P, T60A, S71R, A74S, S79Y, K83R, V89L | nd | nd | nd | nd | 74.0 | 100 |

Intermediate variant F010704099 with mutations A14P, T60A, S71R, A74S, S79Y, K83R showed a similar affinity on hTSLP and a 2-fold lower affinity on cyno TSLP compared to the parental ISVD F0107529F10. The Tm showed an overall increase of 11.4° C. compared to the parental ISVD. Two additional mutations, i.e. L11V and V89L, were introduced into variant F010704099 to minimize pre-existing antibody binding, resulting in the final variant F027400021. The % framework identity in the framework regions for F027400021 is 89.9% based on the AbM definition and 88.5% based on the Kabat definition.

6.4 Multispecific ISVD Construct F027400161

The above identified optimized ISVDs F027100019 (optimized variant of F0107004802), F027100183 (optimized variant of F0107004806), F027400021 (optimized variant of F0107529F10), and F027400160 (optimized version of F0107501A02) were used for the generation of multispecific ISVD construct F027400161. The optimized monovalent

TABLE 20

Results of the analysis of the sequence optimization (SO) variants of anti-TSLP ISVD F0107501A02.

| ISVD ID | Mutation(s) | Koff hTSLP (s-1) | koff cyno TSLP (s-1) | Ternary complex AlphaScreen IC50 (M) | Tm (° C.) at pH 7 TSA | SE-HPLC % main peak |
|---|---|---|---|---|---|---|
| F0107501A02 | WT | 5.4E−05 | 1.5E−03 | 2.8E−10 | 68.5 | 100 |
| F010704076 | A14P, E16G, A74S, K83R | 6.2E−05 | 1.6E−03 | 2.7E−10 | 70.8 | 99.3 |
| F027400160 | L11V, A14P, E16G, A74S, K83R, V89L | 1.2E−04 | 4.3e−03 | nd | 70.0 | 100 |

Intermediate variant F010704076 with mutations A14P, E16G, A74S, K83R showed a similar off-rate on hTSLP and on cyno TSLP compared to the parental ISVD F0107501A02 and a similar potency in ternary complex Alphascreen. The Tm showed an overall increase of 12.3° C. compared to the parental ISVD. Two additional mutations i.e., L11V and V89L, were introduced into variant F010704076 to minimize pre-existing antibody binding, resulting in the final variant F027400160.

The % framework identity in the framework regions for F027400160 is 83.1% based on the AbM definition and 80.5% based on the Kabat definition.

building blocks used in F027400161 are designated in the following in an abbreviated form according to their ISVD origin as 04B02, 04B06, 529F10, and 501A02, respectively.

6.4.1 Example 15: Multispecific ISVD Construct Generation

Identification of ISVD-containing polypeptide F027400161 (SEQ ID NO: 1) binding to IL-13 and TSLP resulted from a data-driven bispecific engineering and formatting campaign in which several anti-TLSP building blocks, several anti-IL13 building blocks and the anti-HSA

TABLE 21

Amino acid sequences of SO version of ISVD F0107004B02, F0107004B06, F0107501A02 and F107529F10.

| ISVD ID | ISVD description | Sequence |
|---|---|---|
| F010704076 (SEQ ID NO: 160) | F0107501A02 (A14P, E16G, A74S, K83R)* | EVQLVESGGGLVQPGGSLRLSCAASGSGFGVNILYWYRQA AGIERELIASITSGGITNYVDSVKGRFTISRDNSENTMYLQM NSLRAEDTGVYYCASRNIFDGTTEWGQGTLVTVSS |
| F010704099 (SEQ ID NO: 161) | F0107529F10 (A14P, T60A, S71R, A74S, S79Y, K83R)* | EVQLVESGGGLVQPGGSLRLSCAASGFTFADYDYDIGWFR QAPGKEREGVSCISNRDGSTYYADSVKGRFTISRDNSKNTV YLQMNSLRPEDTAVYYCAVEIHCDDYGVENFDFDPWGQG TLVTVSS |
| F027100019 (SEQ ID NO: 162) | F0107004B02 (E1D, L11V, A14P, N64K, S65G, A74S, K83R, I89L)* | DVQLVESGGGVVQPGGSLRLSCAASGRTFSSYRMGWFRQ APGKEREFVAALSGDGYSTYTANSVKGRFTISRDNSKNTVYL QMNSLRPEDTALYYCAAKLQYVSGWSYDYPYWGQGTLVT VSSAAA |
| F027100183 (SEQ ID NO: 163) | F0107004B06 (L11V, R74S, K83R, V89L)* | EVQLVESGGGVVQPGGSLRLSCAASGFTFNNYAMKWVRQ APGKGLEWVSSITTGGGSTDYADSVKGRFTISRDNSKNTLYL QMNSLRPEDTALYYCANVPFGYYSEHFSGLSFDYRGQGTLV TVSS |
| F027400021 (SEQ ID NO: 164) | F0107529F10 (L11V, A14P, T60A, S71R, A74S, S79Y, K83R, V89L)* | EVQLVESGGGVVQPGGSLRLSCAASGFTFADYDYDIGWFR QAPGKEREGVSCISNRDGSTYYADSVKGRFTISRDNSKNTV YLQMNSLRPEDTALYYCAVEIHCDDYGVENFDFDPWGQGT LVTVSS |
| F027400160 (SEQ ID NO: 165) | F0107501A02 (L11V, A14P, E16G, A74S, K83R, V89L)* | EVQLVESGGGVVQPGGSLRLSCAASGSGFGVNILYWYRQA AGIERELIASITSGGITNYVDSVKGRFTISRDNSENTMYLQM NSLRAEDTGLYYCASRNIFDGTTEWGQGTLVTVSS |

*( )indicates the amino acid substitutions introduced into the (parental) monovalent building block.

building block ALB23002 were included. Different positions/orientations of the building blocks and different linker lengths (9GS vs 35GS) were applied and proofed to be critical for different parameters (potency, cross-reactivity, expression yield, etc.).

A large panel of different ISVD constructs was transformed in *Pichia Pastoris* for small scale productions. Induction of ISVD expression occurred by stepwise addition of methanol. Clarified medium with secreted ISVD was used as starting material for purification via Protein A affinity chromatography followed by desalting. The purified samples were used for functional characterisation and expression evaluation.

Some constructs showed impaired potencies depending on linker length and relative position of ISVD building blocks. For example: potency for cyno TSLP of the anti-TSLP biparatopic combinations 501A02-529F10 is strongly impaired when linked with a short 9GS linker. Some constructs showed low expression levels depending on the combination and order of the building blocks. For the bispecifics comprising 4B02-4B06 expression was best in combination with 501A02-529F10.

TABLE 22

Selection of different multispecific ISVD formats evaluated. BB = building block, ALB = ALB23002

| ISVD ID | BB1 | linker 1 | BB2 | linker 2 | BB3 | linker 3 | BB4 | linker 4 | BB5 |
|---|---|---|---|---|---|---|---|---|---|
| F027400161 | 4B02 | 35 GS | 4B06 | 9 GS | 501A02 | 9 GS | ALB | 9 GS | 529F10 |
| F027400162 | 4B02 | 9 GS | 501A02 | 9 GS | 4B06 | 9 GS | 529F10 | 9 GS | ALB |
| F027400163 | 501A02 | 9 GS | ALB | 9 GS | 529F10 | 9 GS | 4B02 | 35 GS | 4B06 |
| F027400183 | 501A02 | 35 GS | 529F10 | 9 GS | 4B02 | 9 GS | ALB | 9 GS | 4B06 |
| F027400189 | 4B02 | 9 GS | ALB | 9 GS | 4B06 | 9 GS | 501A02 | 35 GS | 529F10 |
| F027400283 | 501A02 | 9 GS | 4B02 | 9 GS | 529F10 | 9 GS | 4B06 | 35 GS | ALB |
| F027400284 | 501A02 | 35 GS | 4B02 | 35 GS | 529F10 | 35 GS | 4B06 | 35 GS | ALB |
| F027400296 | 4B02 | 9 GS | 501A02 (N73Q)* | 9 GS | 4B06 | 9 GS | 529F10 | 9 GS | ALB |
| F027400298 | 501A02 (N73Q)* | 9 GS | 4B02 | 9 GS | 529F10 | 9 GS | 4B06 | 9 GS | ALB |

*indicates the amino acid substitutions introduced into the (parental) monovalent building block.

Table 23 illustrates that different yields ranging from low to high titer were obtained for six constructs comprising the same building blocks but ordered in different ways and connected with different linker lengths. Highest expression titers are obtained for constructs comprising the IL-13 ISVDs 4B02 and 4B06 linked via a 35GS linker (F027400161 and F027400163). In addition, the solubility of F027400161 and F027400163 was much higher than their respective counterparts F027400296 and 298, of which building blocks are linked with four 9GS linkers and ALB is positioned at the C-terminus.

Subsequently, the large bispecific panel was trimmed down to a panel of 2 bispecific constructs, consisting of ISVD constructs F027400161 and F027400163 proven to be potent on both targets (human and cyno) and having the potential of high expression levels, based on preliminary yield estimates.

Larger scale 2 L and 5 L productions in *Pichia Pastoris* were done for expression yield determination and assessment of biophysical properties and pre-existing antibody reactivity.

Table 24 and example 22 demonstrate that pre-existing antibody reactivity is driven by the orientation of the building blocks and the linker lengths.

TABLE 23

Expression levels and solubility of 6 ISVD constructs with the building blocks of 4B02, 4B06, 501A02 and 529F10 in different orientations and/or with different linker lengths.

| ISVD construct ID | BB1 | linker 1 | BB2 | linker 2 | BB3 | linker 3 | BB4 | linker 4 | BB5 | Yield 5 ml expression (µg/ml) | Yield 5 L fermentation (g/L) | solubility (mg/ml) |
|---|---|---|---|---|---|---|---|---|---|---|---|---|
| F027400161 | 4B02 | 35 GS | 4B06 | 9 GS | 501A02 | 9 GS | ALB | 9 GS | 529F10 | 124 | 4.7 | 145 |
| F027400163 | 501A02 | 9 GS | ALB | 9 GS | 529F10 | 9 GS | 4B02 | 35 GS | 4B06 | 114 | 4.4 | >150 |
| F027400189 | 4B02 | 9 GS | ALB | 9 GS | 4B06 | 9 GS | 501A02 | 35 GS | 529F10 | 77 | | |

TABLE 23-continued

Expression levels and solubility of 6 ISVD constructs with the building blocks of 4B02, 4B06,
501A02 and 529F10 in different orientations and/or with different linker lengths.

| ISVD construct ID | BB1 | linker 1 | BB2 | linker 2 | BB3 | linker 3 | BB4 | linker 4 | BB5 | Yield 5 ml expression (µg/ml) | Yield 5 L fermentation (g/L) | solubility (mg/ml) |
|---|---|---|---|---|---|---|---|---|---|---|---|---|
| F027400183 | 501A02 | 35 GS | 529F10 | 9 GS | 4B02 | 9 GS | ALB | 9 GS | 4B06 | 55 | | |
| F027400296 | 4B02 | 9 GS | 501A02 (N73Q)* | 9 GS | 4B06 | 9 GS | 529F10 | 9 GS | ALB | 80 | 2.4 | Very low |
| F027400298 | 501A02 (N73Q)* | 9 GS | 4B02 | 9 GS | 529F10 | 9 GS | 4B06 | 9 GS | ALB | 80 | 2.4 | 25 |

*indicates the amino acid substitutions introduced into the (parental) monovalent building block.

TABLE 24

Binding of pre-existing antibodies present in 96 human serum samples to F027400161, F027400163
and F027400164 compared to control ISVD construct F027301186.

| Construct ID | BB1 | linker 1 | BB2 | linker 2 | BB3 | linker 3 | BB4 | linker 4 | BB5 | 25% percentile | Median RU levels | 75% percentile |
|---|---|---|---|---|---|---|---|---|---|---|---|---|
| F027301186 | 1E07 | 35 GS | 1E07 | 35 GS | 1C02 | 9 GS | ALB | 9 GS | 1C02 | 61 | 135 | 622 |
| F027400161 | 4B02 | 35 GS | 4B06 | 9 GS | 501A02 | 9 GS | ALB | 9 GS | 529F10-A | 8 | 22 | 34 |
| F027400163 | 501A02 | 9 GS | ALB | 9 GS | 529F10 | 9 GS | 4B02 | 35 GS | 4B06-A | 19 | 34 | 63 |
| F027400164 | 501A02 | 9 GS | 4B02 | 9 GS | 529F10 | 9 GS | 4B06 | 9 GS | ALB-A | 4 | 13 | 24 |

Finally, ISVD construct F027400161 was selected based on potency, reduced binding to pre-existing antibodies and superior expression levels and CMC characteristics

6.4.2 Example 16: Multispecific ISVD Construct Binding Affinity to TSLP, IL13 and Serum Albumin The affinity, expressed as the equilibrium dissociation constant ($K_D$), of F027400161 towards human and cyno TSLP (Human and cyno TSLP sequences are known (Uniprot accession Uniprot accession Q969D9 and NCBI RefSeq XP_005557555.1, respectively). Recombinant protein was used to perform the assay, human IL-13 (Sino Biological cat nr 10369-HNAC), cyno IL-13 (Sino Biological cat nr 11057-CNAH) and rhesus IL-13 (R&D systems cat nr 2674-RM) and human (Sigma Aldrich, cat nr A8763), cyno and mouse (Albumin Bioscience cat nr N1204H1CM) serum albumin was quantified by means of in-solution affinity measurements on a Gyrolab xP Workstation (Gyros).

Under $K_D$-controlled measurements a serial dilution of TSLP or IL-13 (ranging from 1 µM-0.25 fM) or serum albumin (ranging from 100 µM-320 pM) and a fixed amount of F027400161 (5 pM or 10 pM in case of TSLP and IL13 and 20 nM in case of serum albumin) were mixed to allow interaction and incubated for either 48 or 72 hours (in case of TSLP and IL13) or 2 hours (in case of serum albumin) to reach equilibrium.

Under receptor-controlled measurements a serial dilution of TSLP or IL-13 (ranging from 1 µM-0.25 fM) or serum albumin (ranging from 100 µM-320 pM) and a fixed amount of F027400161 (250 pM in case of TSLP, 10 nM in case of IL-13 and 1 µM in case of serum albumin) were mixed to allow interaction and incubated for either 48 or 72 hours (in case of TSLP and IL-13) or 2 hours (in case of serum albumin) to reach equilibrium.

Biotinylated human TSLP/IL-13/serum albumin was captured in the microstructures of a Gyrolab Bioaffy 1000 CD, which contains columns of beads and is used as a molecular probe to capture free F027400161 from the equilibrated solution. The mixture of TLSP/IL-13/serum albumin and F027400161 (containing free TLSP/IL-13/serum albumin, free F027400161 and TLSP/IL-13/serum albumin—F027400161 complexes) was allowed to flow through the beads, and a small percentage of free F027400161 was captured, which is proportional to the free ISVD concentration. A fluorescently labeled anti-$V_{HH}$ antibody, ABH0086-Alexa647, was then injected to label any captured F027400161 and after rinsing away excess of fluorescent probe, the change in fluorescence was determined. Fitting of the dilution series was done using Gyrolab Analysis software, where $K_D$—and receptor-controlled curves were analyzed to determine the $K_D$ value.

The results (Table 25) demonstrate that the multispecific ISVD construct binds human/cyno TSLP and human/cyno/rhesus IL13 with high affinity.

TABLE 25

Binding affinities of F027400161 to human, rhesus and cyno TSLP and IL13 and human, cyno and mouse serum albumin (sequences of cyno and rhesus TSLP and cyno and rhesus albumin are identical).

| | human | | cynomolgus monkey | | rhesus monkey | | |
|---|---|---|---|---|---|---|---|
| Antigen | $K_D$ (pM) | 95% CI (pM) | $K_D$ (pM) | 95% CI (pM) | $K_D$ (pM) | 95% CI (pM) | Incubation time (h) |
| TSLP | 1.8 | 1.2-2.3 | 55.9 | 51-61 | | | 48 |
| | 2.3 | 1.4-3.3 | 44.0 | 26-62 | | | 48 |
| | 1.0 | 0.65-1.4 | 59.0 | 35-83 | | | 72 |
| IL13 | 4.2 | 3.6-48 | 3.8 | 2.8-4.9 | 6.4 | 5.3-7.4 | 48 |
| | 6.3 | 5.3-7.3 | 1.5 | 0.7-2.3 | 1.9 | 0.6-3.1 | 48 |
| | 4.7 | 3.8-5.7 | 3.5 | 2.7-4.2 | 1.5 | 0.5-2.4 | 72 |

| | human | | cynomolgus monkey | | mouse | | |
|---|---|---|---|---|---|---|---|
| Antigen | $K_D$ (nM) | 95% CI (nM) | $K_D$ (nM) | 95% CI (nM) | $K_D$ (nM) | 95% CI (nM) | Incubation time (h) |
| SA | 119 | 99.4-139 | 198 | 185-211 | 1800 | 1700-1900 | 2 |
| | 110 | 56-162 | 133 | 70-196 | | | 2 |
| | 145 | 69-222 | 145 | 78-213 | | | 2 |

6.4.3 Example 17: Multispecific ISVD Construct Binds Selectively to TSLP and IL13

Absence of F027400161 binding to IL-4 and IL-7 as IL13 and TSLP related cytokines was assessed via SPR (Proteon XPR36), respectively.

Cytokines were immobilized on a Proteon GLC sensor chip at 25 μg/mL for 600s using amine coupling, with 80 seconds injection of EDC/NHS for activation and a 150 seconds injection of 1 M Ethanolamine HCl for deactivation (ProteOn Amine Coupling Kit. cat. 176-2410). Flow rate during activation and deactivation was set to 30 μl/min and during ligand injection to 25 μl/min. The pH of the 10 mM Acetate immobilization buffer was 6.0 for IL13 and IL4 (Peprotech cat nr 200-07) and 5.5 for TSLP and IL7 (R&D systems cat nr 204-IL/CF).

Next, 1 μM of F027400161 was injected for 2 minutes and allowed to dissociate for 600s at a flow rate of 45 μL/min. As running buffer PBS (pH7.4)+0.005% Tween 20 was used. As positive controls, 100 nM α-hIL4 Ab and 100 nM α-IL7 Ab were injected. Interaction between F027400161 and the positive controls with the immobilized targets was measured by detection of increases in refractory index which occurs as a result of mass changes on the chip upon binding.

All positive controls did bind to their respective target. No binding was detected of F027400161 to human IL4 and IL7.

In addition, it was investigated if F027400161 could bind to the short form of TSLP. To this end, TSLP and the short form of TSLP (as described in Fornasa, 2015) were immobilized on a proteon GLC sensor chip at 10 μg/mL, respectively 5 μg/ml for 150s using amine coupling as described above. The pH of the 10 mM Acetate immobilization buffer was 5.5 for TSLP and 4.0 for the short form of TSLP.

Next, 500 nM of F027400161 was injected for 2 minutes and allowed to dissociate for 600s at a flow rate of 45 μL/min. As running buffer PBS (pH7.4)+0.005% Tween 20 was used. As reference compound, 500 nM anti-hTSLP reference mAb1 was injected and as positive control 500 nM α-hTSLP pAb (Abcam ab47943).

Whereas the positive control did bind to both the long (normal) and short form of TSLP, no binding was detected of F027400161 and anti-hTSLP reference mAb1 to the short form of TSLP.

6.4.4 Example 18: Simultaneous Binding of Multispecific ISVD Construct to IL13, TSLP and HSA A Biacore T200 instalment was used to determine whether F027400161 can bind simultaneously to hTSLP and hIL13. To this end hTSLP (recombinant human TSLP is commercially available, such as from R&D Systems (cat nr 1398-TS) was immobilized on a CM5 Sensor chip via amine coupling. 100 nM of F027400161 was injected for 2 min at 10 μl/min over the TSLP surface in order to capture the ISVD construct via the TSLP building blocks 501A02-529F10. Subsequently either 100 nM of hIL13 (PeproTech, cat nr 200-13), HSA or hOX40L or 1000 nM of HSA were injected or mixtures of 100 nM IL13+100 nM HSA, 100 nM IL13+1000 nM HSA, 100 nM OX40L+100 nM HSA, 100 nM OX40L+1000 nM HSA or 100 nM IL13+100 nM OX40L, at a flow rate of 10 μl/min for 2 min followed by a subsequent 300 seconds dissociation step. The TSLP surfaces are regenerated with a 1 minute injection of 0.5% SDS+10 mM glycine pH3 at 45 μl/min. The sensorgram (FIG. 1) demonstrates that F027400161 can bind human IL13, human TSLP and HSA simultaneously as shown by the increase in response units after capture on TSLP: ~130 RU increase from IL13 only, ~60 RU increase from 100 nM HSA and ~350 RU from 1000 nM HSA only, ~180 RU increase for the IL13 and 100 nM HSA mixture, and ~500 RU for the IL13 and 1000 nM HSA mixture. Higher concentrations of HSA were needed to see decent RU increase levels, due to the lower affinity of F027400161 for HSA (see example 16).

Example 19: Multispecific ISVD Construct Inhibition of IL13 Induced Eotaxin Release In Vitro Functional activity of soluble IL13 from the different species of interest (human, rhesus and cynomolgus monkey) and inhibition thereof by F027400161 was studied using a cell based assay investigating eotaxin release by A549 human lung carcinoma cells.

To this end, A549 suspension cells were cultured in Ham's F12K medium, supplemented with 10% FCS, and seeded into a 96 well plate at 400.000 cells/well. After 24 hours incubation, a dilution series of F027100161 or reference compounds (anti-hIL-13 reference mAb1 and anti-hIL-13 reference mAb2) were added. After 20 min incubation, human IL13 (Sino Biological cat nr 10369-HNAC), cyno IL13 (Sino Biological cat nr 11057-CNAH) or rhesus IL13 (R&D Systems, cat nr 2674-RM-025) is added to a final concentration of 160 pM. After further incubation for 24 hours in the presence of 30 μM HSA, heparin is added at a final concentration of 50 μg/ml, to enhance the eotaxin expression. After an additional 4 hours of incubation, eotaxin-3, secreted in the cell supernatant was quantified by use of the Human CCL26/Eotaxin-3 DuoSet ELISA (R&D systems, DY346).

Figure 2:
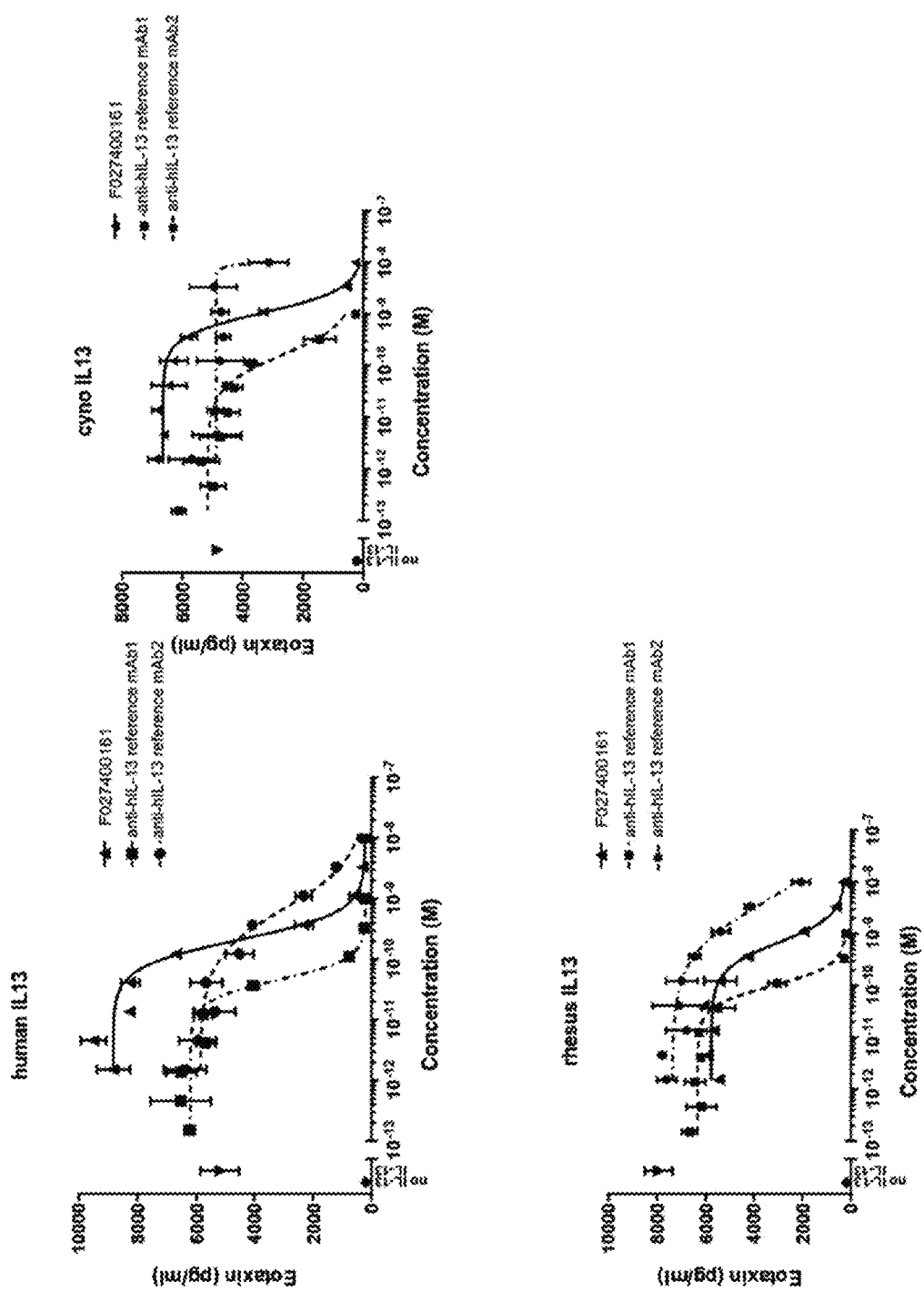
FIG. 2: Inhibition of human, cyno and rhesus IL13 in the eotaxin release assay by $V_{HH}$ F027400161 and the reference compounds anti-hIL-13 mAb1 and anti-hIL-13 mAb2.

F027400161 inhibited human, cyno and rhesus IL13-induced eotaxin-3 release in a concentration-dependent manner with an IC50 of 194 pM (for human IL13), 1040 pM (for cyno IL13) and 713 pM (for rhesus IL13), comparable to the reference compound anti-hIL-13 reference mAb1, and better than the reference compound anti-hIL-13 reference mAb2 (Table 26, FIG. 2).

TABLE 26

IC50 values of F027400161 mediated neutralization of human, cyno and rhesus IL13 in the eotaxin release assay versus the reference compounds anti-hIL-13 reference mAb1 and anti-hIL-13 reference mAb2. nd = not determined

| antigen | F027400161 | | | anti-hIL-13 reference mAb1 | | | anti-hIL-13 reference mAb2 | | |
|---|---|---|---|---|---|---|---|---|---|
| | Human IL13 | Cyno IL13 | Rhesus IL13 | Human IL13 | Cyno IL13 | Rhesus IL13 | Human IL13 | Cyno IL13 | Rhesus IL13 |
| eotaxin release assay (IC50, pM) | 194 | 1040 | 713 | 45 | 160 | 99 | 668 | nd | 3560 |

6.4.5 Example 20: Multispecific ISVD Construct Inhibition of 1113 Induced STAT-6 Activation in HEK-Blue 114/1113 Cells HEK-Blue™ IL-4/IL-13 cells were generated by stable transfection of HEK293 cells with the human STATE gene and a STATE-inducible SEAP reporter gene. Upon IL-4 and IL-13 stimulation, the cells produce STATE-induced SEAP secreted in the supernatant quantified by QUANTI-Blue™.

HEK-Blue™ cells were cultured DMEM, supplemented with 10% FBS and seeded into a 96 well plate at 50.000 cells/well. A dilution series of F027100161 or reference compounds (anti-hIL-13 reference mAb1 and anti-hIL-13 reference mAb2) was pre-incubated with 10 pM hIL13 (Sino Biological cat nr 10369-HNAC) or cyno IL-13 (Sino Biological cat nr 11057-CNAH) for 1 hour at room temperature and added to the cells. After incubation for 22 to 24 hours in the presence of 30 μM HSA, 40 μl of the cell supernatant was mixed with 160 μl QUANTI-Blue™. Secreted SEAP was quantified by measuring absorption at 620 nm on a Clariostar instrument.

Figure 3:
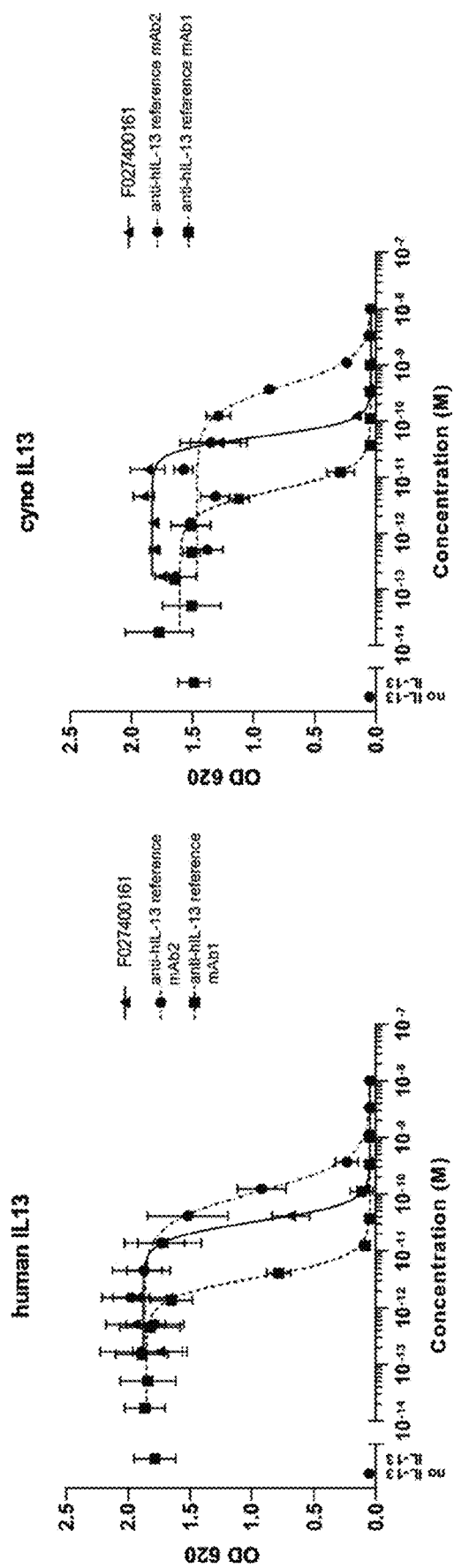
FIG. 3: Inhibition of human and cyno IL13 in the SEAP reporter assay by F027400161 and the reference compounds anti-hIL-13 mAb1 and anti-hIL-13 mAb2.

F027400161 inhibited human and cyno IL-13 induced SEAP secretion in a concentration-dependent manner with an IC50 of 32.8 pM (for human IL-13) and 53.4 pM (for cyno IL-13), better than the reference compound anti-hIL-13 reference mAb2 (Table 27, FIG. 3).

TABLE 27

IC50 values of F027400161 mediated neutralization of human and cyno IL-13 in the SEAP reporter assay versus the reference compounds anti-hIL-13 reference mAb1 and anti-hIL-13 reference mAb2.

| Construct ID | IC50 hIL13 (M) | IC50 cyno IL13 (M) |
|---|---|---|
| F027400161 | 3.28E−11 | 5.34E−11 |
| anti-hIL-13 reference mAb2 | 1.10E−10 | 4.26E−10 |
| anti-hIL-13 reference mAb1 | 3.45E−12 | 5.85E−12 |

6.4.6 Example 21: Multispecific ISVD Construct Inhibition of TSLP-Induced Ba/F3 Cell Proliferation In Vitro Functional activity of soluble TSLP from the different species of interest (human, rhesus and cynomolgus monkey) and inhibition thereof by F027400161 was studied using a cell-based assay investigating proliferation of BaF3 cells transfected with plasmids encoding hTSLPR and hIL7Rα.

Cells were seeded at a density of 15000 cells/well in RPMI 1640 growth medium in cell culture treated white 96 well plates. A dilution series of F027100161 or reference compounds (anti-hTSLP reference mAb1) were added, followed by addition of 5 pM human or cyno TLSP for stimulation of the cells. The human and cyno TSLP sequences are known (Uniprot accession Uniprot accession Q969D9 and NCBI RefSeq XP_005557555.1, respectively). Recombinant protein was used to perform the assay. After incubation for 48 hours in the presence of 30 μM HSA, cell density and viability were monitored using the CellTiter-Glo® Luminescent Cell Viability Assay (Promega, G7571/G7572/G7573) and read-out on an EnVision Multilabel Reader (Perkin Elmer).

Figure 4:
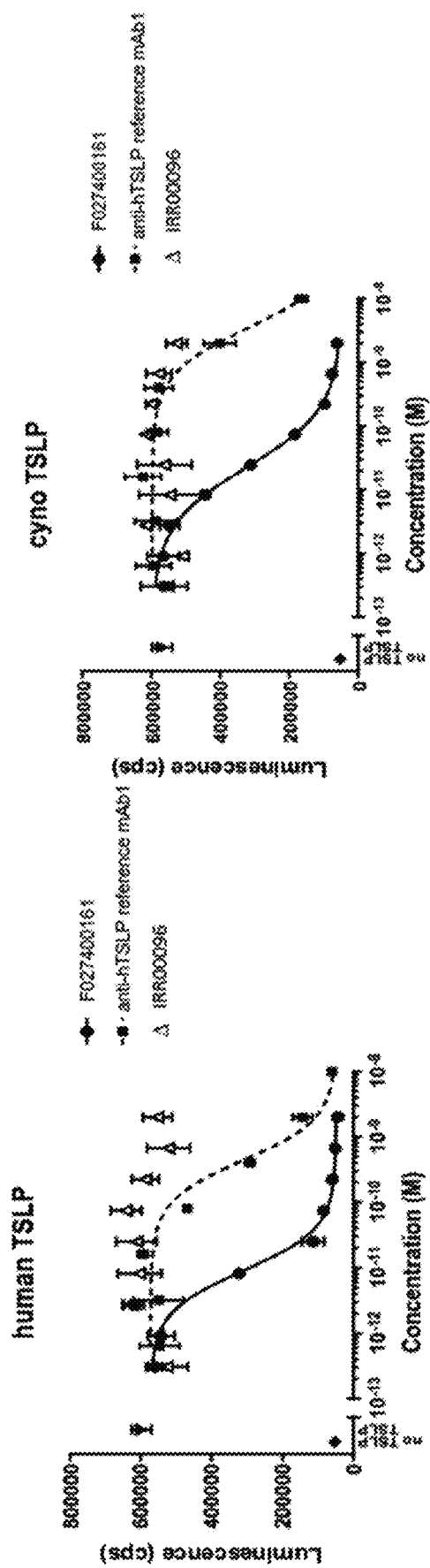
FIG. 4: Inhibition of human and cyno TSLP induced BaF3 proliferation by F027400161 and the reference compound anti-hTSLP mAb1. IRR00096 is a negative control Nb.

F027400161 inhibited human and cyno TSLP dependent proliferation of Ba/F3 cells in a concentration-dependent manner with an IC50 of 7.8 pM (for human TSP) and 24 pM (for cyno TSLP), performing hence much better than the reference compound anti-hTSLP reference mAb1 (Table 28, FIG. 4).

TABLE 28

IC50 values of F027400161 mediated neutralization of human and cyno TSLP induced BaF3 proliferation versus the reference compound anti-hTSLP reference mAb1.

| antigen | F027400161 | | anti-hTSLP reference mAb1 | |
|---|---|---|---|---|
| | Human TSLP | Cyno TSLP | Human TSLP | Cyno TSLP |
| BaF3 proliferation assay (IC50, pM) | 7.8 | 24 | 356 | 3180 |

6.4.7 Example 22: Multispecific ISVD Construct Binding to Pre-Existing Antibodies The pre-existing antibody reactivity of ISVD construct F027400161 was assessed in normal human serum (n=96) using the ProteOn XPR36 (Bio-Rad Laboratories, Inc.). PBS/Tween (phosphate buffered saline, pH7.4, 0.005% Tween20) was used as running buffer and the experiments were performed at 25° C.

ISVDs are captured on the chip via binding of the ALB23002 building block to HSA, which is immobilized on the chip. To immobilize HSA, the ligand lanes of a ProteOn GLC Sensor Chip are activated with EDC/NHS (flow rate 30 μl/min) and HSA is injected at 100 μl/ml in ProteOn Acetate buffer pH4.5 to render immobilization levels of approximately 2900 RU. After immobilization, surfaces are deactivated with ethanolamine HCl (flow rate 34.1/min).

Subsequently, ISVD constructs are injected for 2 min at 45 μl/min over the HSA surface to render an ISVD capture level of approximately 800 RU. The samples containing pre-existing antibodies are centrifuged for 2 minutes at 14,000 rpm and supernatant is diluted 1:10 in PBS-Tween20 (0.005%) before being injected for 2 minutes at 45 μl/min followed by a subsequent 400 seconds dissociation step. After each cycle (i.e. before a new ISVD capture and blood sample injection step) the HSA surfaces are regenerated with a 2 minute injection of HCl (100 mM) at 45 μl/min. Sensorgrams showing pre-existing antibody binding are obtained after double referencing by subtracting 1) ISVD-HSA dissociation and 2) non-specific binding to reference ligand lane. Binding levels of pre-existing antibodies are determined by setting report points at 125 seconds (5 seconds after end of association). Percentage reduction in pre-existing antibody binding is calculated relative to the binding levels at 125 seconds of a reference ISVD.

Figure 5:
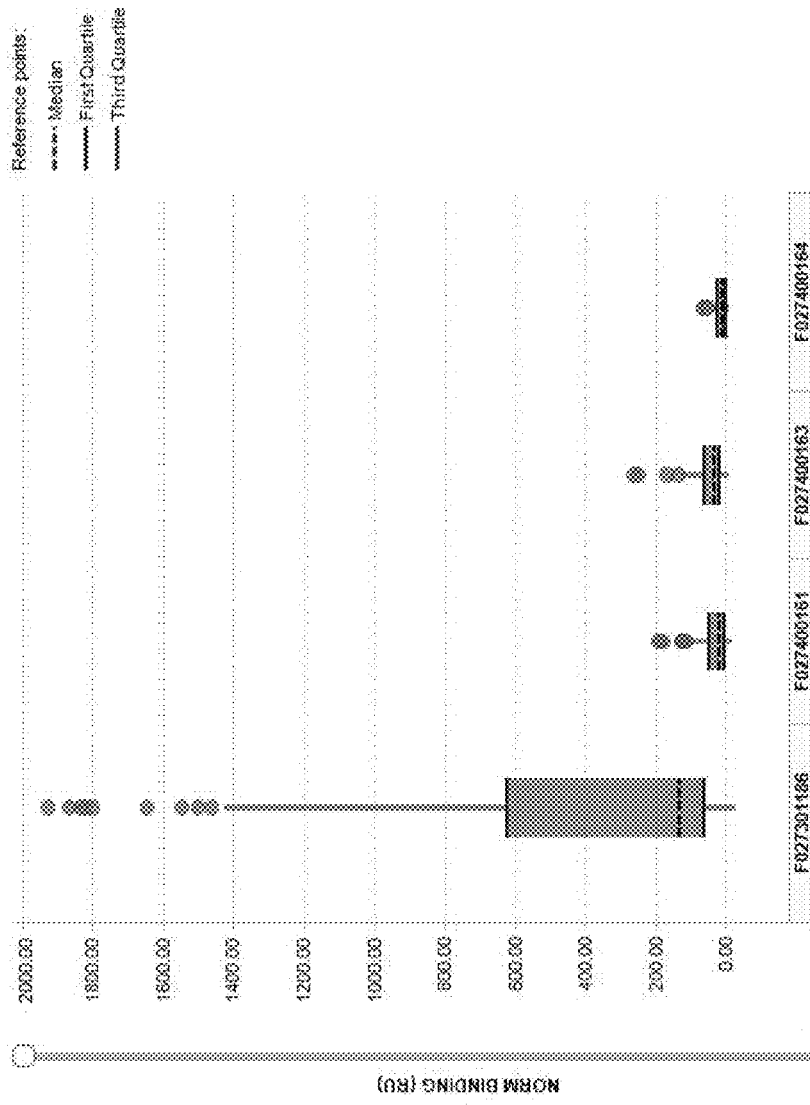
FIG. 5: Box plot showing the binding of pre-existing antibodies present in 96 human serum samples to F027400161, 163 and 164 compared to control F027301186.

The pentavalent ISVD construct F027400161, optimized for reduced pre-existing antibody binding by introduction of mutations L11V and V89L in each building block and a C-terminal alanine, shows substantially less binding to pre-existing antibodies compared to a control non-optimized pentavalent ISVD construct F027301186, (Table 24 and FIG. 5).

Pre-existing antibody binding depends on the orientation of the building blocks and the linker lengths present in the multispecific constructs. Table 24 and FIG. 5 demonstrate that construct F027400161 shows lower pre-existing antibody reactivity than construct F027400163, due to its spe-cific orientation, but that F027400164 shows lower reactivity than F027400161, due to short linkers all over.

6.4.8 Example 23: F027400161 Blocks TSLP-Induced CCL17 in Human Dendritic Cells In Vitro The type 2 inflammation cascade is initiated and propagated by a concerted action of epithelial cells, dendritic cells, type 2 helper T cells (Th2 cells), mast cells and innate lymphoid cells in a context-dependent manner. The cytokine thymic stromal lymphopoietin (TSLP) has been implicated in the initiation and progression of allergic inflammation through its ability to activate dendritic cells (DCs). Upon activation by TSLP, human DCs produce CCL17, a Th2-associated chemokine, and drive Th2 cell differentiation from naïve CD4$^+$ T cells. F027400161 targets both TSLP and IL-13, can block the interaction between TSLP and DCs, and thereby, reduce CCL-17 production and is projected to confer efficacy in type 2 inflammatory diseases and beyond.

The ability of F027400161 to inhibit TSLP-induced CCL17 production was assessed in human DCs isolated from 8 individual healthy donors in comparison to the reference monospecific antibody, anti-hTSLP reference mAb1. Human DCs (CD3$^-$CD14$^-$CD11c$^+$HLA-DR$^{high}$) were isolated and enriched from healthy human PBMCs in buffy coat (human leucocyte pack) samples. A total of 0.5-0.8×10$^6$ DCs/well were incubated with eight 3-fold serially diluted concentrations of F027400161 (400 ng/mL or 5.714 nM top concentration) or eight 4-fold serially diluted concentrations of anti-hTSLP reference mAb1 (4000 ng/mL or 27 nM top concentration) prior to stimulation with 4 ng/mL of recombinant human TSLP for 36 hours in 37° C. cell culture incubator. Recombinant human TSLP is commercially available, such as from R&D Systems (Catalog number 1398-TS). CCL17 production in freshly collected cell culture supernatant was measured by ELISA and IC$_{50}$ values of the ISVD construct and benchmark antibody were calculated in Graphpad Prism.

Figure 6:
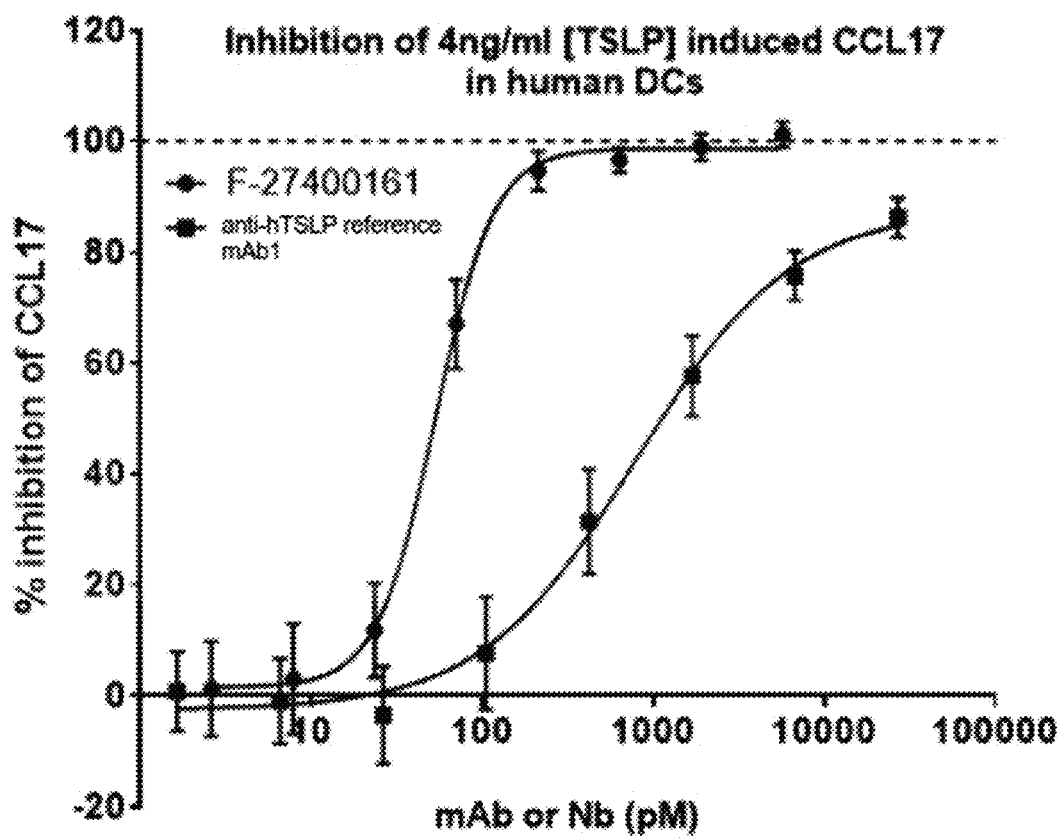
FIG. 6: Dose-response inhibition profiles of F-27400161 (also referred to as F027400161) and comparator antibody anti-hTSLP reference mAb1 on TSLP-induced CCL17 response in human DCs. Enriched human DCs were treated with 4 ng/mL of TSLP and incubated with 8 concentrations of the ISVD construct and anti-hTSLP reference mAb1 for 36 hours. CCL17 concentration in freshly collected supernatant was measured by ELISA. $IC_{50}$ values were calculated by nonlinear regression (log inhibitor vs responses—variable slope four parameters lease squares fit) in Graphpad Prism 8.0 with no constraints. Data are represented as mean±standard error of mean (SEM) of all 8 donors combined from 8 individual experiments.

The collective results of the dose inhibition responses of F027400161 and anti-hTSLP reference mAb1 in human DCs, are shown in FIG. 6. The reference monospecific antibody anti-hTSLP reference mAb1 inhibited TSLP induced CCL17 production at a mean IC$_{50}$ concentration of 793.4 pM, while F027400161 inhibited TSLP induced CCL17 production with a mean IC$_{50}$ of 53.26 pM.

In conclusion, these results demonstrate that the ISVD construct F027400161 is more potent in inhibiting TSLP-induced CCL17 response in human DCs, compared to anti-hTSLP reference mAb1.

6.4.9 Example 24: F027400161 Blocks 0.5 ng/mL [IL-13+TSLP] Induced Synergistic CCL17 in Human PBMCs In Vitro Type 2 cytokines such as thymic stromal lymphopoietin (TSLP) and Interleukin-13 (IL-13) exert unique, additive and synergistic response to drive asthma and atopic dermatitis (AD) pathophysiology. The roles of TSLP as an epithelial cell-derived initiator of the type 2 immune cascade and of IL-13 as a downstream effector cytokine have been extensively validated. F027400161 targets both TSLP and IL-13, thereby projected to confer efficacy in type 2 mediated inflammatory diseases and beyond.

The ability of F027400161 to inhibit 0.5 ng/mL IL-13 and TSLP-induced synergistic production of CCL17 (TARC) was evaluated in human PBMCs from 8 individual healthy donors. The study was designed to evaluate non-inferiority of the ISVD construct versus monospecific biologics, anti-hTSLP reference mAb1 and anti-hIL-13 reference mAb1. One million cells per well of human PBMCs were stimulated with 0.5 ng/mL of recombinant human TSLP (recombinant human TSLP is commercially available, such as from R&D Systems (cat nr 1398-TS) plus IL-13 (R&D Systems, cat nr 213-ILB-005/CF) and incubated with ten 3-fold serially diluted concentrations of the ISVD construct (10 nM top concentration), anti-hIL-13 reference mAb1 (10 nM top concentration) and anti-hTSLP reference mAb1 (100 nM top concentration) in a 96-well plate for 20 hours in 37° C. cell-culture incubator. The assays were performed with technical triplicates within each donor for F027400161. The concentrations of the cytokines used were within 2-fold of the standard error of reported literature values from sera, BAL fluid, sputum and skin of normal humans, asthmatics and atopic dermatitis patients (Berraïes A et al, Immunol Letter 178: 85-91, 2016; Bellini A et al, Mucosal Immunology 5(2):140-9, 2012; Davoodi P et al, Cytokine 60(2):431-7, 2012; Szegedi K et al, J Eur Acad Dermatol Venereol 29(11):2136-44, 2015). CCL17 production in freshly collected cell culture supernatant was measured by Meso Scale Diagnostics (MSD) V-PLEX Human TARC Kit.

Figure 7:
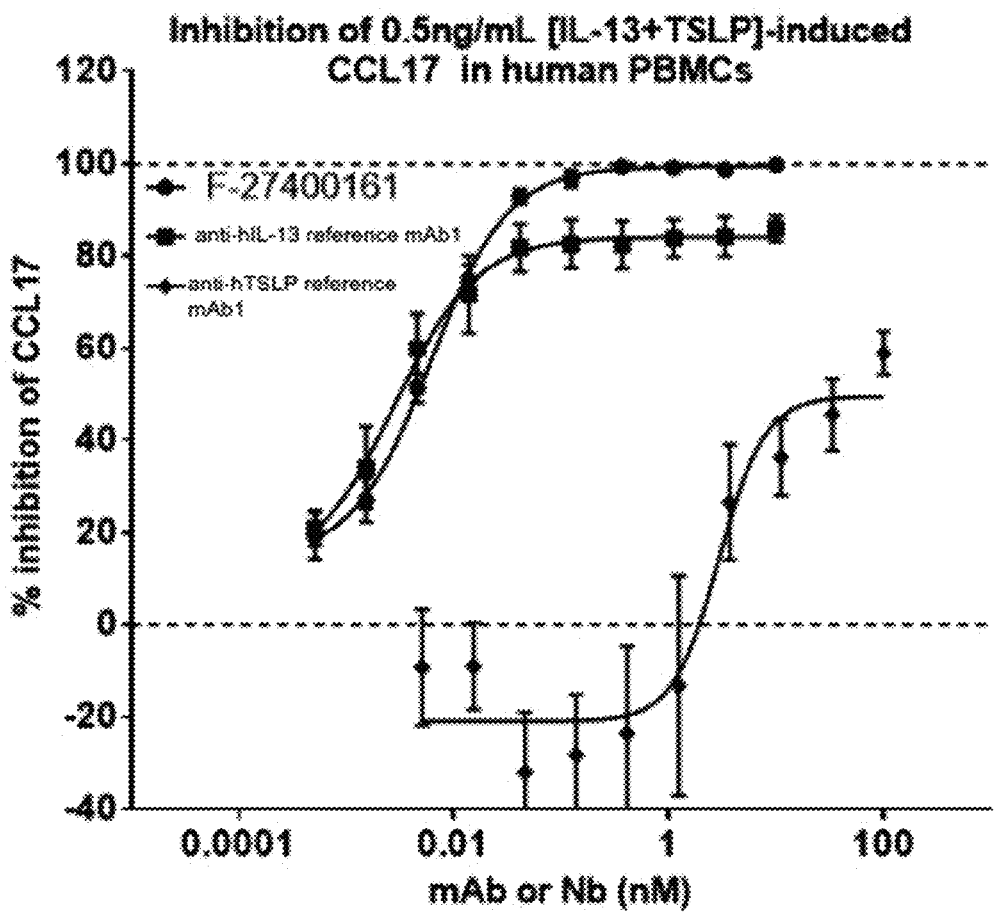
FIG. 7: Dose inhibition responses of F-27400161 (also referred to as F027400161) and comparators Anti-hIL-13 reference mAb1 and anti-hTSLP reference mAb1 on 0.5 ng/mL IL-13 and TSLP-induced synergistic production of CCL17 in human PBMCs. Healthy donor PBMCs were stimulated with 0.5 ng/mL of recombinant IL-13+TSLP and incubated with 10 doses of the ISVD construct (Nb) and comparators for 20 hours. CCL17 concentration in the cell culture supernatant was measured by MSD V-Plex kit. $IC_{50}$ values were calculated by nonlinear regression (log inhibitor vs responses—variable slope four parameters lease squares fit) in Graphpad Prism 8.0 with no constraints. Data are represented as mean±standard error of mean (SEM) of all donors combined from 8 individual experiments.

The collective results of the dose inhibition responses of F027400161 and benchmark antibodies, anti-hIL-13 reference mAb1 and anti-hTSLP reference mAb1, are shown in FIG. 7. F027400161 demonstrated 100% inhibition of 0.5 ng/mL IL-13+TSLP-induced synergistic CCL17 production with a mean $IC_{50}$ of 0.0061 nM. The reference antibody anti-hIL-13 mAb1, despite having a lower mean $IC_{50}$ of 0.0028 nM, was unable to fully block the synergistic CCL17 response at equimolar doses of F027400161 and plateaued at approximately 80% inhibition. On the other hand, anti-hTSLP reference mAb1 was only able to block approximately 50% of the CCL17 production with a mean $IC_{50}$ of 2.932 nM.

In conclusion, these results demonstrate that F027400161 is more potent than anti-hTSLP reference mAb1 and is superior compared to anti-hIL-13 reference mAb1 for blocking pathophysiological relevant concentrations of IL-13 and TSLP-induced synergistic response in human PBMCs, highlighting its therapeutic potential for the treatment of type 2 inflammatory diseases such as asthma and atopic dermatitis.

6.4.10 Example 25: F027400161 Blocks 5 ng/mL [IL-13+TSLP] Induced Synergistic CCL17 in Human PBMCs In Vitro The ability of F027400161 to inhibit 5 ng/mL IL-13+TSLP-induced CCL17 production was evaluated in human PBMCs from 8 healthy individual donors. The study was designed to evaluate non-inferiority of the ISVD construct versus monospecific biologics, anti-hTSLP reference mAb1 and anti-IL-13 reference mAb1. The concentrations of the cytokines used were ~10 fold over the upper end of the pathophysiological ranges of TSLP and IL-13 that have been reported in the literature in normal humans, asthmatics and atopic dermatitis patients (Berraïes A et al, Immunol Letter 178: 85-91, 2016; Bellini A et al, Mucosal Immunology 5(2):140-9, 2012; Davoodi P et al, Cytokine 60(2):431-7, 2012; Szegedi K et al, J Eur Acad Dermatol Venereol 29(11):2136-44, 2015) as hypothetical concentrations during transient inflammatory state. One million cells per well of human PBMCs were stimulated with 5 ng/mL of recombinant human TSLP plus IL-13 (R&D Systems, cat nr 213-ILB-005/CF) and incubated with ten 3-fold serially diluted concentrations of F-27400161 (10 nM top concentrations), anti-hIL-13 reference mAb1 (10 nM top concentration) and anti-hTSLP reference mAb1 (100 nM top dose) in a 96-well plate for 20 hours in 37° C. cell-culture incubator. The assays were performed with technical triplicates within each donor for F027400161. CCL17 production in freshly collected cell culture supernatant was measured by Meso Scale Diagnostics (MSD) V-PLEX Human TARC Kit.

Figure 8:
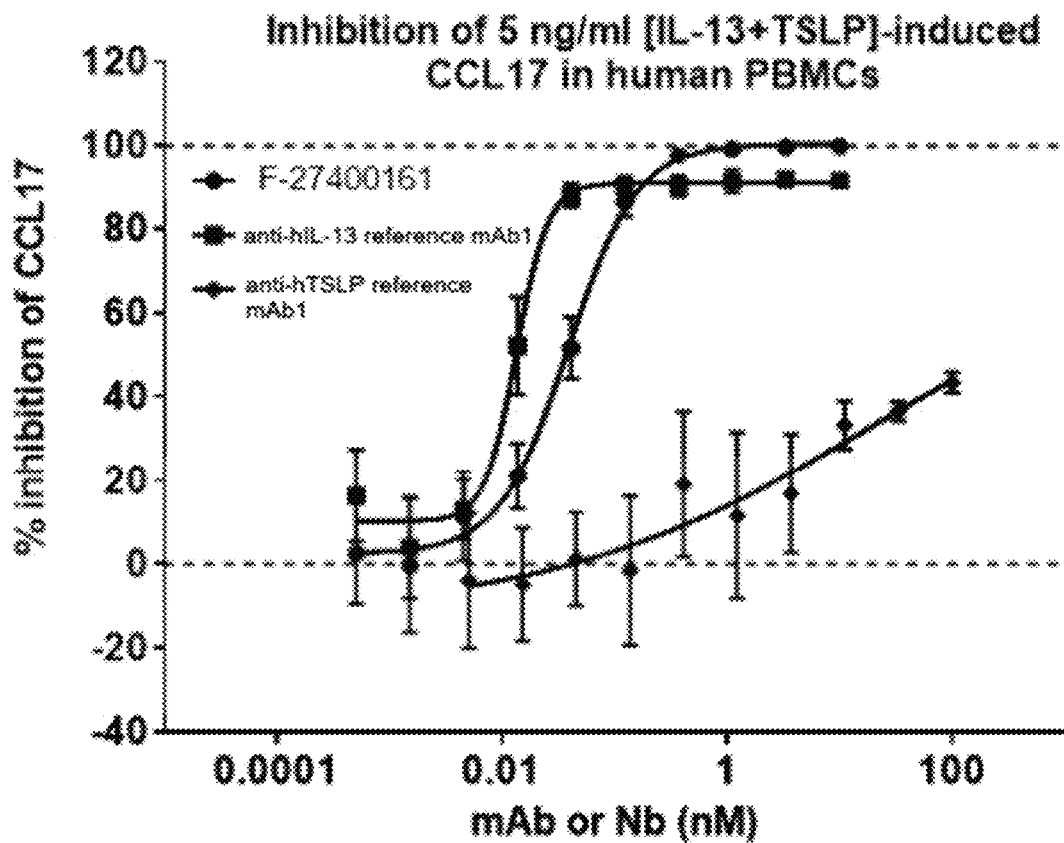
FIG. 8: Dose inhibition responses of F-27400161 (also referred to as F027400161) and comparator antibodies anti-hIL-13 reference mAb1 and anti-hTSLP reference mAb1 on 5 ng/mL IL-13 and TSLP-induced synergistic production of CCL17 in human PBMCs. Healthy donor PBMCs were stimulated with 5 ng/mL of recombinant IL-13+TSLP and incubated with 10 doses of the ISVD construct (Nb) and comparator antibodies for 20 hours. CCL17 concentration in freshly collected supernatant was measured by MSD V-Plex kit. $IC_{50}$ values were calculated by nonlinear regression (log inhibitor vs responses-variable slope four parameters lease squares fit) in Graphpad Prism 8.0 with no constraints. Data are represented as mean±standard error of mean (SEM) of all donors combined from 8 individual experiments.

The collective results of the dose inhibition responses of F027400161 and benchmark antibodies, anti-hIL-13 reference mAb1 and anti-hTSLP reference mAb1, are shown in FIG. 8. F027400161 demonstrated 100% inhibition of 5 ng/mL IL-13+TSLP-induced synergistic CCL17 production with a mean $IC_{50}$ of 0.0387 nM. While PBMCs treated with equimolar doses of the comparator antibody anti-hIL-13 reference mAb1 showed a lower mean $IC_{50}$ of 0.01339 nM, the inhibition response never reached 100% and plateaued at approximately 90% inhibition. On the other hand, anti-hTSLP reference mAb1 only partially blocked approximately 40% of the CCL17 production with a mean $IC_{50}$ of 19 nM.

In conclusion, these results demonstrate that F027400161 is superior to both anti-hTSLP reference mAb1 and anti-hIL-13 reference mAb1 in blocking IL-13 and TSLP-induced synergistic CCL17 response in human PBMCs at [TSLP+IL-13] concentrations 10-fold over the pathophysiological ranges of the cytokines, highlighting its therapeutic potential for the treatment of asthma and atopic dermatitis during acute or inflammatory phases.

6.4.11 Experiment 27: T027400161 Blocks Allergen Der P-Induced Production of IL-5, CCL17, and CCL26 in a Triculture Assay System TSLP drives type 2 immune response by inducing CCL17, IL-5, and IL-13 production. Subsequently, IL-13 triggers CCL26 production by local epithelial cells, leading to the ramification of type 2 immune response mediated inflammatory diseases and beyond.

The ability of F027400161 to inhibit TSLP-induced IL-5 and CCL17, and IL-13-induced CCL26 production was evaluated in a triculture assay system using MRC5 fibroblasts and A549 epithelial cells coculturing with Der P-stimulated human PBMCs from 6 individual normal donors for 6 days. The study was designed to evaluate non-inferiority of the ISVD versus monospecific biologics, anti-hTSLP reference mAb1 and anti-hIL-13 reference mAb1. MRC5 fibroblasts produced ~100 pg/mL endogenous TSLP constitutively, and A549 epithelial cells produced CCL26 in response to IL-13 produced by PBMCs with Der P and endogenous TSLP stimulation. One day prior to coculture with human PBMCs, seventy-five thousand MRC5 fibroblasts and A549 epithelial cells per well were plated. One million cells per well of human PBMCs were added into plated MRC5 fibroblasts and A549 epithelial cells, stimulated with 3 µg/mL of Der P, and incubated with 11.1 nM of ISVD, anti-hIL-13 reference mAb1, or anti-hTSLP reference mAb1 in a 24-well plate for 6 days in a 37° C. cell-culture incubator. The assays were performed with technical triplicates within each donor for F027400161. The production of IL-5, CCL17, and CCL26 in freshly collected cell culture supernatant was measured by Human Magnetic Luminex Assays from RnD System.

Figure 9:
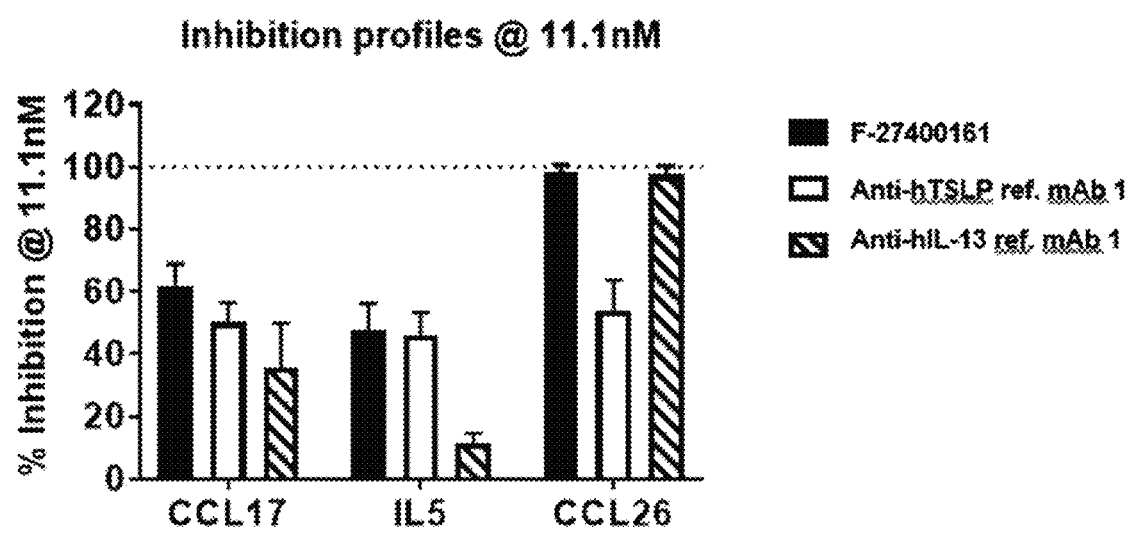
FIG. 9: Inhibition profiles of F-27400161 (also referred to as F027400161) and comparator antibodies anti-hIL-13 reference mAb1 and ant-hTSLP reference mAb1 on allergen Der P-induced IL-5, CCL17, and CCL26 production by human PBMCs in a triculture assay. Normal donor PBMCs cocultured with MRC5 fibroblasts and A549 epithelial cells were stimulated with 3 mg/mL of Der P, and incubated with 11.1 nM of the ISVD, anti-hIL-13 reference mAb1, or anti-hTSLP reference mAb1 in a 24-well plate for 6 days in a 37° C. cell-culture incubator. IL-5, CCL17, and CCL26 concentration in freshly collected supernatant was measured by Human Magnetic Luminex Assays. Percentage of inhibition were calculated relative to unstimulated (min) and stimulated (max) control samples which did not receive either ISVD polypeptides or antibodies. All calculations were performed using GraphPad Prism 8.0. Data are represented as mean±standard error of mean (SEM) of all donors combined from 3 independent experiments.

The collective results of the inhibition responses of F027400161 and benchmark antibodies, anti-hIL-13 reference mAb1 and anti-hTSLP reference mAb1, are shown in FIG. 9. F027400161 demonstrated 60% inhibition of CCL17, 50% inhibition of IL-5, and 95% inhibition of CCL26 production. The reference antibody anti-hTSLP reference mAb1 displayed 50% inhibition of CCL17, 50% inhibition of IL-5, and approximately 55% inhibition of CCL26 production. While anti-hIL-13 reference mAb1 demonstrate comparable 95% inhibition of CCL26 production, this reference antibody was only able to block approximately 35% of the CCL17 production and less than 10% of IL-5 production (FIG. 9). Lack of complete inhibition of IL-5 and CCL17 by these tested molecules may suggest that Der P stimulation triggers PBMCs to elicit pathways other than TSLP and IL-13 to drive the production of IL-5 and CCL17.

In conclusion, these results demonstrate that the anti-TSLP/IL-13 ISVD F027400161 is superior than anti-hTSLP reference mAb1 and anti-hIL-13 reference mAb1 by its ability to block three cytokines and chemokines (CCL17, IL-5 and CCL26) in a complex assay system comprising of human PBMCs cocultured with tissue structural cells, highlighting its therapeutic potential for the treatment of type 2 inflammatory diseases such as asthma and atopic dermatitis, as well as a broad range of immunological disease indications.

6.4.12 Example 26: NSG-SGM3 Mouse Model to Evaluate F027400161 Mediated Target Occupancy and Pharmacodynamics In Vivo F027400161 targets both human TSLP and IL-13 and does not cross react with the murine orthologs. Hence, to evaluate the biological activities of F027400161, a xenografted, humanized model system was used. Female NSG-SGM3 (NOD/SCID-IL2Rγ-/-, NOD.Cg-PrkdcscidIl2rγtm1Wjl/SzJ) were obtained from Jackson Labs, Bar Harbor, ME, USA. These mice express human hematopoietic cytokines: stem cell factor (SCF), granulocyte/macrophage stimulating factor (GM-CSF), and interleukin-3 (IL-3), all driven by a human cytomegalovirus promoter/enhancer sequence. The triple transgenic mouse produces above cytokines constitutively, providing cell proliferation and survival signals, supporting the stable engraftment of CD33+ myeloid lineages, and several types of lymphoid cells. Briefly, the protocol followed for engraftment is as follows:

On day 0 of the study, mice were irradiated with 150 centiGray at a rate of 120 rads/minute for 1 minute and 15 seconds. Mice were engrafted with $1 \times 10^5$ cord blood CD34+ stem/progenitor cells by the intravenous (IV) route in 200 µl of Dulbecco's phosphate buffered saline (DPBS) approximately 6 hours post-engraftment. One group of mice were irradiated in the same manner, but not engrafted. These mice are considered irradiated naïve mice. On day 88 post engraftment, mice received a hydrodynamic (HDD) i.v. injection of either saline (engrafted control mice) or 50 µg of IL-4 minicircle DNA in combination with 50 µg of TSLP minicircle DNA. On day 91, a submandibular bleed was performed, and 100 to 150 µl of blood was collected from each mouse and placed into lithium heparin tubes. An engraftment check was performed by flow cytometry and the plasma levels of IL-4 and TSLP were evaluated. Information from the engraftment check and/or the cytokine determination was used to select (assign or eliminate) mice from the study. Mice from the engrafted control group with less than 25% human CD45+ cells were removed from the study. Similarly, engrafted mice that received minicircle DNA and showed plasma TSLP levels 1 standard deviation below the mean were also removed from the study. Mice that received minicircle DNA by HDD i.v. injection received subcutaneous doses of either vehicle (20 mM phosphate, 125 mM L-arginine HCL, and 0.01% tween 20 pH 7.0) or F027400161 (0.01, 0.05, 0.1, or 10 mg/kg) on days 95, 97, 99, and 101. On day 103, mice were anesthetized by isoflurane anesthesia. While under isoflurane anesthesia, blood was collected by retro-orbital bleeds. Following blood collection and while still under isoflurane anesthesia, the mice were terminated by cervical dislocation. A portion of the lung was harvested and placed in RNA later for gene expression evaluation. Plasma levels of human TSLP from the day 103 plasma samples were determined by MSD kit evaluation (Cat #K15067-L-2, Meso Scale Diagnostics, Rockville, MD, USA). Plasma levels of human IL-13 from the day 103 plasma samples were determined by ELISA (Cat #88-7439-88Human IL-13 ELISA kit, Invitrogen/ThermoFischer, Waltham, MA, USA). Internal assay validation experiments demonstrated that both the human TSLP and IL-13 detection kits were not able to detect F027400161 bound hTSLP and hIL-13.

Figure 10:
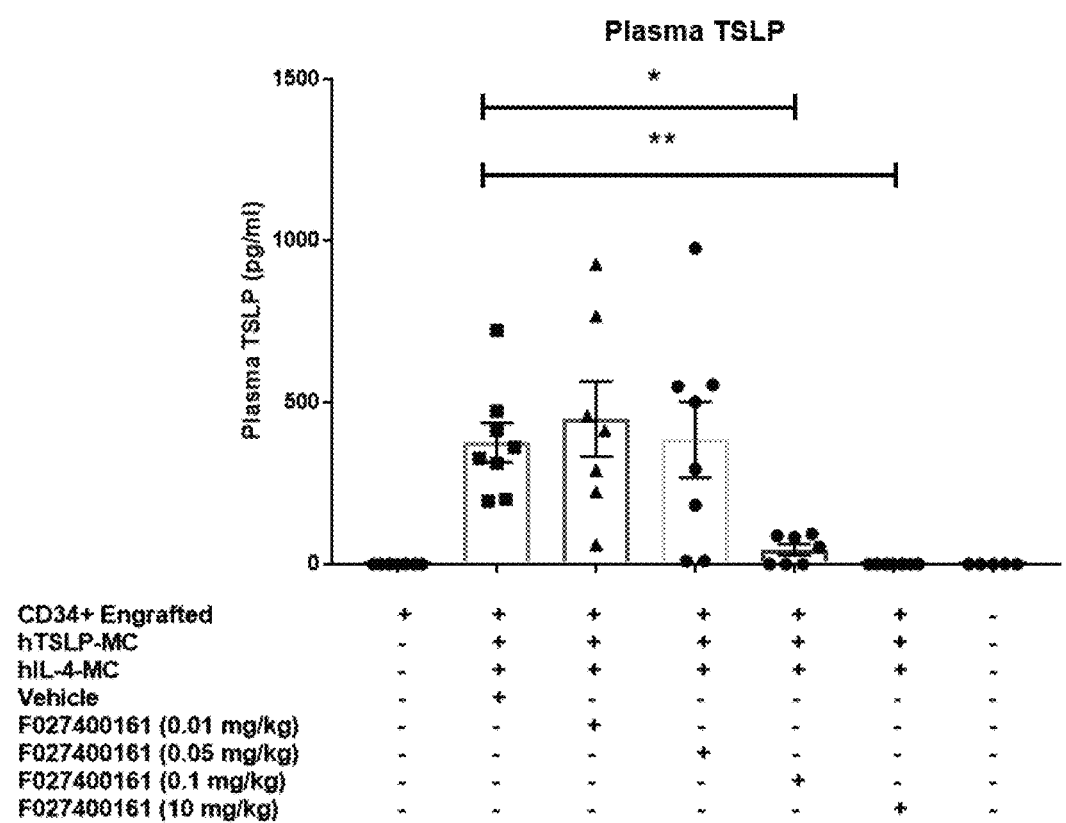
FIG. 10: F027400161 significantly reduced detectable levels of human TSLP in the plasma of NSG-SGM3 mice. When compared to vehicle treated mice (376.166 pg/ml), human plasma TSLP levels were reduced with the 0.1 mg/kg F027400161 dose (45.772 pg/ml) and the 10 mg/kg F027400161 dose (0.072 pg/ml), demonstrating that the TSLP arm of F027400161 can bind to human TSLP in the plasma of humanized NSG-SGM3 mice.
Figure 11:
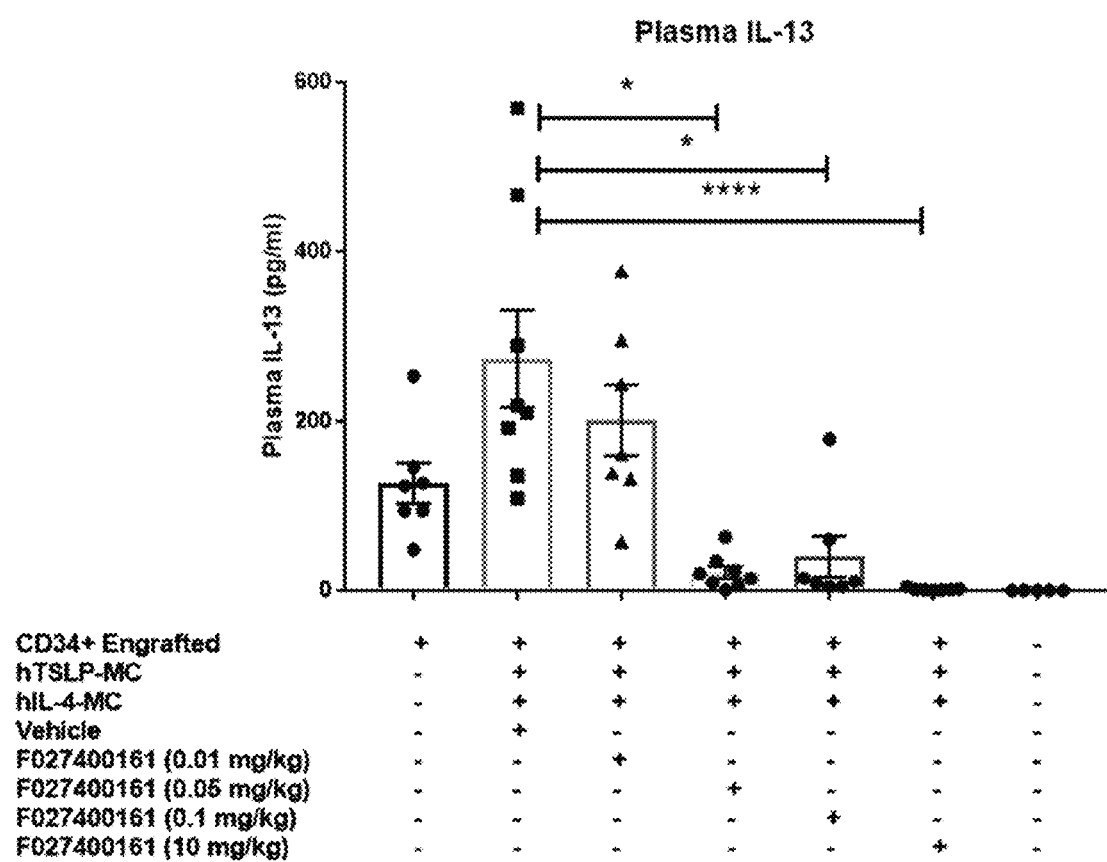
FIG. 11: F027400161 significantly reduced detectable levels of human IL-13 in the plasma of NSG-SGM3 mice. When compared to vehicle treated mice (274.052 pg/ml), human IL-13 levels were reduced with the 0.01 mg/kg F027400161 dose (201.286 pg/ml), 0.05 mg/kg F027400161 dose (22.028 pg/ml), 0.1 mg/kg F027400161 dose (40.740 pg/ml), and with the 10 mg/kg F027400161 dose (1.777 pg/ml), demonstrating that the IL-13 arm of F27400161 can bind to human IL-13 in the plasma of humanized NSG-SGM3 mice.

The collective results of these experiments as shown in FIG. 10 and FIG. 11 demonstrate that F027400161 was able to significantly inhibit detectable levels of human TSLP and IL-13 in the plasma of humanized NSG-SGM3 mice, demonstrating target occupancy for both human TSLP and human IL-13.

In the NSG-SGM3 mouse model, hydrodynamic delivery of TSLP and IL-4 cDNAs turn on the expression of human IL-13 (FIG. 11). Pharmacodynamic effects of F027400161 were studied using samples derived from the NSG-SGM3 study by taking advantage of the ability of human IL-13 to signal through the mouse IL-13 receptor (Hershey GK. 2003, J Allergy Clin Immunol.; 111(4):677-90). In these studies, the impact of F027400161 treatment on human IL-13 regulated mouse gene transcripts were studied. Mouse lung tissues from the above study were used in this analysis.

The lungs from treated and control NSG-SGM3 mice were harvested and processed to make RNA as detailed in the attached protocol. The RNAs were processed for quantification by TaqMan and the data analyzed as described in the protocols. In brief, lungs harvested from the mice were stored in RNALater, processed and purified according to standard protocols to generate high quality RNA. Purified lung RNA was then reverse transcribed to cDNA using Quanta 0-Script 5x master mix according to manufacturer's protocol. Obtained lung cDNA was used to quantify the transcript expression levels of the human IL-13 responsive mouse target genes (mouse Retnla and mouse Clca1) and an endogenous control (Rpl37a) using a TaqMan assay according to manufacturer's protocols. Data analysis was performed in Quantstudio 6&7 flex software. For each probe, $C_T$ values and delta $C_T$ values (against Rpl37a) were exported into excel and relative expression values for each gene were calculated using the following formula:

$$\text{Normalized relative expression} = (\text{Power}(2, -(\text{delta } CT))) * 1000.$$

The two human IL-13 regulated mouse genes evaluated were Retnla (Resistin like alpha), that plays a role in pulmonary vascular remodeling and Clca1 (chloride channel accessory 1) (Lewis CC, 2009, J Allergy Clin Immunol.; 123(4):795-804).

Figure 12:
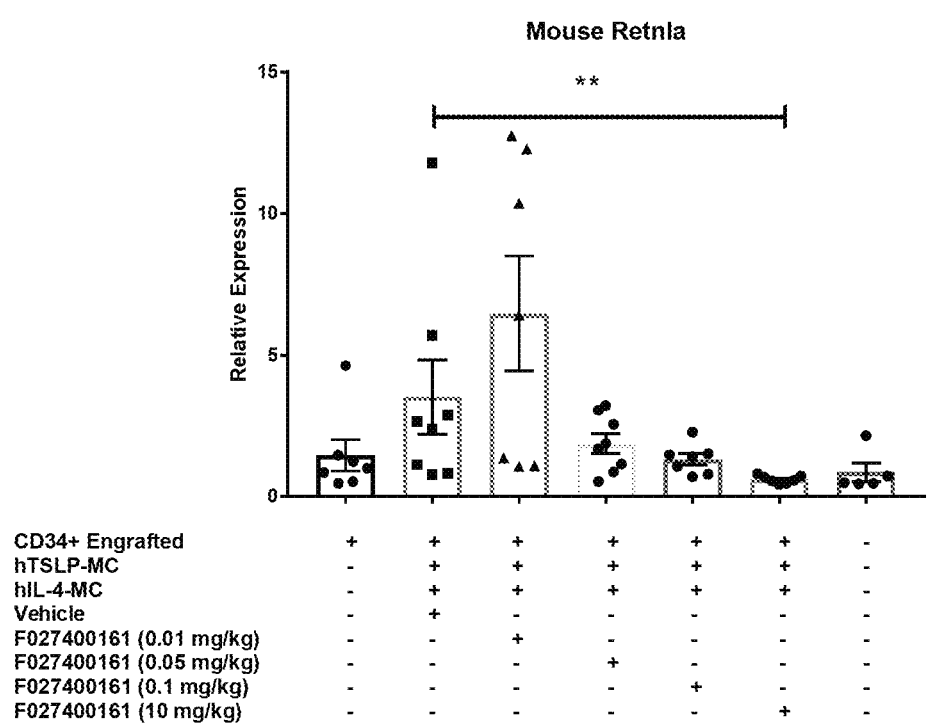
FIGS. 12 and 13: F027400161 Significantly reduced mouse Retnla and Clca1 transcript expression in the lungs of NSG-SGM3 mice that received hydrodynamic delivery of hTSLP and hIL-4. Overexpression of human TSLP and IL-4 in the NSG-SGM3 mice induces the production of hIL-13 from human immune cells derived from the precursor CD34$^+$. Neutralization of the human IL-13 by F027400161 resulted in the inhibition of the mouse Retnla and Clca1 marker genes at the 10 mg/Kg dose.
Figure 13:
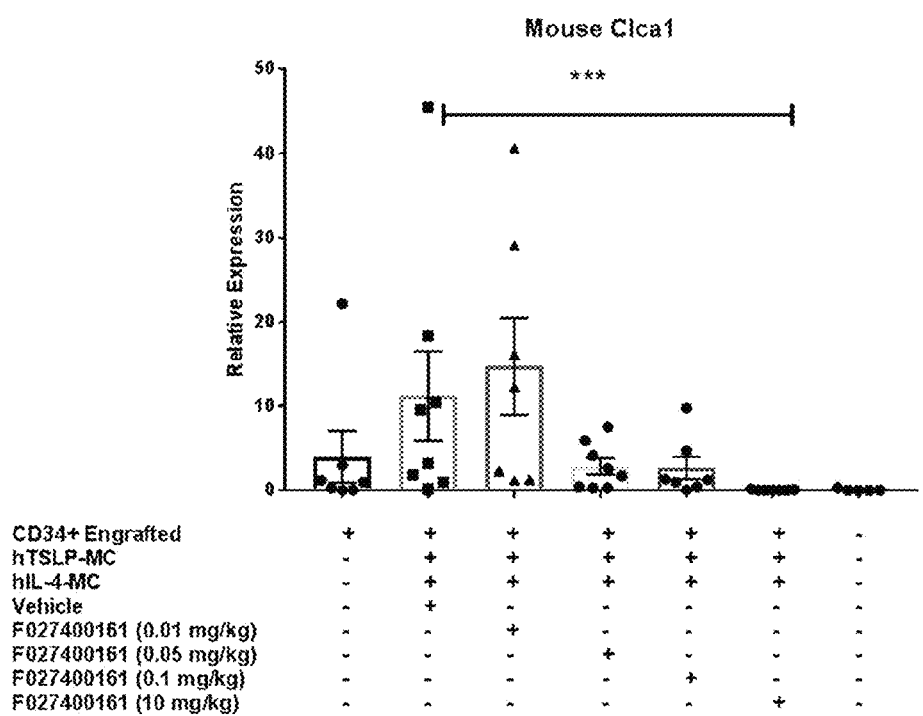
Figure 14:
FIG. 14: Schematic presentation of ISVD construct F027400161 showing from the N-terminus to the C-terminus the monovalent building blocks/ISVDs 4B02, 4B06, 501A02, 529F10, as well as the albumin binder ALB23002. Whereas 4B02 and 4B06 are connected via a 35GS linker, the remaining building block are linked via 9GS linkers.

The collective results of these experiments as shown in FIGS. 12 and 13 demonstrate that F027400161 was able to significantly inhibit mouse Retnla and mouse Clca1 transcript expression, demonstrating the in vivo pharmacodynamics effect of F027400161 on human IL-13 driven mouse transcript responses.

Methods:

Sample Homogenate Preparation:

Lungs were harvested from the mice and stored in RNA later. Lung lobes were then dried and transferred to fastprep lysing Matrix A tubes (for homogenizing lungs) containing 1 mL RLT+2-ME. Samples were homogenized in MP-Bio homogenizer using program 1 (Two 40 second cycles separated by 5 minutes to avoid sample heatup). Samples were then spun at 10,000 g for 3 minutes. Collected 350 ul of lysate [in RLT+2ME (1% v/v)]. Pipette using a multichannel multiple times (~20×) to lyse the cells.

RNA-Preparation:

For RNA purification, 350 ul homogenate was used. 1× volume (350 ul) of 70% Ethanol was added and the homogenate mixed thoroughly and transferred to a 96 well RNeasy spin plate placed in elution plate and RNA was prepared using the Qiagen RNA mini tissue RNA extraction protocol with following modifications. The 96 well plate was covered with sealable aluminum foil and centrifuged for 2 minutes at 4000×g. To wash the column, 400 µl Buffer RWT was added to the RNeasy spin columns and the spin-column plate was centrifuged for 2 minutes at RT at 4000×g. DNAse I digestion was carried out by adding 80 ul of 1×DNAse I mix and incubating at RT for 15 minutes. The DNAse I was washed off by adding 400 ul buffer RWT and spinning the plate at 4000×g for 2 minutes. This was followed by washing the spin-plate with 500 ul each of buffer RPE and 80% ethanol. This was followed by drying of column membranes by spinning at 4000×g for 4 minutes. RNA was then eluted in 40 µl Tris HCl (10 mM; pH-8.0). RNA was quantified using Nanodrop and 500 ng RNA was used for cDNA preparation.

First Strand Synthesis:

Quanta Q-Script 5× master mix was used and cDNA was synthesized using manufacturer's protocol. Final concentration of cDNA was 25 ng/ul. cDNA was stored at −20 Celsius till the TaqMan assay was performed.

TagMan Assay:

TaqMan multiplex master mix was prepared in a 1.5 ml microcentrifuge tube by adding the components in the following order. Three separate master mixes made for each probe-set along with the internal Rpl37a control. Each multiplex qPCR reaction was conducted in a 10 µl reaction volume.

| Component | Single Rxn (ul) | For 40 Rxns (ul) |
|---|---|---|
| 50 × RPL37A Primer/Probe | 0.3 | 10 |
| 20 × Target Gene Primer/Probe | 0.6 | 24 |
| Water | 2.8 | 4 |
| TaqMan Fast Advanced Mastermix; 2× | 5.0 | 200 |
| Total | 8.7 | 238 |

A total of 8.8 ul of the master mix was added for each sample into the appropriate wells of a 384-well optical plate. 30 ng (1.2 ul) cDNA samples were added to each well. TaqMan assay was set-up on QuantStudio 7K. The conditions in the thermo cycler were: pre-denaturation at 95° C. for 3 min, 40 cycles of denaturation at 95° C. for 2 s, and annealing and extension at 60° C. for 5 s. Fluorescent measurements were carried out during the extension step.

Data Analysis:

Data analysis was performed in Quantstudio 6&7 flex software.

For each probe, CT values and delta CT values (against Rpl37a) were exported into excel and relative expression values for each gene were calculated using the following formula:

Normalized relative expression=(power(2,−(delta CT)))*1000

REFERENCES

Liu, Y. J. 2006, J Exp Med.; 203(2):269-73. Thymic stromal lymphopoietin: master switch for allergic inflammation.

Hershey G K. 2003, J Allergy Clin Immunol.; 111(4):677-90. IL-13 receptors and signaling pathways: an evolving web.

Lewis C C, Aronow B, Hutton J, Santeliz J, Dienger K, Herman N, Finkelman F D, Wills-Karp M. 2009, J Allergy Clin Immunol.; 123(4):795-804. Unique and overlapping gene expression patterns driven by IL-4 and IL-13 in the mouse lung.

INDUSTRIAL APPLICABILITY

The polypeptides, nucleic acid molecules encoding the same, vectors comprising the nucleic acids and compositions described herein may be used for example in the treatment of subjects suffering from inflammatory diseases.

The invention claimed is:

1. A method of treating asthma, wherein said method comprises administering, to a subject in need thereof, an effective amount of a polypeptide that comprises at least one immunoglobulin single variable domain (ISVD) that specifically binds to IL13 or TSLP, wherein said ISVD comprises three complementarity determining regions (CDR1 to CDR3, respectively); and wherein the at least one ISVD comprises:
  a) a CDR1 that comprises the amino acid sequence of SEQ ID NO: 7;
    a CDR2 that comprises the amino acid sequence of SEQ ID NO: 12; and
    a CDR3 that comprises the amino acid sequence of SEQ ID NO: 17,
  b) a CDR1 that comprises the amino acid sequence of SEQ ID NO: 8;
    a CDR2 that comprises the amino acid sequence of SEQ ID NO: 13; and
    a CDR3 that comprises the amino acid sequence of SEQ ID NO: 18,
  c) a CDR1 that comprises the amino acid sequence of SEQ ID NO: 9;
    a CDR2 that comprises the amino acid sequence of SEQ ID NO: 14; and
    a CDR3 that comprises the amino acid sequence of SEQ ID NO: 19, or
  d) a CDR1 that comprises the amino acid sequence of SEQ ID NO: 11;
    a CDR2 that comprises the amino acid sequence of SEQ ID NO: 16; and
    a CDR3 that comprises the amino acid sequence of SEQ ID NO: 21.

2. The method according to claim 1, wherein said at least one IS VD that specifically binds to IL-13 or TSLP comprises:
  a) the amino acid sequence of SEQ ID NO: 2,
  b) the amino acid sequence of SEQ ID NO: 3,
  c) the amino acid sequence of SEQ ID NO: 4, or
  d) the amino acid sequence of SEQ ID NO: 6.

3. The method according to claim 1, wherein the polypeptide comprises at least two ISVDs, wherein each of said ISVDs comprises three complementarity determining regions (CDR1 to CDR3, respectively), and wherein:
  a) a first and a second ISVD specifically binds to IL-13 and comprises
    i. a CDR1 that comprises the amino acid sequence of SEQ ID NO: 7;
    ii. a CDR2 that comprises the amino acid sequence of SEQ ID NO: 12; and iii. a CDR3 that comprises the amino acid sequence of SEQ ID NO: 17,
b) a first and a second ISVD specifically binds to IL-13 and comprises
 i. a CDR1 that comprises the amino acid sequence of SEQ ID NO: 8;
 ii. a CDR2 that comprises the amino acid sequence of SEQ ID NO: 13; and
 iii. a CDR3 that comprises the amino acid sequence of SEQ ID NO: 18,
c) a first ISVD specifically binds to IL-13 and comprises
 i. a CDR1 that comprises the amino acid sequence of SEQ ID NO: 7;
 ii. a CDR2 that comprises the amino acid sequence of SEQ ID NO: 12; and
 iii. a CDR3 that comprises the amino acid sequence of SEQ ID NO: 17, and
 a second ISVD specifically binds to IL-13 and comprises
 iv. a CDR1 that comprises the amino acid sequence of SEQ ID NO: 8;
 v. a CDR2 that comprises the amino acid sequence of SEQ ID NO: 13; and
 vi. a CDR3 that comprises the amino acid sequence of SEQ ID NO: 18,
d) a first ISVD specifically binds to IL-13 and comprises
 i. a CDR1 that comprises the amino acid sequence of SEQ ID NO: 8;
 ii. a CDR2 that comprises the amino acid sequence of SEQ ID NO: 13; and
 iii. a CDR3 that comprises the amino acid sequence of SEQ ID NO: 18, and
 a second ISVD specifically binds to IL-13 and comprises
 iv. a CDR1 that comprises the amino acid sequence of SEQ ID NO: 7;
 v. a CDR2 that comprises the amino acid sequence of SEQ ID NO: 12; and
 vi. a CDR3 that comprises the amino acid sequence of SEQ ID NO: 17,
e) a first ISVD specifically binds to TSLP and comprises
 i. a CDR1 that comprises the amino acid sequence of SEQ ID NO: 11;
 ii. a CDR2 that comprises the amino acid sequence of SEQ ID NO: 16; and
 iii. a CDR3 that comprises the amino acid sequence of SEQ ID NO: 21, and
 a second ISVD specifically binds to TSLP and comprises
 iv. a CDR1 that comprises the amino acid sequence of SEQ ID NO: 9;
 v. a CDR2 that comprises the amino acid sequence of SEQ ID NO: 14; and
 vi. a CDR3 that comprises the amino acid sequence of SEQ ID NO: 19, or
f) a first ISVD specifically binds to TSLP and comprises
 i. a CDR1 that comprises the amino acid sequence of SEQ ID NO: 9;
 ii. a CDR2 that comprises the amino acid sequence of SEQ ID NO: 14; and
 iii. a CDR3 that comprises the amino acid sequence of SEQ ID NO: 19, and
 a second ISVD specifically binds to TSLP and comprises
 iv. a CDR1 that comprises the amino acid sequence of SEQ ID NO: 11;

v. a CDR2 that comprises the amino acid sequence of SEQ ID NO: 16; and
 vi. a CDR3 that comprises the amino acid sequence of SEQ ID NO: 21,
wherein the order of the ISVDs indicates their relative position to each other considered from the N-terminus to the C-terminus of said polypeptide.

4. The method according to claim 3, wherein the polypeptide comprises:
 a) the amino acid sequence of SEQ ID NO: 148,
 b) the amino acid sequence of SEQ ID NO: 149,
 c) the amino acid sequence of SEQ ID NO: 150,
 d) the amino acid sequence of SEQ ID NO: 151,
 e) the amino acid sequence of SEQ ID NO: 152,
 f) the amino acid sequence of SEQ ID NO: 153,
 g) the amino acid sequence of SEQ ID NO: 154,
 h) the amino acid sequence of SEQ ID NO: 155,
 i) the amino acid sequence of SEQ ID NO: 156,
 j) the amino acid sequence of SEQ ID NO: 157,
 k) the amino acid sequence of SEQ ID NO: 158, or
 l) the amino acid sequence of SEQ ID NO: 159.

5. The method of claim 3, wherein the at least two ISVDs are linked via one or more peptidic linkers.

6. The method according to claim 1, wherein the polypeptide comprises at least four ISVDs, wherein each of said ISVDs comprises three complementarity determining regions (CDR1 to CDR3, respectively), and wherein:
 a) a first ISVD specifically binds to IL-13 and comprises
  i. a CDR1 that comprises the amino acid sequence of SEQ ID NO: 7;
  ii. a CDR2 that comprises the amino acid sequence of SEQ ID NO: 12; and
  iii. a CDR3 that comprises the amino acid sequence of SEQ ID NO: 17,
 b) a second ISVD specifically binds to IL-13 and comprises
  iv. a CDR1 that comprises the amino acid sequence of SEQ ID NO: 8;
  v. a CDR2 that comprises the amino acid sequence of SEQ ID NO: 13; and
  vi. a CDR3 that comprises the amino acid sequence of SEQ ID NO: 18,
 c) a third ISVD specifically binds to TSLP and comprises
  vii. a CDR1 that comprises the amino acid sequence of SEQ ID NO: 9;
  viii. a CDR2 that comprises the amino acid sequence of SEQ ID NO: 14; and
  ix. a CDR3 that comprises the amino acid sequence of SEQ ID NO: 19, and
 d) a fourth ISVD specifically binds to TSLP and comprises
  x. a CDR1 that comprises the amino acid sequence of SEQ ID NO: 11;
  xi. a CDR2 that comprises the amino acid sequence of SEQ ID NO: 16; and
  xii. a CDR3 that comprises the amino acid sequence of SEQ ID NO: 21,
wherein the order of the ISVDs indicates their relative position to each other considered from the N-terminus to the C-terminus of said polypeptide.

7. The method according to claim 6, wherein:
 a) said first ISVD comprises the amino acid sequence of SEQ ID NO: 2;
 b) said second ISVD comprises the amino acid sequence of SEQ ID NO: 3;

c) said third ISVD comprises the amino acid sequence of SEQ ID NO: 4; and
d) said fourth ISVD comprises the amino acid sequence of SEQ ID NO: 6.

8. The method according to claim 6, wherein the polypeptide comprises the amino acid sequence of SEQ ID NO: 1.

9. The method according to claim 8, wherein the polypeptide consists of the amino acid sequence of SEQ ID NO: 1.

10. The method of claim 6, wherein the at least four ISVDs are linked via one or more peptidic linkers.

11. The method according to claim 1, wherein said polypeptide further comprises one or more other groups, residues, moieties or binding units, in which said one or more other groups, residues, moieties or binding units provide the polypeptide with increased half-life, compared to the corresponding polypeptide without said one or more other groups, residues, moieties or binding units.

12. The method according to claim 11, in which said one or more other groups, residues, moieties or binding units that provide the polypeptide with increased half-life is selected from the group consisting of binding units that bind to serum albumin and a serum immunoglobulin.

13. The method according to claim 12, in which said binding unit that provides the polypeptide with increased half-life is an ISVD that binds to human serum albumin, wherein the ISVD that binds to human serum albumin comprises a CDR1 that comprises the amino acid sequence of SEQ ID NO: 10, a CDR2 that comprises the amino acid sequence of SEQ ID NO: 15 and a CDR3 that comprises the amino acid sequence of SEQ ID NO: 20.

14. The method according to claim 13, wherein the amino acid sequence of said ISVD binding to human serum albumin comprises a sequence identity of more than 90% with SEQ ID NO: 5.

15. The method according to claim 13, wherein said ISVD binding to human serum albumin comprises the amino acid sequence of SEQ ID NO: 5.

16. The method claim 12, wherein the serum immunoglobulin is an IgG.

17. The method of claim 11, wherein the one or more other groups, residues, moieties or binding units one or more other groups, residues, moieties or binding units are linked to an ISVD of the polypeptide via one or more peptidic linkers.

18. The method according to claim 1, wherein the polypeptide is in a pharmaceutical composition.

* * * * *

UNITED STATES PATENT AND TRADEMARK OFFICE
CERTIFICATE OF CORRECTION

PATENT NO. : 11,840,566 B2
APPLICATION NO. : 17/530800
DATED : December 12, 2023
INVENTOR(S) : Heidi Rommelaere et al.

It is certified that error appears in the above-identified patent and that said Letters Patent is hereby corrected as shown below:

In the Claims

Claim 2, at Column 186, Lines 52-53, should read:
--one ISVD that specifically binds to IL-13 or TSLP comprises:--

Signed and Sealed this
Twentieth Day of February, 2024

Katherine Kelly Vidal
*Director of the United States Patent and Trademark Office*